(12) United States Patent
Myers et al.

(10) Patent No.: US 11,124,534 B2
(45) Date of Patent: Sep. 21, 2021

(54) LINCOSAMIDE ANTIBIOTICS AND USES THEREOF

(71) Applicant: President and Fellows of Harvard College, Cambridge, MA (US)

(72) Inventors: Andrew G. Myers, Cambridge, MA (US); Matthew James Mitcheltree, Cambridge, MA (US); Katherine J. Silvestre, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 35 days.

(21) Appl. No.: 16/637,647

(22) PCT Filed: Aug. 10, 2018

(86) PCT No.: PCT/US2018/046167
§ 371 (c)(1),
(2) Date: Feb. 7, 2020

(87) PCT Pub. No.: WO2019/032936
PCT Pub. Date: Feb. 14, 2019

(65) Prior Publication Data
US 2020/0339620 A1    Oct. 29, 2020

Related U.S. Application Data

(60) Provisional application No. 62/650,822, filed on Mar. 30, 2018, provisional application No. 62/585,271, filed on Nov. 13, 2017, provisional application No. 62/568,657, filed on Oct. 5, 2017, provisional application No. 62/557,893, filed on Sep. 13, 2017, provisional application No. 62/558,143, filed on Sep. 13, 2017, provisional application No. 62/543,808, filed on Aug. 10, 2017.

(51) Int. Cl.
*C07H 15/14*    (2006.01)
*A61P 31/04*    (2006.01)

(52) U.S. Cl.
CPC ............. *C07H 15/14* (2013.01); *A61P 31/04* (2018.01)

(58) Field of Classification Search
None
See application file for complete search history.

(56) References Cited

U.S. PATENT DOCUMENTS

| | | |
|---|---|---|
| 5,004,730 A | 4/1991 | Philippe et al. |
| 7,199,106 B2 * | 4/2007 | Lewis .................. C07D 405/12 514/24 |
| 7,361,743 B2 | 4/2008 | Lewis et al. |
| 7,879,808 B2 | 2/2011 | Wakiyama et al. |
| 2009/0156512 A1 | 6/2009 | Umemura et al. |
| 2010/0184746 A1 | 7/2010 | Umemura et al. |
| 2010/0210570 A1 | 8/2010 | Wakiyama et al. |
| 2012/0028222 A1 | 2/2012 | Abdennour et al. |

OTHER PUBLICATIONS

Invitation to Pay Additional Fees, dated Sep. 24, 2018, in connection with Application No. PCT/US2018/046200.
International Search Report and Written Opinion, dated Dec. 11, 2018, in connection with Application No. PCT/US2018/046200.
International Preliminary Report on Patentability, dated Feb. 20, 2020, in connection with Application No. PCT/US2018/046200.
International Search Report and Written Opinion, dated Sep. 26, 2018, in connection with Application No. PCT/US2018/046167.
International Preliminary Report on Patentability, dated Feb. 20, 2020, in connection with Application No. PCT/US2018/046167.
Invitation to Pay Additional Fees, dated Sep. 21, 2018, in connection with Application No. PCT/US2018/046178.
International Search Report and Written Opinion, dated Nov. 26, 2018, in connection with Application No. PCT/US2018/046178.
International Preliminary Report on Patentability, dated Feb. 20, 2020, in connection with Application No. PCT/US2018/046178.
Belanger et al., Stereocontrolled synthesis of triazacyclopenta[cd]pentalenes by intramolecular 1,3-dipolar cycloaddition reactions of azomethine imines. J Org Chem. Nov. 1, 2002;67(22):7880-3.
U.S. Appl. No. 16/637,477, filed Feb. 7, 2020, Myers et al.
U.S. Appl. No. 16/637,644, filed Feb. 7, 2020, Myers et al.
PCT/US2018/046200, Sep. 24, 2018, Invitation to Pay Additional Fees.
PCT/US2018/046200, Dec. 11, 2018, International Search Report and Written Opinion.
PCT/US2018/046200, Feb. 20, 2020, International Preliminary Report on Patentability.
PCT/US2018/046167, Sep. 26, 2018, International Search Report and Written Opinion.
PCT/US2018/046167, Feb. 20, 2020, International Preliminary Report on Patentability.
PCT/US2018/046178, Sep. 21, 2018, Invitation to Pay Additional Fees.

* cited by examiner

*Primary Examiner* — Traviss C McIntosh, III
(74) *Attorney, Agent, or Firm* — Wolf, Greenfield & Sacks, P.C.

(57) ABSTRACT

Provided are lincosamide compounds for the treatment of infectious diseases. The lincosamides described herein are modified at the amino acid (southern) region. The lincosamides may have further modification at the C-1 and C-7 positions of the aminooctose (northern) region, thus distinguishing them from lincomycin and clindamycin. Also provided are methods for preparing the lincosamide compounds, pharmaceutical compositions comprising the lincosamide compounds, and methods of treating infectious diseases using the disclosed lincosamide compounds.

20 Claims, No Drawings

LINCOSAMIDE ANTIBIOTICS AND USES THEREOF

RELATED APPLICATIONS

This application is a national stage filing under 35 U.S.C. § 371 of international PCT application, PCT/US2018/046167, filed Aug. 10, 2018, which claims priority under 35 U.S.C. § 119(e) to U.S. Provisional Applications, U.S. Ser. No. 62/543,808, filed Aug. 10, 2017; U.S. Ser. No. 62/557,893, filed Sep. 13, 2017; U.S. Ser. No. 62/558,143, filed Sep. 13, 2017; U.S. Ser. No. 62/568,657, filed Oct. 5, 2017; U.S. Ser. No. 62/585,271, filed Nov. 13, 2017; and U.S. Ser. No. 62/650,822, filed Mar. 30, 2018, each of which is incorporated herein by reference.

BACKGROUND

Emerging resistance to existing antibiotics is rapidly developing as a crisis of global proportions, especially for infections originating from drug-resistant Gram-negative bacteria. Pathogenic bacteria can transmit genes coding for antibiotic resistance both vertically (to their progeny) and horizontally (to neighboring bacteria of different lineages), and as a result antibiotic resistance can evolve quickly, particularly in nosocomial (hospital) settings. See, e.g., Wright, *Chem. Commun.* (2011) 47:4055-4061. More than 99,000 people die annually in the U.S. from healthcare-associated infections, more than all casualties from car accidents, HIV, and breast cancer combined, creating an estimated burden of up to $45 billion in U.S. healthcare costs. See, e.g., Klevens et al., *Public Health Rep* (2007) 122:160-166. The current crisis is exacerbated by decreased research in the development of new antibiotics by most major pharmaceutical companies. See, e.g., Projan, *Curr. Opin. Microbiol.* (2003) 6:427-430. The current rate of introduction of new antibiotics does not adequately address growing resistance, and with the ease of international travel and increasing population densities, the need for innovation in the field has never been higher.

The lincosamides are a class of antibiotics that prevent bacteria growth by interfering with the synthesis of proteins. They bind to the 23s portion of the 50S subunit of bacterial ribosomes and cause premature dissociation of the peptidyl-tRNA from the ribosome. Lincosamides do not interfere with protein synthesis in human cells (or those of other eukaryotes) because human ribosomes are structurally different from those of bacteria.

The first lincosamide to be discovered was lincomycin, but the use of lincomycin as an antibiotic has been largely superseded by clindamycin, which exhibits improved antibacterial activity. Clindamycin also exhibits some activity against parasitic protozoa and has been used to treat toxoplasmosis and malaria. Lincosamides are typically used to treat *Staphylococcus* and *Streptococcus* infections but have also proved to be useful in treating *Bacteroides fragilis* and other anaerobic infections. They are used in the treatment of toxic shock syndrome and thought to directly block the M protein production that leads to the severe inflammatory response.

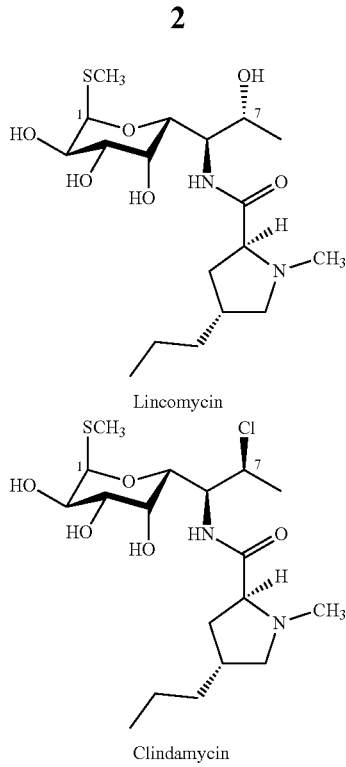

Lincomycin

Clindamycin

Target bacteria may alter the drug's binding site leading to resistance (similar to resistance found with macrolides and streptogramins). The resistance mechanism is methylation of the 23s binding site. If this occurs, then the bacteria are resistant to both macrolides and lincosamides. In rare instances, enzymatic inactivation of clindamycin has also been reported.

In addition, lincosamide antibiotics are associated with pseudomembranous colitis caused by *Clostridium difficile* (*C. difficile*). Pseudomembranous colitis is inflammation of the colon associated with an overgrowth of *C. difficile*. This overgrowth of *C. difficile* is most often related to recent lincosamide antibiotic use. For example, clindamycin, currently the only lincosamide in clinical use, carries a black-box warning for its tendency to promote *C. difficile*-associated diarrhea (CDAD).

Accordingly, the discovery and development of new antibiotics effective against drug-resistant bacteria, particularly lincosamides, represents a currently unmet medical need.

SUMMARY

A powerful synthetic platform for the discovery of new synthetic lincosamide antibiotics is disclosed herein. This platform enables the production of lincosamides bearing unprecedented modifications to both constituent halves of the lincosamides, namely the aminooctose (northern) and amino-acid (southern) portions. Lincosamides generated using this platform demonstrate potent activity against high-priority, clinically relevant pathogens including clindamycin- and azithromycin-resistant strains of *S. aureus, S. pneumoniae,* and *E. faecalis*-strains against which effective new antibiotics are in demand. Moreover, the disclosed lincosamides show potential promise as safer alternatives to clindamycin, owing to a diminished negative impact on commensal gut flora due to increased activity against *C. difficile*. The disclosed synthetic lincosamides also demonstrate activity against Gram-negative pathogens like *E. coli*.

In one aspect, the present disclosure provides compounds of Formula (I):

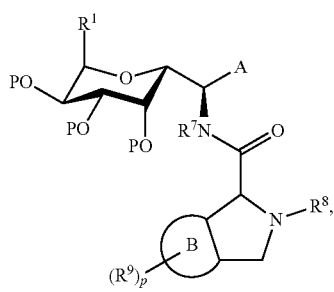

and pharmaceutically acceptable salts thereof, wherein:
P is independently hydrogen or a protecting group;
A is substituted or unsubstituted carbocyclyl, substituted or unsubstituted heterocyclyl, substituted or unsubstituted aryl, substituted or unsubstituted heteroaryl, substituted or unsubstituted alkyl, substituted or unsubstituted alkenyl, or substituted or unsubstituted alkynyl;
B is a carbocyclic or heterocyclic ring;
$R^1$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, substituted or unsubstituted heteroaliphatic, —$OR^A$, —$N(R^A)_2$, or —$SR^A$;
$R^7$ is hydrogen or unsubstituted alkyl; or A and $R^7$ are joined to form a substituted or unsubstituted heterocyclic ring;
$R^8$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaliphatic, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —S(O)$_2R^A$, or a nitrogen protecting group;
each occurrence of $R^9$ is independently, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, substituted or unsubstituted heteroaliphatic, —$OR^A$, —N($R^A$)$_2$, —$SR^A$, —CN, —SCN, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —NO$_2$, —$NR^A$C(=O)$R^A$, —$NR^A$C(=O)$OR^A$, —$NR^A$C(=O)N($R^A$)$_2$, —$NR^A$C(=$NR^A$)N($R^A$)$_2$, —OC(=O)$R^A$, —OC(=O)$OR^A$, —OC(=O)N($R^A$)$_2$, —$NR^A$S(O)$_2R^A$, —OS(O)$_2R^A$, or —S(O)$_2R^A$; or two $R^9$ groups are joined to form a substituted or unsubstituted heterocyclyl ring, or a substituted or unsubstituted carbocyclyl ring;
p is 0-4;
each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted carbocyclylalkyl, substituted or unsubstituted heterocyclyl, substituted or unsubstituted aryl, substituted or unsubstituted aralkyl, substituted or unsubstituted heteroaryl, substituted or unsubstituted hetaralkyl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclyl ring, or a substituted or unsubstituted heteroaryl ring.

In certain embodiments, the present disclosure provides compounds of Formulae (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), (I-s), (I-t), (I-u), (I-v), and (I-w):

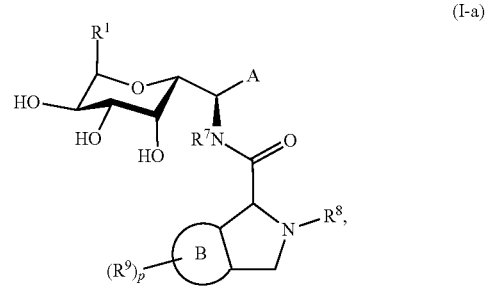

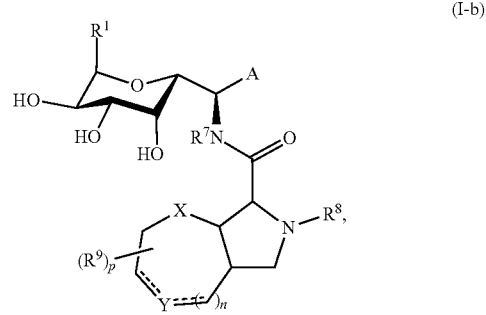

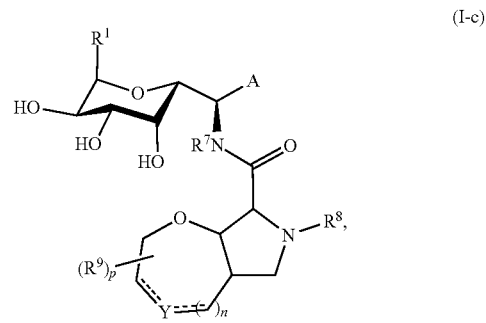

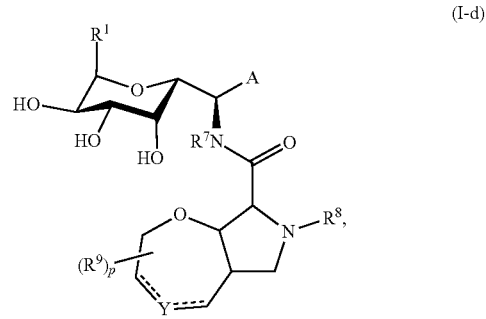

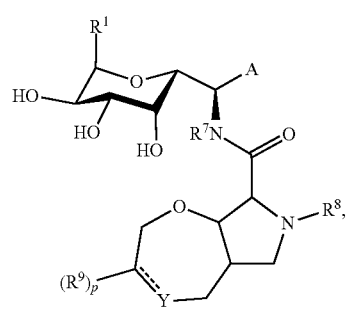
(I-e)
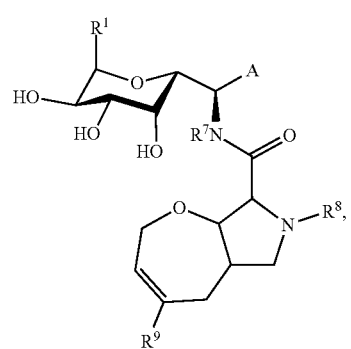
(I-f)
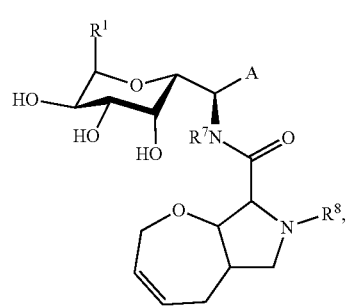
(I-g)
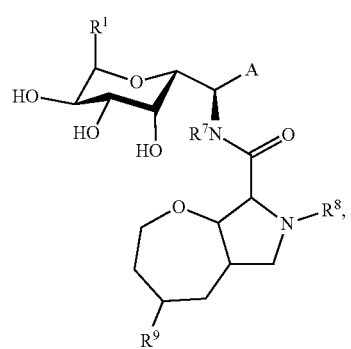
(I-h)
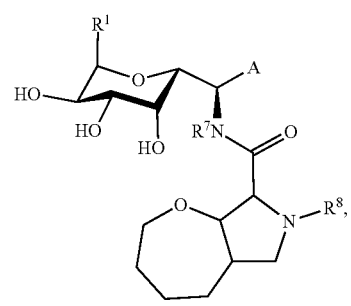
(I-i)
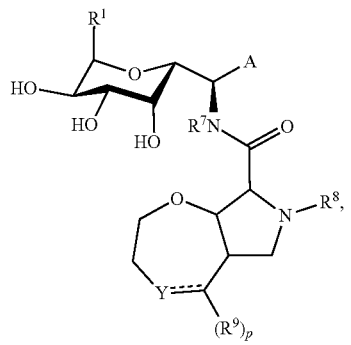
(I-j)
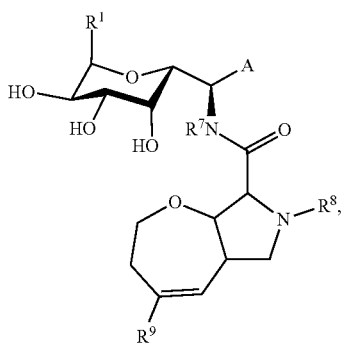
(I-k)
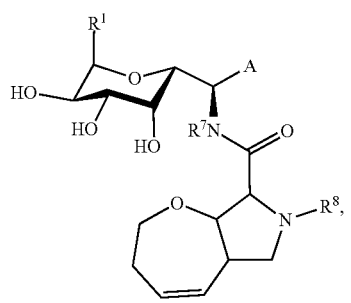
(I-l)
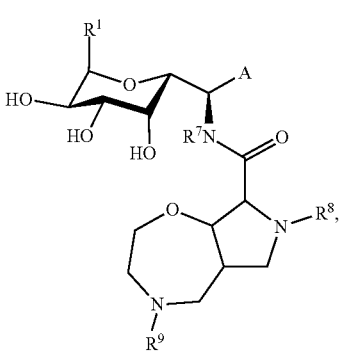
(I-m)
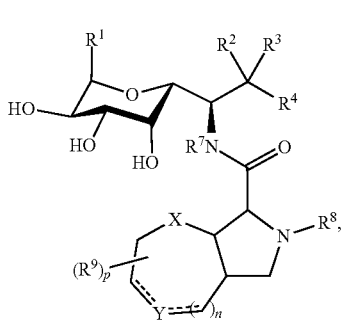
(I-n)

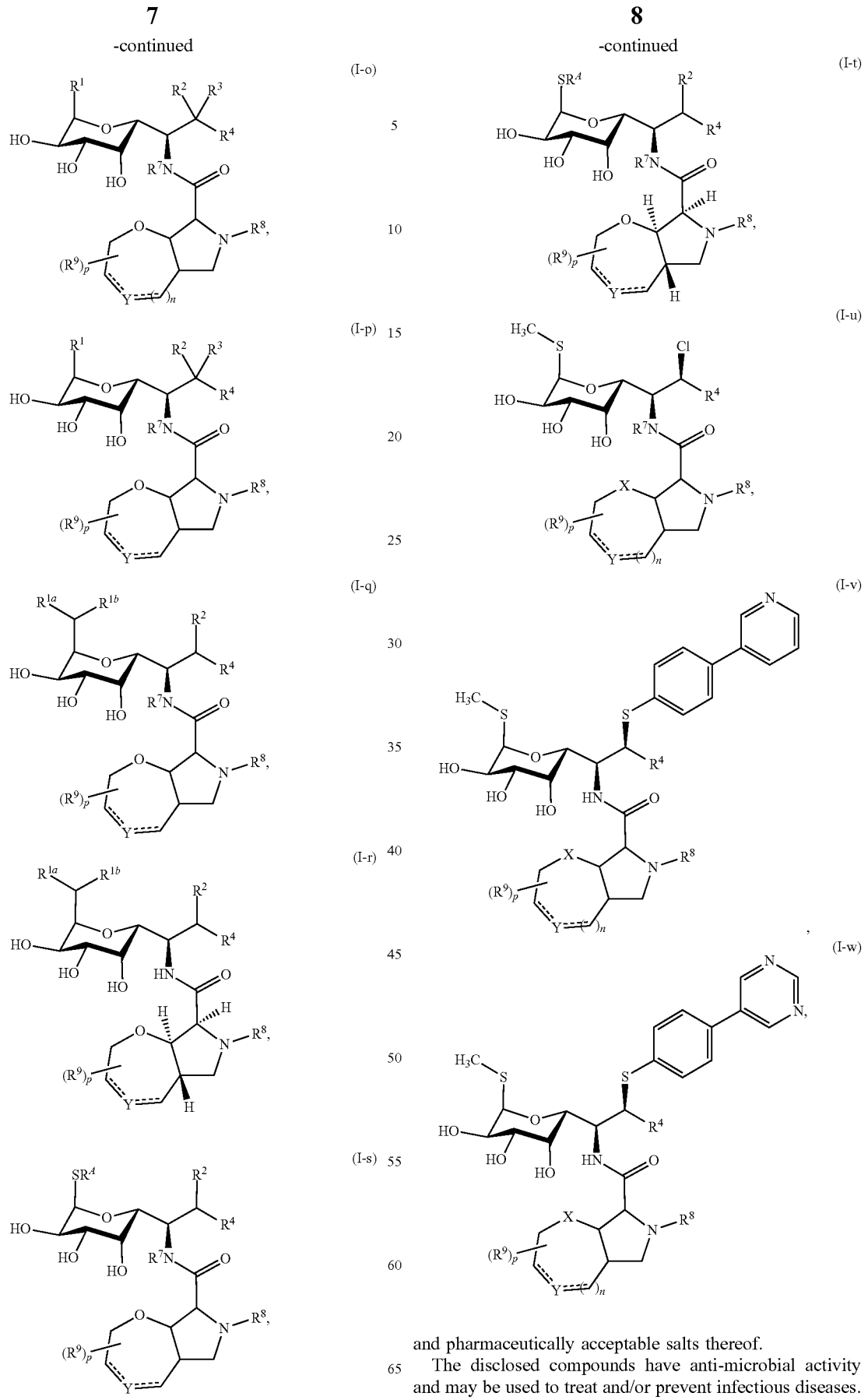
and pharmaceutically acceptable salts thereof.
The disclosed compounds have anti-microbial activity and may be used to treat and/or prevent infectious diseases. Pharmaceutical compositions of the compounds, kits comprising the compounds and/or compositions, and methods of treatment using the compounds or compositions thereof are provided herein. Infectious diseases which may be treated with compounds of the invention include, but are not limited to, bacterial infections caused by *Staphylococcus*, *Streptococcus*, *Enterococcus*, *Acinetobacter*, *Clostridium*, *Bacteriodes*, *Klebsiella*, *Escherichia*, *Pseudomonas*, and *Haemophilus* species.

Methods of preparing the disclosed compounds are also provided herein. In certain embodiments, the disclosed compounds are prepared by an amide coupling of the aminooctose (northern) and amino-acid (southern) portions (e.g., Scheme 1).

The details of certain embodiments of the invention are set forth in the Detailed Description of Certain Embodiments, as described below. Other features, objects, and advantages of the invention will be apparent from the Definitions, Examples, and Claims.

DETAILED DESCRIPTION OF CERTAIN EMBODIMENTS

The compounds disclosed herein include lincosamide analogues. The disclosed compounds have increased structural diversity over known lincosamides, such as lincomycin and clindamycin. In particular, the disclosed compounds have structures that have a fused bicyclic ring at the amino-acid (southern) region, and also may be modified at the C-1 and C-7 positions of the aminooctose (northern) region. The disclosed lincosamides provide unexpected and potent activity against various microorganisms, including Gram negative bacteria. The disclosed lincosamides are non-hemolytic, non-toxic, and possess improved activity profiles relative to clindamycin, such as increased activity against resistant strains of bacteria, including *Clostridium difficile*. Also disclosed are methods for the preparation of the disclosed compounds, pharmaceutical compositions comprising the compounds, uses of the compounds, and methods of using the compounds (e.g., treatment of an infectious disease, prevention of an infectious disease).

In one aspect, provided are compounds of Formula (I):

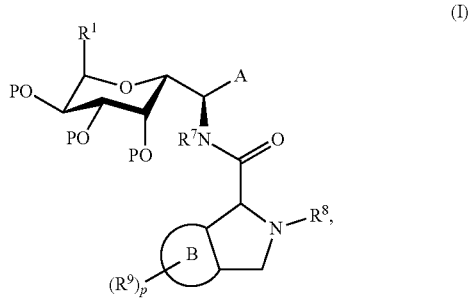

(I)

and pharmaceutically acceptable salts thereof, wherein:

P is independently hydrogen or a protecting group;

A is substituted or unsubstituted carbocyclyl, substituted or unsubstituted heterocyclyl, substituted or unsubstituted aryl, substituted or unsubstituted heteroaryl, substituted or unsubstituted alkyl, substituted or unsubstituted alkenyl, or substituted or unsubstituted alkynyl;

B is a carbocyclyl or heterocyclyl ring;

$R^1$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, substituted or unsubstituted heteroaliphatic, —$OR^4$, —$N(R^4)_2$, or —$SR^4$;

$R^7$ is hydrogen or unsubstituted alkyl; or A and $R^7$ are joined to form a substituted or unsubstituted heterocyclic ring;

$R^8$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaliphatic, —$C(=NR^4)R^4$, —$C(=NR^4)OR^4$, —$C(=NR^4)N(R^4)_2$, —$C(=O)R^4$, —$C(=O)OR^4$, —$C(=O)N(R^4)_2$, —$S(O)_2R^4$, or a nitrogen protecting group;

each occurrence of $R^9$ is independently, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaliphatic, —$OR^4$, —$N(R^4)_2$, —$SR^4$, —CN, —SCN, —$C(=NR^4)R^4$, —$C(=NR^4)OR^4$, —$C(=NR^4)N(R^4)_2$, —$C(=O)R^4$, —$C(=O)OR^4$, —$C(=O)N(R^4)_2$, —$NO_2$, —$NR^4C(=O)R^4$, —$NR^4C(=O)OR^4$, —$NR^4C(=O)N(R^4)_2$, —$NR^4C(=NR^4)N(R^4)_2$, —$OC(=O)R^4$, —$OC(=O)OR^4$, —$OC(=O)N(R^4)_2$, —$NR^4S(O)_2R^4$, —$OS(O)_2R^4$, or —$S(O)_2R^4$; or two $R^9$ groups are joined to form a substituted or unsubstituted heterocyclyl ring, or a substituted or unsubstituted carbocyclyl ring;

p is 0-4; and each occurrence of $R^4$ is, independently, hydrogen, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted carbocyclylalkyl, substituted or unsubstituted heterocyclyl, substituted or unsubstituted aryl, substituted or unsubstituted aralkyl, substituted or unsubstituted heteroaryl, substituted or unsubstituted hetaralkyl, a nitrogen protecting group when attached to a nitrogen atom, an oxygen protecting group when attached to an oxygen atom, or a sulfur protecting group when attached to a sulfur atom, or two $R^4$ groups are joined to form a substituted or unsubstituted heterocyclyl ring, or a substituted or unsubstituted heteroaryl ring.

In certain embodiments of the compound of Formula (I), each P is hydrogen.

Unless otherwise stated, any formulae described herein are also meant to include salts, solvates, hydrates, polymorphs, co-crystals, tautomers, stereoisomers, and isotopically labeled derivatives thereof. In certain embodiments, the provided compound is a salt of any of the formulae described herein. In certain embodiments, the provided compound is a pharmaceutically acceptable salt of any of the formulae described herein. In certain embodiments, the provided compound is a solvate of any of the formulae described herein. In certain embodiments, the provided compound is a hydrate of any of the formulae described herein. In certain embodiments, the provided compound is a polymorph of any of the formulae described herein. In certain embodiments, the provided compound is a co-crystal of any of the formulae described herein. In certain embodiments, the provided compound is a tautomer of any of the formulae described herein. In certain embodiments, the provided compound is a stereoisomer of any of the formulae described herein. In certain embodiments, the provided compound is of an isotopically labeled form of any of the formulae described herein. For example, compounds having the present structures except for the replacement of hydrogen by deuterium or tritium, replacement of $^{19}$F with $^{18}$F, or the replacement of a $^{12}$C by a $^{13}$C or $^{14}$C are within the scope of the disclosure. In certain embodiments, the provided compound is a deuterated form of any of the formulae or compounds described herein.

Group A

As generally defined herein, A is substituted or unsubstituted carbocyclyl, substituted or unsubstituted heterocyclyl, substituted or unsubstituted aryl, substituted or unsubstituted heteroaryl, substituted or unsubstituted alkyl, substituted or unsubstituted alkenyl, or substituted or unsubstituted alkynyl; or A and $R^7$ are joined to form a substituted or unsubstituted heterocyclic ring.

In certain embodiments, A is substituted or unsubstituted carbocyclyl, substituted or unsubstituted heterocyclyl,

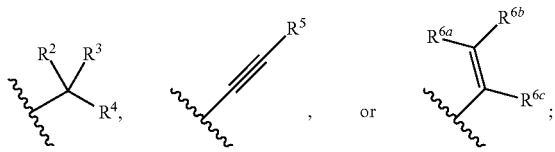

$R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —OR$^A$, —N$_3$, —N(R$^A$)$_2$, —SR$^A$, —CN, —SCN, —C(=NR$^A$)R$^A$, —C(=NR$^A$)OR$^A$, —C(=NR$^A$)N(R$^A$)$_2$, —C(=O)R$^A$, —C(=O)OR$^A$, —C(=O)N(R$^A$)$_2$, —NO$_2$, —NR$^A$C(=O)R$^A$, —NR$^A$C(=O)OR$^A$, —NR$^A$C(=O)N(R$^A$)$_2$, —NR$^A$C(=NR$^A$)N(R$^A$)$_2$, —OC(=O)R$^A$, —OC(=O)OR$^A$, —OC(=O)N(R$^A$)$_2$, —NR$^A$S(O)$_2$R$^A$, —OS(O)$_2$R$^A$, or —S(O)$_2$R$^A$;

$R^3$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

$R^4$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

$R^5$ is hydrogen, halogen, substituted or unsubstituted alkyl, substituted or unsubstituted carbocyclyl, substituted or unsubstituted heterocyclyl, substituted or unsubstituted aryl, substituted or unsubstituted heteroaryl, or substituted or unsubstituted heteroaliphatic; and $R^{6a}$, $R^{6b}$, and $R^{6c}$ are each independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or unsubstituted heteroaliphatic, or substituted or unsubstituted acyl.

In certain embodiments, A is

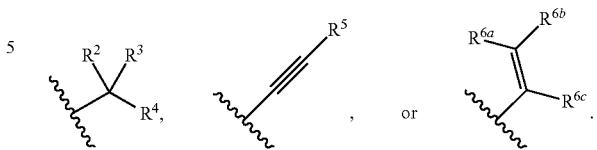

In certain embodiments, A is

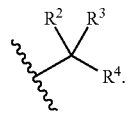

In certain embodiments, $R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaryl, substituted or unsubstituted heteroalkyl, —OR$^A$, —N$_3$, —N(R$^A$)$_2$, —SR$^A$, —NR$^A$C(=O)R$^A$, or —OC(=O)N(R$^A$)$_2$.

In certain embodiments, $R^2$ is halogen, substituted or unsubstituted alkyl, substituted or unsubstituted alkenyl, substituted or unsubstituted heteroaryl, —OR$^A$, —N$_3$, —N(R$^A$)$_2$, —SR$^A$, —NR$^A$C(=O)R$^A$, or —OC(=O)N(R$^A$)$_2$. In certain embodiments, $R^2$ is substituted or unsubstituted heteroaryl. In certain embodiments, $R^2$ is substituted or unsubstituted 5-membered heteroaryl. In certain embodiments, $R^2$ is substituted or unsubstituted pyrrolyl, imidazolyl, pyrazolyl, or triazolyl.

In certain embodiments, $R^2$ is halogen, substituted or unsubstituted alkyl, —OR$^A$, —N$_3$, —N(R$^A$)$_2$, or —SR$^A$. In certain embodiments, $R^2$ is halogen or —SR$^A$. In certain embodiments, $R^2$ is —Cl or —SCH$_3$. In certain embodiments, $R^2$ is —Cl. In certain embodiments, $R^2$ is —SCH$_3$.

In certain embodiments, $R^3$ is hydrogen, halogen, substituted or unsubstituted alkyl, or substituted or unsubstituted alkenyl. In certain embodiments, $R^3$ is hydrogen or substituted or unsubstituted alkyl. In certain embodiments, $R^3$ is hydrogen. In certain embodiments, $R^3$ is substituted or unsubstituted C$_{1-6}$ alkyl. In certain embodiments, $R^3$ is unsubstituted C$_{1-6}$ alkyl. In certain embodiments, $R^3$ is unsubstituted C$_{1-3}$ alkyl. In certain embodiments, $R^3$ is unsubstituted C$_{1-2}$ alkyl. In certain embodiments, $R^3$ is ethyl. In certain embodiments, $R^3$ is methyl.

In certain embodiments, $R^4$ is hydrogen, halogen, substituted or unsubstituted alkyl, or substituted or unsubstituted alkenyl. In certain embodiments, $R^4$ is hydrogen or substituted or unsubstituted alkyl. In certain embodiments, $R^4$ is hydrogen. In certain embodiments, $R^4$ is substituted or unsubstituted C$_{1-6}$ alkyl. In certain embodiments, $R^4$ is unsubstituted C$_{1-6}$ alkyl. In certain embodiments, $R^4$ is unsubstituted C$_{1-3}$ alkyl. In certain embodiments, $R^4$ is unsubstituted C$_{1-2}$ alkyl. In certain embodiments, $R^4$ is ethyl. In certain embodiments, $R^4$ is methyl.

In certain embodiments, $R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaryl, substituted or unsubstituted heteroalkyl, —OR$^A$, —N$_3$, —N(R$^A$)$_2$, —SR$^A$, —NR$^A$C(=O)R$^A$, or —OC(=O)N(R$^A$)$_2$; $R^3$ is hydrogen, halogen, substituted or unsubstituted alkyl, or substituted or unsubstituted alkenyl; and $R^4$ is hydrogen, halogen, substituted or unsubstituted alkyl, substituted or unsubstituted alkenyl.

In certain embodiments, $R^2$ is halogen, substituted or unsubstituted alkyl, substituted or unsubstituted alkenyl, substituted or unsubstituted heteroaryl, —$OR^A$, —$N_3$, —$N(R^A)_2$, —$SR^A$, —$NR^AC(=O)R^A$, or —$OC(=O)N(R^A)_2$; $R^3$ is hydrogen, halogen, substituted or unsubstituted alkyl, or substituted or unsubstituted alkenyl; and $R^4$ is hydrogen, halogen, substituted or unsubstituted alkyl, substituted or unsubstituted alkenyl.

In certain embodiments, $R^2$ is halogen, substituted or unsubstituted alkyl, —$OR^A$, —$N_3$, —$N(R^A)_2$, or —$SR^A$; $R^3$ is hydrogen, halogen, substituted or unsubstituted alkyl, or substituted or unsubstituted alkenyl; and $R^4$ is hydrogen, halogen, substituted or unsubstituted alkyl, substituted or unsubstituted alkenyl.

In certain embodiments, $R^2$ is halogen, substituted or unsubstituted alkyl, —$OR^A$, —$N_3$, —$N(R^A)_2$, or —$SR^A$; $R^3$ is hydrogen or substituted or unsubstituted alkyl; and $R^4$ is hydrogen or substituted or unsubstituted alkyl.

In certain embodiments, $R^2$ is halogen, —$OR^A$, or —$SR^A$; $R^3$ is hydrogen or substituted or unsubstituted alkyl; and $R^4$ is hydrogen or substituted or unsubstituted alkyl. In certain embodiments, $R^2$ is halogen or —$SR^A$; $R^3$ is substituted or unsubstituted alkyl; and $R^4$ is hydrogen. In certain embodiments, $R^2$ is —Cl or —$SCH_3$; $R^3$ is substituted or unsubstituted alkyl; and $R^4$ is hydrogen.

In certain embodiments, $R^2$ is halogen; $R^3$ is halogen; and $R^4$ is hydrogen or halogen. In certain embodiments, $R^2$ is halogen; $R^3$ is halogen; and $R^4$ is halogen. In certain embodiments, $R^2$ is —F; $R^3$ is —F; and $R^4$ is —F. In certain embodiments, $R^2$ is —F; $R^3$ is —F; and $R^4$ is hydrogen. In certain embodiments, $R^2$ is —F; $R^3$ is hydrogen; and $R^4$ is hydrogen.

In certain embodiments, A is —$CF_3$, —$CHF_2$, or $CH_2F$. In certain embodiments, A is —$CF_3$. In certain embodiments, A is —$CHF_2$. In certain embodiments, A is $CH_2F$.

In certain embodiments, A is

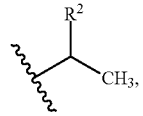

wherein $R^4$ is hydrogen, halogen, $C_{1-4}$ alkyl, or $C_{1-4}$haloalkyl. In certain embodiments, A is

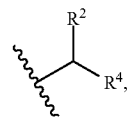

wherein $R^4$ is hydrogen, fluorine, chlorine or $C_{1-4}$ alkyl.

In certain embodiments, A is

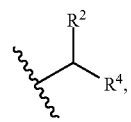

wherein $R^2$ is halogen, —$OR^A$, or —$SR^A$. In certain embodiments, A is

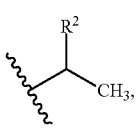

wherein $R^2$ is halogen, —$OR^A$, or —$SR^A$; and $R^A$ is substituted or unsubstituted aryl, substituted or unsubstituted heteroaryl, substituted or unsubstituted alkyl, or hydrogen.

In certain embodiments, A is

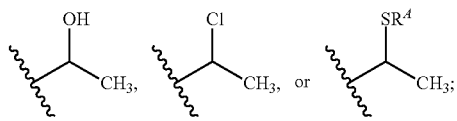

and $R^A$ is substituted or unsubstituted aryl, or substituted or unsubstituted alkyl.

In certain embodiments, A is

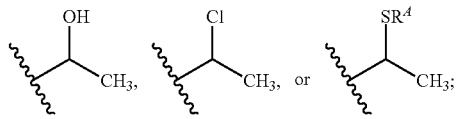

and $R^A$ is substituted or unsubstituted aryl.

In certain embodiments, A is

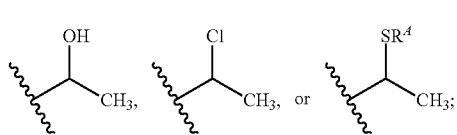

and $R^A$ is substituted aryl.

In certain embodiments, A is

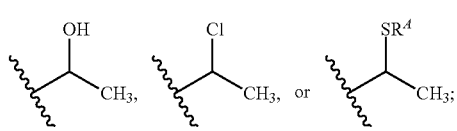

and $R^A$ is substituted phenyl.

In certain embodiments, A is of the formula:

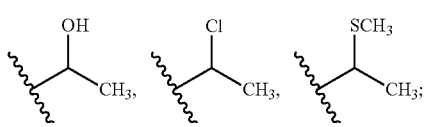

-continued

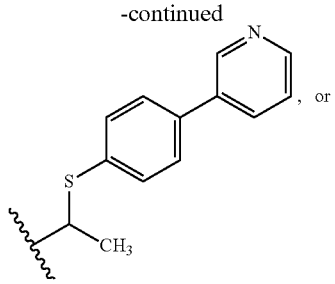, or

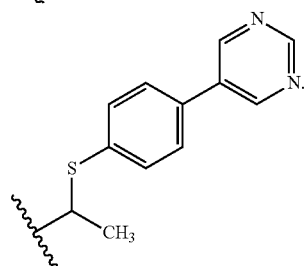

In certain embodiments, A is

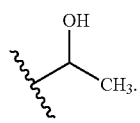 [SMILES: *C(C)O]

In certain embodiments, A is

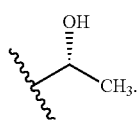

In certain embodiments, A is

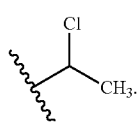 [SMILES: *C(C)Cl]

In certain embodiments, A is

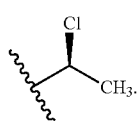

In certain embodiments, A is

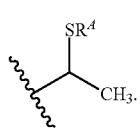

In certain embodiments, A is

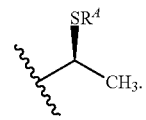

In certain embodiments, A is

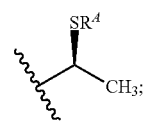

and $R^A$ is substituted or unsubstituted aryl, or substituted or unsubstituted alkyl.

In certain embodiments, A is of the formula:

, or

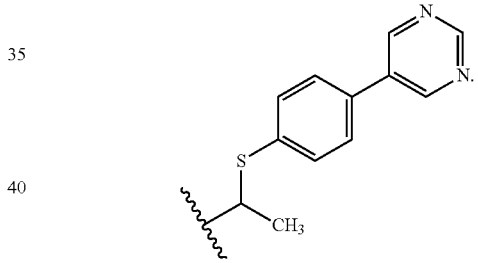

In certain embodiments, A is of the formula:

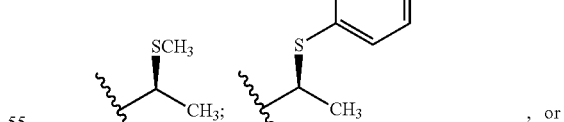, or

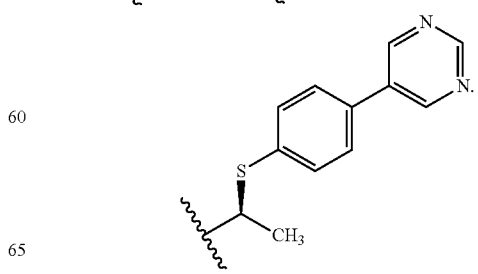

In certain embodiments, A is of the formula:
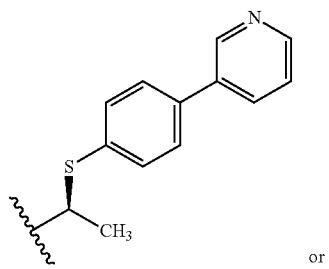
or
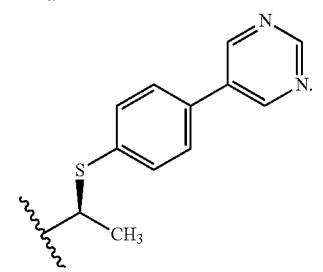
In certain embodiments, A is of the formula:
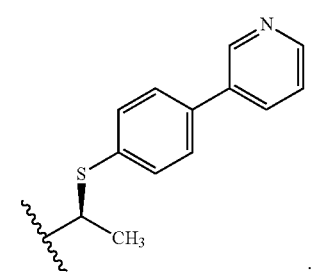 [SMILES: *[C@H](C)Sc1ccc(-c2cccnc2)cc1]
In certain embodiments, A is of the formula:
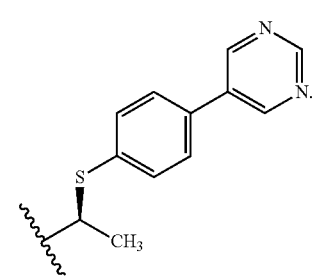 [SMILES: *[C@H](C)Sc1ccc(-c2cncnc2)cc1]
In certain embodiments, A is of the formula:
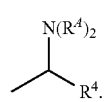
In certain embodiments, A is of the formula:
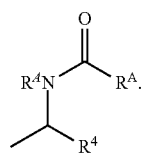
In certain embodiments, A is of the formula:
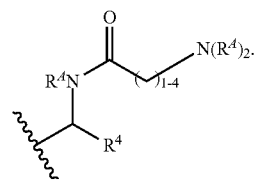
In certain embodiments, A is of the formula:
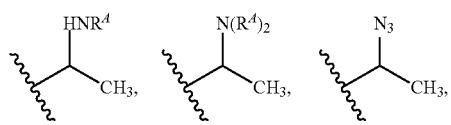
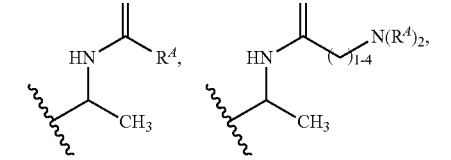
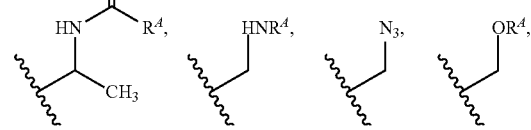
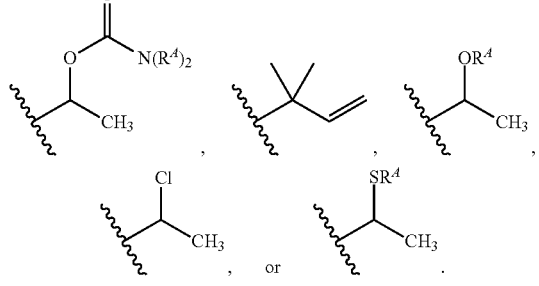
In certain embodiments, A is of the formula:
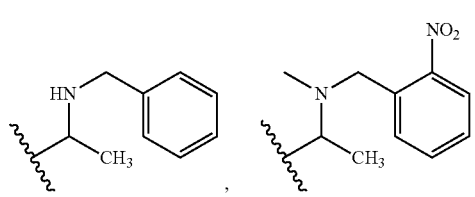

-continued
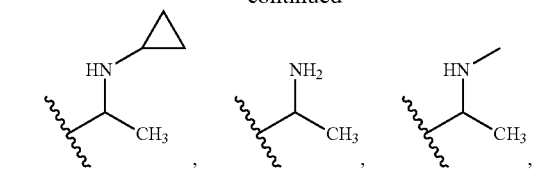
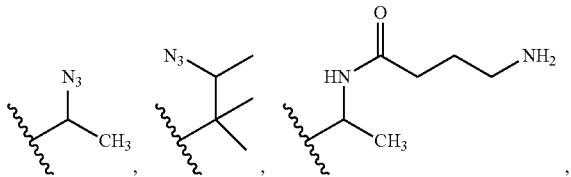
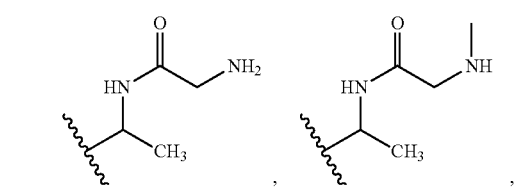
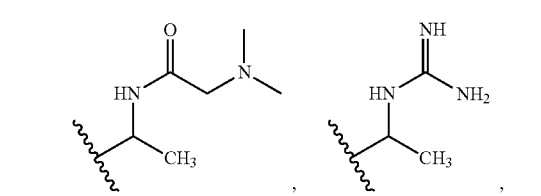
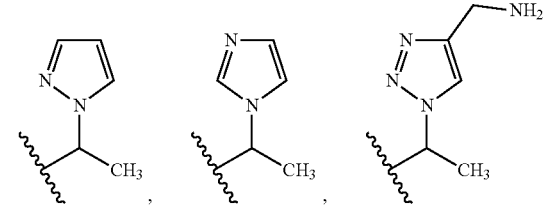
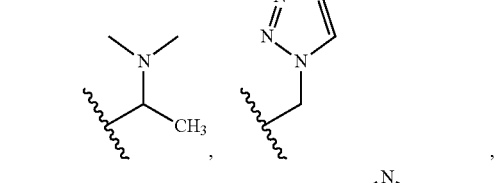
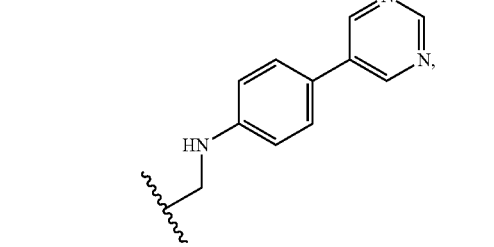
-continued
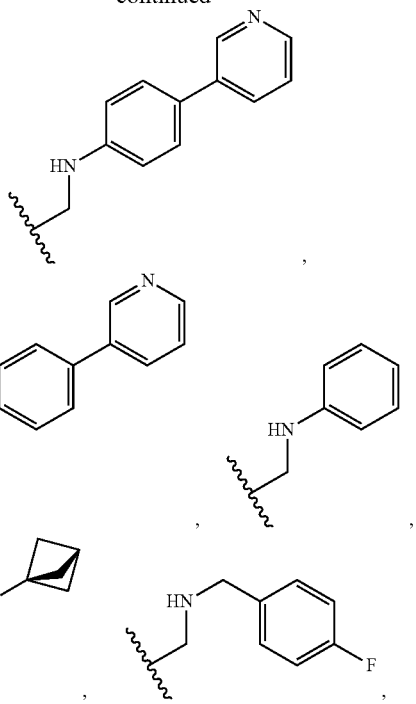
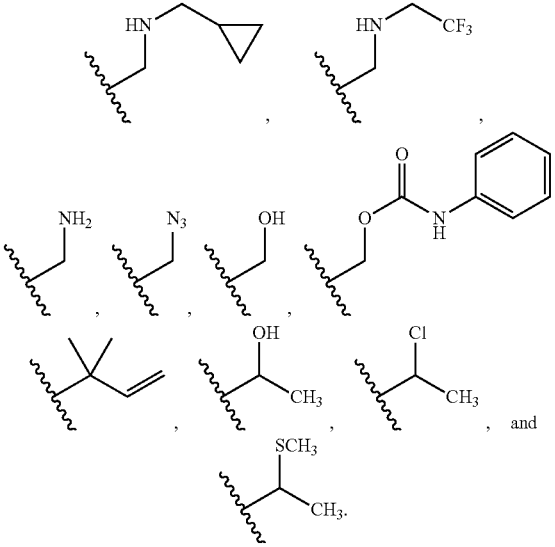
In certain embodiments, A is of the formula:
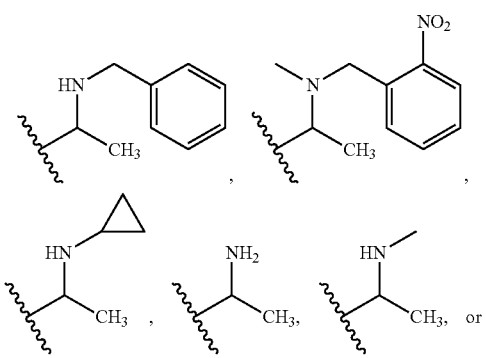
or

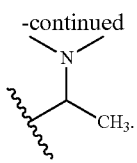
In certain embodiments, A is of the formula:
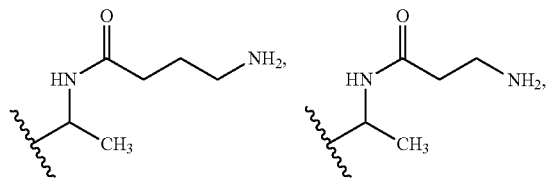
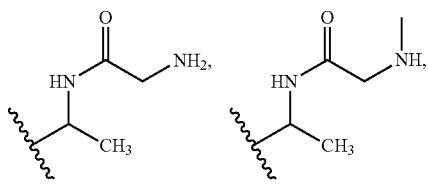
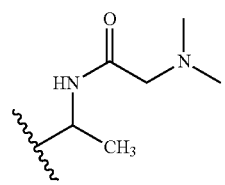
In certain embodiments, A is of the formula:
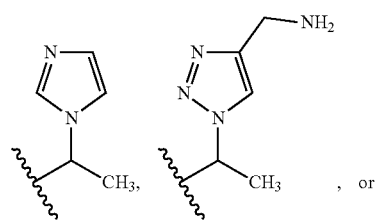, or
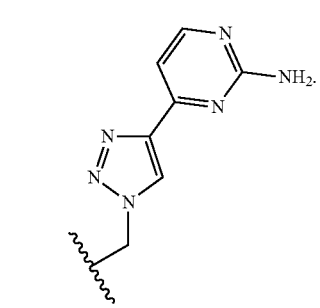
In certain embodiments, A is of the formula:
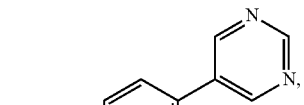
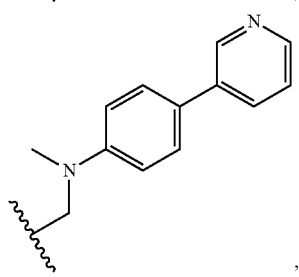
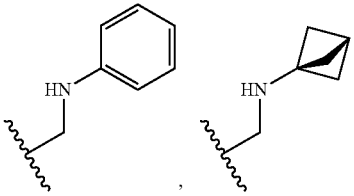
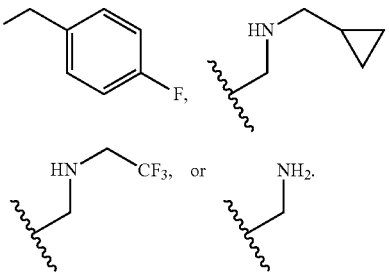
In certain embodiments, A is of the formula:
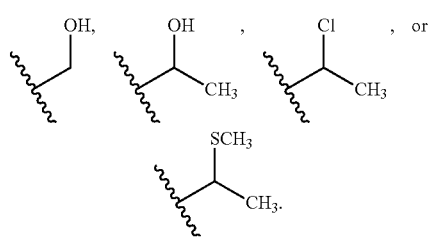

In certain embodiments, A is of the formula:

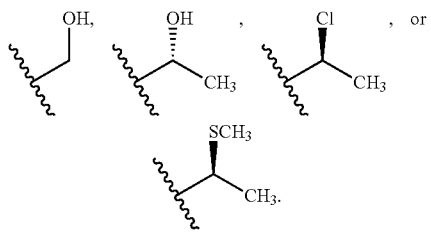

In certain embodiments, A is of the formula:

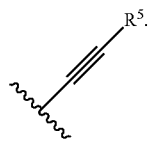

In certain embodiments, $R^5$ is hydrogen, halogen, substituted or unsubstituted alkyl, substituted or unsubstituted aryl, or substituted or unsubstituted heteroaryl. In certain embodiments, $R^5$ is substituted or unsubstituted aryl, or substituted or unsubstituted heteroaryl. In certain embodiments, $R^5$ is substituted or unsubstituted aryl. In certain embodiments, $R^5$ is substituted or unsubstituted phenyl. In certain embodiments, $R^5$ is substituted or unsubstituted heteroaryl. In certain embodiments, $R^5$ is substituted or unsubstituted pyrazolyl, imidazolyl, triazolyl, tetrazolyl, pyrrolyl, oxazolyl, isoxazolyl, thienyl, furanyl, pyridyl, pyrimidinyl, pyrazinyl, pyridazinyl, or triazolinyl. In certain embodiments, $R^5$ is hydrogen.

In certain embodiments, A is of the formula:

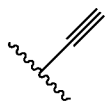

In certain embodiments, A is of the formula:

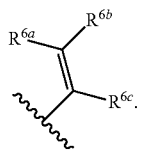

In certain embodiments, $R^{6a}$, $R^{6b}$, and $R^{6c}$ are each independently hydrogen, halogen, substituted or unsubstituted alkyl, substituted or unsubstituted aryl, substituted or unsubstituted heteroaryl, or substituted or unsubstituted acyl. In certain embodiments, $R^{6a}$, $R^{6b}$, and $R^{6c}$ are each hydrogen.

In certain embodiments, A is of the formula:

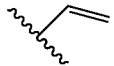

In certain embodiments, A is substituted or unsubstituted carbocyclyl, or substituted or unsubstituted heterocyclyl. In certain embodiments, A is substituted or unsubstituted carbocyclyl. In certain embodiments, A is substituted or unsubstituted cycloalkyl or cycloalkenyl. In certain embodiments, A is substituted or unsubstituted $C_{3-6}$ cycloalkyl or $C_{3-6}$ cycloalkenyl. In certain embodiments, A is substituted or unsubstituted $C_{3-6}$ cycloalkyl. In certain embodiments, A is substituted or unsubstituted $C_{3-6}$ cycloalkenyl. In certain embodiments, A is substituted or unsubstituted heterocyclyl. In certain embodiments, A is substituted or unsubstituted 4-7 membered heterocyclyl. In certain embodiments, A is substituted or unsubstituted 5-6 membered heterocyclyl. In certain embodiments, A is substituted or unsubstituted dihydropyrrolyl or tetrahydropyridyl.

In certain embodiments, A is of the formula:

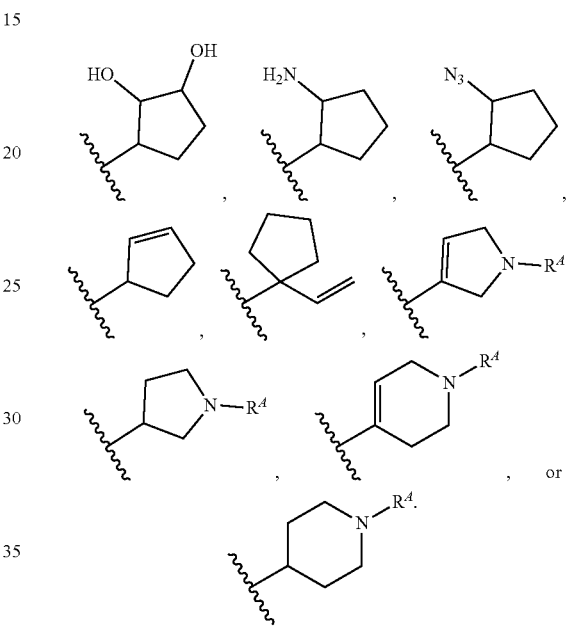

Group $R^1$

As generally defined herein, $R^1$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, substituted or unsubstituted heteroaliphatic, —$OR^A$, —$N(R^A)_2$, or —$SR^A$.

In certain embodiments, $R^1$ is substituted or unsubstituted alkyl, substituted or unsubstituted alkenyl, substituted or unsubstituted carbocyclyl, substituted or unsubstituted heterocyclyl, substituted or unsubstituted heteroaryl, substituted or unsubstituted heteroaralkyl, substituted or unsubstituted heteroalkyl, —$OR^A$, —$N(R^A)_2$, or —$SR^A$.

In certain embodiments, $R^1$ is substituted or unsubstituted alkyl, substituted or unsubstituted carbocyclyl, substituted or unsubstituted heteroaralkyl, or —$SR^A$.

In certain embodiments, $R^1$ is substituted or unsubstituted alkyl, substituted or unsubstituted carbocyclyl, or —$SR^A$.

In certain embodiments, $R^1$ is

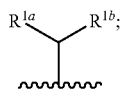

wherein $R^{1a}$ and $R^{1b}$ are each independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —$OR^A$, —$N_3$, —$N(R^A)_2$, —$SR^A$, —CN, —SCN, —C(=$NR^A$)$R^A$, —C(=$NR^A$)$OR^A$, —C(=$NR^A$)$N(R^A)_2$, —C(=O)$R^A$, —C(=O)$OR^A$, —C(=O)$N(R^A)_2$, —$NO_2$, —$NR^A$C(=O)$R^A$, —$NR^A$C(=O)$OR^A$, —$NR^A$C(=O)$N(R^A)_2$, —$NR^A$C(=$NR^A$)$N(R^A)_2$, —OC(=O)$R^A$, —OC(=O)$OR^A$, —OC(=O)$N(R^A)_2$, —$NR^A$S(O)$_2R^A$, —OS(O)$_2R^A$, or —S(O)$_2R^A$, or $R^{1a}$ and $R^{1b}$ are joined to form a substituted or unsubstituted heterocyclic ring, or a substituted or unsubstituted carbocyclic ring.

In certain embodiments, $R^{1a}$ and $R^{1b}$ are each independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —$OR^A$, —OS(O)$_2R^A$, —$N_3$, —$N(R^A)_2$, or $R^{1a}$ and $R^{1b}$ are joined to form a substituted or unsubstituted carbocyclic ring.

In certain embodiments, $R^{1a}$ and $R^{1b}$ are each independently hydrogen, halogen, substituted or unsubstituted alkyl, substituted or unsubstituted heteroaryl, or —$N(R^A)_2$; or $R^{1a}$ and $R^{1b}$ are joined to form a substituted or unsubstituted carbocyclic ring.

In certain embodiments, $R^{1a}$ and $R^{1b}$ together with the carbon to which they are attached, form an optionally substituted cycloalkyl or optionally substituted heterocyclyl.

In certain embodiments, $R^{1a}$ and $R^{1b}$ together with the carbon to which they are attached, form an optionally substituted cycloalkyl. In certain embodiments, $R^{1a}$ and $R^{1b}$ together with the carbon to which they are attached, form an optionally substituted $C_{3-6}$ cycloalkyl. In certain embodiments, $R^{1a}$ and $R^{1b}$ together with the carbon to which they are attached, form an optionally substituted $C_{3-5}$ cycloalkyl. In certain embodiments, $R^{1a}$ and $R^{1b}$ together with the carbon to which they are attached, form an optionally substituted $C_{3-4}$ cycloalkyl. In certain embodiments, $R^{1a}$ and $R^{1b}$ together with the carbon to which they are attached, form an optionally substituted cyclopentyl. In certain embodiments, $R^{1a}$ and $R^{1b}$ together with the carbon to which they are attached, form an optionally substituted cyclobutyl. In certain embodiments, $R^{1a}$ and $R^{1b}$ together with the carbon to which they are attached, form an optionally substituted cyclopropyl. In certain embodiments, $R^{1a}$ and $R^{1b}$ together with the carbon to which they are attached, form an unsubstituted cyclopropyl.

In certain embodiments, $R^{1a}$ and $R^{1b}$ together with the carbon to which they are attached, form an optionally substituted heterocyclyl. In certain embodiments, $R^{1a}$ and $R^{1b}$ together with the carbon to which they are attached, form an optionally substituted 3-7 membered heterocyclyl. In certain embodiments, $R^{1a}$ and $R^{1b}$ together with the carbon to which they are attached, form an optionally substituted 4-7 membered heterocyclyl. In certain embodiments, $R^{1a}$ and $R^{1b}$ together with the carbon to which they are attached, form an optionally substituted 4-6 membered heterocyclyl. In certain embodiments, $R^{1a}$ and $R^{1b}$ together with the carbon to which they are attached, form an optionally substituted 4-6 membered heterocyclyl with at least one nitrogen atom in the ring. In certain embodiments, $R^{1a}$ and $R^{1b}$ together with the carbon to which they are attached, form an optionally substituted azetidine, pyrrolidine, or piperidine. In certain embodiments, $R^{1a}$ and $R^{1b}$ together with the carbon to which they are attached, form a substituted azetidine, pyrrolidine, or piperidine.

In certain embodiments, $R^1$ is of the formula:

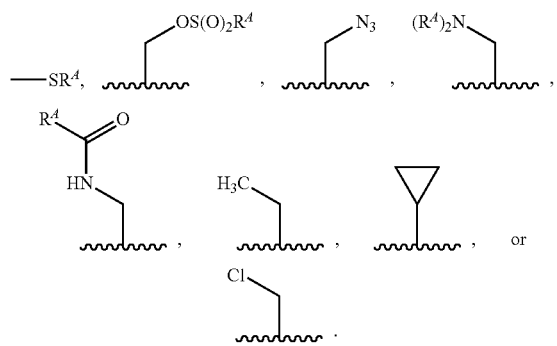

In certain embodiments, $R^1$ is of the formula:

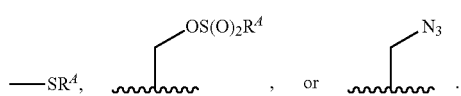

In certain embodiments, $R^1$ is of the formula:

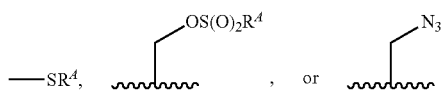

and $R^A$ is substituted or unsubstituted aryl or substituted or unsubstituted alkyl.

In certain embodiments, $R^1$ is —$SR^A$. In certain embodiments, $R^1$ is —$SR^A$; and $R^A$ is a substituted or unsubstituted alkyl. In certain embodiments, $R^1$ is —$SR^A$; and $R^A$ is an unsubstituted alkyl. In certain embodiments, $R^1$ is —$SR^A$; and $R^1$ is an unsubstituted $C_{1-4}$ alkyl. In certain embodiments, $R^1$ is —$SCH_3$.

Group $R^7$

As generally defined herein, $R^7$ is hydrogen or unsubstituted alkyl; or A and $R^7$ are joined to form a substituted or unsubstituted heterocyclic ring.

In certain embodiments, $R^7$ is hydrogen or unsubstituted alkyl. In certain embodiments, $R^7$ is unsubstituted alkyl. In certain embodiments, $R^7$ is unsubstituted $C_{1-6}$ alkyl. In certain embodiments, $R^7$ is unsubstituted $C_{1-4}$ alkyl. In certain embodiments, $R^7$ is unsubstituted $C_{1-3}$ alkyl. In certain embodiments, $R^7$ is unsubstituted $C_{1-2}$ alkyl. In certain embodiments, $R^7$ is ethyl. In certain embodiments, $R^7$ is methyl. In certain embodiments, $R^7$ is hydrogen.

In certain embodiments, A and $R^7$ are joined to form a substituted or unsubstituted heterocyclic ring. In certain embodiments, A and $R^7$ are joined to form a substituted or unsubstituted pyrrolidine, piperidine, piperazine, azepine, or azepane. In certain embodiments, A and $R^7$ are joined to form a substituted or unsubstituted pyrrolidine.

In certain embodiments, A and $R^7$ are joined to form

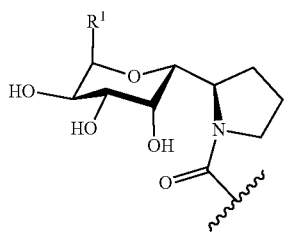

Group $R^8$

As generally defined herein, $R^8$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaliphatic, $-C(=NR^4)R^4$, $-C(=NR^4)OR^4$, $-C(=NR^4)N(R^4)_2$, $-C(=O)R^4$, $-C(=O)OR^4$, $-C(=O)N(R^4)_2$, $-S(O)_2R^4$, or a nitrogen protecting group.

In certain embodiments, $R^8$ is hydrogen, substituted or unsubstituted alkyl, or $-C(=O)R^4$. In certain embodiments, $R^8$ is hydrogen or substituted or unsubstituted alkyl. In certain embodiments, $R^8$ is hydrogen or unsubstituted alkyl. In certain embodiments, $R^8$ is hydrogen or unsubstituted $C_{1-6}$ alkyl. In certain embodiments, $R^8$ is hydrogen or unsubstituted $C_{1-4}$ alkyl. In certain embodiments, $R^8$ is hydrogen or unsubstituted $C_{1-3}$ alkyl. In certain embodiments, $R^8$ is hydrogen or unsubstituted $C_{1-2}$ alkyl. In certain embodiments, $R^8$ is hydrogen or ethyl. In certain embodiments, $R^8$ is hydrogen or methyl. In certain embodiments, $R^8$ is hydrogen.

In certain embodiments, $R^8$ is unsubstituted $C_{1-6}$ alkyl. In certain embodiments, $R^8$ is unsubstituted $C_{1-4}$ alkyl. In certain embodiments, $R^8$ is unsubstituted $C_{1-3}$ alkyl. In certain embodiments, $R^8$ is unsubstituted $C_{1-2}$ alkyl. In certain embodiments, $R^8$ is ethyl. In certain embodiments, $R^8$ is methyl.

Ring B

As generally defined herein, Ring B is a carbocyclyl or heterocyclyl ring. In certain embodiments, B is cycloalkyl, cycloalkenyl, or heterocyclyl. In certain embodiments, B is heterocyclyl. In certain embodiments, B is a 5-8 membered cycloalkyl, cycloalkenyl, or heterocyclyl ring. In certain embodiments, B is a 5-8 membered heterocyclyl ring. In certain embodiments, B is a 5-7 membered cycloalkyl, cycloalkenyl, or heterocyclyl ring. In certain embodiments, B is a 5-7 membered heterocyclyl ring. In certain embodiments, B is a 6-7 membered cycloalkyl, cycloalkenyl, or heterocyclyl ring. In certain embodiments, B is a 6-7 membered heterocyclyl ring. In certain embodiments, B is a 6-membered cycloalkyl, cycloalkenyl, or heterocyclyl ring. In certain embodiments, B is a 6-membered heterocyclyl ring. In certain embodiments, B is a 7-membered cycloalkyl, cycloalkenyl, or heterocyclyl ring. In certain embodiments, B is a 7-membered heterocyclyl ring.

In certain embodiments, B is of the formula:

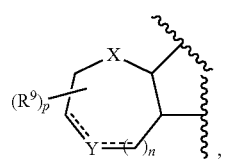

wherein:
X is O, S, $NR^9$ or $C(R^9)_2$;
Y is O, S, $NR^9$, $C(R^9)_2$, $CR^9$, $CH_2$, or CH;
n is 0 or 1;
p is 0-3; and
⁓ represents a single or double bond.

In certain embodiments, X is O, S, $NR^9$ or $C(R^9)_2$. In certain embodiments, X is O, S, or $NR^9$. In certain embodiments, X is O or S. In certain embodiments, X is O.

In certain embodiments, Y is O, S, $NR^9$, $C(R^9)_2$, $CR^9$, $CHR^9$, $CH_2$, or CH. In certain embodiments, Y is O, $NR^9$, $C(R^9)_2$, $CR^9$, $CHR^9$, $CH_2$, or CH. In certain embodiments, Y is $NR^9$, $C(R^9)_2$, $CR^9$, $CHR^9$, $CH_2$, or CH. In certain embodiments, Y is $C(R^9)_2$, $CR^9$, $CHR^9$, $CH_2$, or CH. In certain embodiments, Y is $C(R^9)_2$, $CR^9$, $CHR^9$, $CH_2$, or CH. In certain embodiments, Y is $C(R^9)_2$, $CHR^9$, or $CH_2$. In certain embodiments, Y is $C(R^9)_2$. In certain embodiments, Y is $CHR^9$. In certain embodiments, Y is $CH_2$. In certain embodiments, Y is $CR^9$ or CH. In certain embodiments, Y is $CR^9$. In certain embodiments, Y is CH.

In certain embodiments, n is 0. In certain embodiments, n is 1.

In certain embodiments, p is 0-4. In certain embodiments, p is 0-3. In certain embodiments, p is 0-2. In certain embodiments, p is 0-1. In certain embodiments, p is 1-2. In certain embodiments, p is 0 or 2. In certain embodiments, p is 0. In certain embodiments, p is 1. In certain embodiments, p is 2.

In certain embodiments, X is O; Y is $NR^9$, $C(R^9)_2$, $CR^9$, $CHR^9$, $CH_2$, or CH; n is 1; and p is 0-2. In certain embodiments, X is O; Y is $C(R^9)_2$, $CR^9$, $CHR^9$, $CH_2$, or CH; n is 1; and p is 0-2. In certain embodiments, X is O; Y is $CR^9$ or CH; n is 1; and p is 1. In certain embodiments, X is O; Y is $C(R^9)_2$, $CHR^9$, or $CH_2$; n is 1; and p is 0-2.

In certain embodiments, B is of the formula:

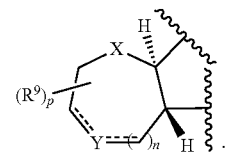

In certain embodiments, B is of the formula:

In certain embodiments, B is of the formula:

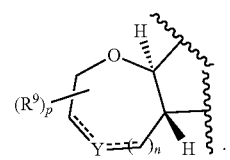

In certain embodiments, B is of the formula:


In certain embodiments, B is of the formula:

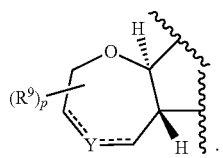

In certain embodiments, B is of the formula:


In certain embodiments, B is of the formula:

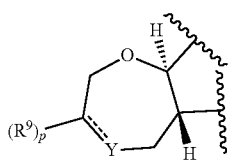

In certain embodiments, B is of the formula:

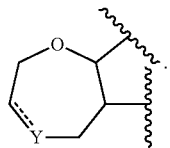

In certain embodiments, B is of the formula:

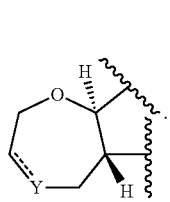

In certain embodiments, B is of the formula:

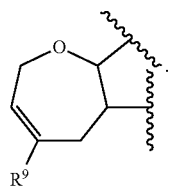

In certain embodiments, B is of the formula:

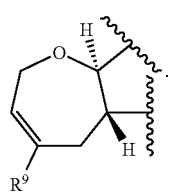

In certain embodiments, B is of the formula:

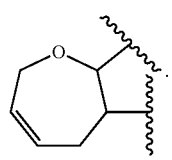 [SMILES: *C1CC=CCOC1*]

In certain embodiments, B is of the formula:

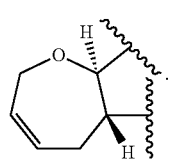 [SMILES: *[C@@H]1CC=CCO[C@H]1*]

In certain embodiments, B is of the formula:

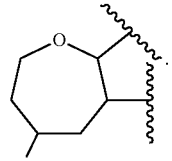

In certain embodiments, B is of the formula:

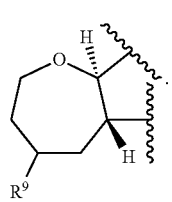

In certain embodiments, B is of the formula:

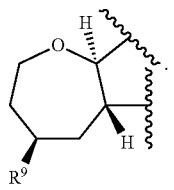

In certain embodiments, B is of the formula:

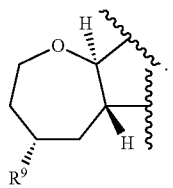

In certain embodiments, B is of the formula:

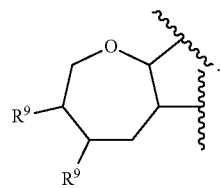

In certain embodiments, B is of the formula:

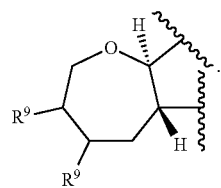

In certain embodiments, B is of the formula:

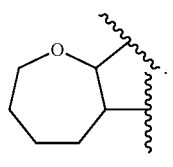 [SMILES: *C1CCCCOC1*]

In certain embodiments, B is of the formula:

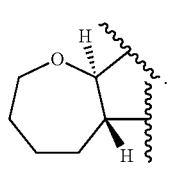 [SMILES: *[C@@H]1CCCCO[C@H]1*]

In certain embodiments, B is of the formula:

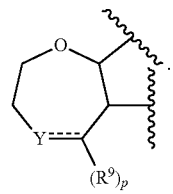

In certain embodiments, B is of the formula:

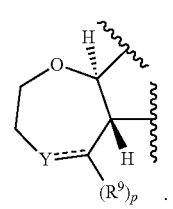

In certain embodiments, B is of the formula:

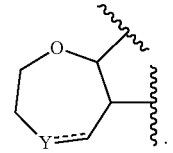

In certain embodiments, B is of the formula:

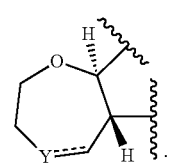

In certain embodiments, B is of the formula:

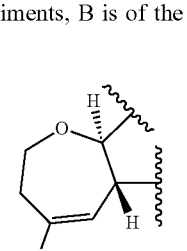

In certain embodiments, B is of the formula:

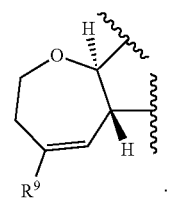

In certain embodiments, B is of the formula:

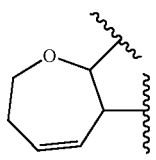

In certain embodiments, B is of the formula:

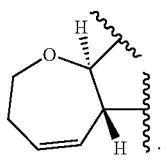 [SMILES: *[C@@H]1C=CCCO[C@H]1*]

In certain embodiments, B is of the formula:

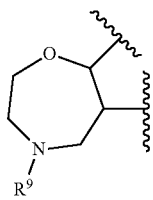

In certain embodiments, B is of the formula:

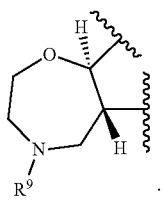

Group $R^9$

As generally defined herein, each occurrence of $R^9$ is independently, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, substituted or unsubstituted heteroaliphatic, —$OR^A$, —$N(R^A)_2$, —$SR^A$, —CN, —SCN, —C(=$NR^A$)$R^A$, —C(=$NR^A$)$OR^A$, —C(=$NR^A$)$N(R^A)_2$, —C(=O)$R^A$, —C(=O)$OR^A$, —C(=O)$N(R^A)_2$, —$NO_2$, —$NR^A$C(=O)$R^A$, —$NR^A$C(=O)$OR^A$, —$NR^A$C(=O)$N(R^A)_2$, —$NR^A$C(=$NR^A$)$N(R^A)_2$, —OC(=O)$R^A$, —OC(=O)$OR^A$, —OC(=O)$N(R^A)_2$, —$NR^A$S(O)$_2R^A$, —OS(O)$_2R^A$, or —S(O)$_2R^A$; or two $R^9$ groups are joined to form a substituted or unsubstituted heterocyclyl ring, or a substituted or unsubstituted carbocyclyl ring.

In certain embodiments, $R^9$ is halogen, substituted or unsubstituted alkyl, substituted or unsubstituted alkenyl, substituted or unsubstituted alkynyl, substituted or unsubstituted heterocyclyl, substituted or unsubstituted aryl, substituted or unsubstituted aralkyl, substituted or unsubstituted heteroaryl, substituted or unsubstituted heteroaralkyl, —$OR^A$, or —$N(R^A)_2$; or two $R^9$ groups are joined to form a substituted or unsubstituted heterocyclyl ring, or a substituted or unsubstituted carbocyclyl ring.

In certain embodiments, $R^9$ is halogen, substituted or unsubstituted alkyl, substituted or unsubstituted alkenyl, substituted or unsubstituted alkynyl, substituted or unsubstituted aryl, substituted or unsubstituted aralkyl, substituted or unsubstituted heteroaryl, substituted or unsubstituted heteroaralkyl, —C(=O)$OR^A$, —C(=O)$N(R^A)_2$, —C(=$NR^A$)$N(R^A)_2$, —$OR^A$, or —$N(R^A)_2$; or two $R^9$ groups are joined to form a substituted or unsubstituted heterocyclyl ring, or a substituted or unsubstituted carbocyclyl ring.

In certain embodiments, $R^9$ is halogen, substituted or unsubstituted alkenyl, substituted alkynyl, substituted or unsubstituted aryl, substituted or unsubstituted aralkyl; or two $R^9$ groups are joined to form a substituted or unsubstituted carbocyclyl ring.

In certain embodiments, $R^9$ is halogen, unsubstituted ethenyl, substituted or unsubstituted phenethynyl, substituted or unsubstituted phenyl, substituted or unsubstituted benzyl, substituted or unsubstituted phenethyl; or two $R^9$ groups are joined to form a unsubstituted cycloalkyl ring.

In certain embodiments, $R^9$ is substituted or unsubstituted alkyl, substituted or unsubstituted aryl, or substituted or unsubstituted aralkyl. In certain embodiments, $R^9$ is substituted or unsubstituted aryl or substituted or unsubstituted aralkyl. In certain embodiments, $R^9$ is substituted or unsubstituted phenyl or substituted or unsubstituted phenethyl.

In certain embodiments, $R^9$ is of the formula:

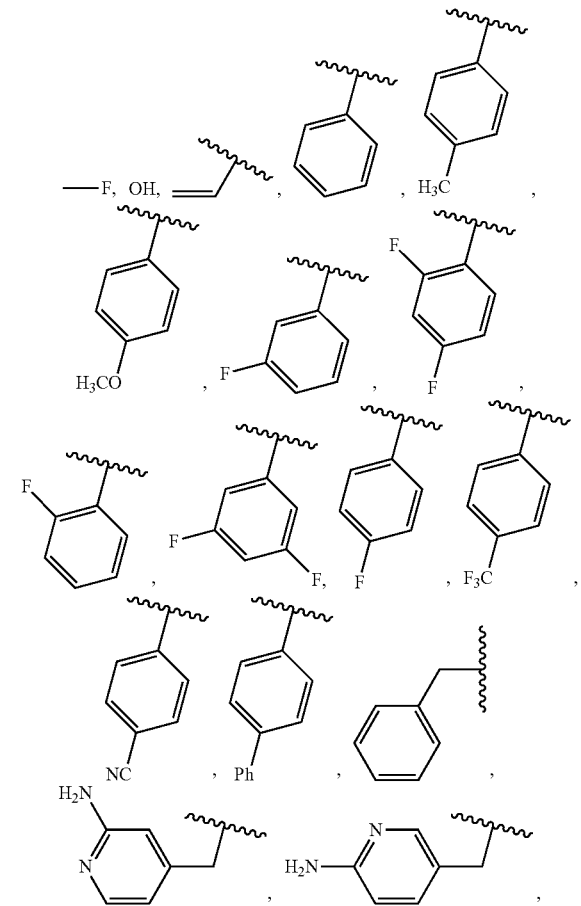

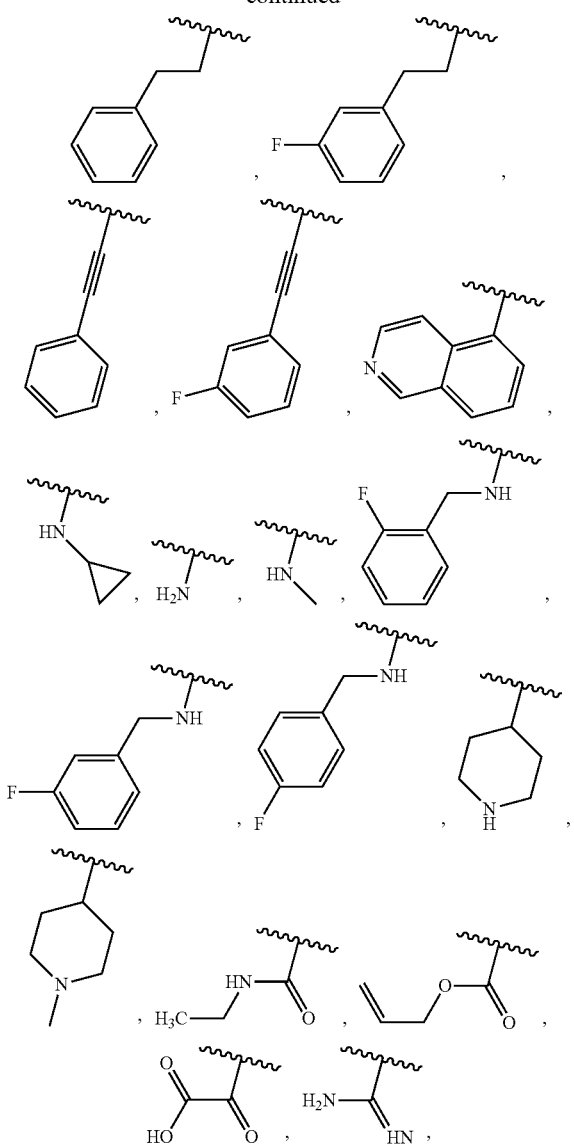
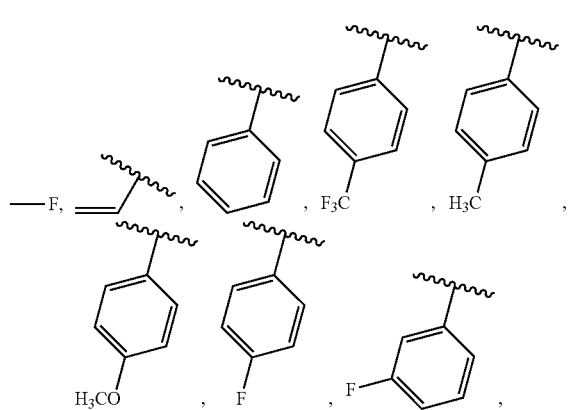
methyl, or propyl; or two R⁹ groups are joined to form an unsubstituted cyclopropyl ring.
In certain embodiments, R⁹ is of the formula:
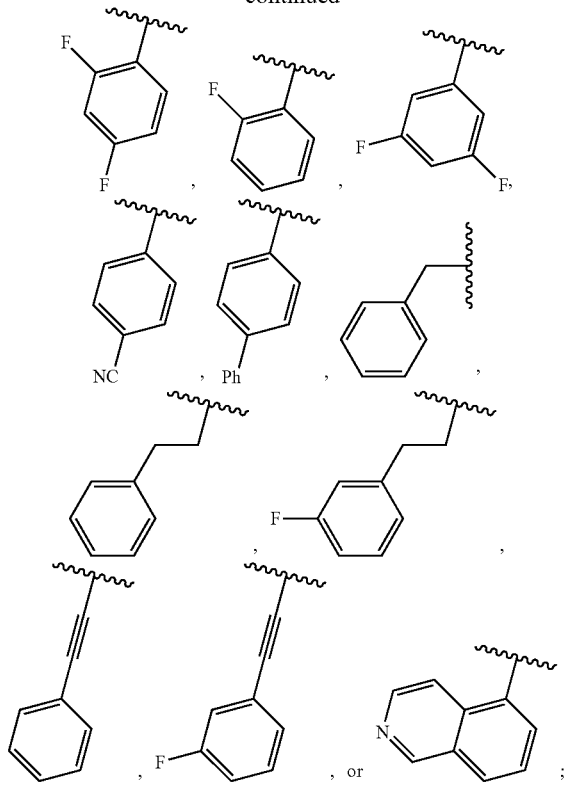
or two R⁹ groups are joined to form an unsubstituted cyclopropyl ring.
In certain embodiments, R⁹ is of the formula:
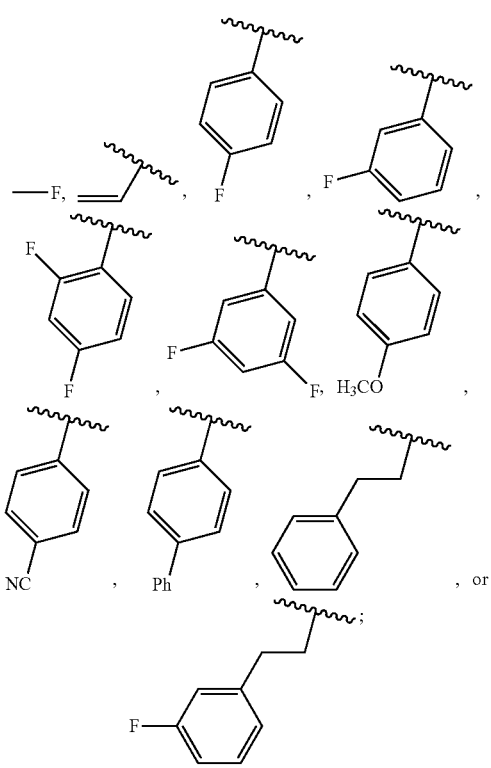

or two $R^9$ groups are joined to form an unsubstituted cyclopropyl ring.

In certain embodiments, $R^9$ is of the formula:

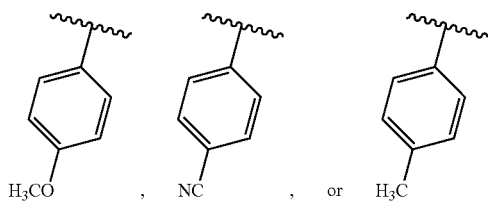

Embodiments of Formula (I)

In certain embodiments, the compound of Formula (I) is a compound of Formula (I-a):

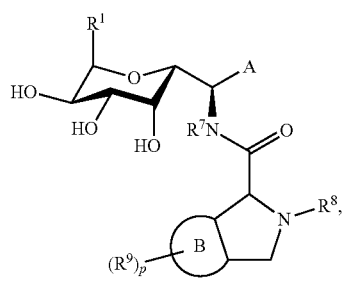

(I-a)

or a pharmaceutically acceptable salt thereof, wherein A, $R^1$, $R^7$, $R^8$, $R^9$, B, and p are as defined herein.

In certain embodiments of the compound of Formula (I-a), $R^1$ is —$SR^A$; $R^7$ is hydrogen; $R^8$ is hydrogen or methyl; and p is 0-2. In certain embodiments of the compound of Formula (I-a), $R^1$ is —$SCH_3$; $R^7$ is hydrogen; $R^8$ is hydrogen or methyl; and p is 0-2. In certain embodiments of the compound of Formula (I-a), $R^1$ is —$SCH_3$; $R^7$ is hydrogen; $R^8$ is hydrogen; and p is 0-2. In certain embodiments of the compound of Formula (I-a), $R^1$ is —$SCH_3$; $R^7$ is hydrogen; $R^8$ is methyl; and p is 0-2.

In certain embodiments, the compound of Formula (I) is a compound of Formula (I-b):

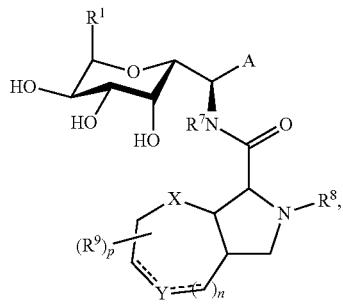

(I-b)

or a pharmaceutically acceptable salt thereof, wherein A, $R^1$, $R^7$, $R^8$, $R^9$, X, Y, n, and p are as defined herein.

In certain embodiments of the compound of Formula (I-b), $R^1$ is —$SR^A$; $R^7$ is hydrogen; $R^8$ is hydrogen or methyl; X is O; and p is 0-2. In certain embodiments of the compound of Formula (I-b), $R^1$ is —$SCH_3$; $R^7$ is hydrogen; $R^8$ is hydrogen or methyl; X is O; and p is 0-2. In certain embodiments of the compound of Formula (I-b), $R^1$ is —$SCH_3$; $R^7$ is hydrogen; $R^8$ is hydrogen; X is O; and p is 0-2. In certain embodiments of the compound of Formula (I-b), $R^1$ is —$SCH_3$; $R^7$ is hydrogen; $R^8$ is methyl; X is O; and p is 0-2.

In certain embodiments, the compound of Formula (I) is a compound of Formula (I-c):

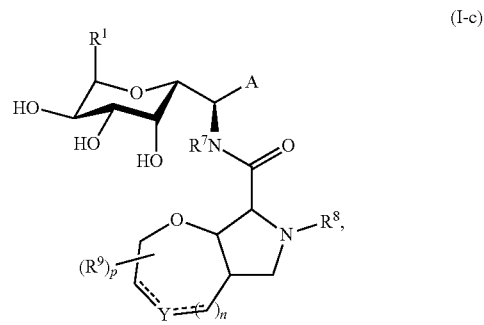

(I-c)

or a pharmaceutically acceptable salt thereof, wherein A, $R^1$, $R^7$, $R^8$, $R^9$, Y, n, and p are as defined herein.

In certain embodiments of the compound of Formula (I-c), $R^1$ is —$SR^A$; $R^7$ is hydrogen; $R^8$ is hydrogen or methyl; and p is 0-2. In certain embodiments of the compound of Formula (I-c), $R^1$ is —$SCH_3$; $R^7$ is hydrogen; $R^8$ is hydrogen or methyl; and p is 0-2. In certain embodiments of the compound of Formula (I-c), $R^1$ is —$SCH_3$; $R^7$ is hydrogen; $R^8$ is hydrogen; and p is 0-2. In certain embodiments of the compound of Formula (I-c), $R^1$ is —$SCH_3$; $R^7$ is hydrogen; $R^8$ is methyl; and p is 0-2. In certain embodiments of the compound of Formula (I-c), $R^1$ is —$SCH_3$; $R^7$ is hydrogen; $R^8$ is methyl; and p is 1. In certain embodiments of the compound of Formula (I-c), $R^1$ is —$SCH_3$; $R^7$ is hydrogen; $R^8$ is methyl; and p is 0.

In certain embodiments, the compound of Formula (I) is a compound of Formula (I-d):

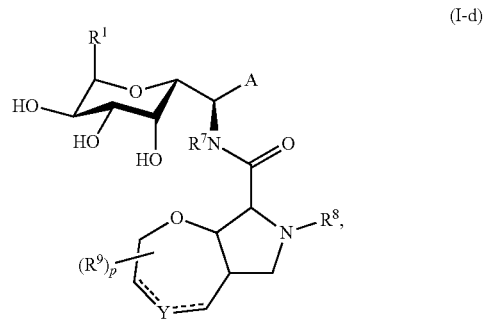

(I-d)

or a pharmaceutically acceptable salt thereof, wherein A, $R^1$, $R^7$, $R^8$, $R^9$, Y, and p are as defined herein.

In certain embodiments of the compound of Formula (I-d), $R^1$ is —$SR^A$; $R^7$ is hydrogen; $R^8$ is hydrogen or methyl; and p is 0-2. In certain embodiments of the compound of Formula (I-d), $R^1$ is —$SCH_3$; $R^7$ is hydrogen; $R^8$ is hydrogen or methyl; and p is 0-2. In certain embodiments of the compound of Formula (I-d), $R^1$ is —$SCH_3$; $R^7$ is hydrogen; $R^8$ is hydrogen; and p is 0-2. In certain embodiments of the compound of Formula (I-c), $R^1$ is —$SCH_3$; $R^7$ is hydrogen; $R^8$ is methyl; and p is 0-2. In certain embodiments of the compound of Formula (I-d), $R^1$ is —$SCH_3$; $R^7$ is hydrogen; $R^8$ is methyl; and p is 1. In certain embodiments of the compound of Formula (I-d), $R^1$ is —$SCH_3$; $R^7$ is hydrogen; $R^8$ is methyl; and p is 0.

In certain embodiments, the compound of Formula (I) is a compound of Formula (I-e):

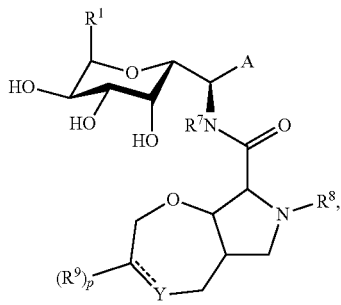

(I-e)

or a pharmaceutically acceptable salt thereof, wherein A, $R^1$, $R^7$, $R^8$, $R^9$, Y, and p are as defined herein.

In certain embodiments of the compound of Formula (I-e), $R^1$ is —$SR^A$; $R^7$ is hydrogen; $R^8$ is hydrogen or methyl; and p is 0-2. In certain embodiments of the compound of Formula (I-e), $R^1$ is —$SCH_3$; $R^7$ is hydrogen; $R^8$ is hydrogen or methyl; and p is 0-2. In certain embodiments of the compound of Formula (I-e), $R^1$ is —$SCH_3$; $R^7$ is hydrogen; $R^8$ is hydrogen; and p is 0-2. In certain embodiments of the compound of Formula (I-e), $R^1$ is —$SCH_3$; $R^7$ is hydrogen; $R^8$ is methyl; and p is 0-2. In certain embodiments of the compound of Formula (I-e), $R^1$ is —$SCH_3$; $R^7$ is hydrogen; $R^8$ is methyl; and p is 1. In certain embodiments of the compound of Formula (I-e), $R^1$ is —$SCH_3$; $R^7$ is hydrogen; $R^8$ is methyl; and p is 0.

In certain embodiments, the compound of Formula (I) is a compound of Formula (I-f):

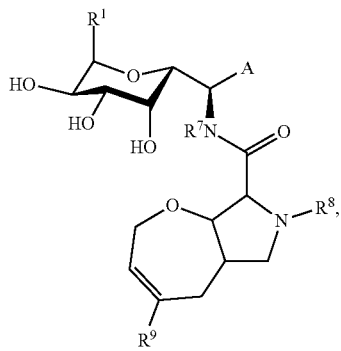

(I-f)

or a pharmaceutically acceptable salt thereof, wherein A, $R^1$, $R^7$, $R^8$, and $R^9$ areas defined herein.

In certain embodiments of the compound of Formula (I-f), $R^1$ is —$SR^A$; $R^7$ is hydrogen; and $R^8$ is hydrogen or methyl. In certain embodiments of the compound of Formula (I-f), $R^1$ is —$SCH_3$; $R^7$ is hydrogen; and $R^8$ is hydrogen or methyl. In certain embodiments of the compound of Formula (I-f), $R^1$ is —$SCH_3$; $R^7$ is hydrogen; and $R^8$ is hydrogen. In certain embodiments of the compound of Formula (I-f), $R^1$ is —$SCH_3$; $R^7$ is hydrogen; and $R^8$ is methyl.

In certain embodiments, the compound of Formula (I) is a compound of Formula (I-g):

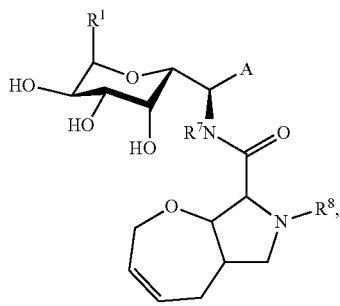

(I-g)

or a pharmaceutically acceptable salt thereof, wherein A, $R^1$, $R^7$, and $R^8$ are as defined herein.

In certain embodiments of the compound of Formula (I-g), $R^1$ is —$SR^A$; $R^7$ is hydrogen; and $R^8$ is hydrogen or methyl. In certain embodiments of the compound of Formula (I-g), $R^1$ is —$SCH_3$; $R^7$ is hydrogen; and $R^8$ is hydrogen or methyl. In certain embodiments of the compound of Formula (I-g), $R^1$ is —$SCH_3$; $R^7$ is hydrogen; and $R^8$ is hydrogen. In certain embodiments of the compound of Formula (I-g), $R^1$ is —$SCH_3$; $R^7$ is hydrogen; and $R^8$ is methyl.

In certain embodiments, the compound of Formula (I) is a compound of Formula (I-h):

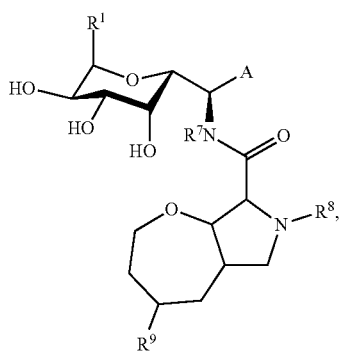

(I-h)

or a pharmaceutically acceptable salt thereof, wherein A, $R^1$, $R^7$, $R^8$, and $R^9$ are as defined herein.

In certain embodiments of the compound of Formula (I-h), $R^1$ is —$SR^A$; $R^7$ is hydrogen; and $R^8$ is hydrogen or methyl. In certain embodiments of the compound of Formula (I-h), $R^1$ is —$SCH_3$; $R^7$ is hydrogen; and $R^8$ is hydrogen or methyl. In certain embodiments of the compound of Formula (I-h), $R^1$ is —$SCH_3$; $R^7$ is hydrogen; and $R^8$ is hydrogen. In certain embodiments of the compound of Formula (I-h), $R^1$ is —$SCH_3$; $R^7$ is hydrogen; and $R^8$ is methyl.

In certain embodiments, the compound of Formula (I) is a compound of Formula (I-i):

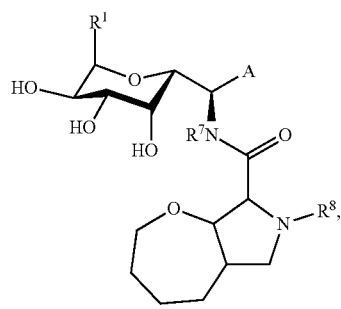

(I-i)

or a pharmaceutically acceptable salt thereof, wherein A, $R^1$, $R^7$, and $R^8$ are as defined herein.

In certain embodiments of the compound of Formula (I-i), $R^1$ is —$SR^4$; $R^7$ is hydrogen; and $R^8$ is hydrogen or methyl. In certain embodiments of the compound of Formula (I-i), $R^1$ is —$SCH_3$; $SR^4$; $R^7$ is hydrogen; and $R^8$ is hydrogen or methyl. In certain embodiments of the compound of Formula (I-i), $R^1$ is —$SCH_3$; $SR^4$; $R^7$ is hydrogen; and $R^8$ is hydrogen. In certain embodiments of the compound of Formula (I-i), $R^1$ is —$SCH_3$; $SR^4$; $R^7$ is hydrogen; and $R^8$ is methyl.

In certain embodiments, the compound of Formula (I) is a compound of Formula (I-j):

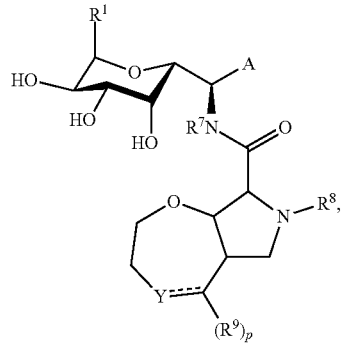

(I-j)

or a pharmaceutically acceptable salt thereof, wherein A, $R^1$, $R^7$, $R^8$, $R^9$, Y, and p are as defined herein.

In certain embodiments of the compound of Formula (I-j), $R^1$ is —$SR^4$; $R^7$ is hydrogen; $R^8$ is hydrogen or methyl; and p is 0-2. In certain embodiments of the compound of Formula (I-j), $R^1$ is —$SCH_3$; $R^7$ is hydrogen; $R^8$ is hydrogen or methyl; and p is 0-2. In certain embodiments of the compound of Formula (I-j), $R^1$ is —$SCH_3$; $R^7$ is hydrogen; $R^8$ is hydrogen; and p is 0-2. In certain embodiments of the compound of Formula (I-j), $R^1$ is —$SCH_3$; $R^7$ is hydrogen; $R^8$ is methyl; and p is 0-2. In certain embodiments of the compound of Formula (I-j), $R^1$ is —$SCH_3$; $R^7$ is hydrogen; $R^8$ is methyl; and p is 1. In certain embodiments of the compound of Formula (I-j), $R^1$ is —$SCH_3$; $R^7$ is hydrogen; $R^8$ is methyl; and p is 0.

In certain embodiments, the compound of Formula (I) is a compound of Formula (I-k):

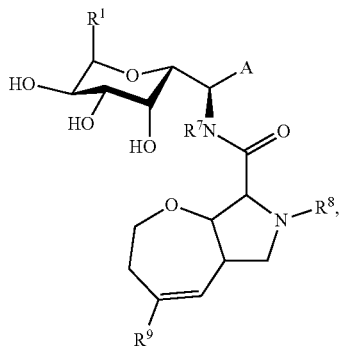

(I-k)

or a pharmaceutically acceptable salt thereof, wherein A, $R^1$, $R^7$, $R^8$, and $R^9$ areas defined herein.

In certain embodiments of the compound of Formula (I-k), $R^1$ is —$SR^4$; $R^7$ is hydrogen; and $R^8$ is hydrogen or methyl. In certain embodiments of the compound of Formula (I-k), $R^1$ is —$SCH_3$; $R^7$ is hydrogen; and $R^8$ is hydrogen or methyl. In certain embodiments of the compound of Formula (I-k), $R^1$ is —$SCH_3$; $R^7$ is hydrogen; and $R^8$ is hydrogen. In certain embodiments of the compound of Formula (I-k), $R^1$ is —$SCH_3$; $R^7$ is hydrogen; and $R^8$ is methyl.

In certain embodiments, the compound of Formula (I) is a compound of Formula (I-1):

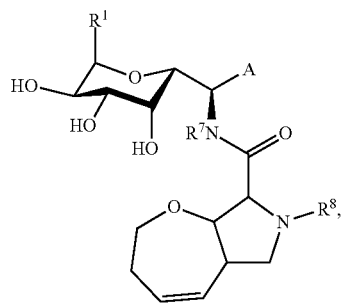

(I-l)

or a pharmaceutically acceptable salt thereof, wherein A, $R^1$, $R^7$, and $R^8$ are as defined herein.

In certain embodiments of the compound of Formula (I-1), $R^1$ is —$SR^4$; $R^7$ is hydrogen; and $R^8$ is hydrogen or methyl. In certain embodiments of the compound of Formula (I-1), $R^1$ is —$SR^1$; $R^7$ is hydrogen; and $R^8$ is hydrogen or methyl. In certain embodiments of the compound of Formula (I-1), $R^1$ is —$SR^4$; $R^7$ is hydrogen; and $R^8$ is hydrogen. In certain embodiments of the compound of Formula (I-1), $R^1$ is —$SR^4$; $R^7$ is hydrogen; and $R^8$ is methyl.

In certain embodiments, the compound of Formula (I) is a compound of Formula (I-m):

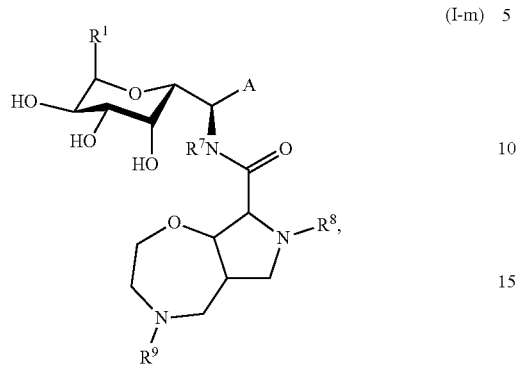

(I-m)

or a pharmaceutically acceptable salt thereof, wherein A, $R^1$, $R^7$, $R^8$, and $R^9$ areas defined herein.

In certain embodiments of the compound of Formula (I-m), $R^1$ is —$SR^A$; $R^7$ is hydrogen; and $R^8$ is hydrogen or methyl. In certain embodiments of the compound of Formula (I-m), $R^1$ is —$SR^A$; $R^7$ is hydrogen; and $R^8$ is hydrogen or methyl. In certain embodiments of the compound of Formula (I-m), $R^1$ is —$SR^A$; $R^7$ is hydrogen; and $R^8$ is hydrogen. In certain embodiments of the compound of Formula (I-m), $R^1$ is —$SR^A$; $R^7$ is hydrogen; and $R^8$ is methyl.

In certain embodiments, the compound of Formula (I) is a compound of Formula (I-n):

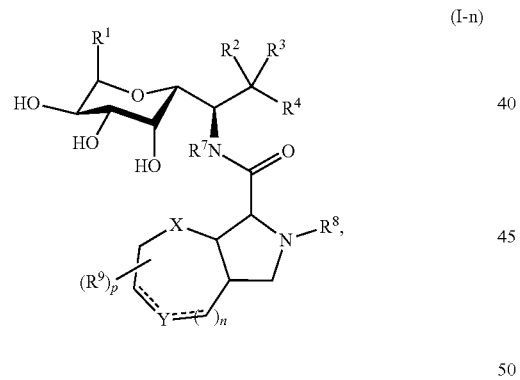

(I-n)

or a pharmaceutically acceptable salt thereof, wherein $R^1$, $R^2$, $R^3$, $R^4$, $R^7$, $R^8$, $R^9$, X, Y, n, and p are as defined herein.

In certain embodiments of the compound of Formula (I-n), $R^1$ is —$SR^A$; $R^7$ is hydrogen; $R^8$ is hydrogen or methyl; X is O; and p is 0-2. In certain embodiments of the compound of Formula (I-n), $R^1$ is —$SCH_3$; $R^7$ is hydrogen; $R^8$ is hydrogen or methyl; X is O; and p is 0-2. In certain embodiments of the compound of Formula (I-n), $R^1$ is —$SCH_3$; $R^7$ is hydrogen; $R^8$ is hydrogen; X is O; and p is 0-2. In certain embodiments of the compound of Formula (I-n), $R^1$ is —$SCH_3$; $R^7$ is hydrogen; $R^8$ is methyl; X is O; and p is 0-2. In certain embodiments of the compound of Formula (I-n), $R^1$ is —$SCH_3$; $R^7$ is hydrogen; $R^8$ is methyl; X is O; and p is 1. In certain embodiments of the compound of Formula (I-n), $R^1$ is —$SCH_3$; $R^7$ is hydrogen; $R^8$ is methyl; X is O; and p is 0.

In certain embodiments, the compound of Formula (I) is a compound of Formula (I-o):

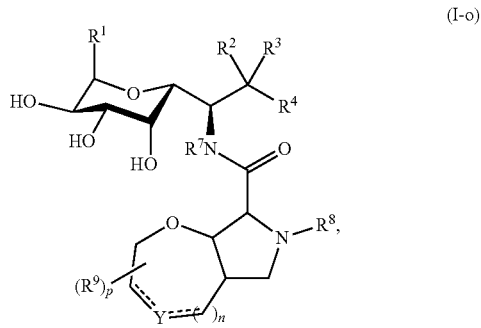

(I-o)

or a pharmaceutically acceptable salt thereof, wherein $R^1$, $R^2$, $R^3$, $R^4$, $R^7$, $R^8$, $R^9$, Y, n, and p are as defined herein.

In certain embodiments of the compound of Formula (I-o), $R^1$ is —$SR^A$; $R^7$ is hydrogen; $R^8$ is hydrogen or methyl; and p is 0-2. In certain embodiments of the compound of Formula (I-o), $R^1$ is —$SCH_3$; $R^7$ is hydrogen; $R^8$ is hydrogen or methyl; and p is 0-2. In certain embodiments of the compound of Formula (I-o), $R^1$ is —$SCH_3$; $R^7$ is hydrogen; $R^8$ is hydrogen; and p is 0-2. In certain embodiments of the compound of Formula (I-o), $R^1$ is —$SCH_3$; $R^7$ is hydrogen; $R^8$ is methyl; and p is 0-2. In certain embodiments of the compound of Formula (I-o), $R^1$ is —$SCH_3$; $R^7$ is hydrogen; $R^8$ is methyl; and p is 1. In certain embodiments of the compound of Formula (I-o), $R^1$ is —$SCH_3$; $R^7$ is hydrogen; $R^8$ is methyl; and p is 0.

In certain embodiments, the compound of Formula (I) is a compound of Formula (I-op):

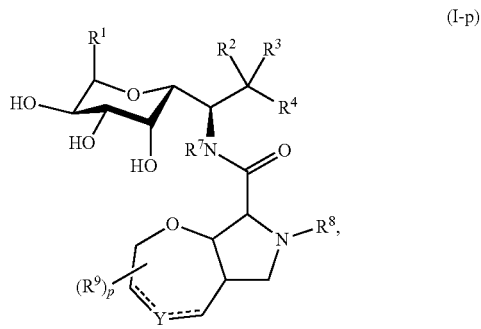

(I-p)

or a pharmaceutically acceptable salt thereof, wherein $R^1$, $R^2$, $R^3$, $R^4$, $R^7$, $R^8$, $R^9$, Y, n, and p are as defined herein.

In certain embodiments of the compound of Formula (I-p), $R^1$ is —$SR^A$; $R^7$ is hydrogen; $R^8$ is hydrogen or methyl; and p is 0-2. In certain embodiments of the compound of Formula (I-p), $R^1$ is —$SCH_3$; $R^7$ is hydrogen; $R^8$ is hydrogen or methyl; and p is 0-2. In certain embodiments of the compound of Formula (I-p), $R^1$ is —$SCH_3$; $R^7$ is hydrogen; $R^8$ is hydrogen; and p is 0-2. In certain embodiments of the compound of Formula (I-p), $R^1$ is —$SCH_3$; $R^7$ is hydrogen; $R^8$ is methyl; and p is 0-2. In certain embodiments of the compound of Formula (I-p), $R^1$ is —$SCH_3$; $R^7$ is hydrogen; $R^8$ is methyl; and p is 1. In certain embodiments of the compound of Formula (I-p), $R^1$ is —$SCH_3$; $R^7$ is hydrogen; $R^8$ is methyl; and p is 0.

In certain embodiments, the compound of Formula (I) is a compound of Formula (I-q):

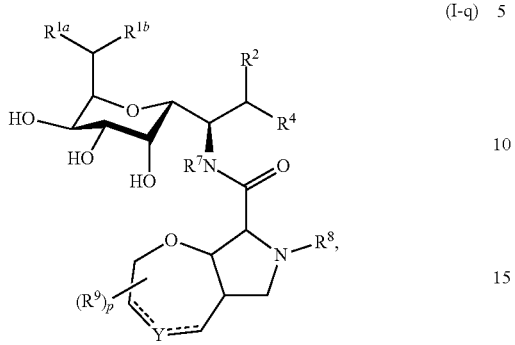

(I-q)

or a pharmaceutically acceptable salt thereof, wherein $R^{1a}$, $R^{1b}$, $R^2$, $R^4$, $R^7$, $R^8$, $R^9$, Y, and p are as defined herein.

In certain embodiments of the compound of Formula (I-q), $R^7$ is hydrogen; $R^8$ is hydrogen or methyl; and p is 0-2. In certain embodiments of the compound of Formula (I-q), $R^7$ is hydrogen; $R^8$ is hydrogen or methyl; and p is 0-2. In certain embodiments of the compound of Formula (I-q), $R^7$ is hydrogen; $R^8$ is hydrogen; and p is 0-2. In certain embodiments of the compound of Formula (I-q), $R^7$ is hydrogen; $R^8$ is methyl; and p is 0-2. In certain embodiments of the compound of Formula (I-q), $R^7$ is hydrogen; $R^8$ is methyl; and p is 1. In certain embodiments of the compound of Formula (I-q), $R^7$ is hydrogen; $R^8$ is methyl; and p is 0.

In certain embodiments, the compound of Formula (I) is a compound of Formula (I-r):

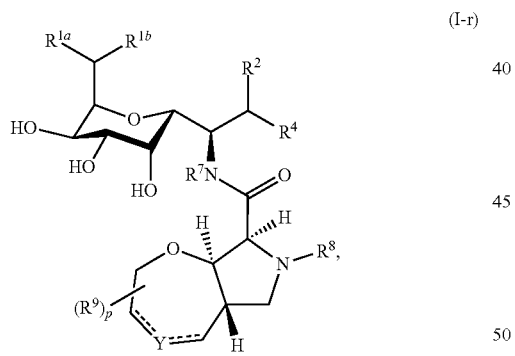

(I-r)

or a pharmaceutically acceptable salt thereof, wherein $R^{1a}$, $R^{1b}$, $R^2$, $R^4$, $R^7$, $R^8$, $R^9$, Y, and p are as defined herein.

In certain embodiments of the compound of Formula (I-r), $R^7$ is hydrogen; $R^8$ is hydrogen or methyl; and p is 0-2. In certain embodiments of the compound of Formula (I-r), $R^7$ is hydrogen; $R^8$ is hydrogen or methyl; and p is 0-2. In certain embodiments of the compound of Formula (I-r), $R^7$ is hydrogen; $R^8$ is hydrogen; and p is 0-2. In certain embodiments of the compound of Formula (I-r), $R^7$ is hydrogen; $R^8$ is methyl; and p is 0-2. In certain embodiments of the compound of Formula (I-r), $R^7$ is hydrogen; $R^8$ is methyl; and p is 1. In certain embodiments of the compound of Formula (I-r), $R^7$ is hydrogen; $R^8$ is methyl; and p is 2.

In certain embodiments, the compound of Formula (I) is a compound of Formula (I-s):

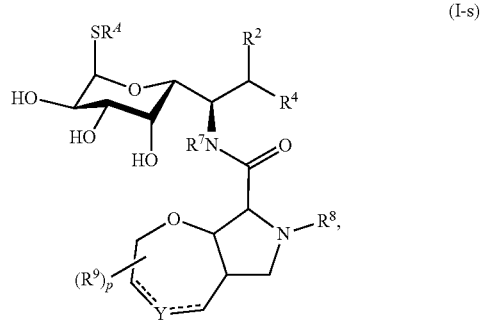

(I-s)

or a pharmaceutically acceptable salt thereof, wherein $R^A$, $R^2$, $R^4$, $R^7$, $R^8$, $R^9$, Y, and p are as defined herein.

In certain embodiments of the compound of Formula (I-s), $R^A$ is substituted or unsubstituted alkyl; $R^7$ is hydrogen; $R^8$ is hydrogen or methyl; and p is 0-2. In certain embodiments of the compound of Formula (I-s), $R^A$ is —$CH_3$; $R^7$ is hydrogen; $R^8$ is hydrogen or methyl; and p is 0-2. In certain embodiments of the compound of Formula (I-s), $R^A$ is —$CH_3$; $R^7$ is hydrogen; $R^8$ is hydrogen; and p is 0-2. In certain embodiments of the compound of Formula (I-s), $R^A$ is —$CH_3$; $R^7$ is hydrogen; $R^8$ is methyl; and p is 0-2. In certain embodiments of the compound of Formula (I-s), $R^A$ is —$CH_3$; $R^7$ is hydrogen; $R^8$ is methyl; and p is 1. In certain embodiments of the compound of Formula (I-s), $R^A$ is —$CH_3$; $R^7$ is hydrogen; $R^8$ is methyl; and p is 0.

In certain embodiments, the compound of Formula (I) is a compound of Formula (I-t):

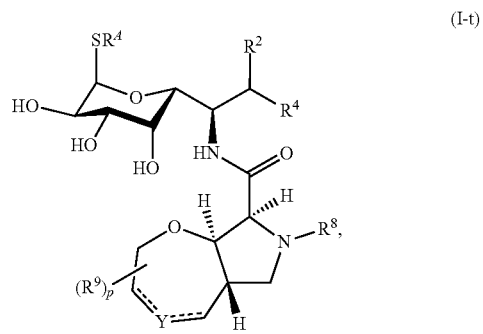

(I-t)

or a pharmaceutically acceptable salt thereof, wherein $R^A$, $R^2$, $R^4$, $R^8$, $R^9$, Y, and p are as defined herein.

In certain embodiments of the compound of Formula (I-t), $R^A$ is substituted or unsubstituted alkyl; $R^8$ is hydrogen or methyl; and p is 0-2. In certain embodiments of the compound of Formula (I-t), $R^A$ is —$CH_3$; $R^8$ is hydrogen or methyl; and p is 0-2. In certain embodiments of the compound of Formula (I-t), $R^A$ is —$CH_3$; $R^8$ is hydrogen; and p is 0-2. In certain embodiments of the compound of Formula (I-t), $R^A$ is —$CH_3$; $R^8$ is methyl; and p is 0-2. In certain embodiments of the compound of Formula (I-t), $R^A$ is —$CH_3$; $R^8$ is methyl; and p is 1. In certain embodiments of the compound of Formula (I-t), $R^A$ is —$CH_3$; $R^8$ is methyl; and p is 0.

In certain embodiments, the compound of Formula (I) is a compound of Formula (I-u):

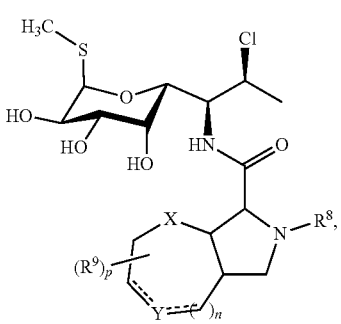

(I-u)

or a pharmaceutically acceptable salt thereof, wherein $R^8$, $R^9$, X, Y, p, and n are as defined herein.

In certain embodiments of the compound of Formula (I-u), $R^8$ is hydrogen or methyl; X is O; n is 1; and p is 0-2. In certain embodiments of the compound of Formula (I-u), $R^8$ is hydrogen or methyl; X is O; Y is $C(R^9)_2$, $CR^9$, $CHR^9$, $CH_2$, or CH; n is 1; and p is 0-2. In certain embodiments of the compound of Formula (I-u), $R^8$ is hydrogen; X is O; Y is $C(R^9)_2$, $CR^9$, $CHR^9$, $CH_2$, or CH; n is 1; and p is 0-2. In certain embodiments of the compound of Formula (I-u), $R^8$ is methyl; X is O; Y is $C(R^9)_2$, $CR^9$, $CHR^9$, $CH_2$, or CH; n is 1; and p is 0-2. In certain embodiments of the compound of Formula (I-u), $R^8$ is methyl; X is O; Y is $C(R^9)_2$, $CR^9$, $CHR^9$, $CH_2$, or CH; n is 1; and p is 1. In certain embodiments of the compound of Formula (I-u), $R^8$ is methyl; X is O; Y is $C(R^9)_2$, $CR^9$, $CHR^9$, $CH_2$, or CH; n is 1; and p is 0.

In certain embodiments, the compound of Formula (I) is a compound of Formula (I-v):

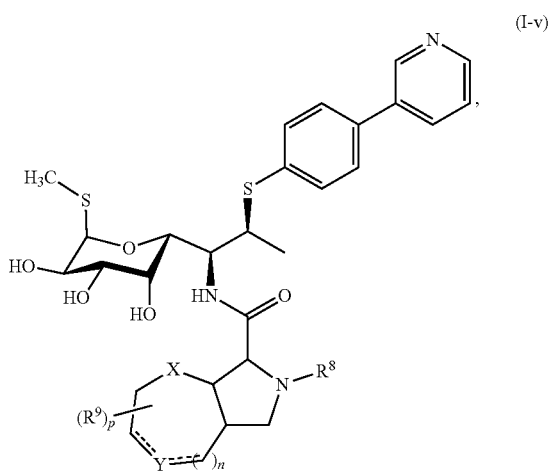

(I-v)

or a pharmaceutically acceptable salt thereof, wherein $R^8$, $R^9$, X, Y, p, and n are as defined herein.

In certain embodiments of the compound of Formula (I-v), $R^8$ is hydrogen or methyl; X is O; n is 1; and p is 0-2. In certain embodiments of the compound of Formula (I-v), $R^8$ is hydrogen or methyl; X is O; Y is $C(R^9)_2$, $CR^9$, $CHR^9$, $CH_2$, or CH; n is 1; and p is 0-2. In certain embodiments of the compound of Formula (I-v), $R^8$ is hydrogen; X is O; Y is $C(R^9)_2$, $CR^9$, $CHR^9$, $CH_2$, or CH; n is 1; and p is 0-2. In certain embodiments of the compound of Formula (I-v), $R^8$ is methyl; X is O; Y is $C(R^9)_2$, $CR^9$, $CHR^9$, $CH_2$, or CH; n is 1; and p is 0-2. In certain embodiments of the compound of Formula (I-v), $R^8$ is methyl; X is O; Y is $C(R^9)_2$, $CR^9$, $CHR^9$, $CH_2$, or CH; n is 1; and p is 1. In certain embodiments of the compound of Formula (I-v), $R^8$ is methyl; X is O; Y is $C(R^9)_2$, $CR^9$, $CHR^9$, $CH_2$, or CH; n is 1; and p is 0.

In certain embodiments, the compound of Formula (I) is a compound of Formula (I-w):

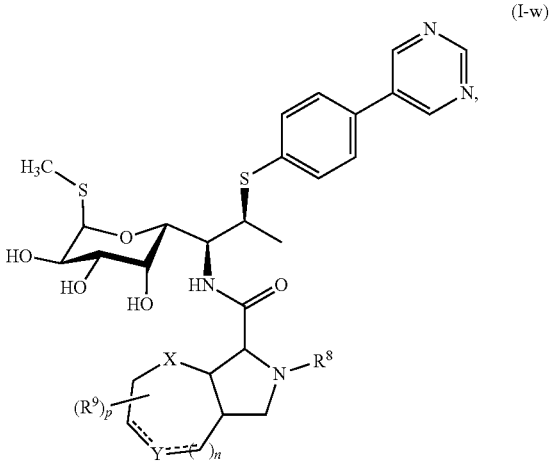

(I-w)

or a pharmaceutically acceptable salt thereof, wherein $R^8$, $R^9$, X, Y, p, and n are as defined herein.

In certain embodiments of the compound of Formula (I-w), $R^8$ is hydrogen or methyl; X is O; n is 1; and p is 0-2. In certain embodiments of the compound of Formula (I-w), $R^8$ is hydrogen or methyl; X is O; Y is $C(R^9)_2$, $CR^9$, $CHR^9$, $CH_2$, or CH; n is 1; and p is 0-2. In certain embodiments of the compound of Formula (I-w), $R^8$ is hydrogen; X is O; Y is $C(R^9)_2$, $CR^9$, $CHR^9$, $CH_2$, or CH; n is 1; and p is 0-2. In certain embodiments of the compound of Formula (I-w), $R^8$ is methyl; X is O; Y is $C(R^9)_2$, $CR^9$, $CHR^9$, $CH_2$, or CH; n is 1; and p is 0-2. In certain embodiments of the compound of Formula (I-v), $R^8$ is methyl; X is O; Y is $C(R^9)_2$, $CR^9$, $CHR^9$, $CH_2$, or CH; n is 1; and p is 1. In certain embodiments of the compound of Formula (I-w), $R^8$ is methyl; X is O; Y is $C(R^9)_2$, $CR^9$, $CHR^9$, $CH_2$, or CH; n is 1; and p is 0.

Exemplary Compounds

Exemplary compounds of Formula (I) include, but are not limited to, the compounds listed in Table 1.

TABLE 1

Exemplary compounds of Formula (I)

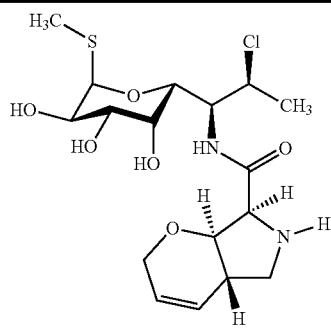

FSA-24039

TABLE 1-continued
Exemplary compounds of Formula (I)
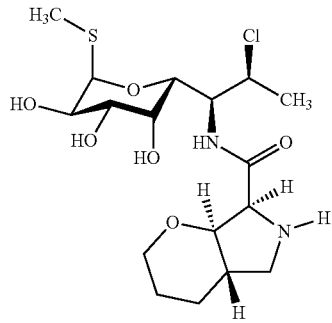
FSA-24041
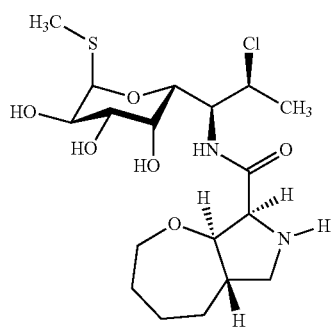
FSA-22091
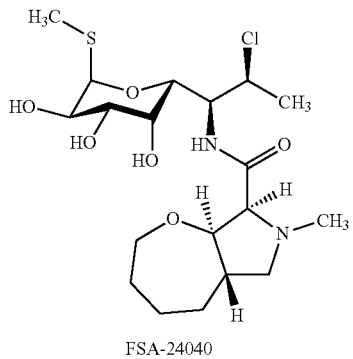
FSA-24040
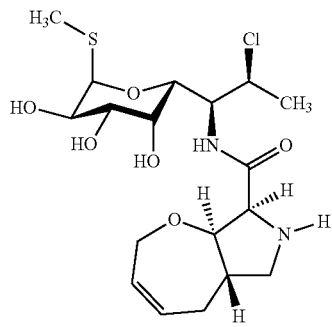
FSA-24035
TABLE 1-continued
Exemplary compounds of Formula (I)
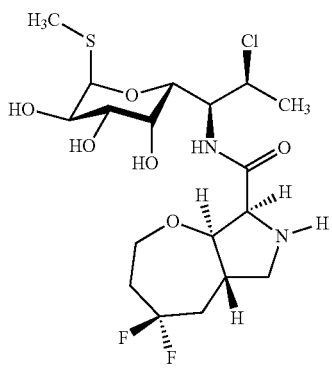
FSA-24036
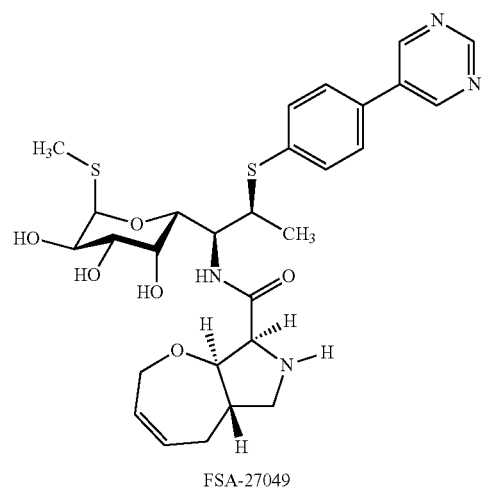
FSA-27049
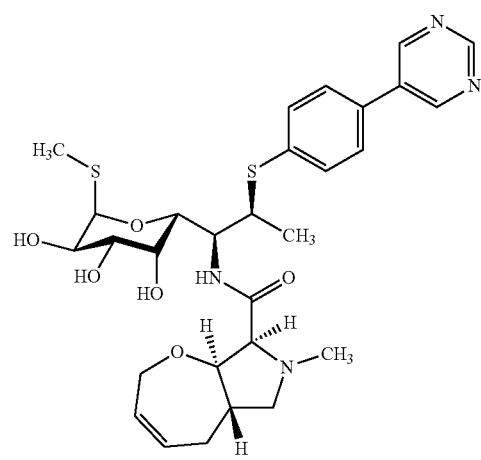
FSA-212034

TABLE 1-continued
Exemplary compounds of Formula (I)
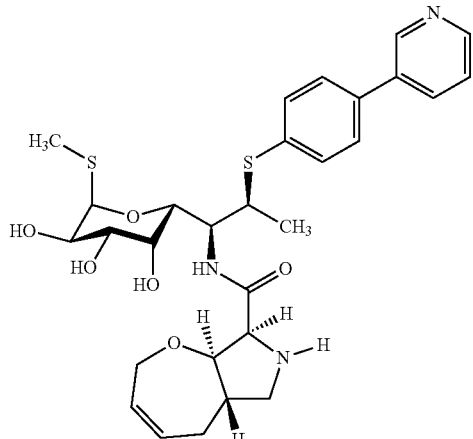
FSA-213061
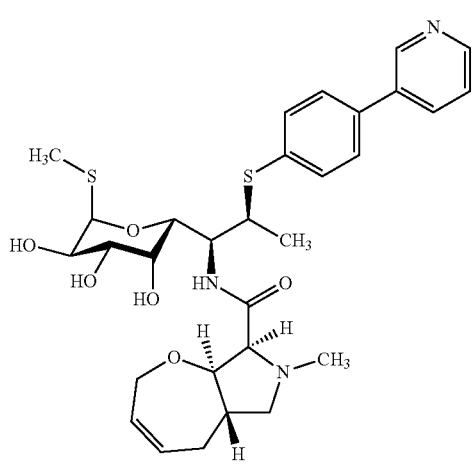
FSA-213064
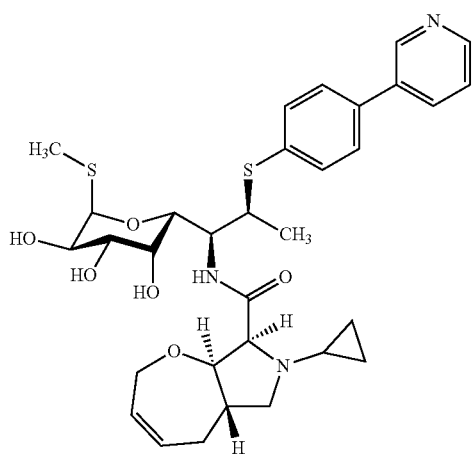
FSA-214009a
TABLE 1-continued
Exemplary compounds of Formula (I)
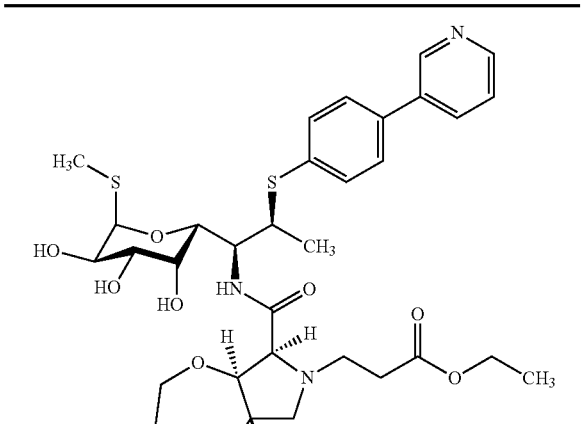
FSA-214009b
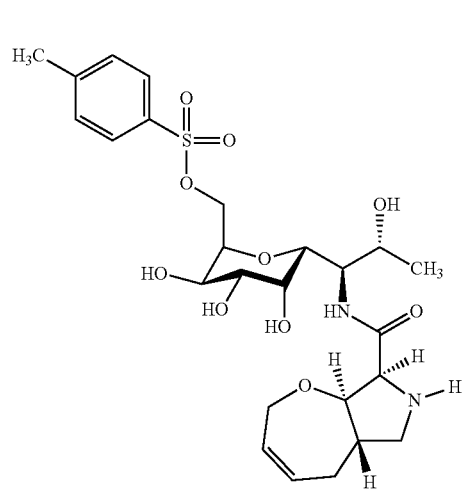
FSA-211030
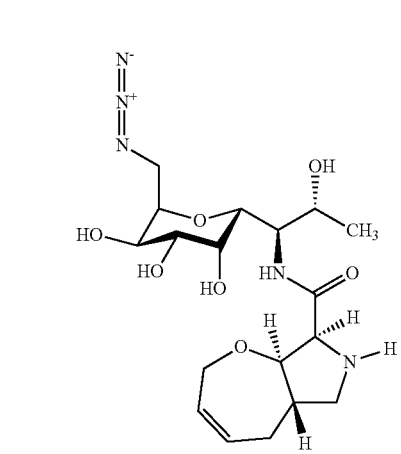
FSA-211064

TABLE 1-continued

Exemplary compounds of Formula (I)

FSA-501076

FSA-501099

FSA-504059

FSA-504062

FSA-507051

FSA-507007

FSA-507041

FSA-507031

TABLE 1-continued
Exemplary compounds of Formula (I)
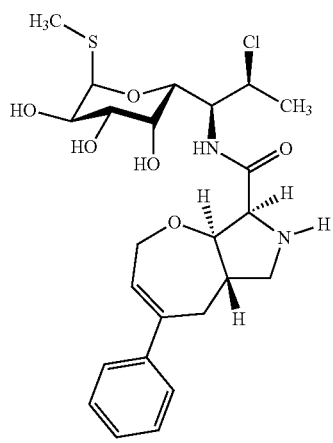
FSA-507056
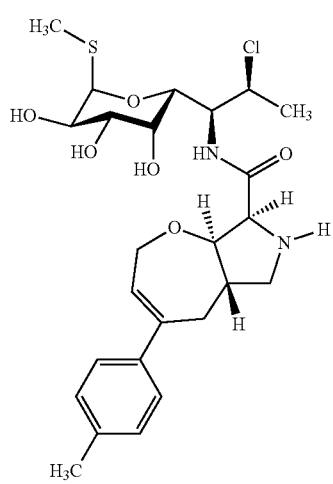
FSA-511019
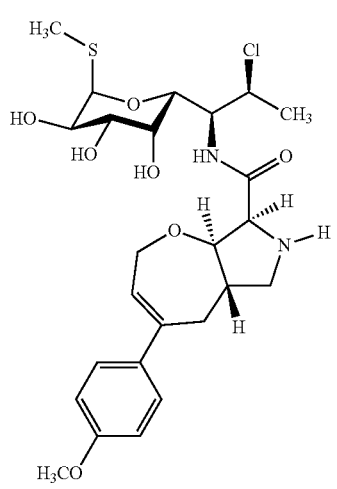
FSA-511020
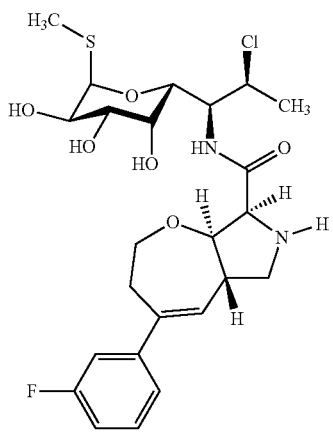
FSA-511071
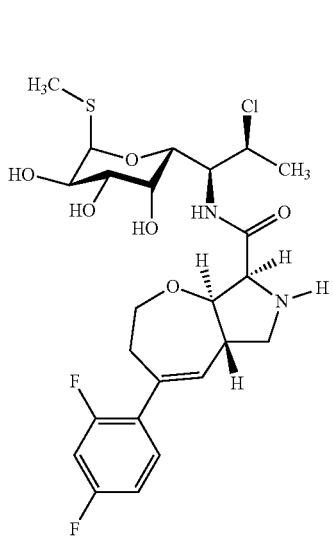
FSA-511072
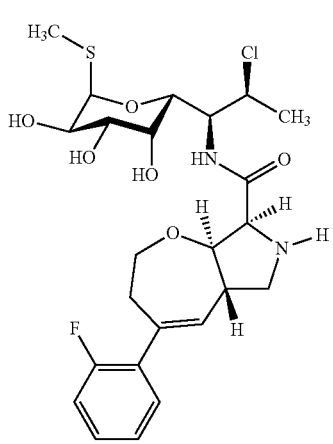
FSA-511073

TABLE 1-continued
Exemplary compounds of Formula (I)
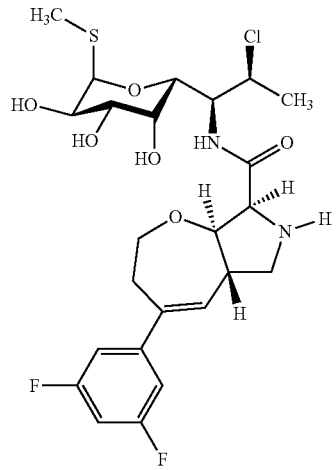
FSA-511074
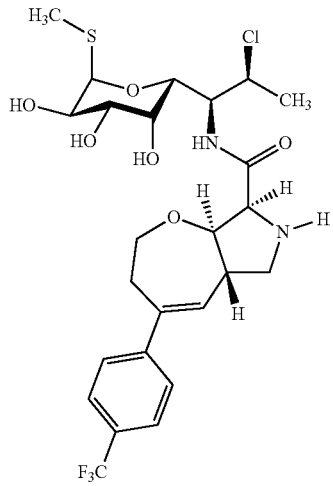
FSA-507053
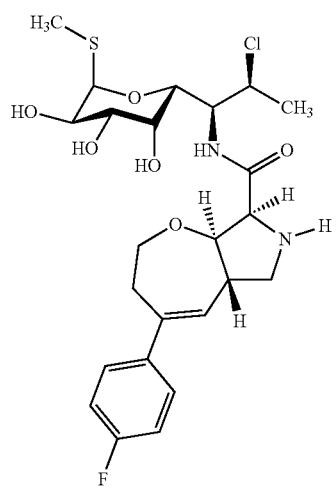
FSA-507052
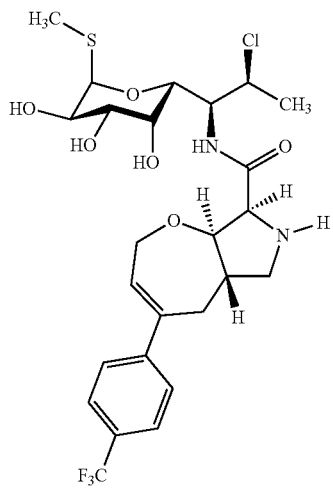
FSA-507060
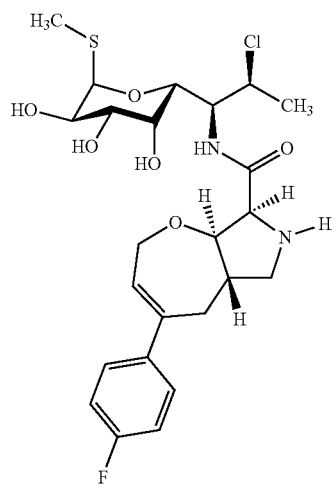
FSA-507057
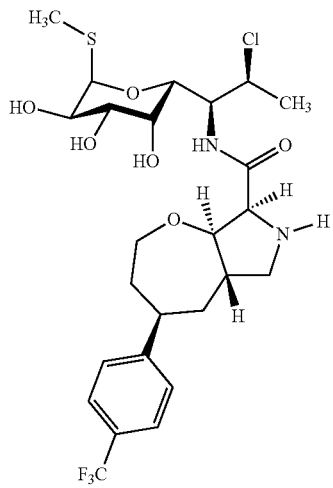
FSA-509019

TABLE 1-continued
Exemplary compounds of Formula (I)
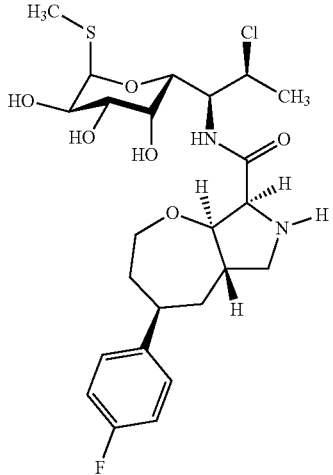
FSA-507061
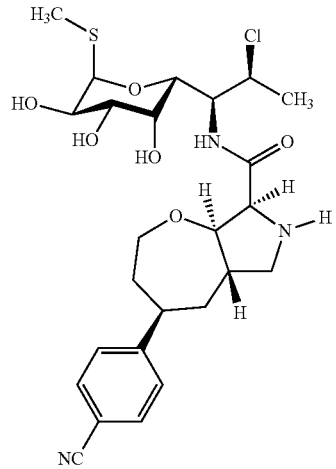
FSA-511046
FSA-511044
FSA-511077
FSA-511045
FSA-511078

TABLE 1-continued
Exemplary compounds of Formula (I)
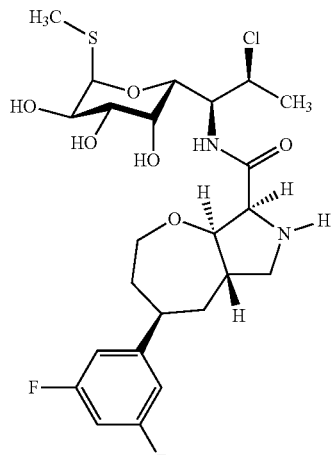
FSA-511080
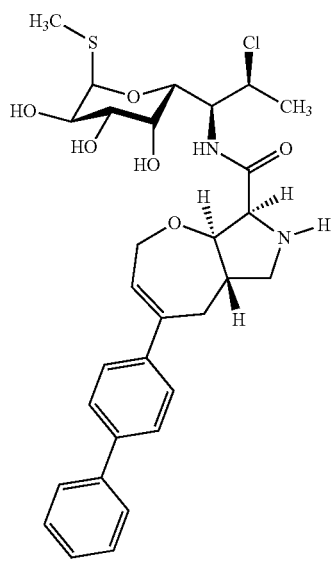
FSA-510001
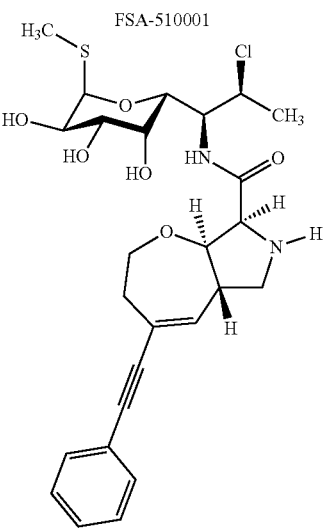
FSA-510002
TABLE 1-continued
Exemplary compounds of Formula (I)
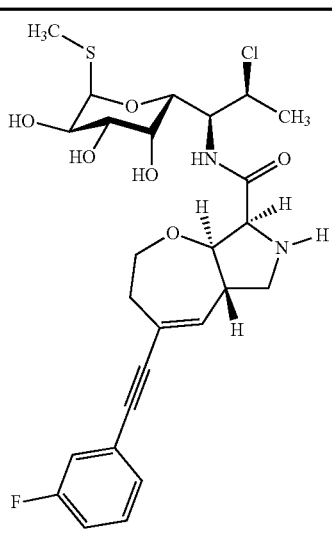
FSA-510003
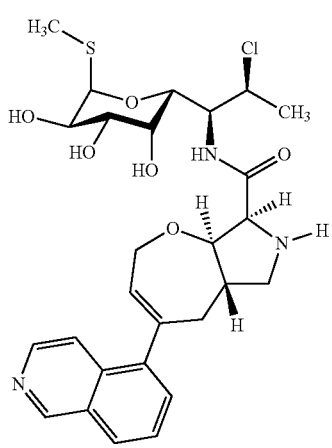
FSA-510006
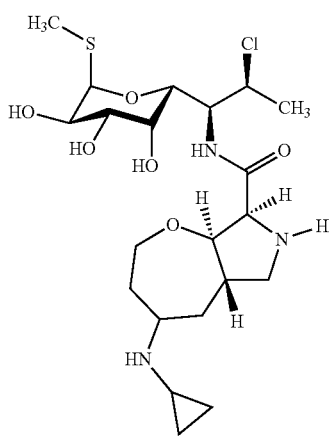
FSA-510011

TABLE 1-continued
Exemplary compounds of Formula (I)
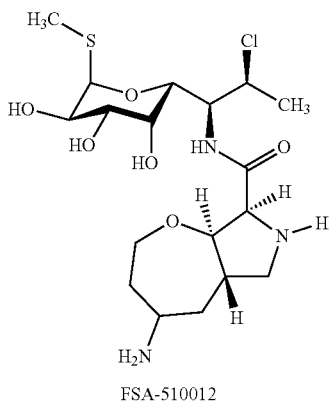
FSA-510012
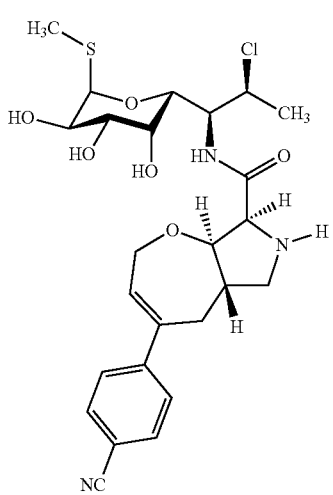
FSA-511033
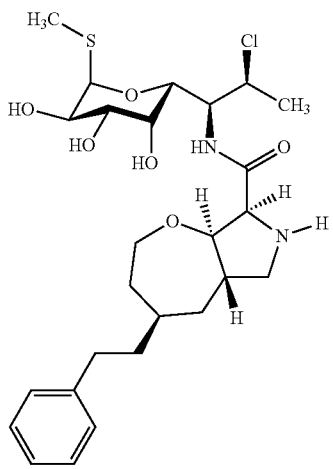
FSA-510021
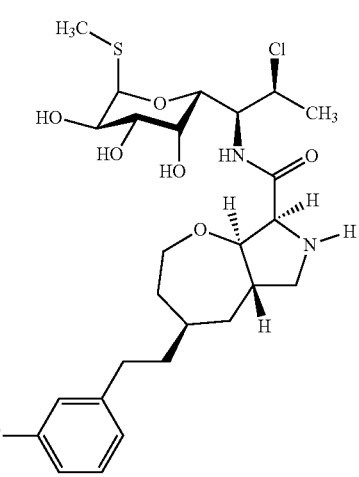
FSA-510022
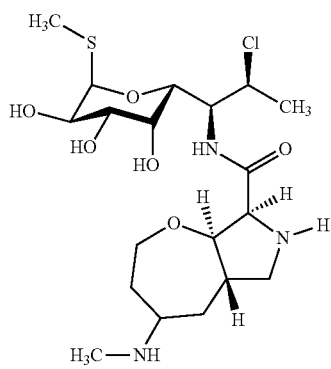
FSA-510065
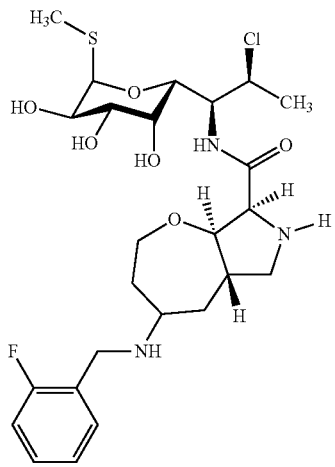
FSA-510072

TABLE 1-continued
Exemplary compounds of Formula (I)
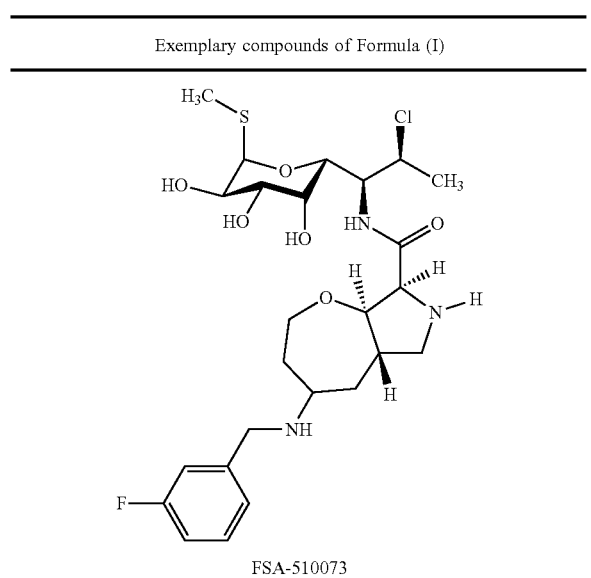
FSA-510073
FSA-510074
FSA-503001
TABLE 1-continued
Exemplary compounds of Formula (I)
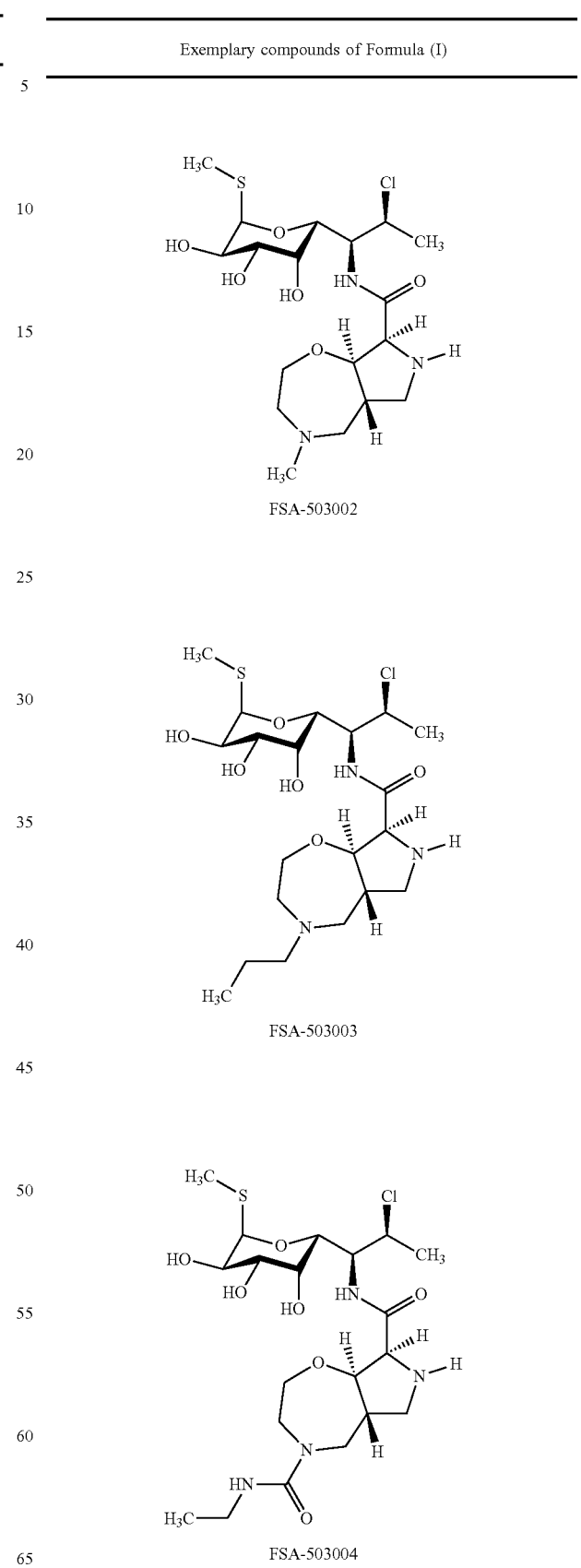
FSA-503002
FSA-503003
FSA-503004

TABLE 1-continued
Exemplary compounds of Formula (I)
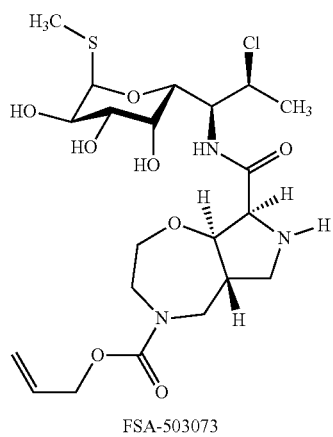
FSA-503073
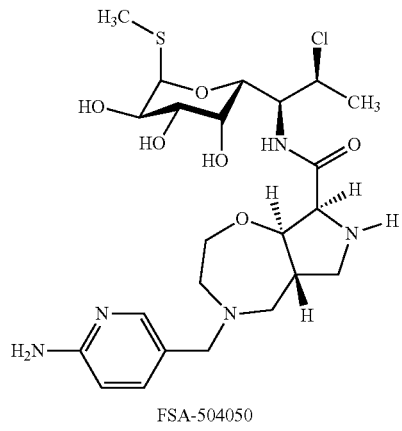
FSA-504050
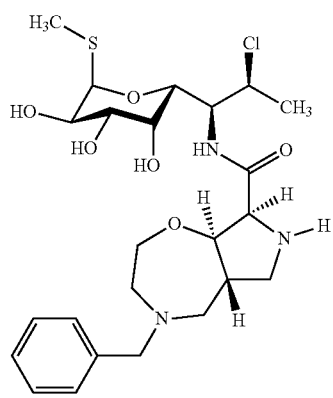
FSA-502002
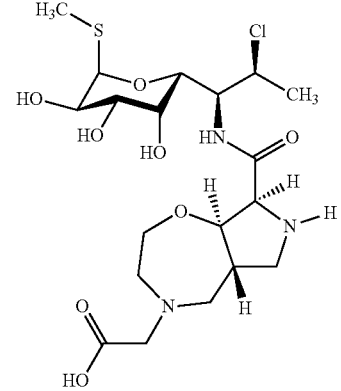
FSA-504063
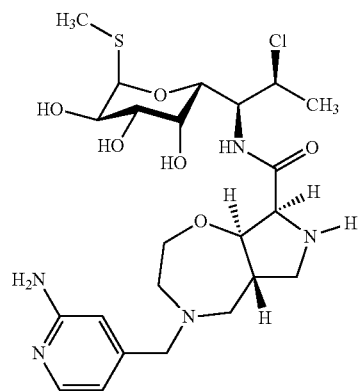
FSA-504049
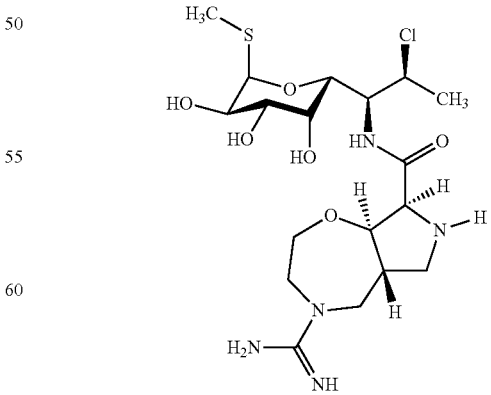
FSA-504057

TABLE 1-continued
Exemplary compounds of Formula (I)
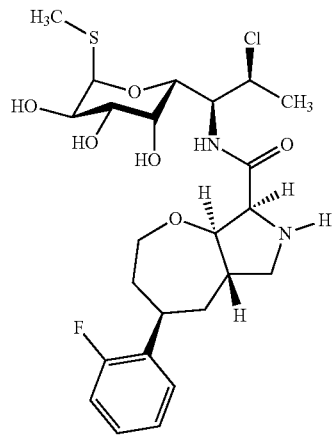
FSA-511100
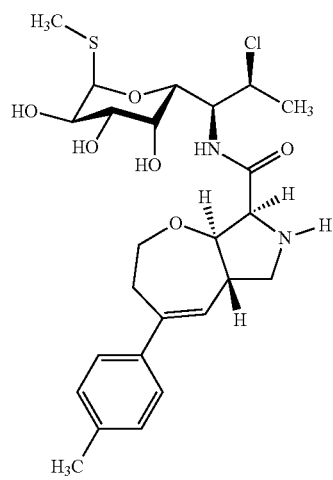
FSA-512075
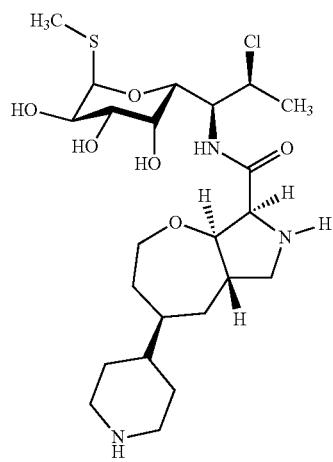
FSA-512011
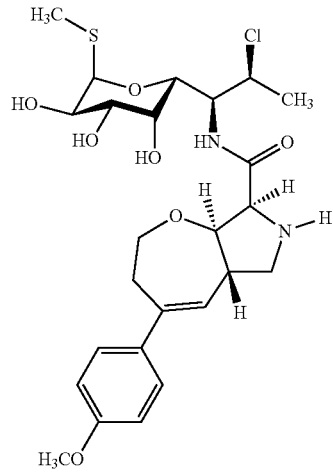
FSA-512076
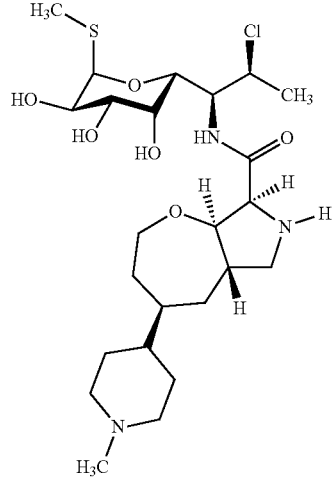
FSA-512012
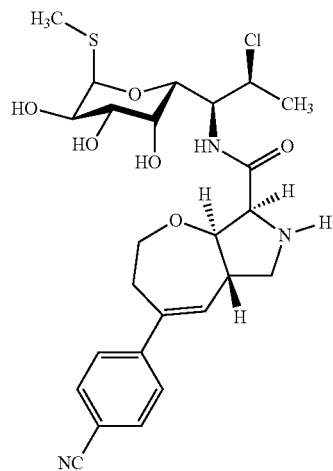
FSA-512077

TABLE 1-continued
Exemplary compounds of Formula (I)
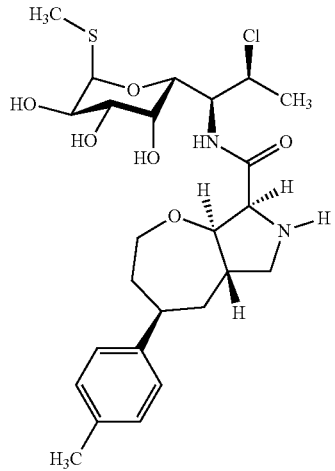
FSA-512079b
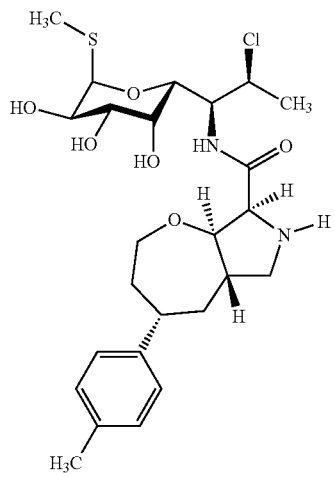
FSA-512079c
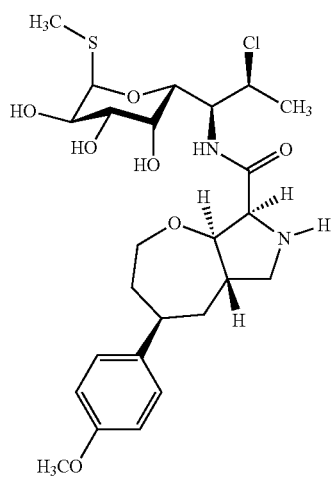
FSA-512080b
TABLE 1-continued
Exemplary compounds of Formula (I)
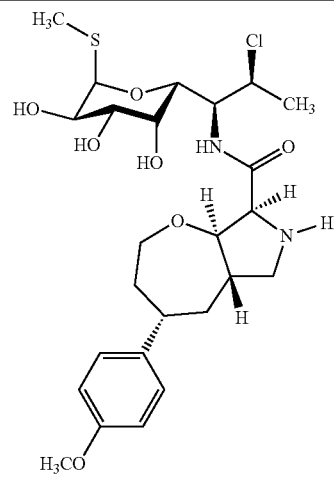
FSA-512080c
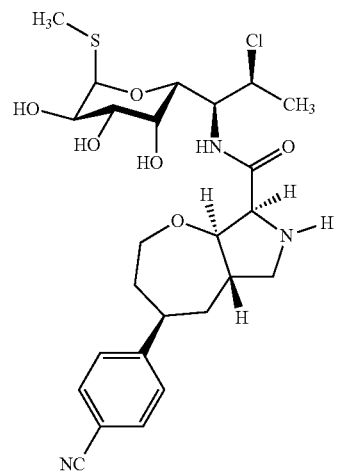
FSA-512081a
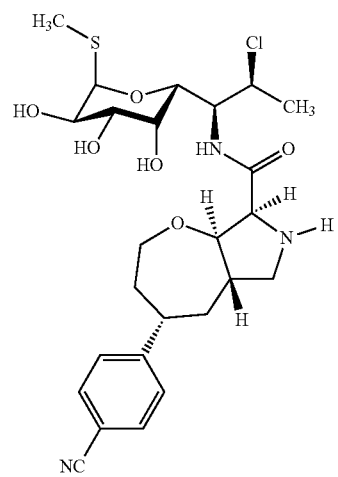
FSA-512081b
Additional Formulae
Provided herein are certain intermediates that may be useful in the preparation of a compound described herein.

In one aspect, the present disclosure provides an compound of Formula (B):

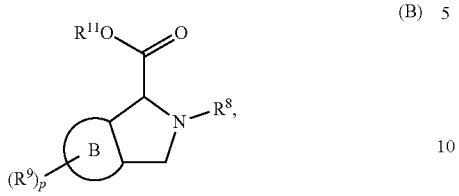
(B)

or salt thereof, wherein B, $R^8$, $R^9$, and p are as defined for compounds of Formula (I);

$R^{11}$ is hydrogen, substituted or unsubstituted alkyl, substituted or unsubstituted aryl, substituted or unsubstituted heteroaryl, or an oxygen protecting group; and ⚌ represents a single or double bond.

In certain embodiments of the compound of Formula (B), $R^{11}$ is hydrogen.

In certain embodiments, the compound of Formula (B) is a compound of Formula (B-1):

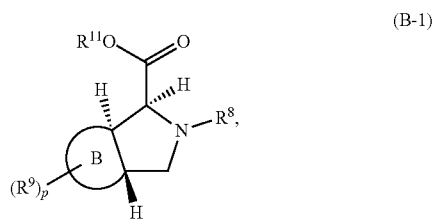
(B-1)

or salt thereof, wherein X, Y, $R^8$, $R^9$, $R^{11}$, p, and n are as defined herein; and ⚌ represents a single or double bond.

In certain embodiments of the compound of Formula (B-1), $R^{11}$ is hydrogen.

In another aspect, the present disclosure provides an intermediate of Formula (C):

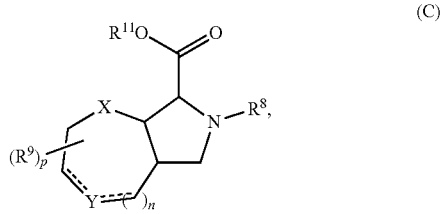
(C)

or salt thereof, wherein X, Y, $R^8$, $R^9$, p, and n are as defined for compounds of Formula (I);

$R^{11}$ is hydrogen, substituted or unsubstituted alkyl, substituted or unsubstituted aryl, substituted or unsubstituted heteroaryl, or an oxygen protecting group; and ⚌ represents a single or double bond.

In certain embodiments of the compound of Formula (C), $R^{11}$ is hydrogen.

In certain embodiments, the compound of Formula (C) is a compound of Formula (C-1):

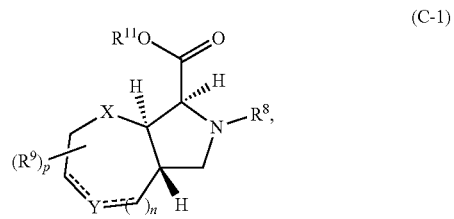
(C-1)

or salt thereof, wherein X, Y, $R^8$, $R^9$, $R^{11}$, p, and n are as defined herein; and ⚌ represents a single or double bond.

In certain embodiments of the compound of Formula (C-1), $R^{11}$ is hydrogen.

In certain embodiments, the compound of Formula (C) is a compound of Formula (C-2):

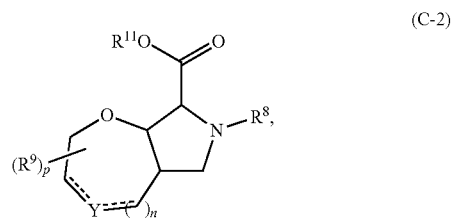
(C-2)

or salt thereof, wherein Y, $R^8$, $R^9$, $R^{11}$, p, and n are as defined herein; and ⚌ represents a single or double bond.

In certain embodiments of the compound of Formula (C-2), $R^{11}$ is hydrogen.

In certain embodiments, the compound of Formula (C) is a compound of Formula (C-3):

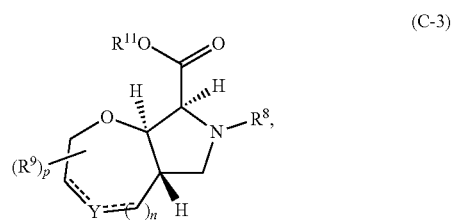
(C-3)

or salt thereof, or salt thereof, wherein Y, $R^8$, $R^9$, $R^{11}$, p, and n are as defined herein.

In certain embodiments of the compound of Formula (C-3), $R^{11}$ is hydrogen.

In certain embodiments, the compound of Formula (C) is a compound of Formula (C-4):

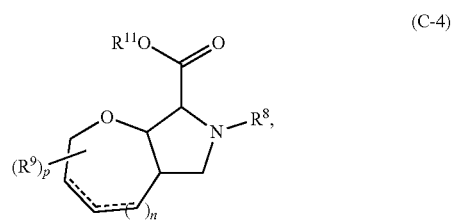
(C-4)

or salt thereof, or salt thereof, wherein Y, $R^8$, $R^9$, $R^{11}$, p, and n are as defined herein.

In certain embodiments of the compound of Formula (C-3), $R^{11}$ is hydrogen.

Preparation of Compounds of Formula (I)

In another aspect, compounds of the present disclosure are prepared by coupling a compound of Formula (A) and a compound of Formula (B) as depicted in Scheme 1.

Exemplary methods that may be used in the preparation of a compound of the present disclosure are described below, and are not to be construed as limiting. The compounds herein may be prepared by other methods of synthesis known in the art, and the procedures described herein may be modified or combined with other known methods.

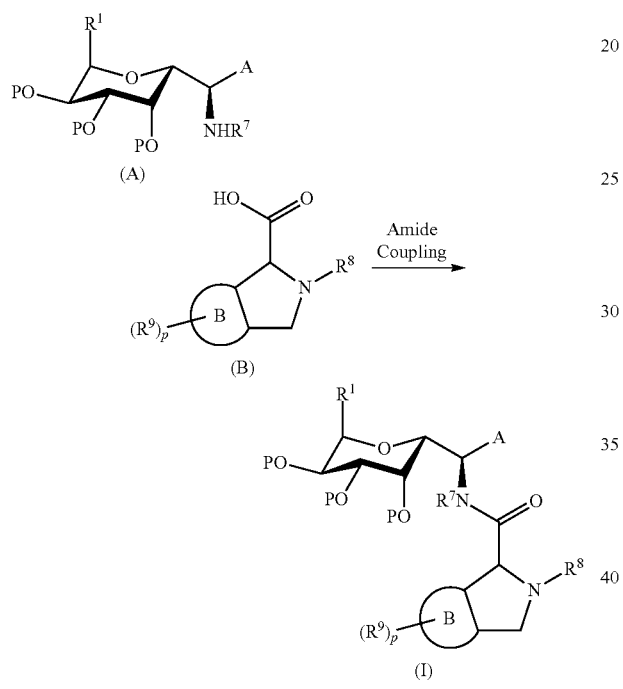

For all intermediates, A, P. $R^1$, $R^7$, $R^8$, $R^9$, n, and p are as defined herein for a compound of Formula (I), unless otherwise stated.

In certain embodiments, the amide bond formation is promoted by an amide coupling reagent (e.g., 1-[bis(dimethylamino)methylene]-1H-1,2,3-triazolo[4,5-b]pyridinium 3-oxid hexafluorophosphate (HATU). 1-ethyl-3-(3-dimethylaminopropyl)carbodiimide (EDC), hydroxybenzotriazole (HOBt)). In certain embodiments, the amide coupling reagent (e.g., HATU, EDC, HOBt) is reacted with the compound of Formula (B). In certain embodiments, the amide coupling reagent (e.g., HATU, EDC, HOBt) is reacted with the compound of Formula (B) prior to reacting with the compound of Formula (A). In certain embodiments, the amide coupling reagent is HATU.

In certain embodiments, the method comprises adding up to 1.0, 1.1, 1.2, 1.3, 1.4, 1.5, 1.6, 1.7, 1.8. 1.9, 2.0, 2.1, 2.2, 2.3, 2.4, 2.5, 2.6, 2.7, 2.8. 2.9, or 3.0 equivalents of the amide coupling reagent. In certain embodiments, the method comprises performing the coupling reaction at room temperature, ambient temperature, or elevated temperature. In certain embodiments, the method comprises performing the coupling reaction at 20-60° C., 20-50° C., 20-40° C., 20-30° C., 20-25° C., or 25-30° C.

In certain embodiments, an additional reagent may be added to the amide bond forming reaction. In certain embodiments, the additional reagent may facilitate amide coupling by protecting the free hydroxyls of the compound of Formula (A). In certain embodiments, the additional reagent is a silylating reagent. In certain embodiments, the silylating reagent reacts with the free hydroxyl groups of the compound of Formula (A) to form silyl protecting groups in situ during the reaction. In certain embodiments, the additional reagent is added to the compound of Formula (A) before the amide coupling. In certain embodiments, the method comprises adding up to 1.0, 1.1, 1.2, 1.3, 1.4, 1.5, 1.6, 1.7, 1.8. 1.9, 2.0, 2.1, 2.2, 2.3, 2.4, 2.5, 2.6, 2.7, 2.8. 2.9, 3.0, or more equivalents of the silylating reagent. In certain embodiments, the silylating reagent is N,O-bis(trimethylsilyl)trifluoroacetamide.

In another aspect, the present disclosure provides methods of preparing compounds of Formula (B), e.g., compounds of Formula (C-2):

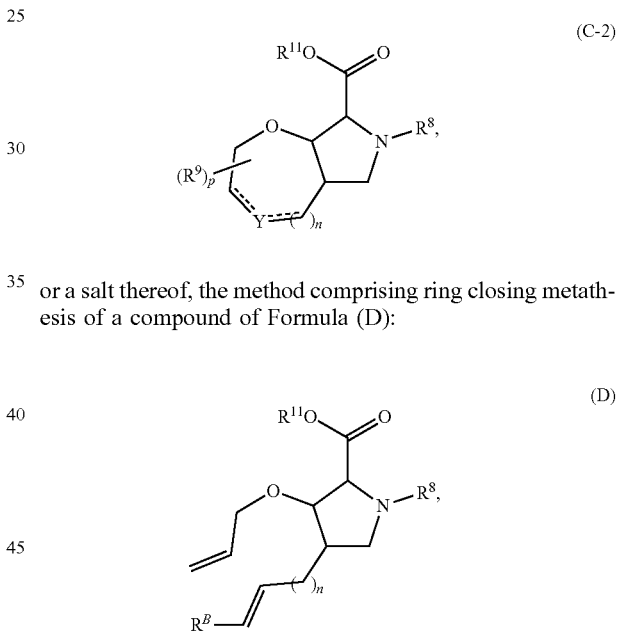

or a salt thereof, the method comprising ring closing metathesis of a compound of Formula (D):

or salt thereof, wherein Y, $R^8$, $R^9$, $R^{11}$, p, and n are as defined herein; and $R^B$ is hydrogen or methyl.

In certain embodiments, the compound of Formula (C-2) is the compound of Formula (C-4):

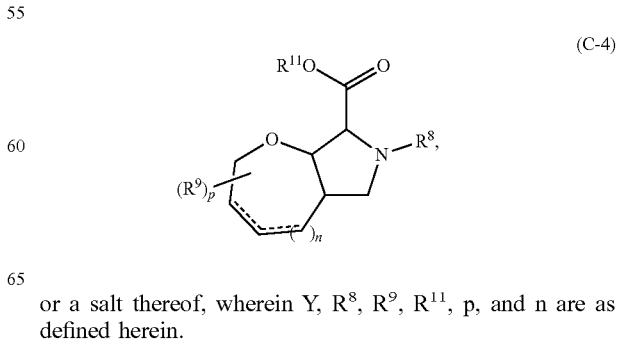

or a salt thereof, wherein Y, $R^8$, $R^9$, $R^{11}$, p, and n are as defined herein.

In certain embodiments, the ring closing metathesis is achieved through use of a transition metal catalyst. In certain embodiments, the transition metal catalyst is a tungsten (W), molybdenum (Mo), or ruthenium (Ru) catalyst. In certain embodiments, the catalyst is a ruthenium catalyst.

For examples of olefin metathesis reagents, catalysts, and reaction conditions useful in the present methods, see, e.g., Schrodi, Y.; Pederson, R. L. *Aldrichimica Acta* 2007, 40, 45; *Adv. Synth. Catal.* 2007, 349, 1-268; Grubbs, R. H. *Tetrahedron* 2004, 60, 7117; *Handbook of Metathesis*; Grubbs, R. H., Ed.; Wiley-VCH: Weinheim, 2003; Vols. 1-3; Trnka, T. M.; Grubbs, R. H. Acc. *Chem. Res.* 2001, 34, 18; Fürstner, A. *Angew. Chem., Int. Ed.* 2000, 39, 3012; Schuster, M.; Blechert, S. *Angew. Chem., Int. Ed.* 1997, 36, 2036; Ritter, T. et al. *Organometallics* 2006, 25, 5740; Chatterjee, A. K. et al. *J. Am. Chem. Soc.* 2000, 122, 3783; Chatterjee, A. K.; Grubbs, R. H. *Org. Lett.* 1999, 1, 1751; Murelli, R. P.; Snapper, M. L. *Org. Lett.* 2007, 9, 1749; Stewart, I. C. et al. *Org. Lett.* 2007, 9, 1589; Ung, T. et al. *Organometallics* 2004, 23, 5399; Benitez, D.; Goddard, W. A., III. *J. Am. Chem. Soc.* 2005, 127, 12218; Love, J. A. et al. Angew. *Chem., Int. Ed.* 2002, 41, 4035; Sanford, M. S. et al. *Organometallics* 2001, 20, 5314; Choi, T.-L.; Grubbs, R. H. *Angew. Chem.* 2003, 115, 1785; Ritter, T. et al. *Organometallics* 2006, 25, 5740; and references cited therein; each of which is incorporated herein by reference.

In certain embodiments, the metathesis catalyst is a Grubbs catalyst. In certain embodiments, the Grubbs catalyst is of the formula:

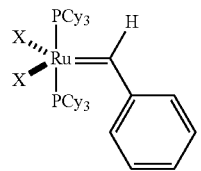

X = Cl; Br; I
Cy = cyclohexyl

Benzylidenebis-(tricyclohexylphosphine)-dichlororuthenium (X=Cl); Benzylidenebis-(tricyclohexylphosphine)-dibromoruthenium (X=Br); Benzylidenebis-(tricyclohexylphosphine)-diiodoruthenium (X=I);

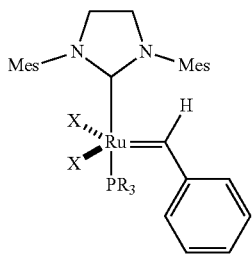

X = Cl; Br; I
R = cyclohexyl (Cy); phenyl (Ph); benzyl (Bn)

1,3-(Bis(mesityl)-2-imidazolidinylidene)dichloro-(phenylmethylene) (tricyclohexyl-phosphine)ruthenium (X=Cl; R=cyclohexyl); 1,3-(Bis(mesityl)-2-imidazolidinylidene)dibromo-(phenylmethylene) (tricyclohexyl-phosphine)ruthenium (X=Br; R=cyclohexyl); 1,3-(Bis(mesityl)-2-imidazolidinylidene)diiodo-(phenylmethylene) (tricyclohexyl-phosphine)ruthenium (X=I; R=cyclohexyl); 1,3-(Bis(mesityl)-2-imidazolidinylidene)dichloro-(phenylmethylene) (triphenylphosphine)ruthenium (X=Cl; R=phenyl); 1,3-(Bis(mesityl)-2-imidazolidinylidene)dichloro-(phenylmethylene) (tribenzylphosphine)ruthenium (X=Cl; R=benzyl);

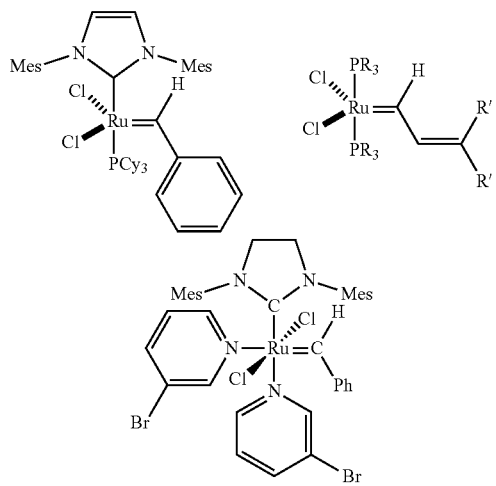

R = cylohexyl (Cy); phenyl (Ph)
R' = methyl; phenyl

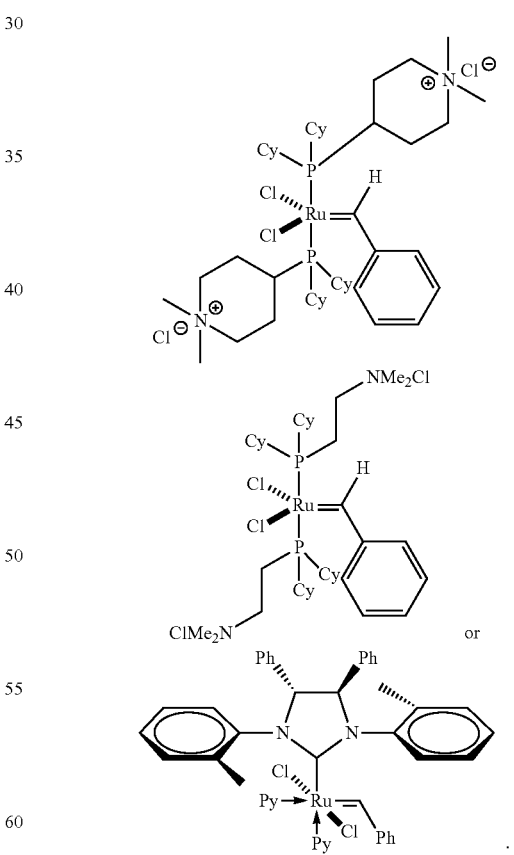

Py = pyridine
Ph = phenyl

In certain embodiments, the metathesis catalyst is a Grubbs-Hoveyda catalyst. In certain embodiments, the Grubbs-Hoveyda catalyst is of the formula:

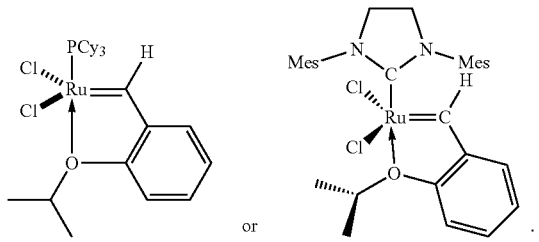

In certain embodiments, the method further comprises allylation of a compound of Formula (E):

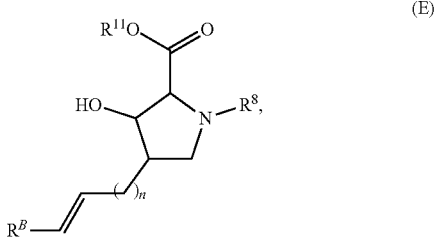

or salt thereof, to provide the compound of Formula (D).

In certain embodiments, the method further comprises a tandem aldol coupling-cyclization between a compound of Formula (G):

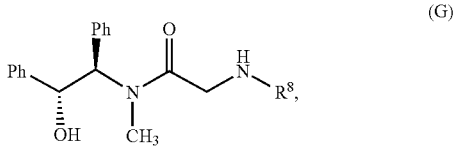

or a salt thereof, and a compound of Formula (H):

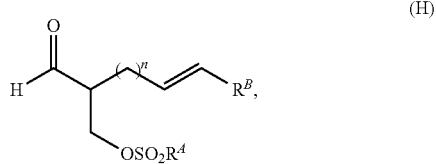

or a salt thereof.

In certain embodiments, the method comprises treating the compound of Formula (G) with a base prior to reacting with a compound of Formula (H). In certain embodiments, the base is an organolithium reagent. In certain embodiments, the base is lithium hexamethyldisilazide, lithium diisopropylamide, lithium tetramethylpiperidide. In certain embodiments, the base is lithium hexamethyldisilazide.

In certain embodiments, the method comprises reacting the compound of Formula (G) with the compound of Formula (H) at a temperature of less than 0° C., less than −10° C., less than −20° C., less than −30° C., less than −40° C., less than −50° C., less than −60° C., less than −70° C., less than −75° C., less than −80° C., or less than −85° C.

In certain embodiments of the compound of Formula (H), $R^A$ is substituted or unsubstituted aryl. In certain embodiments of the compound of Formula (H), $R^A$ is substituted or unsubstituted phenyl. In certain embodiments of the compound of Formula (H), $R^A$ is substituted phenyl. In certain embodiments of the compound of Formula (H), $R^A$ is tosyl or mesityl. In certain embodiments of the compound of Formula (H), $R^A$ is mesityl. In certain embodiments of the compounds of Formulae (G) and (H), $R^A$ is mesityl, and $R^8$ is hydrogen.

Pharmaceutical Compositions and Administration

The present disclosure provides pharmaceutical compositions comprising a compound as described herein, or a pharmaceutically acceptable salt thereof, and a pharmaceutically acceptable excipient.

Pharmaceutically acceptable excipients include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the compound of the present disclosure. The amount of the compound is generally equal to the dosage of the compound which would be administered to a subject and/or a convenient fraction of such a dosage such as, for example, one-half or one-third of such a dosage.

Relative amounts of the compound, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) compound.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the compounds, the liquid dosage forms may comprise inert diluents commonly used in the art such as, for example, water or other solvents, solubilizing agents, and emulsifiers, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium.

Solid dosage forms for oral administration include capsules, tablets, pills, powders, and granules. In such solid dosage forms, the compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Dosage forms for topical and/or transdermal administration of a compound of this invention may include ointments, pastes, creams, lotions, gels, powders, solutions, sprays, inhalants and/or patches. Generally, the compound is admixed under sterile conditions with a pharmaceutically acceptable carrier and/or any needed preservatives and/or buffers as can be required.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily amount of the compound will be decided by the attending physician within the scope of sound medical judgment. The specific therapeutically effective dose level for any particular subject will depend upon a variety of factors including the disease, disorder, or condition being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In general, the most appropriate route of administration will depend upon a variety of factors including the nature of the agent, the therapeutic regimen, and/or the condition of the subject. Oral administration is the preferred mode of administration. However, in certain embodiments, the subject may not be in a condition to tolerate oral administration, and thus intravenous, intramuscular, and/or rectal administration are also preferred alternative modes of administration.

An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein.

It will be also appreciated that a compound or composition, as described herein, can be administered in combination with one or more additional therapeutically active agents.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In certain embodiments, the levels utilized in combination will be lower than those utilized individually.

Exemplary additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins.

Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, the additional therapeutically active agent is an antibiotic. Exemplary antibiotics include, but are not limited to, penicillins (e.g., penicillin, amoxicillin), cephalosporins (e.g., cephalexin), compounds (e.g., erythromycin, clarithormycin, azithromycin, troleandomycin), fluoroquinolones (e.g., ciprofloxacin, levofloxacin, ofloxacin), sulfonamides (e.g., co-trimoxazole, trimethoprim), tetracyclines (e.g., tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline)), aminoglycosides (e.g., gentamicin, tobramycin, paromomycin), aminocyclitol (e.g., spectinomycin), chloramphenicol, sparsomycin, and quinupristin/dalfoprisin (Syndercid™).

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In certain embodiments, provided kits may optionally further include a second container comprising a pharmaceutical excipient for dilution or suspension of an inventive pharmaceutical composition or compound. In certain embodiments, the inventive pharmaceutical composition or compound provided in the container and the second container are combined to form one unit dosage form.

Methods of Treatment and Uses

The present disclosure contemplates using compounds of the present invention for the treatment of infectious diseases, for example, fungal, bacterial, viral, and/or parasitic infections. Lincosamides are generally known to exhibit antibacterial activity.

Thus, as generally described herein, provided is a method of treating an infectious disease comprising administering an effective amount of a compound of the present disclosure, or a pharmaceutically acceptable salt thereof, to a subject in need thereof. Such a method can be conducted in vivo (i.e., by administration to a subject). Treating, as used herein, encompasses therapeutic treatment and prophylactic treatment.

In certain embodiments, the effective amount is a therapeutically effective amount. For example, in certain embodiments, the method slows the progress of an infectious disease in the subject. In certain embodiments, the method improves the condition of the subject suffering from an infectious disease. In certain embodiments, the subject has a suspected or confirmed infectious disease.

In certain embodiments, the effective amount is a prophylactically effective amount. For example, in certain embodiments, the method prevents or reduces the likelihood of an infectious disease, e.g., in certain embodiments, the method comprises administering a compound of the present invention to a subject in need thereof in an amount sufficient to prevent or reduce the likelihood of an infectious disease. In certain embodiments, the subject is at risk of an infectious disease (e.g., has been exposed to another subject who has a suspected or confirmed infectious disease or has been exposed or thought to be exposed to a pathogen).

In one aspect, provided is a method of killing a microorganism (e.g., fungus, bacterium, virus, parasite) comprising contacting the microorganism with an effective amount of a compound of the present disclosure. The compound may contact the microorganism in vivo (e.g., in a subject in need thereof) or in vitro.

In another aspect, provided is a method of inhibiting the growth of a microorganism (e.g., fungus, bacterium, virus, parasite) comprising contacting the microorganism with an effective amount of a compound of the present disclosure. The compound may contact the microorganism in vivo (e.g., in a subject in need thereof) or in vitro.

In another aspect, provided is an in vitro method of inhibiting pathogenic growth comprising contacting an effective amount of the compound of the present invention with a pathogen (e.g., a bacteria, virus, fungus, or parasite) in a cell culture.

In another aspect, provided is an in vitro method of inhibiting pathogenic growth comprising contacting a pathogen (e.g., a bacteria, virus, fungus, or parasite) with an effective amount of a compound of the present disclosure. In another aspect, provided is a method of inhibiting protein synthesis (e.g., by interfering with the synthesis of proteins by binding to the 23s portion of the 50S subunit of the bacterial ribosome and causing premature dissociation of the peptidyl-tRNA from the ribosome) with an effective amount of a compound of the present disclosure. In certain embodiments, inhibiting protein synthesis comprises inhibiting the ribosome of bacteria with an effective amount of a compound of the present disclosure. Protein synthesis may be inhibited in vivo or in vitro.

As used herein, "infectious disease" and "microbial infection" are used interchangeably, and refer to an infection with a pathogen, such as a fungus, bacteria, virus, or a parasite. In certain embodiments, the infectious disease is caused by a fungus, bacteria, or a parasite. In certain embodiments, the infectious disease is caused by a pathogen resistant to other treatments. In certain embodiments, the infectious disease is caused by a pathogen that is multi-drug tolerant or resistant, e.g., the infectious disease is caused by a pathogen that neither grows nor dies in the presence of or as a result of other treatments.

In certain embodiments, the infectious disease is a bacterial infection. For example, in certain embodiments, provided is a method of treating a bacterial infection comprising administering an effective amount of a compound of the present invention, or a pharmaceutically acceptable salt thereof, to a subject in need thereof.

In certain embodiments, the compound has a mean inhibitory concentration (MIC), with respect to a particular bacteria, of less than 50 µg/mL, less than 25 µg/mL, less than 20 µg/mL, less than 10 µg/mL, less than 5 µg/mL, or less than 1 µg/mL.

In certain embodiments, the bacteria is susceptible (e.g., responds to) or resistant to known commercial compounds, such as azithromycin, lincomycin, clindamycin, telithromycin, erythromycin, spiramycin, and the like. In certain embodiments, the bacteria is resistant to a known compound. For example, in certain embodiments, the bacteria is lincomycin or clindamycin resistant.

In certain embodiments, the bacterial infection is resistant to other antibiotics (e.g., non-compound) therapy. For example, in certain embodiments, the pathogen is vancomycin resistant (VR). In certain embodiments, the pathogen is methicillin-resistant (MR), e.g., in certain embodiments, the bacterial infection is an methicillin-resistant *S. aureus* infection (a MRSA infection). In certain embodiments, the pathogen is quinolone resistant (QR). In certain embodiments, the pathogen is fluoroquinolone resistant (FR).

Exemplary bacterial infections include, but are not limited to, infections with a Gram positive bacteria (e.g., of the phylum Actinobacteria, phylum Firmicutes, or phylum Tenericutes); Gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacterial infection is an infection with a Gram positive bacterium.

In certain embodiments, the Gram positive bacterium is a bacterium of the phylum Firmicutes.

In certain embodiments, the bacteria is a member of the phylum Firmicutes and the genus *Enterococcus*, i.e., the bacterial infection is an *Enterococcus* infection. Exemplary Enterococci bacteria include, but are not limited to, *E. avium, E. durans, E. faecalis, E. faecium, E. gallinarum, E. solitarius, E. casseliflavus,* and *E. raffinosus*.

In certain embodiments, the bacteria is a member of the phylum Firmicutes and the genus *Staphylococcus*, i.e., the bacterial infection is a *Staphylococcus* infection. Exemplary Staphylococci bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri,* and *S. xylosus*. In certain embodiments, the *Staphylococcus* infection is a *S. aureus* infection.

In certain embodiments, the *S. aureus* has an efflux (e.g., mef, msr) genotype. Bacteria of the efflux genotypes actively pump drug out of the cell via efflux pumps.

In certain embodiments, the *S. aureus* has a methylase (e.g., erm) genotype. In certain embodiments, erm is the bacterial gene class coding for erythromycin ribosomal methylase, which methylates a single adenine in 23S rRNA, itself a component of 50S rRNA.

In certain embodiments, the bacteria is a member of the phylum Firmicutes and the genus *Bacillus*, i.e., the bacterial infection is a *Bacillus* infection. Exemplary *Bacillus* bacteria include, but are not limited to, *B. alcalophilus, B. alvei, B. aminovorans, B. amyloliquefaciens, B. aneurinolyticus, B. anthracis, B. aquaemaris, B. atrophaeus, B. boroniphilus, B. brevis, B. caldolyticus, B. centrosporus, B. cereus, B. circulans, B. coagulans, B. firmus, B. flavothermus, B. fusiformis, B. globigii, B. infernus, B. larvae, B. laterosporus, B. lentus, B. licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis,* and *B. weihenstephanensis*. In certain embodiments, the *Bacillus* infection is a *B. subtilis* infection. In certain embodiments, the *B. subtilis* has an efflux (e.g., mef, msr) genotype. In certain embodiments, the *B. subtilis* has a methylase (e.g., erm) genotype.

In certain embodiments, the bacteria is a member of the phylum Firmicutes and the genus *Streptococcus*, i.e., the bacterial infection is a *Strepococcus* infection. Exemplary *Streptococcus* bacteria include, but are not limited to, *S. agalactiae, S. anginosus, S. bovis, S. canis, S. constellatus, S. dysgalactiae, S. equinus, S. iniae, S. intermedius, S. mitis, S. mutans, S. oralis, S. parasanguinis, S. peroris, S. pneumoniae, S. pyogenes, S. ratti, S. salivarius, S. thermophilus, S. sanguinis, S. sobrinus, S. suis, S. uberis, S. vestibularis, S. viridans,* and *S. zooepidemicus*. In certain embodiments, the *Strepococcus* infection is an *S. pyogenes* infection. In certain embodiments, the *Strepococcus* infection is an *S. pneumoniae* infection. In certain embodiments, the *S. pneumoniae* has an efflux (e.g., mef, msr) genotype. In certain embodiments, the *S. pneumoniae* has a methylase (e.g., erm) genotype.

In certain embodiments, the bacteria is a member of the phylum Firmicutes and the genus *Clostridium*, i.e., the bacterial infection is a *Clostridium* infection. Exemplary Clostridia bacteria include, but are not limited to, *C. botulinum, C. difficile, C. perfringens, C. tetani,* and *C. sordellii*.

In certain embodiments, the compounds of the disclosure are a safer alternative to clindamycin, due to reduced incidence of pseudomembranous colitis. In certain embodiments, the compounds of the disclosure have increased activity against *Clostridium difficile* (*C. difficile*) in comparison to clindamycin. In certain embodiments, the compounds have a mean inhibitory concentration (MIC), with respect to *C. difficile*, of less than 50 µg/mL, less than 25 µg/mL, less than 20 µg/mL, less than 10 µg/mL, less than 5 µg/mL, or less than 1 µg/mL.

In certain embodiments, the bacterial infection is an infection with a Gram negative bacteria.

In certain embodiments, the Gram negative bacteria is a bacteria of the phylum Proteobacteria and the genus *Escherichia*. i.e., the bacterial infection is an *Escherichia* infection. Exemplary *Escherichia* bacteria include, but are not limited to, *E. albertii, E. blattae, E. coli, E. fergusonii, E. hermannii,* and *E. vulneris*. In certain embodiments, the *Escherichia* infection is an *E. coli* infection.

In certain embodiments, the Gram negative bacteria is a bacteria of the phylum Proteobacteria and the genus *Haemophilus*. i.e., the bacterial infection is an *Haemophilus* infection. Exemplary *Haemophilus* bacteria include, but are not limited to, *H. aegyptius, H. aphrophilus, H. avium, H. ducreyi, H. felis, H. haemolyticus, H. influenzae, H. parainfluenzae, H. paracuniculus, H. parahaemolyticus, H. pittmaniae, Haemophilus segnis,* and *H. somnus*. In certain embodiments, the *Haemophilus* infection is an *H. influenzae* infection.

In certain embodiments, the Gram negative bacteria is a bacteria of the phylum Proteobacteria and the genus *Acinetobacter*. i.e., the bacterial infection is an *Acinetobacter* infection. Exemplary *Acinetobacter* bacteria include, but are not limited to, *A. baumanii, A. haemolyticus,* and *A. lwoffii*. In certain embodiments, the *Acinetobacter* infection is an *A. baumanii* infection.

In certain embodiments, the Gram negative bacteria is a bacteria of the phylum Proteobacteria and the genus *Klebsiella*. i.e., the bacterial infection is a *Klebsiella* infection. Exemplary *Klebsiella* bacteria include, but are not limited to, *K. granulomatis, K. oxytoca, K. michiganensis, K. pneumoniae, K. quasipneumoniae,* and *K. variicola*. In certain embodiments, the *Klebsiella* infection is a *K. pneumoniae* infection.

In certain embodiments, the Gram negative bacteria is a bacteria of the phylum Proteobacteria and the genus *Pseudomonas*. i.e., the bacterial infection is a *Pseudomonas* infection. Exemplary *Pseudomonas* bacteria include, but are not limited to, *P. aeruginosa, P. oryzihabitans, P. plecoglissicida, P. syringae, P. putida,* and *P. fluoroscens*. In certain embodiments, the *Pseudomonas* infection is a *P. aeruginosa* infection.

In certain embodiments, the Gram negative bacteria is a bacteria of the phylum Bacteroidetes and the genus *Bacteroides*. i.e., the bacterial infection is a *Bacteroides* infection. Exemplary *Bacteroides* bacteria include, but are not limited to, *B. fragilis, B. distasonis, B. ovatus, B. thetaiotaomicron,* and *B. vulgatus*. In certain embodiments, the *Bacteroides* infection is a *B. fragilis* infection.

In certain embodiments, the bacteria is an atypical bacteria, i.e., are neither Gram positive nor Gram negative.

In certain embodiments, the infectious disease is an infection with a parasitic infection. Thus, in certain embodiments, provided is a method of treating a parasitic infection comprising administering an effective amount of a compound of the present invention, or a pharmaceutically acceptable salt thereof, to a subject in need thereof.

In certain embodiments, the compound has an $IC_{50}$ (uM) with respect to a particular parasite, of less than 50 uM, less than 25 uM, less than 20 uM, less than 10 uM, less than 5 uM, or less than 1 uM.

Exemplary parasites include, but are not limited to, *Trypanosoma* spp. (e.g., *Trypanosoma cruzi, Trypansosoma brucei*), *Leishmania* spp., *Giardia* spp., *Trichomonas* spp., *Entamoeba* spp., *Naegleria* spp., *Acanthamoeba* spp., *Schistosoma* spp., *Plasmodium* spp. (e.g., *P. flaciparum*), *Crytosporidium* spp., *Isospora* spp., *Balantidium* spp., *Pneumocystis* spp., *Babesia, Loa Loa, Ascaris lumbricoides, Dirofilaria immitis,* and *Toxoplasma* ssp. (e.g. *T. gondii*).

As generally described herein, the present disclosure further provides a method of treating an inflammatory condition comprising administering an effective amount of a compound of the present disclosure, or a pharmaceutically acceptable salt thereof, to a subject in need thereof. Such a method can be conducted in vivo (i.e., by administration to a subject) or in vitro (e.g., upon contact with the pathogen, tissue, or cell culture). Treating, as used herein, encompasses therapeutic treatment and prophylactic treatment.

In certain embodiments, the effective amount is a therapeutically effective amount. For example, in certain embodiments, the method slows the progress of an inflammatory condition in the subject. In certain embodiments, the method improves the condition of the subject suffering from an inflammatory condition. In certain embodiments, the subject has a suspected or confirmed inflammatory condition.

In certain embodiments, the effective amount is a prophylactically effective amount. For example, in certain embodiments, the method prevents or reduces the likelihood of an inflammatory condition, e.g., in certain embodiments, the method comprises administering a compound of the present invention to a subject in need thereof in an amount sufficient to prevent or reduce the likelihood of an inflammatory condition. In certain embodiments, the subject is at risk to an inflammatory condition.

The term "inflammatory condition" refers to those diseases, disorders, or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent). Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

In certain embodiments, the inflammatory condition is an acute inflammatory condition (e.g., for example, inflammation resulting from an infection). In certain embodiments, the inflammatory condition is a chronic inflammatory condition. In certain embodiments, the inflammatory condition is inflammation associated with cancer.

As generally described herein, the present disclosure further provides a method of treating a central nervous system disorder comprising administering an effective amount of a compound of the present disclosure, or a pharmaceutically acceptable salt thereof, to a subject in need thereof. Such a method can be conducted in vivo (i.e., by administration to a subject) or in vitro (e.g., upon contact with a tissue or cell culture). Treating, as used herein, encompasses therapeutic treatment and prophylactic treatment.

In certain embodiments, the effective amount is a therapeutically effective amount. For example, in certain embodiments, the method slows the progress of a central nervous system disorder in the subject. In certain embodiments, the method improves the condition of the subject suffering from a central nervous system disorder. In certain embodiments, the subject has a suspected or confirmed central nervous system disorder.

In certain embodiments, the effective amount is a prophylactically effective amount. For example, in certain embodiments, the method prevents or reduces the likelihood of a central nervous system disorder, e.g., in certain embodiments, the method comprises administering a compound of the present disclosure to a subject in need thereof in an amount sufficient to prevent or reduce the likelihood of a central nervous system disorder. In certain embodiments, the subject is at risk of developing a central nervous system disorder.

In certain embodiments, compounds of the present disclosure may treat a central nervous system disorder by modulating the serotonin $5\text{-HT}_{2C}$ receptor. In certain embodiments, the compounds of the present disclosure are allosteric modulators of the serotonin $5\text{-HT}_{2C}$ receptor, e.g., see Zhou et al. *ACS Chemical Neuroscience* 2012, 3, 538-545, and Dinh et al. *Molecular Pharmacology* 2003, 64, 78-84.

In certain embodiments, the central nervous system disorder is addiction, anxiety, depression, obesity, eating disorders, Parkinson's disease, or schizophrenia.

DEFINITIONS

Chemical Terms

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N.Y., 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⁓ is a single bond where the stereochemistry of the moieties immediately attached thereto is not specified, - - - is absent or a single bond, and === or ≡≡≡ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In certain embodiments, an alkyl group has 1 to 9 carbon atoms ("$C_{1-9}$ alkyl"). In certain embodiments, an alkyl group has 1 to 8 carbon atoms ("$C_{1-8}$ alkyl"). In certain embodiments, an alkyl group has 1 to 7 carbon atoms ("$C_{1-7}$ alkyl"). In certain embodiments, an alkyl group has 1 to 6 carbon atoms ("$C_{1-6}$ alkyl"). In certain embodiments, an alkyl group has 1 to 5 carbon atoms ("$C_{1-8}$ alkyl"). In certain embodiments, an alkyl group has 1 to 4 carbon atoms ("$C_{1-4}$ alkyl"). In certain embodiments, an alkyl group has 1 to 3 carbon atoms ("$C_{1-3}$ alkyl"). In certain embodiments, an alkyl group has 1 to 2 carbon atoms ("$C_{1-2}$ alkyl"). In certain embodiments, an alkyl group has 1 carbon atom ("$C_1$ alkyl"). In certain embodiments, an alkyl group has 2 to 6 carbon atoms ("$C_{2-6}$ alkyl"). Examples of $C_{1-6}$ alkyl groups include methyl ($C_1$), ethyl (C), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl (C) (e.g., n-hexyl). Additional examples of alkyl groups include n-heptyl ($C_7$), n-octyl (C), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In certain embodiments, the haloalkyl moiety has 1 to 8 carbon atoms ("$C_{1-8}$ haloalkyl"). In certain embodiments, the haloalkyl moiety has 1 to 6 carbon atoms ("$C_{1-6}$ haloalkyl"). In certain embodiments, the haloalkyl moiety has 1 to 4 carbon atoms ("$C_{1-4}$ haloalkyl"). In certain embodiments, the haloalkyl moiety has 1 to 3 carbon atoms ("$C_{1-3}$ haloalkyl"). In certain embodiments, the haloalkyl moiety has 1 to 2 carbon atoms ("$C_{1-2}$ haloalkyl"). Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In certain embodiments, a heteroalkyl group is a saturated group having 1 to 9 carbon atoms and 1 or more heteroatoms within the parent chain ("hetero$C_{1-9}$ alkyl"). In certain embodiments, a heteroalkyl group is a saturated group having 1 to 8 carbon atoms and 1 or more heteroatoms within the parent chain ("hetero$C_{1-8}$ alkyl"). In certain embodiments, a heteroalkyl group is a saturated group having 1 to 7 carbon atoms and 1 or more heteroatoms within the parent chain ("hetero$C_{1-7}$ alkyl"). In certain embodiments, a heteroalkyl group is a saturated group having 1 to 6 carbon atoms and 1 or more heteroatoms within the parent chain ("hetero$C_{1-6}$ alkyl"). In certain embodiments, a heteroalkyl group is a saturated group having 1 to 5 carbon atoms and 1 or 2 heteroatoms within the parent chain ("hetero$C_{1-5}$ alkyl"). In certain embodiments, a heteroalkyl group is a saturated group having 1 to 4 carbon atoms and 1 or 2 heteroatoms within the parent chain ("heteroC$_{1-4}$ alkyl"). In certain embodiments, a heteroalkyl group is a saturated group having 1 to 3 carbon atoms and 1 heteroatom within the parent chain ("heteroC$_{1-3}$ alkyl"). In certain embodiments, a heteroalkyl group is a saturated group having 1 to 2 carbon atoms and 1 heteroatom within the parent chain ("heteroC$_{1-2}$ alkyl"). In certain embodiments, a heteroalkyl group is a saturated group having 1 carbon atom and 1 heteroatom ("heteroC$_1$ alkyl"). In certain embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In certain embodiments, an alkenyl group has 2 to 9 carbon atoms ("C$_{2-9}$ alkenyl"). In certain embodiments, an alkenyl group has 2 to 8 carbon atoms ("C$_{2-8}$ alkenyl"). In certain embodiments, an alkenyl group has 2 to 7 carbon atoms ("C$_{2-7}$ alkenyl"). In certain embodiments, an alkenyl group has 2 to 6 carbon atoms ("C$_{2-6}$ alkenyl"). In certain embodiments, an alkenyl group has 2 to 5 carbon atoms ("C$_{2-5}$ alkenyl"). In certain embodiments, an alkenyl group has 2 to 4 carbon atoms ("C$_{2-4}$ alkenyl"). In certain embodiments, an alkenyl group has 2 to 3 carbon atoms ("C$_{2-3}$ alkenyl"). In certain embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C), and the like. Additional examples of alkenyl include heptenyl (C$_7$), octenyl (C), octatrienyl (C), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In certain embodiments, a heteroalkenyl group has 2 to 9 carbon atoms at least one double bond, and 1 or more heteroatoms within the parent chain ("heteroC$_{2-9}$ alkenyl"). In certain embodiments, a heteroalkenyl group has 2 to 8 carbon atoms, at least one double bond, and 1 or more heteroatoms within the parent chain ("heteroC$_{2-8}$ alkenyl"). In certain embodiments, a heteroalkenyl group has 2 to 7 carbon atoms, at least one double bond, and 1 or more heteroatoms within the parent chain ("heteroC$_{2-7}$ alkenyl"). In certain embodiments, a heteroalkenyl group has 2 to 6 carbon atoms, at least one double bond, and 1 or more heteroatoms within the parent chain ("heteroC$_{2-6}$ alkenyl"). In certain embodiments, a heteroalkenyl group has 2 to 5 carbon atoms, at least one double bond, and 1 or 2 heteroatoms within the parent chain ("heteroC$_{2-5}$ alkenyl"). In certain embodiments, a heteroalkenyl group has 2 to 4 carbon atoms, at least one double bond, and 1 or 2 heteroatoms within the parent chain ("heteroC$_{2-4}$ alkenyl"). In certain embodiments, a heteroalkenyl group has 2 to 3 carbon atoms, at least one double bond, and 1 heteroatom within the parent chain ("heteroC$_{2-3}$ alkenyl"). In certain embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In certain embodiments, an alkynyl group has 2 to 9 carbon atoms ("C$_{2-9}$ alkynyl"). In certain embodiments, an alkynyl group has 2 to 8 carbon atoms ("C$_{2-8}$ alkynyl"). In certain embodiments, an alkynyl group has 2 to 7 carbon atoms ("C$_{2-7}$ alkynyl"). In certain embodiments, an alkynyl group has 2 to 6 carbon atoms ("C$_{2-6}$ alkynyl"). In certain embodiments, an alkynyl group has 2 to 5 carbon atoms ("C$_{2-5}$ alkynyl"). In certain embodiments, an alkynyl group has 2 to 4 carbon atoms ("C$_{2-4}$ alkynyl"). In certain embodiments, an alkynyl group has 2 to 3 carbon atoms ("C$_{2-3}$ alkynyl"). In certain embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In certain embodiments, a heteroalkynyl group has 2 to 9 carbon atoms, at least one triple bond, and 1 or more heteroatoms within the parent chain ("heteroC$_{2-9}$ alkynyl"). In certain embodiments, a heteroalkynyl group has 2 to 8 carbon atoms, at least one triple bond, and 1 or more heteroatoms within the parent chain ("heteroC$_{2-8}$ alkynyl"). In certain embodiments, a heteroalkynyl group has 2 to 7 carbon atoms, at least one triple bond, and 1 or more heteroatoms within the parent chain ("heteroC$_2$-7 alkynyl"). In certain embodiments, a heteroalkynyl group has 2 to 6 carbon atoms, at least one triple bond, and 1 or more heteroatoms within the parent chain ("heteroC$_{2-6}$ alkynyl"). In certain embodiments, a heteroalkynyl group has 2 to 5 carbon atoms, at least one triple bond, and 1 or 2 heteroatoms within the parent chain ("heteroC$_{2-5}$ alkynyl"). In certain embodiments, a heteroalkynyl group has 2 to 4 carbon atoms, at least one triple bond, and 1 or 2 heteroatoms within the parent chain ("heteroC$_{2-4}$ alkynyl"). In certain embodiments, a heteroalkynyl group has 2 to 3 carbon atoms, at least one triple bond, and 1 heteroatom within the parent chain ("heteroC$_{2-3}$ alkynyl"). In certain embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In certain embodiments, a carbocyclyl group has 3 to 10 ring carbon atoms ("C$_{3-10}$ carbocyclyl"). In certain embodiments, a carbocyclyl group has 3 to 8 ring carbon atoms ("$_C$ carbocyclyl"). In certain embodiments, a carbocyclyl group has 3 to 7 ring carbon atoms ("C$_{3-7}$ carbocyclyl"). In certain embodiments, a carbocyclyl group has 3 to 6 ring carbon atoms ("C$_{3-6}$ carbocyclyl"). In certain embodiments, a carbocyclyl group has 4 to 6 ring carbon atoms ("C$_{4-6}$ carbocyclyl"). In certain embodiments, a carbocyclyl group has 5 to 6 ring carbon atoms ("C$_{5-6}$ carbocyclyl"). In certain embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C), cyclopropenyl (C), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C), cyclooctenyl (C), bicyclo[2.2.1]heptanyl (C$_7$), bicyclo[2.2.2]octanyl (C), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In certain embodiments, "carbocyclyl" is a monocyclic, saturated carbocyclyl group having from 3 to 14 ring carbon atoms ("C$_{3-14}$ cycloalkyl"). In certain embodiments, a cycloalkyl group has 3 to 10 ring carbon atoms ("C$_{3-10}$ cycloalkyl"). In certain embodiments, a cycloalkyl group has 3 to 8 ring carbon atoms ("C$_{3-8}$ cycloalkyl"). In certain embodiments, a cycloalkyl group has 3 to 6 ring carbon atoms ("C$_{3-6}$ cycloalkyl"). In certain embodiments, a cycloalkyl group has 4 to 6 ring carbon atoms ("C$_{4-6}$ cycloalkyl"). In certain embodiments, a cycloalkyl group has 5 to 6 ring carbon atoms ("C$_{5-6}$ cycloalkyl"). In certain embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

"Carbocyclylalkyl" is a subset of "alkyl" and refers to an alkyl group substituted by a carbocyclyl group, wherein the point of attachment is on the alkyl moiety.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In certain embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In certain embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In certain embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In certain embodiments, the 5-6 membered heterocyclyl has 1-3 ring heteroatoms selected from nitrogen, oxygen, and sulfur. In certain embodiments, the 5-6 membered heterocyclyl has 1-2 ring heteroatoms selected from nitrogen, oxygen, and sulfur. In certain embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

"Heterocyclylalkyl" is a subset of "alkyl" and refers to an alkyl group substituted by an heterocyclyl group, wherein the point of attachment is on the alkyl moiety.

The term "aryl" refers to a radical of a monocyclic or polycyclic (e.g., bicyclic or tricyclic) 4n+2 aromatic ring system (e.g., having 6, 10, or 14 T electrons shared in a cyclic array) having 6-14 ring carbon atoms and zero heteroatoms provided in the aromatic ring system ("$C_{6-14}$ aryl"). In certain embodiments, an aryl group has 6 ring carbon atoms ("$C_6$ aryl"; e.g., phenyl). In certain embodiments, an aryl group has 10 ring carbon atoms ("$C_{10}$ aryl"; e.g., naphthyl such as 1-naphthyl and 2-naphthyl). In certain embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In certain embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In certain embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In certain embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In certain embodiments, the 5-6 membered heteroaryl has 1-3 ring heteroatoms selected from nitrogen, oxygen, and sulfur. In certain embodiments, the 5-6 membered heteroaryl has 1-2 ring heteroatoms selected from nitrogen, oxygen, and sulfur. In certain embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —C(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal $R^{19}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R—, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$CO$_2$$R^{aa}$, —N$R^{bb}$C(=O)N($R^{bb}$)$_2$, —N$R^{bb}$C(=N$R^{bb}$)N($R^{bb}$)$_2$, —N$R^{bb}$SO$_2$$R^{aa}$, —N$R^{bb}$P(=O)(O$R^{cc}$)$_2$, and —N$R^{bb}$P(=O)(N$R^{bb}$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$$X^-$, wherein $R^{bb}$ and $X^-$ are as defined herein.

The term "sulfonyl" refers to a group selected from —SO$_2$N($R^{bb}$)$_2$, —SO$_2$$R^{aa}$, and —SO$_2$O$R^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "acyl" refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, and —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "silyl" refers to the group —Si($R^{aa}$)$_3$, wherein $R^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$R, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=N$R^{cc}$)$R^{aa}$, —C(=N$R^{cc}$)O$R^{11}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{aa})OR^{aa}$, $-C(=NR^{bb})N(R^{bb})_2$, $-S(=O)R^{aa}$, $-SO_2R^{aa}$, $-Si(R^{cc})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl (TBDMS), t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R$, —$C(=O)N(R^{bb})_2$, —$C(=NR^{bb})$ $R^{aa}$, —$C(=NR^{bb})OR^{aa}$, —$C(=NR^{bb})N(R^{bb})_2$, —$S(=O)$ $R^{aa}$, —$SO_2R^{aa}$, —$Si(R^{aa})_3$, —$P(R^{cc})_2$, —$P(R^{cc})_3$, —$P(=O)_2R^{cc}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March *Advanced Organic Chemistry* 6th ed. (501-502). Exemplary leaving groups include, but are not limited to, halo (e.g., chloro, bromo, iodo), —$OR^{aa}$ (when the O atom is attached to a carbonyl group, wherein $R^{aa}$ is as defined herein), —$O(C=O)R^{LG}$, or —$O(SO)_2R^{LG}$ (e.g., tosyl, mesyl, besyl), wherein $R^{LG}$ is optionally substituted alkyl, optionally substituted aryl, or optionally substituted heteroaryl. In certain embodiments, the leaving group is a halogen. In certain embodiments, the leaving group is I.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., $2^4$) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an a anomer, the —OH substituent on the anomeric carbon rests on the opposite side (trans) of the ring from the —$CH_2OH$ side branch. The alternative form, in which the —$CH_2OH$ substituent and the anomeric hydroxyl are on the same side (cis) of the plane of the ring, is called a anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, or rutinose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

These and other exemplary substituents are described in more detail in the Detailed Description, Examples, and claims. The invention is not intended to be limited in any manner by the above exemplary listing of substituents.

Other Definitions

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\,alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.xH_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R.0.5H_2O$)), and polyhydrates (x is a number greater than 1, e.g., dihydrates ($R.2H_2O$) and hexahydrates ($R.6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_{1-8}$ alkyl, $C_{2-8}$ alkenyl, $C_{2-8}$ alkynyl, aryl, $C_{7-12}$ substituted aryl, and $C_7$-$C_{12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal "Disease," "disorder," and "condition" are used interchangeably herein.

The term "administer," "administering," or "administration" refers to implanting, absorbing, ingesting, injecting, inhaling, or otherwise introducing a compound described herein, or a composition thereof, in or on a subject.

As used herein, and unless otherwise specified, the terms "treat," "treating" and "treatment" contemplate an action that occurs while a subject is suffering from the specified infectious disease or inflammatory condition, which reduces the severity of the infectious disease or inflammatory condition, or retards or slows the progression of the infectious disease or inflammatory condition ("therapeutic treatment"), and also contemplates an action that occurs before a subject begins to suffer from the specified infectious disease or inflammatory condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of an infectious disease or inflammatory condition, or to delay or minimize one or more symptoms associated with the infectious disease or inflammatory condition. A therapeutically effective amount of a compound means an amount of therapeutic agent, alone or in combination with other therapies, which provides a therapeutic benefit in the treatment of the infectious disease or inflammatory condition. The term "therapeutically effective amount" can encompass an amount that improves overall therapy, reduces or avoids symptoms or causes of infectious disease or inflammatory condition, or enhances the therapeutic efficacy of another therapeutic agent.

As used herein, and unless otherwise specified, a "prophylactically effective amount" of a compound is an amount sufficient to prevent an infectious disease or inflammatory condition, or one or more symptoms associated with the infectious disease or inflammatory condition, or prevent its recurrence. A prophylactically effective amount of a compound means an amount of a therapeutic agent, alone or in combination with other agents, which provides a prophylactic benefit in the prevention of the infectious disease or inflammatory condition. The term "prophylactically effective amount" can encompass an amount that improves overall prophylaxis or enhances the prophylactic efficacy of another prophylactic agent.

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Synthesis of Lincosamide Analogues

General Experimental Procedures:

All reactions were performed in oven- or flame-dried round-bottomed or modified Schlenk flasks fitted with rubber septa under a positive pressure of argon (dried by passage through a column of Drierite calcium sulfate desiccant), unless otherwise noted. Air- and moisture-sensitive liquids and solutions were transferred via syringe or stainless steel cannula. When necessary (so noted), solutions were deoxygenated by three cycles of freezing (liquid nitrogen), evacuation, and thawing under static vacuum. Organic solutions were concentrated by rotary evaporation (house vacuum, ~60 Torr) at 23-30° C. Flash-column chromatography was performed as described by Still et al., (Still, W. C.; Kahn, M.; Mitra, A., *J. Org. Chem.* 1978, 43 (14), 2923-2925), employing silica gel (60-Å pore size, 230-400 mesh, Agela Technologies, Chicago, Ill.; or RediSep silica cartridges, Teledyne Isco, Lincoln, Nebr.). Analytical thin-layer chromatography (TLC) was performed using glass plates pre-coated with silica gel (0.25 mm, 60-A pore size, 230-400 mesh, Merck KGA) impregnated with a fluorescent indicator (254 nm). In special cases (so noted), analytical TLC was performed with aminopropyl-modified silica gel ($NH_2$ silica gel, 60-Å pore size, Wako Chemicals USA) impregnated with a fluorescent indicator (254 nm). TLC plates were visualized by exposure to ultraviolet light (UV) and/or exposure to iodine vapor ($I_2$), basic aqueous potassium permanganate solution ($KMnO_4$), acidic ethanolic para-anisaldehyde solution (PAA), acidic aqueous ceric ammonium molybdate solution (CAM), or ethanolic solution of phosphomolybdic acid (PMA) followed by brief heating on a hot plate as needed (~200° C., ≤15 s). In some cases, reaction monitoring was carried out by analytical liquid chromatography-mass spectrometry (LCMS), or by flow-injection analysis-high-resolution mass spectrometry (FIA-HRMS).

Materials:

Commercial reagents and solvents were used as received, unless mentioned otherwise. Dichloromethane, diethyl ether, tetrahydrofuran, 1,4-dioxane, N,N-dimethylformamide, toluene, and benzene were purified by passage through $Al_2O_3$ under argon, according to the method of Pangborn et al. (Pangborn, A. B.; Giardello, M. A.; Grubbs, R. H.; Rosen, R. K.; Timmers, F. J. *Organometallics* 1996, 15 (5), 1518-1520) Ethynyltriisopropylsilane, triethylphosphonoacetate, 1,8-diazabicyclo[5.4.0]undec-7-ene, (−)-diethyl-D-tartrate, tert-butyldiphenylchlorosilane, imidazole, trimethyl phosphite, sodium triacetoxyborohydride, trifluoroacetic acid, 1-[2-(trimethylsilyl)ethoxycarbonyloxy]pyrrolidin-2,5-dione (Teoc-OSu), Oxone monopersulfate compound, and HATU were purchased from Oakwood Products, Inc. (Estill, S.C., USA). Tungsten hexacarbonyl (99%, <0.3% molybdenum) was purchased from Strem Chemicals, Inc. (Newburyport, Mass., USA). N-Boc-β-alanine N-hydroxysuccinimide ester was purchased from Santa Cruz Biotechnology (Dallas, Tex., USA). 1-Chloro-3-methyl-2-butene (prenyl chloride) and ethynyltrimethylsilane were purchased from Alfa Aesar (Haverhill, Mass., USA). 4-Pyrimidin-5-ylaniline was purchased from Enamine Ltd. (Monmouth Jct., N.J., USA). 4-Pyridin-3-ylaniline was purchased from Maybridge Chemical Company (Altrincham, UK). 4-Ethynylpyrimidin-2-amine was prepared according to literature procedures (Tibiletti, F.; Simonetti, M.; Nicholas, K. M.; Palmisano, G.; Parravicini, M.; Imbesi, F.; Tollari, S.; Penoni, A. *Tetrahedron* 2010, 66 (6), 1280-1288.). All other chemicals and reagents were purchased from Sigma-Aldrich Corporation (Natick, Mass., USA).

Instrumentation:

Proton nuclear magnetic resonance ($^1H$ NMR) spectra and carbon nuclear magnetic resonance ($^{13}C$ NMR) spectra were recorded on Varian Mercury 400 (400 MHz/100 MHz), Varian Inova 500 (500 MHz/125 MHz), or Varian Inova 600 (600 MHz/150 MHz) NMR spectrometers at 23° C. Proton chemical shifts are expressed in parts per million (ppm, δ scale) and are referenced to residual protium in the NMR solvent ($CHCl_3$, δ 7.26; $CHD_2OD$, δ 3.31; $C_6H_5D$, δ 7.16). Carbon chemical shifts are expressed as parts per million (ppm, δ scale) and are referenced to the carbon resonance of the NMR solvent ($CDCl_3$, δ 77.2; $CD_3OD$, δ 49.0; $C_6D_6$, δ 128.1). Data are reported as follows: Chemical shift, multiplicity (s=singlet, d=doublet, t=triplet, q=quartet, qn=quintet, dd=doublet of doublets, td=triplet of doublets, ABq=AB quartet, m=multiplet, br=broad, app=apparent), integration, and coupling constant (J) in Hertz (Hz). Infrared transmittance (IR) spectra were obtained using a Bruker ALPHA FTIR spectrophotometer referenced to a polystyrene standard. Data are represented as follows: Frequency of absorption ($cm^{-1}$), and intensity (s=strong, m=medium, br=broad). Melting points were determined using a Thomas Scientific capillary melting point apparatus. High-resolution mass spectrometry (including FIA-HRMS reaction monitoring) was performed at the Harvard University Mass Spectrometry Facility using a Bruker micrOTOF-QII mass spectrometer. X-ray crystallographic analysis was performed at the Harvard University X-Ray Crystallographic Laboratory by Dr. Shao-Liang Zheng. Ultra high-performance liquid chromatography-mass spectrometry (LCMS) was performed using an Agilent Technologies 1260-series analytical HPLC system in tandem with an Agilent Technologies 6120 Quadrupole mass spectrometer; a Zorbax Eclipse Plus reverse-phase C$_{18}$ column (2.1×50 mm, 1.8 μm pore size, 600 bar rating; Agilent Technologies, Santa Clara, Calif.) was employed as stationary phase. LCMS samples were eluted at a flow rate of 650 μL/min, beginning with 5% acetonitrile-water containing 0.1% formic acid, grading linearly to 100% acetonitrile containing 0.1% formic acid over 3 minutes, followed by 100% acetonitrile containing 0.1% formic acid for 2 minutes (5 minute total run time).

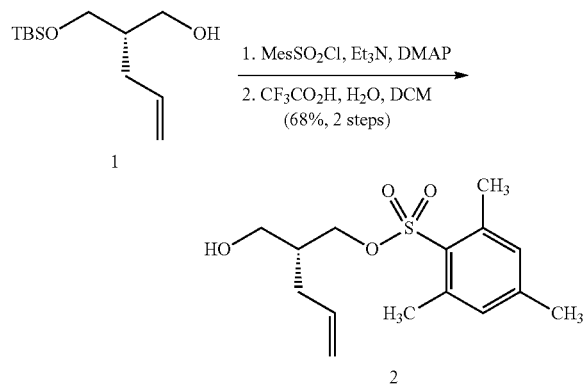

A magnetically stirred solution of (−)-1 (15.0 g, 65.1 mmol, 1 equiv) in dichloromethane (325 mL) was cooled to 0° C. before it was treated sequentially with triethylamine (11.8 mL, 85.0 mmol, 1.3 equiv), 4-(dimethylamino)pyridine (795 mg, 6.51 mmol, 0.100 equiv), and 2,4,6-trimethylbenzenesulfonyl chloride (17.1 g, 78.0 mmol, 1.20 equiv). The mixture was stirred at 0° C. for 15 min before the ice-water cooling bath was removed, and the mixture was allowed to warm to 23° C. overnight. After 15 h, TLC analysis (20% ethyl acetate-hexanes, KMnO$_4$) showed that no starting material remained. The mixture was poured into a separatory funnel containing water, and the mixture was shaken vigorously. The layers were separated, and the aqueous layer was extracted with ether (4×300 mL). The combined organic phases were then washed with saturated aqueous sodium bicarbonate solution (200 mL), dried over sodium sulfate, filtered, and concentrated to give tert-butyldimethylsilyl mesitylenesulfonate ester intermediate as a milky yellow oil.

This crude residue was transferred to a 2000-mL round-bottomed flask, where it was dissolved in dichloromethane (650 mL). Water (7.20 mL) was added, and the mixture was chilled to 0° C. before trifluoroacetic acid (36.0 mL) was introduced. The mixture was stirred at 0° C. for 15 minutes before the ice-water cooling bath was removed and the mixture was allowed to warm to 23° C. After 1.5 h, TLC (20% ethyl acetate-hexanes, UV+KMnO$_4$) showed that no tert-butyldimethylsilyl ether intermediate remained. The mixture was diluted with toluene (250 mL), and the diluted mixture was concentrated in vacuo. The residue thus obtained was purified by flash-column chromatography (1.0 kg silica gel, eluting with 20% diethyl ether-hexanes, grading to 50% diethyl ether-hexanes) to furnish the product as a colorless oil (13.3 g, 68%, 2 steps). $^1$H NMR (500 MHz, CDCl$_3$) δ 6.98 (s, 2H), 5.70 (ddt, J=17.4, 9.8, 7.2 Hz, 1H), 5.05-5.01 (m, 2H), 4.05 (dd, J=9.9, 4.7 Hz, 1H), 3.97 (dd, J=9.9, 5.8 Hz, 1H), 3.67 (dd, J=11.2, 4.8 Hz, 1H), 3.60 (dd, J=11.1, 6.5 Hz, 1H), 2.63 (s, 6H), 2.32 (s, 3H), 2.15-2.06 (m, 2H), 1.97-1.89 (m, 1H). HRMS (ESI+, m/z): [M+H]$^+$ calcd for C$_{15}$H$_{22}$O$_4$S, 299.1312; found 299.1322.

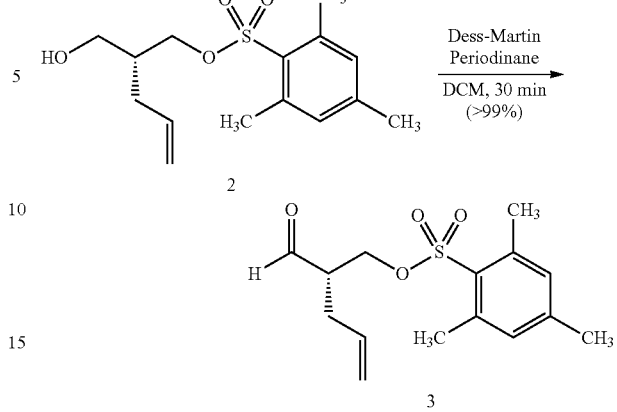

A magnetically stirred solution of alcohol 2 (3.00 g, 10.1 mmol, 1 equiv) in dichloromethane (50.3 mL) was cooled to 0° C. in an ice-water bath before Dess-Martin periodinane (4.26 g, 10.1 mmol, 1.00 equiv) was added in one portion. After stirring for 5 min at 0° C., the cooling bath was removed and the mixture was allowed to warm to 23° C. After 30 min, TLC analysis (40% ethyl acetate-hexanes, UV+KMnO$_4$) indicated that no starting material remained. Saturated aqueous sodium bicarbonate (25 mL) was added, and the mixture was stirred at 23° C. for 3 min before aqueous sodium thiosulfate solution (4.0 M, 25 mL) was added. The resulting mixture was stirred vigorously at 23° C. for 30 min before it was transferred to a separatory funnel, where the layers were separated. The aqueous phase was extracted with dichloromethane (2×20 mL), and the combined organic layers were washed sequentially with fresh saturated aqueous sodium bicarbonate solution (20 mL) and saturated aqueous sodium chloride solution (20 mL). The washed organic solution was then dried over sodium sulfate, filtered, and concentrated to provide the product as a cloudy oil (3.01 g, 101%). This material analytically pure, and was suitable for use without further processing. $^1$H NMR (600 MHz, CDCl$_3$) δ 9.63 (d, J=1.0 Hz, 1H), 6.98 (s, 2H), 5.67 (ddt, J=17.2, 10.3, 7.0 Hz, 1H), 5.10-5.06 (m, 2H), 4.20 (dd, J=10.2, 6.0 Hz, 1H), 4.16 (dd, J=10.2, 5.0 Hz, 1H), 2.76-2.71 (m, 1H), 2.59 (s, 6H), 2.49 (dtt, 14.6, 6.6, 1.4 Hz, 1H), 2.34-2.29 (m, 1H), 2.31 (s, 3H). HRMS (ESI+, m/z): [M+Na]$^+$ calcd for C$_{15}$H$_{20}$O$_4$S, 319.0975; found 319.0971.

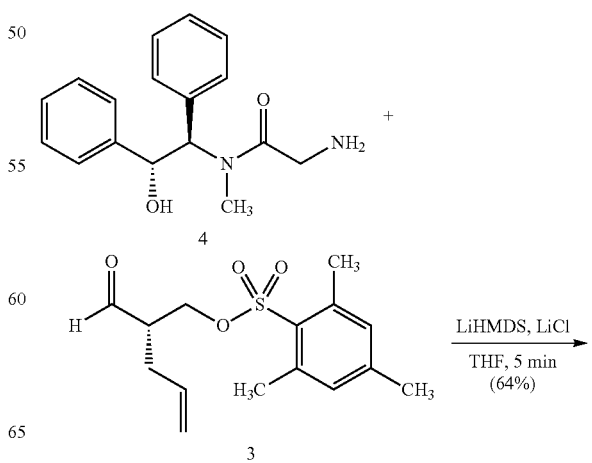

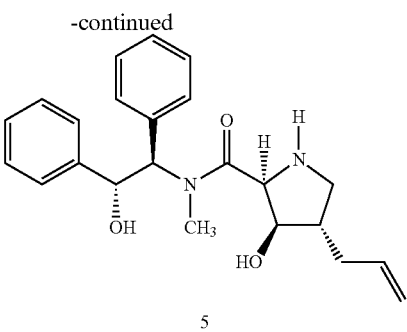

5

An oven-dried 500-mL round-bottomed flask was charged with a magnetic stir bar and anhydrous lithium chloride (6.23 g, 147 mmol, 15.6 equiv). The vessel was then evacuated (0.1 mmHg), heated with a gentle flame for 2 min in order to drive off any residual moisture from the lithium chloride, and allowed to cool to room temperature before it was back-filled with argon. Next, (R,R)-pseudoephenamine glycinamide (4, 3.48 g, 12.3 mmol, 1.30 equiv) and tetrahydrofuran (131 mL) were added, and the mixture was stirred for 5 min at 23° C., until all pseudoephenamine glycinamide had dissolved (lithium chloride does not completely dissolve). The mixture was then chilled to −78° C. in a dry ice-acetone bath, and a freshly prepared solution of lithium hexamethyldisilazide (1.00 M in tetrahydrofuran, 23.6 mL, 23.6 mmol, 2.50 equiv) was added dropwise over a period of 3-4 min. The resulting yellow mixture was stirred at −78° C. for 5 min before it was warmed to 0° C. for a period of 30 min. The glycinamide enolate solution was then chilled to −90° C. in an acetone bath cooled with liquid nitrogen, and a solution of aldehyde 3 (2.79 g, 9.42 mmol, 1 equiv) in tetrahydrofuran (10.1 mL) was added via cannula over 2 min. After stirring at −90° C. for 5 min following complete addition of the electrophile, the reaction was quenched with the addition of half-saturated aqueous ammonium chloride solution (1.00 mL), causing the vibrant yellow color to darken to orange-yellow. The cooling bath was removed, and the mixture was warmed to 23° C. before the mixture was transferred to a separatory funnel containing half-saturated aqueous ammonium chloride solution (200 mL) and ethyl acetate (200 mL). The layers were shaken, then separated, and the aqueous phase was extracted with additional portions of ethyl acetate (3×100 mL). The combined organic extracts were washed with saturated sodium chloride solution, dried over sodium sulfate, filtered, and concentrated to provide a foaming straw-colored solid, which was purified by flash-column chromatography (330 g silica gel, eluting with 1% ammonium hydroxide-3% methanol-dichloromethane initially, grading to 1% ammonium hydroxide-4% methanol-dichloromethane) to provide the product as a snow-white, foaming solid (2.31 g, 64%), along with recovered pseudoephenamine glycinamide (1.28 g).

Crystals suitable for single-crystal X-ray diffraction analysis were prepared as follows: In a 1-mL glass sample vial, pure 5 (10 mg) was deposited, and this material was dissolved in a minimal quantity of methanol. A drop of benzene was added to this solution, and the vial was partially sealed with a screw cap, leaving the cap slightly ajar so as to allow slow evaporation of solvent. After several days of standing at 23° C., needle-shaped crystals had formed. X-ray diffraction analysis confirmed the structure of 5. Melting point: 135-137° C. $^1$H NMR (52:48 mixture of rotamers, asterisks [*] denote minor rotameric signals that could be resolved, 600 MHz, CD$_3$OD) δ 7.40-7.32 (m, 4H), 7.24-7.12 (m, 6H), 5.93 (ddt, J=17.0, 10.2, 6.9 Hz, 1H), 5.90 (d, J=8.5 Hz, 1H),* 5.81 (ddt, J=16.9, 10.2, 6.7 Hz, 1H),* 5.46 (d, J=8.7 Hz, 1H),* 5.45 (d, J=10.1 Hz, 1H), 5.19 (d, J=10.3 Hz, 1H), 5.18 (app dq, J=17.0, 1.7 Hz, 1H), 5.10 (ddt, J=10.4, 2.2, 1.1 Hz, 1H),* 5.07 (app dq, J=16.9, 1.5 Hz, 1H), 5.01 (ddt, J=10.2, 2.0, 1.1 Hz, 1H), 4.62 (dd, J=5.8, 4.0 Hz, 1H),* 4.36 (d, J=5.8 Hz, 1H),* 4.18 (dd, J=6.2, 3.7 Hz, 1H), 4.04 (d, J=6.1 Hz, 1H), 3.36 (dd, J=11.6, 7.3 Hz, 1H), 3.30 (dd, J=12.9, 6.5 Hz, 1H),* 3.08 (s, 3H), 3.06 (s, 3H),* 2.48 (dd, J=11.6, 8.2 Hz, 1H), 2.43 (dd, J=11.4, 6.6 Hz, 1H), 2.42-2.37 (m, 1H),* 2.30-2.25 (m, 2H), 2.17 (app pd, J=74, 3.9 Hz, 1H),* 2.08-2.03 (m, 2H). HRMS (ESI+, m/z): [M+H]$^+$ calcd for C$_{23}$H$_{28}$N$_2$O$_3$, 381.2173; found 381.2182.

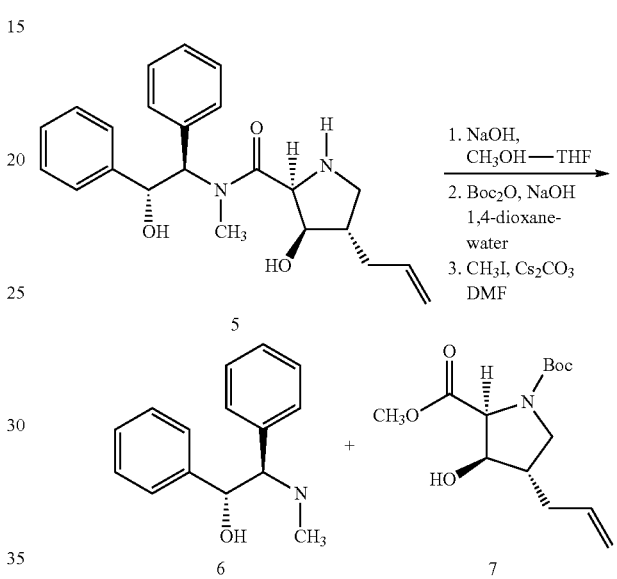

A magnetically stirred solution of hydroxyprolinamide 5 (2.31 g, 6.07 mmol, 1 equiv) in 50% v/v methanol-tetrahydrofuran (30.4 mL) was chilled to 0° C. before aqueous sodium hydroxide solution (1.00 M, 6.19 mL, 6.19 mmol, 1.02 equiv) was added dropwise. The cooling bath was then removed, and the mixture was allowed to warm to 23° C. overnight. After 18 h, LCMS analysis showed that not all starting material had been consumed (estimated 80% conversion), and the mixture was heated to 40° C. for 5 h to drive the reaction to completion. Once it was confirmed that no starting material remained, the reaction mixture was concentrated in vacuo to give a tan-colored sludge, which was re-dissolved in water (100 mL). In order to recover the chiral auxiliary, this aqueous mixture was extracted with dichloromethane (4×25 mL), and the combined dichloromethane extracts were dried over sodium sulfate, filtered, and concentrated to provide analytically pure (R,R)-pseudoephenamine (6, 1.31 g, 95%).5 The aqueous mixture was concentrated separately, and residual water was removed by azeotropic distillation from methanol in vacuo. This provided the sodium pyrrolidinecarboxylate salt as a dull brown solid (1.21 g, 103%).

A portion of this this crude residue (0.900 g, 4.66 mmol) was transferred to a 200-mL round-bottomed flask, where it was dissolved in 50% v/v 1,4-dioxane-water (38.8 mL). Aqueous sodium hydroxide (1.00 M, 6.99 mL, 6.99 mmol, 1.50 equiv) and di-tert-butyl dicarbonate (2.16 mL, 9.32 mmol, 2.00 equiv) were added, and the mixture was stirred at 23° C. After 2.5 h, LCMS analysis showed that N-Boc protection was complete, and the mixture was diluted with water (100 mL). The diluted mixture was washed with ether (3×30 mL) in order to remove excess di-tert-butyl dicarbonate before the washed aqueous solution was chilled to 0° C. The aqueous solution was acidified to pH=2 with the dropwise addition of 1N aqueous hydrogen chloride solution, and the acidified mixture was extracted with ethyl acetate (4×25 mL) to recover N-Boc-protected amino acid as a white solid.

This material was finally transferred to a 100-mL round-bottomed flask, where it was dissolved in N,N-dimethylformamide (17.2 mL). Cesium carbonate (1.59 g, 4.88 mmol, 1.05 equiv) was added in one portion, followed by methyl iodide (348 µL, 5.57 mmol, 1.20 equiv), which was added dropwise at 23° C. After 1 h of stirring, LCMS analysis showed that methylation of the starting material was complete, and the mixture was diluted with ethyl acetate (50 mL), causing a white precipitate to form. This suspension was transferred to a separatory funnel containing saturated aqueous sodium bicarbonate solution (50 mL), and the layers were shaken. The layers were then separated, the aqueous phase was extracted with additional ethyl acetate (3×20 mL), and the combined organic layers were washed with saturated aqueous sodium chloride (2×20 mL). The washed organic solution was then dried over sodium sulfate, filtered, and concentrated to provide a viscous oil, which was purified by flash-column chromatography (80 g silica gel, eluting with 30% ethyl acetate-hexanes initially, grading to 40% ethyl acetate-hexanes) to furnish N-Boc-protected hydroxyproline methyl ester 7 as a colorless, highly viscous oil (1.29 g, 97%, 2 steps). $^1$H NMR (60:40 mixture of rotamers, asterisks [*] denote minor rotameric signals that could be resolved, 600 MHz, CDCl$_3$) δ 5.80 (ddt, J=16.9, 10.0, 7.34 Hz, 1H), 5.11 (d, J=17.0 Hz, 1H), 5.06 (d, J=10.2 Hz, 1H), 4.46 (d, J=7.8 Hz, 1H),* 4.38 (d, J=7.5 Hz, 1H), 4.18 (app dtd, J=12.9, 7.5, 4.9 Hz, 1H), 3.79 (dd, J=10.9, 7.5 Hz, 1H), 3.77 (s, 3H),* 3.76 (s, 3H), 3.72 (dd, J=10.8, 7.7 Hz, 1H),* 3.07 (dd, J=10.7, 7.6 Hz, 1H), 3.04 (dd, J=8.6, 2.5 Hz, 1H),* 2.39-2.30 (m, 2H), 2.25-2.15 (m, 1H), 2.13-2.06 (m, 1H), 1.45 (s, 9H)*1.40 (s, 9H). HRMS (ESI+, m/z): [M+Na]$^+$ calcd for C$_{14}$H$_{23}$NO$_5$, 308.1468; found 308.1476.

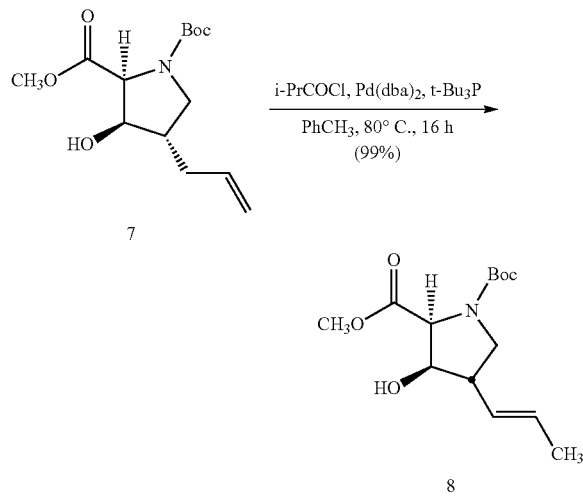

In a 5-10 mL glass microwave vial, olefin 7 (450 mg, 1.58 mmol, 1 equiv) and bis(dibenzylideneacetone)palladium(0) (27.2 mg, 47.3 µmol, 0.0300 equiv) were dissolved in toluene. Argon gas was bubbled through this solution for 5 min in order to sparge it of any dissolved dioxygen, and to the degassed solution were then added tri-tert-butylphosphine solution (1.0 M in toluene, 47 µL, 47 µmol, 0.030 equiv) and isobutyryl chloride solution (0.473 M in toluene, 100 µL, 47.3 µmol, 0.0300 equiv) sequentially at 23° C. The vial was sealed, and the reaction mixture was heated to 80° C. in a pre-heated oil bath. Upon heating, the burgundy-colored solution changed to straw-yellow. Progress was monitored by aliquot NMR: Approximately 50-µL portions of the reaction solution were periodically removed by syringe, diluted with chloroform-d, and analyzed by $^1$H NMR. After 16 h, no starting material was observed, and the reaction was judged to be complete. The mixture was cooled to 23° C., the cooled solution was concentrated in vacuo, and the residue was purified by flash-column chromatography (24 g silica gel, eluting with 30% ethyl acetate-hexanes initially, grading to 40% ethyl acetate-hexanes) to provide the product as a colorless oil (447 mg, 99%). $^1$H NMR (60:40 mixture of rotamers, asterisk [*] denotes minor rotamer signals that could be resolved, 500 MHz, CDCl$_3$) δ 5.60 (dq, J=13.2, 6.4 Hz, 1H), 5.26 (dd, J=15.2, 8.0 Hz, 1H), 4.40 (d, J=7.7 Hz, 1H),* 4.32 (d, J=7.7 Hz, 1H), 4.13 (app t, J=8.5 Hz, 1H), 3.76-3.67 (m, 4H), 3.07 (ddd, J=11.8, 9.6, 2.8 Hz, 1H), 3.01 (dd, J=14.3, 4.3 Hz, 1H), 2.88-2.77 (m, 1H), 1.64 (d, J=6.5 Hz, 3H), 1.40 (s, 9H),* 1.35 (s, 9H). HRMS (ESI+, m/z): [M+H]$^+$ calcd for C$_{14}$H$_{23}$NO$_5$, 286.1649; found 286.1654.

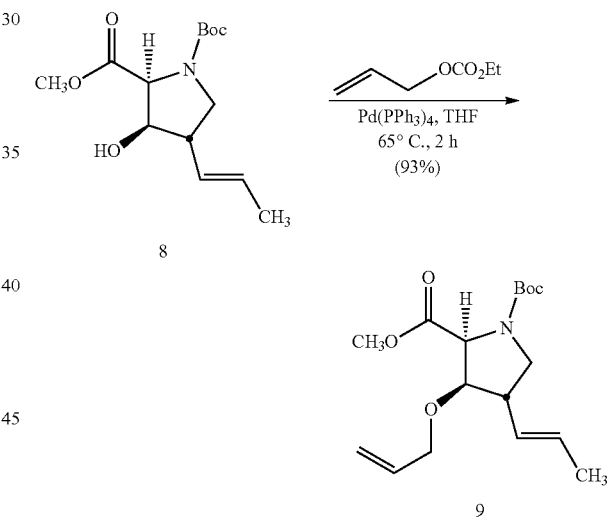

In a 2-5 mL glass microwave vial, alcohol 8 (17 mg, 60 µmol, 1 equiv) and allyl ethyl carbonate (16 µL, 120 µmol, 2.0 equiv) were dried together by azeotropic removal of benzene. A separate 4-mL glass vial was charged with tetrakis(triphenylphosphine)palladium(0) (1.7 mg, 1.4 µmol, 0.025 equiv), and this precatalyst was dissolved in tetrahydrofuran (600 µL). The precatalyst solution was added to the reaction vial containing the starting materials via cannula, and the reaction vial was sealed. The mixture was heated to 65° C. in a pre-heated oil bath. After 2 h, TLC analysis (30% ethyl acetate-hexanes, UV+KMnO$_4$) showed that etherification was complete, and the mixture was cooled to 23° C. before it was concentrated to dryness in vacuo. The crude residue was then purified by flash-column chromatography (4 g silica gel, eluting with 10% ethyl acetate-hexanes) to provide the product as a colorless oil (18 mg, 93%). $^1$H NMR (60:40 mixture of rotamers, asterisks [*] denote minor rotameric signals that could be resolved, 600 MHz, CDCl₃) δ 5.87-5.79 (m, 1H), 5.65-5.58 (m, 1H), 5.31-5.27 (m, 1H), 5.26 (dq, J=17.2, 1.6 Hz, 1H), 5.18 (ddq, J=10.5, 3.0, 1.4 Hz, 1H), 4.55 (d, J=7.6 Hz, 1H),* 4.45 (d, J=7.6 Hz, 1H), 4.17-4.12 (m, 1H), 4.05-4.02 (m, 1H), 3.87 (ddd, J=10.8, 9.1, 7.6 Hz, 1H), 3.76-3.71 (m, 1H), 3.74 (s, 3H),* 3.73 (s, 3H), 3.09-3.04 (m, 1H), 3.02-2.92 (m, 1H), 1.68 (dd, J=6.7, 1.8 Hz, 1H), 1.44 (s, 9H),* 1.40 (s, 9H).

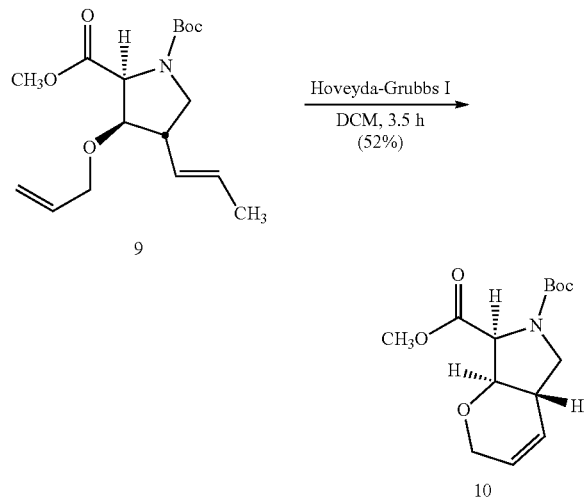

In a 10-mL round-bottomed flask fused to a reflux condenser, diene 9 (18 mg, 55 μmol, 1 equiv) and dichloro(2-isopropoxyphenylmethylene)(tricyclohexylphosphine)ruthenium(II) (first-generation Hoveyda-Grubbs catalyst, 1.6 mg, 2.8 μmol, 0.050 equiv) were dissolved in dichloromethane (1.1 mL). The resulting solution was heated to reflux in a pre-heated oil bath (55° C. bath temperature), and after 3.5 h, TLC analysis (30% ethyl acetate-hexanes, KMnO₄) indicated that no starting material remained. The mixture was concentrated to dryness, and the residue was purified by flash-column chromatography (4 g silica gel, eluting with 20% ethyl acetate-hexanes) to furnish the product as a colorless oil (8.2 mg, 52%). ¹H NMR (60:40 mixture of rotamers, asterisks [*] denote minor rotameric signals that could be resolved, 600 MHz, CDCl₃) δ 5.99 (app dq, J=10.1, 2.1 Hz, 1H), 5.95 (app dq, J=10.0, 2.2 Hz, 1H),* 5.69-5.66 (m, 1H), 4.49 (d, J=7.9 Hz, 1H),* 4.41-4.39 (m, 2H), 3.92-3.89 (m, 1H), 3.83-3.79 (m, 1H), 3.78 (s, 3H),* 3.77 (s, 3H), 2.92-2.86 (m, 1H), 1.46 (s, 9H),* 1.41 (s, 9H). HRMS (ESI+, m/z): [M+Na]⁺ calcd for C₁₄H₂₁NO₅, 306.1312; found 306.1319.

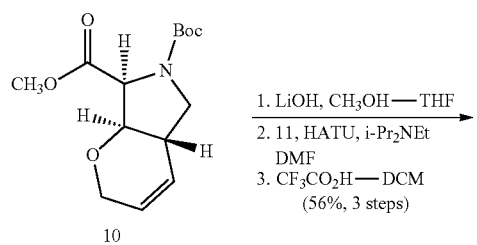

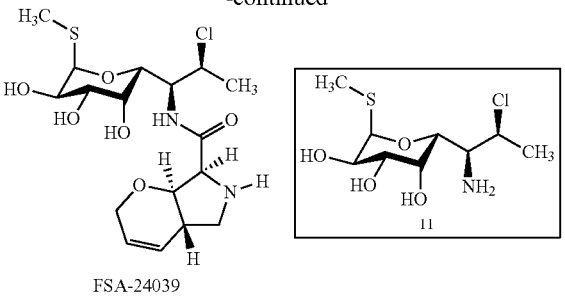

FSA-24039

A magnetically stirred solution of methyl ester 10 (45 mg, 0.16 mmol, 1 equiv) in 50% v/v methanol-tetrahydrofuran (790 μL) was treated with aqueous lithium hydroxide solution (1.0 M, 190 μL, 190 μmol, 1.2 equiv) at 23° C. After stirring for 18 h at ambient temperature, LCMS analysis indicated that saponification was complete. The reaction mixture was consequently diluted with water (3 mL), the diluted solution was chilled to 0° C., and the cooled mixture was acidified to pH=2 with the addition of 1N aqueous hydrogen chloride solution. The acidified mixture was then extracted with ethyl acetate (5×2 mL), and the combined extracts were dried over sodium sulfate. The dried organic product solution was filtered, and the filtrate was concentrated to afford carboxylic acid saponification product as a white solid.

This residue was then transferred to a 2-5 mL glass microwave vial, where it was dried by azeotropic removal of benzene. The dried carboxylic acid was dissolved in N,N-dimethylformamide (930 μL), and the solution was treated with HATU (78 mg, 0.20 mmol, 1.1 equiv). The colorless solution was stirred at 23° C. for 10 min before 7-chloromethylthiolincosamine (11, 76 mg, 0.28 mmol, 1.5 equiv) (U.S. Pat. No. 7,361,743) was added. A light cream-yellow suspension formed, and this mixture was stirred at 23° C. for 20 min before N,N-diisopropylethylamine (81 μL, 0.46 mmol, 2.5 equiv) was added dropwise. After 30 min of additional stirring at 23° C., LCMS analysis showed no trace of carboxylic acid or activated-ester intermediate. The mixture was concentrated in vacuo, and the dried residue was purified by flash-column chromatography (4 g silica gel, eluting with dichloromethane initially, grading to 5% methanol-dichloromethane). Fractions containing the coupled, N-Boc-protected product were identified by TLC (R_f=0.50, 10% methanol-dichloromethane, PMA); these fractions were pooled and concentrated to provide N-Boc-protected lincosamide as a white film.

Finally, this residue was dissolved in dichloromethane (1.6 mL), and the solution was chilled to 0° C. Dimethyl sulfide (120 μL) and trifluoroacetic acid (200 μL) were added sequentially, and then the mixture was allowed to warm to 23° C. gradually over 4 h. At this point, LCMS analysis showed that Boc removal was complete. The reaction mixture was diluted with toluene (3 mL), and the diluted mixture was concentrated in vacuo. The residue was then re-dissolved in methanol (1.5 mL), the solution was chilled to 0° C., and Amberlyst A26 ion-exchange resin (hydroxide form, 500 mg) was added. The mixture was stirred at 0° C. for 30 min before the beads were filtered off, and the filtrate was concentrated. The residue obtained was then purified by flash-column chromatography (4 g silica gel, eluting with 1% ammonium hydroxide-5% methanol-dichloromethane initially, grading to 1% ammonium hydroxide-10% methanol-dichloromethane) to provide FSA-24039 as a white powder (38 mg, 56%, 3 steps). ¹H NMR (500 MHz, CD₃OD) δ 6.01 (app dq, J=10.1, 2.1 Hz, 1H), 5.74 (app dq, J=10.1, 2.5 Hz, 1H), 5.29 (d, J=5.7 Hz, 1H), 4.60 (qd, J=6.8, 1.6 Hz, 1H), 4.44-4.41 (m, 3H), 4.19 (dd, J=10.0, 1.1 Hz, 1H), 4.08 (dd, J=10.2, 5.6 Hz, 1H), 3.92 (d, J=8.5 Hz, 1H), 3.84-3.80 (m, 2H), 3.56 (dd, J=10.2, 3.4 Hz, 1H), 3.25 (dd, J=8.9, 6.5 Hz, 1H), 2.58 (dd, J=12.2, 8.9 Hz, 1H), 2.52 (br, 1H), 2.15 (s, 3H), 1.49 (d, J=6.8 Hz, 3H). HRMS (ESI+, m/z): [M+H]⁺ calcd for $C_{17}H_{27}ClN_2O_6S$, 423.1351; found 423.1344.

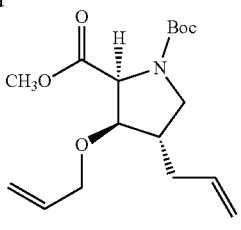

12

In a 50-mL round-bottomed flask containing a magnetic stir bar, alcohol 7 (500 mg, 1.75 mmol, 1 equiv) and allyl ethyl carbonate (461 μL, 3.50 mmol, 2.00 equiv) were dissolved in tetrahydrofuran (8.75 mL), and the flask was fitted with a reflux condenser. In a separate pear-shaped flask, tetrakis(triphenylphosphine)palladium(0) (51.0 g, 44.2 μmol, 0.0250 equiv) was dissolved in tetrahydrofuran (8.75 mL). The precatalyst solution was then added via cannula to the flask containing the starting materials, the apparatus was shielded from light with aluminum foil, and the reaction mixture was heated to reflux in a pre-heated oil bath (75° C. bath temperature). Over 30 min, the reaction mixture changed color from very faint yellow to sunset orange. After 2 h, TLC analysis showed that no starting material remained. The mixture was cooled to 23° C. before it was passed through a plug of silica gel. Upon exposure to silica gel, the reaction mixture attained a cherry-red color. The filter pad was rinsed with tert-butyl methyl ether (2×15 mL), and the combined filtrates were concentrated to give a yellow residue. This crude product was purified by flash-column chromatography (30 g silica gel, eluting with hexanes initially, grading to 10% ethyl acetate-hexanes) to furnish the product as a faint yellow viscous oil (539 mg, 95%). ¹H NMR (60:40 mixture of rotamers, asterisks [*] denote minor rotameric signals that could be resolved, 500 MHz, CDCl₃) δ 5.85 (ddt, J=17.0, 10.3, 5.8 Hz, 1H), 5.80-5.71 (m, 1H), 5.27 (app dq, J=17.2, 1.4 Hz, 1H), 5.19 (ddt, J=10.3, 2.8, 1.4 Hz, 1H), 5.08-5.00 (m, 2H), 4.56 (d, J=7.5 Hz, 1H),* 4.47 (d, J=7.5 Hz, 1H), 4.16 (dddt, J=12.4, 8.3, 5.4, 1.5 Hz, 1H), 3.99 (ddt, J=12.5, 6.1, 1.3 Hz, 1H), 3.82 (ddd, J=16.2, 8.9, 7.6 Hz, 1H), 3.80-3.75 (m, 1H), 3.73 (s, 3H),* 3.72 (s, 3H), 3.70 (dd, J=10.2, 7.8 Hz, 1H), 2.97 (td, J=11.0, 9.0 Hz, 1H), 2.50-2.41 (m, 1H), 2.40-2.34 (m, 1H), 2.05-1.97 (m, 1H), 1.44 (s, 9H),* 1.39 (s, 9H). HRMS (ESI+, m/z): [M+H]⁺ calcd for $C_{17}H_{27}NO_5$, 326.1962; found 326.1969.

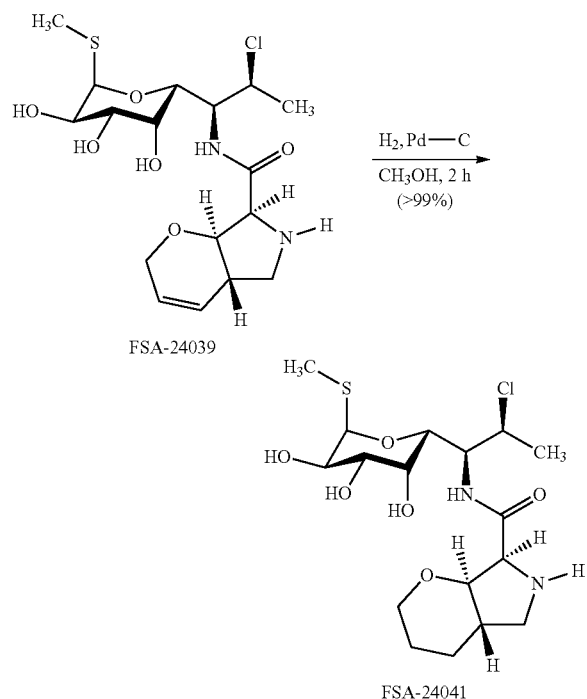

FSA-24039

FSA-24041

In a 2-5 mL glass microwave vial, FSA-24039 (6.7 mg, 16 μmol, 1 equiv) was dissolved in methanol (160 μL). To this solution was added palladium on carbon (10% w/w, 1.0 mg), and the headspace of the reaction vial was replaced with hydrogen gas supplied by a balloon. After stirring for 2 h at 23° C., LCMS analysis showed that hydrogenation was complete, and the mixture was filtered through a pad of Celite to remove the heterogeneous catalyst. The filtrate was concentrated to provide the product as a white film (7.0 mg, 104%). ¹H NMR (400 MHz, CD₃OD) δ 5.29 (d, J=5.6 Hz, 1H), 4.60 (qd, J=6.5, 1.4 Hz, 1H), 4.42 (dd, J=9.8, 1.4 Hz, 1H), 4.18 (d, J=10.4 Hz, 1H), 4.11-4.06 (m, 2H), 3.89 (d, J=8.7 Hz, 1H), 3.85 (d, J=3.3 Hz, 1H), 3.59-3.47 (m, 3H), 3.14 (dd, J=9.7, 6.7 Hz, 1H), 2.54 (dd, J=11.5, 9.7 Hz, 1H), 2.14 (s, 3H), 2.06-2.03 (m, 1H), 1.75-1.67 (m, 1H), 1.65-1.58 (m, 2H), 1.50 (d, J=6.8 Hz, 3H), 1.40-1.32 (m, 1H). MS (ESI+, m/z): [M+H]⁺ calcd for $C_{17}H_{29}ClN_2O_6S$, 425.2; found 425.2.

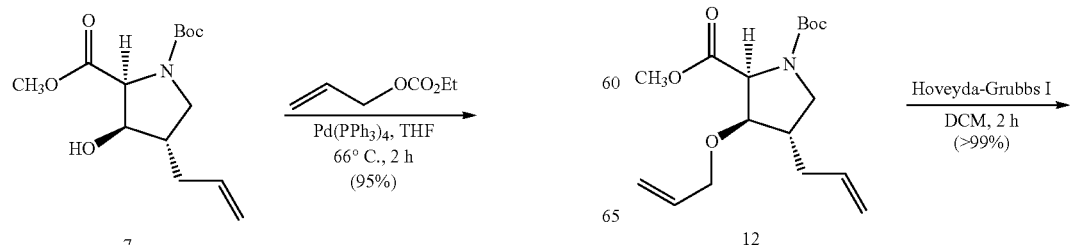

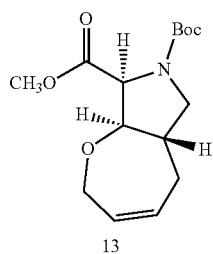

13

In a 100-mL round-bottomed flask to which a reflux condenser had been affixed, a solution of diene 12 (539 mg, 1.66 mmol, 1 equiv) and dichloro(2-isopropoxyphenylmethylene)(tricyclohexylphosphine)ruthenium(II) (first-generation Hoveyda-Grubbs catalyst, 50.0 mg, 83.3 µmol, 0.0500 equiv) in dichloromethane (33.1 mL) was heated to reflux in a pre-heated oil bath (55° C. bath temperature). After 2 h, TLC analysis (30% ethyl acetate-hexanes, KMnO$_4$) showed that no starting material remained. The mixture was cooled to 23° C. before it was concentrated to dryness to give a thick brown oil. This crude residue was purified by flash-column chromatography (30 g silica gel, eluting with hexanes first, grading to 20% ethyl acetate-hexanes) to provide the product as a leather-brown oil (499 mg, 101%). $^1$H NMR (60:40 mixture of rotamers, asterisks [*] denote minor rotameric signals that could be resolved, 500 MHz, CDCl$_3$) δ 5.86-5.80 (m, 1H), 5.75-5.69 (m, 1H), 4.53 (d, J=8.3 Hz, 1H),* 4.44 (d, J=8.3 Hz, 1H), 4.32 (dd, J=6.3, 1.2 Hz, 1H),* 4.29 (dd, J=6.2, 1.3 Hz, 1H), 4.09-4.03 (m, 1H), 3.93-3.88 (m, 1H), 3.88-3.86 (m, 1H),* 3.83-3.78 (m, 1H), 3.76 (s, 3H),* 3.74 (s, 3H), 2.91 (app td, J=10.6, 4.0 Hz, 1H), 2.55-2.41 (m, 2H), 2.04-1.96 (m, 1H), 1.44 (s, 9H),* 1.40 (s, 9H). HRMS (ESI+, m/z): [M+Na]$^+$ calcd for C$_{15}$H$_{23}$NO$_5$, 320.1468; found 320.1477.

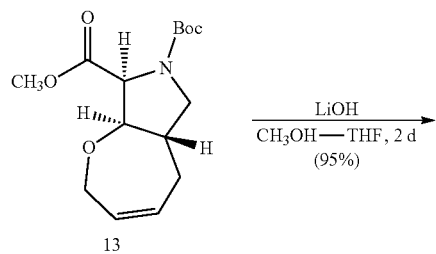

13 → 14

To a magnetically stirred solution of methyl ester 13 (73 mg, 0.25 mmol, 1 equiv) in 50% v/v methanol-tetrahydrofuran (1.2 mL) was added aqueous lithium hydroxide solution (1.0 M, 270 µL, 0.27 mmol, 1.1 equiv) at 23° C. After stirring at ambient temperature for 2 d, LCMS analysis showed that saponification was complete. The reaction mixture was diluted with water (2 mL), and the diluted solution was chilled to 0° C. before being acidified to pH=2 with the dropwise addition of 1N aqueous hydrogen chloride solution. The acidified aqueous mixture was extracted with ethyl acetate (5×2 mL), and the combined extracts were dried over sodium sulfate. The dried solution was filtered, and the filtrate was concentrated to provide carboxylic acid saponification product as a dull white solid (66 mg, 95%). $^1$H NMR (70:30 mixture of rotamers, asterisks [*] denote minor rotameric signals that could be resolved, 600 MHz, CDCl$_3$) δ 10.93 (br, 1H), 5.82 (app dtt, J=13.6, 8.1, 2.7 Hz, 1H), 5.72 (app ddt, J=11.9, 5.9, 2.9 Hz, 1H), 4.52 (d, J=8.3 Hz, 1H),* 4.43 (d, J=8.3 Hz, 1H), 4.31 (ddd, J=15.1, 8.6, 6.2 Hz, 1H), 4.06 (app dq, J=15.7, 3.0 Hz, 1H), 3.93 (app td, J=9.9, 8.2 Hz, 1H), 3.86 (dd, J=10.7, 8.3 Hz, 1H), 3.77 (dd, J=10.5, 8.5 Hz, 1H),* 2.91 (app td, J=10.6, 1.5 Hz, 1H), 2.51-2.40 (m, 2H), 1.99 (ddd, J=17.0, 11.3, 2.9 Hz, 1H), 1.43 (s, 9H),* 1.39 (s, 9H). HRMS (ESI+, m/z): [M+Na]$^+$ calcd for C$_{14}$H$_{21}$NO$_5$, 306.1312; found 306.1298.

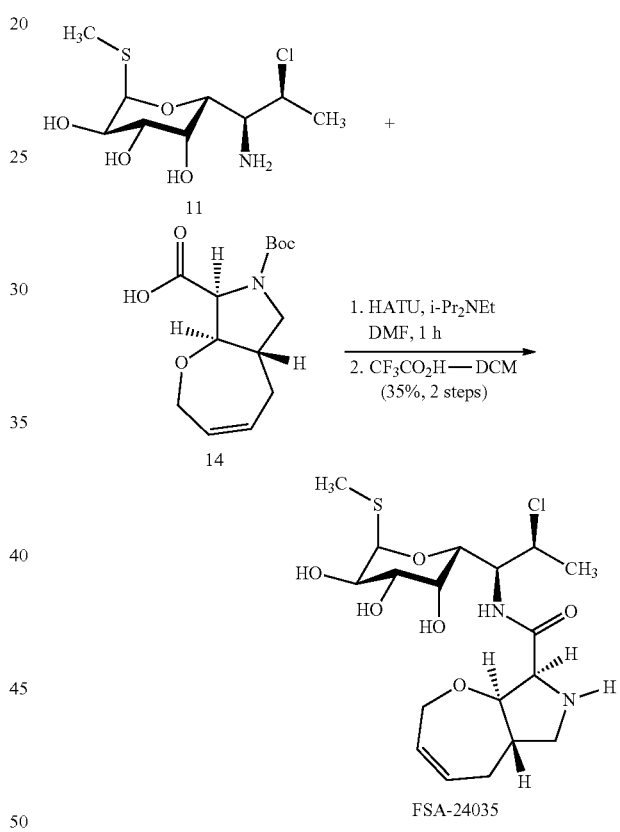

In a 2-5 mL glass microwave vial, carboxylic acid 14 (66 mg, 0.23 mmol, 1 equiv) was dried by azeotropic removal of benzene. The dried starting material was then dissolved in N,N-dimethylformamide (1.2 mL), and HATU (98 mg, 0.26 mmol, 1.1 equiv) was added at 23° C. After stirring this mixture for 10 min, 7-chloro-methylthiolincosamine (11, 96 mg, 0.35 mmol, 1.5 equiv)$^7$ was added next, and the resulting light cream-yellow suspension was stirred at ambient temperature for 20 min. Finally, N,N-diisopropylethylamine (100 µL, 0.59 mmol, 2.5 equiv) was added dropwise. After stirring an additional 1 h, LCMS analysis indicated that no carboxylic acid or activated-ester intermediate remained, and the reaction mixture was concentrated to dryness in vacuo. The residue was purified by flash-column chromatography (12 g silica gel, eluting with dichloromethane initially, grading to 5% methanol-dichloromethane). Fractions containing product were identified by TLC ($R_f$=0.34, 5% methanol-dichloromethane, PMA); these fractions were pooled and concentrated to provide N-Boc-protected product as a white film (100 mg, 79%). Due to substantial amide and carbamate rotamerism observed in the $^1$H-NMR spectrum, this material was carried forward through N-Boc deprotection prior to full characterization.

The N-Boc-protected lincosamide was finally dissolved in dichloromethane (1.4 mL), and dimethyl sulfide (140 μL) was added. This solution was chilled to 0° C., whereupon trifluoroacetic acid (140 μL) was added dropwise. The mixture was allowed to warm gradually to 23° C. over 5 h, at which point LCMS analysis showed that Boc removal was complete. The reaction mixture was consequently diluted with toluene (2 mL), and the diluted mixture was concentrated in vacuo. The residue was purified by flash-column chromatography (10 g silica gel, eluting with 1% ammonium hydroxide-5% methanol-dichloromethane initially, grading to 1% ammonium hydroxide-10% methanol-dichloromethane) to provide FSA-24035 as a white solid (35 mg, 35%, 2 steps). $^1$H NMR (600 MHz, CD$_3$OD) δ 5.84 (ddt, J=12.5, 7.3, 2.7 Hz, 1H), 5.71 (ddt, J=12.1, 6.0, 2.9 Hz, 1H), 5.30 (d, J=5.7 Hz, 1H), 4.59 (qd, J=6.8, 1.6 Hz, 1H), 4.42 (dd, J=10.1, 1.6 Hz, 1H), 4.31 (dd, J=15.9, 6.0 Hz, 1H), 4.19 (dd, J=10.0, 1.2 Hz, 1H), 4.12-4.04 (m, 3H), 3.96 (app t, J=9.0 Hz, 1H), 3.89 (dd, J=3.4, 1.2 Hz, 1H), 3.56 (dd, J=10.2, 3.4 Hz, 1H), 3.28 (dd, J=10.3, 7.1 Hz, 1H), 2.60 (app t, J=10.8 Hz, 1H), 2.47 (ddd, J=16.6, 7.4, 3.2 Hz, 1H), 2.14 (s, 3H), 2.10-2.04 (m, 1H), 2.02-1.97 (m, 1H), 1.50 (d, J=6.8 Hz, 3H). HRMS (ESI+, m/z): [M+H]$^+$ calcd for C$_{18}$H$_{29}$ClN$_2$O$_6$S, 437.1508; found 437.1503.

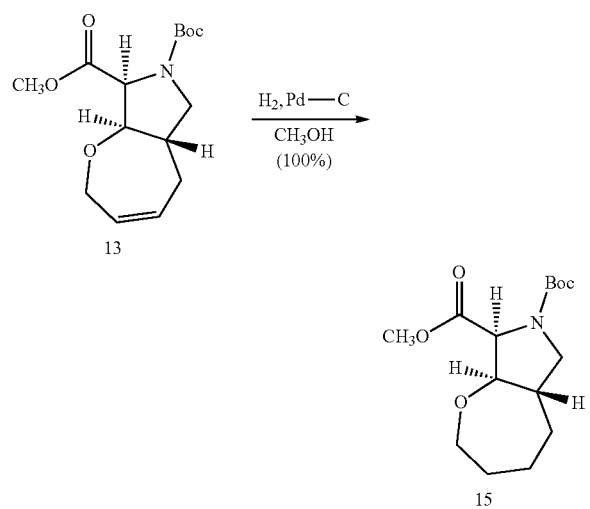

To a magnetically stirred solution of pyrrolidinooxepine 13 (12 mg, 40 μmol, 1 equiv) in methanol (3.0 mL) was added palladium on carbon (10% w/w, 2.1 mg). Hydrogen gas was bubbled through this mixture at 23° C. for 15 min, at which point LCMS analysis indicated that hydrogenation was complete. The black suspension was filtered through a pad of Celite in order to remove the heterogeneous catalyst, and the filter cake was rinsed with fresh portions of methanol (3×1 mL). The filtrate was concentrated to provide pyrrolidinooxepane product as a colorless film (12 mg, 100%). $^1$H NMR (60:40 mixture of rotamers, asterisks [*] denote minor rotameric signals that could be resolved, 500 MHz, CDCl$_3$) δ 4.45 (d, J=8.2 Hz, 1H),* 4.36 (d, J=8.3 Hz, 1H), 4.08-4.03 (m, 1H), 3.87 (d, J=8.6 Hz, 1H), 3.84 (d, J=3.85 Hz, 1H),* 3.81-3.75 (m, 3H), 3.75 (s, 3H),* 3.73 (s, 3H), 2.88 (app td, J=10.6, 2.0 Hz, 1H), 260-2.44 (m, 1H), 2.00-1.91 (m, 1H), 1.86-1.79 (m, 2H), 1.77-1.70 (m, 1H), 1.63-1.51 (m, 2H), 1.43 (s, 9H),* 1.39 (s, 9H), 1.25-1.16 (m, 2H). HRMS (ESI+, m/z): [M+Na] calcd for C$_{15}$H$_{25}$NO$_5$, 322.1625; found 322.1637.

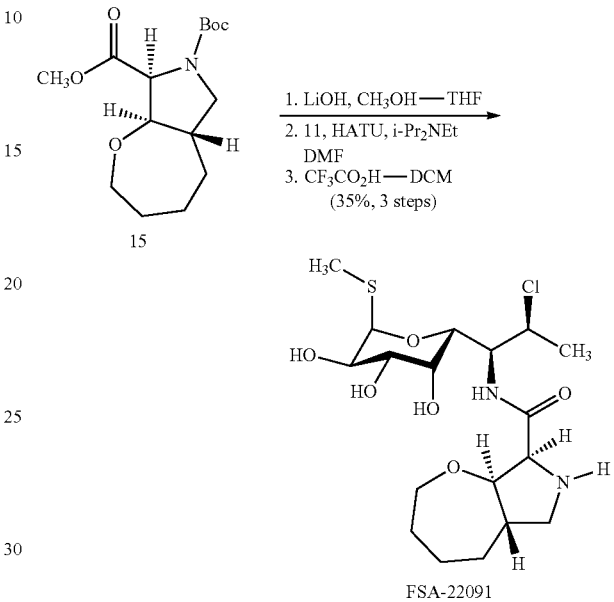

To a magnetically stirred solution of methyl ester 15 (12 mg, 40 μmol, 1 equiv) in 50% v/v methanol-tetrahydrofuran (200 μL) was added aqueous lithium hydroxide solution (1.0 M, 40 μL, 40 μmol, 1.0 equiv) at 23° C. The mixture was then heated to 40° C. with stirring, and LCMS analysis after 7 h indicated that saponification was not complete. Consequently, an additional portion of aqueous lithium hydroxide solution (1.0 M, 40 μL, 40 μmol, 1.0 equiv) was added, and stirring was maintained at 40° C. for an additional 17 h. At this point, LCMS analysis indicated that no methyl ester remained. The mixture was diluted with water (2 mL), and the resulting solution was chilled to 0° C. The ice-cold mixture was acidified to pH=2 with the addition of 1N aqueous hydrogen chloride solution, and the acidified mixture was extracted with ethyl acetate (5×2 mL). The combined organic extracts were dried over sodium sulfate, filtered, and concentrated to provide carboxylic acid intermediate as a white powder.

This residue was transferred to a 2-5 mL glass microwave vial, where it was dissolved in N,N-dimethylformamide (210 μL). To this solution, HATU (18 mg, 46 μmol, 1.1 equiv) was added, and the mixture was stirred at 23° C. for 10 min. Next, 7-chloro-methylthiolincosamine (11, 17 mg, 63 μmol, 1.5 equiv) was added; the resulting light yellow suspension was stirred for 20 min before N,N-diisopropylamine (18 μL, 0.11 mmol, 2.5 equiv) was finally added, causing a canary yellow solution to form. After 35 min, LCMS analysis showed that no carboxylic acid or activated-ester intermediate remained, and the reaction mixture was concentrated in vacuo. The residue was purified by flash-column chromatography (4 g silica gel, eluting with dichloromethane initially, grading to 5% methanol-dichloromethane). Fractions containing N-Boc-protected coupled product were identified by TLC ($R_f$=0.41, 10% methanol-dichloromethane, PMA). These fractions were pooled and concentrated to provide N-Boc-protected lincosamide as a white film.

This residue was finally dissolved in dichloromethane (300 μL). The resulting solution was chilled to 0° C. before trifluoroacetic acid (30 μL) was added; the mixture was stirred at 0° C. for 4.5 h, at which point LCMS analysis showed that Boc removal was complete. The solution was diluted with toluene (5 mL), and the diluted mixture was concentrated in vacuo. The residue was purified by flash-column chromatography (4 g silica gel, eluting with 1% ammonium hydroxide-5% methanol-dichloromethane initially, grading to 1% ammonium hydroxide-10% methanol-dichloromethane) to provide FSA-22091 as a white solid (6.1 mg, 35%, 3 steps). $^1$H NMR (600 MHz, CD$_3$OD) δ 5.30 (d, J=5.6 Hz, 1H), 4.60 (qd, J=6.8, 1.6 Hz, 1H), 4.41 (dd, J=10.1, 1.6 Hz, 1H), 4.20 (dd, J=10.0, 0.8 Hz, 1H), 4.12 (app t, J=9.1 Hz, 1H), 4.08 (dd, J=10.2, 5.6 Hz, 1H), 3.95 (d, J=9.0 Hz, 1H), 3.91 (dd, J=3.5, 1.1 Hz, 1H), 3.87 (ddd, J=11.8, 7.6, 4.2 Hz, 1H), 3.76 (ddd, J=11.7, 5.7, 3.9 Hz, 1H), 3.57 (dd, J=10.2, 3.4 Hz, 1H), 3.26 (dd, J=10.2, 7.2 Hz, 1H), 2.56 (dd, J=11.2, 10.3 Hz, 1H), 2.19-2.12 (m, 1H), 2.14 (s, 3H), 1.94 (app dq, J=13.4, 5.2 Hz, 1H), 1.90-1.76 (m, 3H), 1.67 (app ddt, J=17.5, 8.7, 5.5 Hz, 1H), 1.51 (d, J=6.8 Hz, 3H), 1.26 (dddd, J=14.0, 11.4, 9.0, 5.3 Hz, 1H). HRMS (ESI+, m/z): [M+H]$^+$ calcd for C$_{18}$H$_{31}$ClN$_2$O$_6$S, 439.1664; found 439.1678.

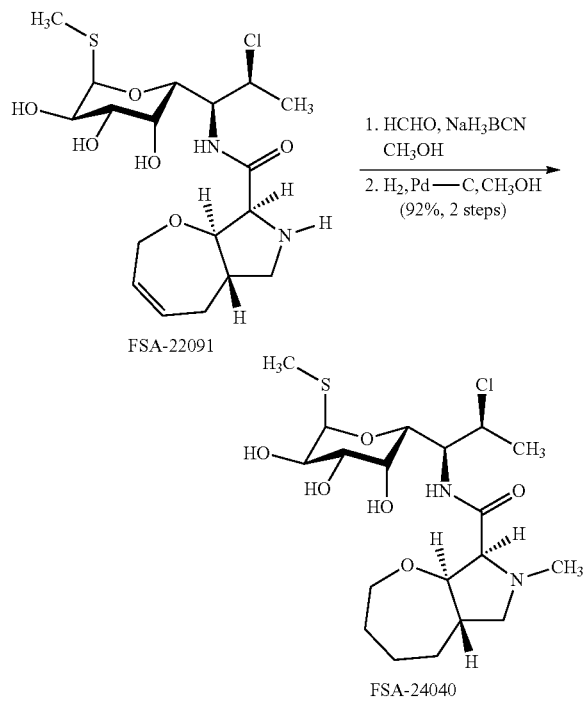

To a solution of FSA-22091 (6.5 mg, 15 μmol, 1 equiv) in methanol (150 μL) was added formalin (2.2 μL, 30 μL, 2.0 equiv) at 23° C. After stirring this mixture for 3 min, sodium cyanoborohydride (1.9 mg, 30 μmol, 2.0 equiv) was added as well; within 20 min, LCMS analysis indicated methylation was complete. The mixture was concentrated to dryness in vacuo, and the residue was passed through a plug of silica gel (~1 g), eluting with 1% ammonium hydroxide-10% methanol-dichloromethane. The filtrate was concentrated to afford methylated pyrrolidinooxepine intermediate.

In a 2-5 mL glass microwave vial, this residue was dissolved in methanol (500 μL), and the solution was treated with palladium on carbon (10% w/w, 1.0 mg). Hydrogen gas, supplied by a balloon, was bubbled through the solution for 5 min, and then the mixture was stirred at 23° C. under a balloon full of hydrogen gas. After 1 h, LCMS analysis indicated that oxepine hydrogenation was complete. The mixture was filtered through a pad of Celite in order to remove the heterogeneous catalyst, and the filter cake was rinsed with methanol (3×1 mL). The combined filtrates were concentrated to provide FSA-24040 as a colorless film (6.2 mg, 92%). $^1$H NMR (600 MHz, CD$_3$OD) δ 5.30 (d, J=5.6 Hz, 1H), 4.63 (qd, J=6.8, 1.6 Hz, 1H), 4.36 (dd, J=9.9, 1.6 Hz, 1H), 4.16-4.05 (m, 4H), 3.91 (ddd, J=11.4, 7.3, 3.2 Hz, 1H), 3.68 (ddd, J=11.8, 6.8, 2.9 Hz, 1H), 3.57 (dd, J=10.2, 3.6 Hz, 1H), 3.19 (d, J=9.8 Hz, 1H), 3.15 (dd, J=8.9, 6.1 Hz, 1H), 2.36 (s, 3H), 2.33-2.28 (m, 1H), 2.16 (dd, J=11.4, 9.1 Hz, 1H), 2.13 (s, 3H), 1.94-1.89 (m, 1H), 1.87-1.83 (m, 1H), 1.81-1.68 (m, 3H), 1.49 (d, J=6.9 Hz, 3H), 1.34-1.28 (m, 1H). HRMS (ESI+, m/z): [M+H]$^+$ calcd for C$_{19}$H$_{33}$ClN$_2$O$_6$S, 453.1821; found 453.1817.

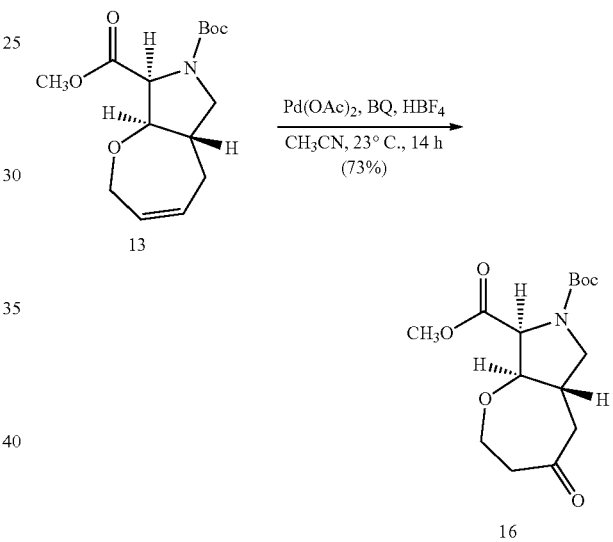

In a 25-mL round-bottomed flask, pyrrolidinooxepine 13 (169 mg, 568 μmol, 1 equiv), palladium acetate (6.38 mg, 28.4 μmol, 0.0500 equiv), and 1,4-benzoquinone (61.0 mg, 568 μmol, 1.00 equiv) were dissolved in acetonitrile (2.49 mL). To this solution were then added water (349 μL) and aqueous tetrafluoroboric acid solution (48% w/w, 102 μL, 784 μmol, 1.38 equiv). The reaction mixture was stirred at 23° C., and after 14 h, TLC analysis (30% ethyl acetate-hexanes, KMnO$_4$) indicated that no starting material remained. The mixture was diluted with saturated aqueous sodium chloride solution (10 mL), and the diluted mixture was extracted with dichloromethane (3×5 mL). The combined organic extracts were dried over sodium sulfate, filtered, and concentrated. The crude residue thus obtained was subjected to flash-column chromatography (12 g silica gel, eluting with 40% ethyl acetate-hexanes) to provide the product as a pale yellow oil (131 mg, 73%). $^1$H NMR (60:40 mixture of rotamers, asterisks [*] denote minor rotameric signals that could be resolved, 500 MHz, CDCl$_3$) δ 4.53 (d, J=8.3, 1H),* 4.45 (d, J=8.4 Hz, 1H), 4.12-4.08 (m, 1H), 3.95-3.89 (m, 2H), 3.84 (dd, J=10.4, 8.3 Hz, 1H),* 3.74 (s, 3H),* 3.73 (s, 3H), 3.65 (app t, J=12.2 Hz, 1H),* 3.66 (app t, J=12.1 Hz, 1H), 2.95-2.89 (m, 2H), 2.86-2.69 (m, 2H), 2.55 (dd, J=15.7, 4.7 Hz, 1H), 2.41 (dd, J=17.8, 12.0 Hz, 1H), 1.41 (s, 9H),* 1.37 (s, 9H). HRMS (ESI+, m/z): [M+H]+ calcd for $C_{15}H_{23}NO_6$, 314.1598; found 314.1599.

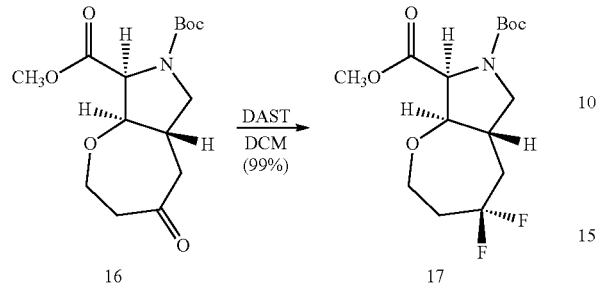

16 → 17
DAST
DCM
(99%)

In a 2-5 mL glass microwave vial, a solution of ketone 16 (20 mg, 64 μmol, 1 equiv) in dichloromethane (430 mL) pre-chilled to −30° C. was treated with diethylaminosulfur trifluoride (DAST, 51 μL, 0.38 mmol, 6.0 equiv), added dropwise over 30 s. The cooling bath was removed, and the reaction mixture was then allowed to warm to 23° C. After 2.5 h, TLC analysis (60% ethyl acetate-hexanes, CAM) indicated that some starting material remained, so the mixture was chilled to 0° C., an additional portion of DAST (42 μL, 0.32 mmol, 5.0 equiv) was added dropwise, and the mixture was then re-warmed to 23° C. as before. The reaction was judged to be complete by TLC analysis 4 h after this second addition of deoxyfluorinating reagent. The reaction mixture was cooled to −5° C., and methanol (200 μL) was added to quench excess DAST. The quenched mixture was stirred at −5° C. for 1 min, and was then diluted with dichloromethane (15 mL). The diluted mixture was washed with saturated aqueous sodium bicarbonate solution (5 mL), the organic phase was dried over sodium sulfate, the dried solution was filtered, and the filtrate was concentrated to give a crude residue. This residue was subjected to flash-column chromatography (4 g silica gel, eluting with 20% ethyl acetate-hexanes initially, grading to 40% ethyl acetate-hexanes) to provide the product as a colorless film, 21 mg, 99%). $^1$H NMR (55:45 mixture of rotamers, asterisks [*] denote minor rotameric signals that could be resolved, 500 MHz, CDCl$_3$) δ 4.50 (d, J=8.1 Hz, 1H),* 4.41 (d, J=8.2 Hz, 1H), 4.08-4.03 (m, 1H), 3.99-3.94 (m, 1H), 3.92 (dd, J=10.6, 8.5 Hz, 1H), 3.85 (dd, J=10.5, 8.4 Hz, 1H),* 3.80-3.78 (m, 1H),* 3.76 (s, 3H), 3.75 (s, 3H), 3.73-3.70 (m, 1H), 2.95-2.89 (m, 1H), 2.81-2.68 (m, 1H), 2.51-2.41 (m, 1H), 2.39-2.27 (m, 1H), 2.00 (app dtd, J=22.3, 14.6, 11.8 Hz, 1H), 1.44 (s, 9H),* 1.40 (s, 9H). $^{19}$F NMR (471 MHz, CDCl$_3$) δ −82.55 (app dddt, J=247.5, 12.4, 8.4, 4.2 Hz, 1F), −84.96 (ddddd, J=247.5, 21.8, 17.5, 8.2, 5.3 Hz, 1F). HRMS (ESI+, m/z): [M+Na]+ calcd for $C_{15}H_{23}F_2NO_5$, 358.1437; found 358.1447.

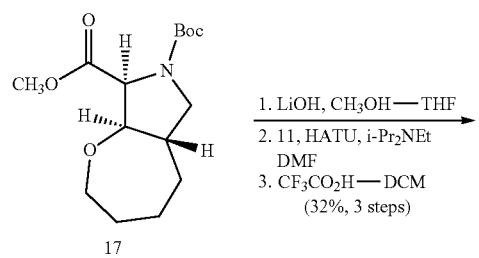

17

1. LiOH, CH$_3$OH — THF
2. 11, HATU, i-Pr$_2$NEt DMF
3. CF$_3$CO$_2$H — DCM
(32%, 3 steps)

FSA-24036

To a solution of methyl ester 17 (21 mg, 63 μmol, 1 equiv) in 50% v/v methanol-tetrahydrofuran (310 μL) was added aqueous lithium hydroxide solution (1.0 M, 75 μL, 75 μmol, 1.2 equiv) at 23° C. After 24 h, LCMS analysis showed that saponification was complete; the reaction mixture was diluted with water (4 mL), was chilled to 0° C., and was acidified to pH=2 by the dropwise addition of aqueous hydrogen chloride solution (1.0 N). The acidified solution was then extracted with ethyl acetate (4×3 mL). The combined extracts were dried over sodium sulfate, filtered, and concentrated to provide carboxylic acid intermediate as a white powder (17 mg, 53 μmol).

This crude carboxylic acid was then transferred to a 2-5 mL glass microwave vial, where it was dissolved in N,N-dimethylformamide (270 μL). To this solution was added HATU (22 mg, 58 μmol, 1.1 equiv). The mixture was stirred at 23° C. for 10 min before 7-chloro-methylthiolincosamine (11, 22 mg, 79 μmol, 1.5 equiv) was added, causing a light cream-yellow suspension to form. This mixture was stirred for 20 min, during which time it gradually became a homogeneous solution. At this point, N,N-diisopropylethylamine (23 μL, 0.13 mmol, 2.5 equiv) was added, causing the mixture to attain a vibrant yellow color. After 25 min of additional stirring, LCMS analysis indicated no trace of carboxylic acid or activated-ester intermediate. The mixture was loaded directly onto a column silica gel (4 g), where it was purified by flash chromatography (eluting with dichloromethane initially, grading to 5% methanol-dichloromethane). Fractions containing the Boc-protected coupling product were identified by TLC ($R_f$=0.44, 10% methanol-dichloromethane, PMA), pooled, and concentrated to afford a white solid residue.

Finally, this residue was transferred to a clean 2-5 mL glass microwave vial, where it was dissolved in dichloromethane (450 μL). Dimethyl sulfide (44 μL) and trifluoroacetic acid (45 μL) were added, and the mixture was stirred at 23° C. for 1.5 h, whereupon LCMS analysis showed that Boc removal was complete. The mixture was concentrated under a stream of argon, and the residue was purified by flash-column chromatography (4 g silica gel, eluting with 1% ammonium hydroxide-5% methanol-dichloromethane initially, grading to 1% ammonium hydroxide-10% methanol-dichloromethane) to provide FSA-24036 as a white film (9.6 mg, 32%, 3 steps). $^1$H NMR (500 MHz, CD$_3$OD) δ 5.30 (d, J=5.6 Hz, 1H), 4.59 (qd, J=6.8, 1.7 Hz, 1H), 4.42 (dd, J=10.0, 1.6 Hz, 1H), 4.20 (dd, J=10.0, 1.1 Hz, 1H), 4.12 (app td, J=9.0, 1.3 Hz, 1H), 4.08 (dd, J=10.2, 5.6 Hz, 1H), 4.01 (d, J=8.9 Hz, 1H), 3.97 (app ddt, J=7.2, 3.9, 1.9 Hz, 1H), 3.89 (dd, J=3.5, 1.2 Hz, 1H), 3.79-3.75 (m, 1H), 3.57 (dd, J=10.2, 3.4 Hz, 1H), 3.30 (dd, J=10.2, 7.1 Hz, 1H), 2.59 (app t, J=10.6 Hz, 1H), 2.47-2.28 (m, 4H), 2.14 (s, 3H), 2.03 (app dt, J=20.0, 14.9, 11.7 Hz, 1H), 1.50 (d, J=6.8 Hz, 3H). $^{19}$F NMR (471 MHz, CD$_3$OD) δ -83.40 (app dqd, J=246.9, 6.9, 3.7 Hz, 1F), -85.69 (app ddq, J=247.1, 11.6, 5.4 Hz, 1F). HRMS (ESI+, m/z): [M+H]$^+$ calcd for C$_{18}$H$_{29}$CF$_2$N$_2$O$_6$S, 475.1476; found 475.1462.

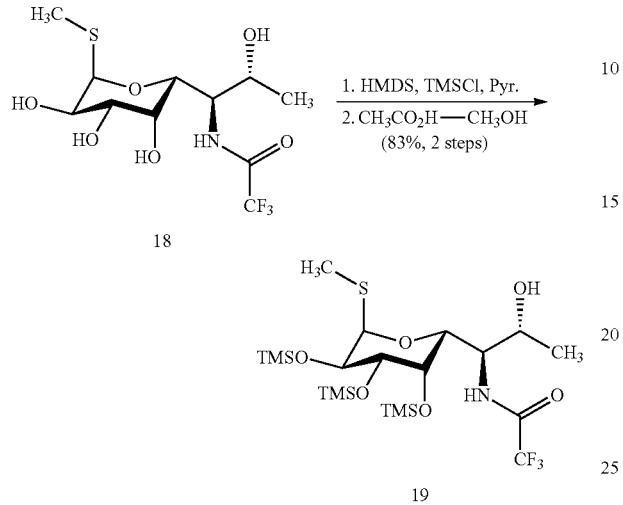

18

19

3H), 0.19 (s, 9H), 0.14 (s, 18H). $^{19}$F NMR (471 MHz, CDCl$_3$) δ -75.5 (s, 3F). HRMS (ESI+, m/z): [M+H]$^+$ calcd for C$_{20}$H$_{42}$F$_3$NO$_6$SSi$_3$, 566.2065; found 566.2082.

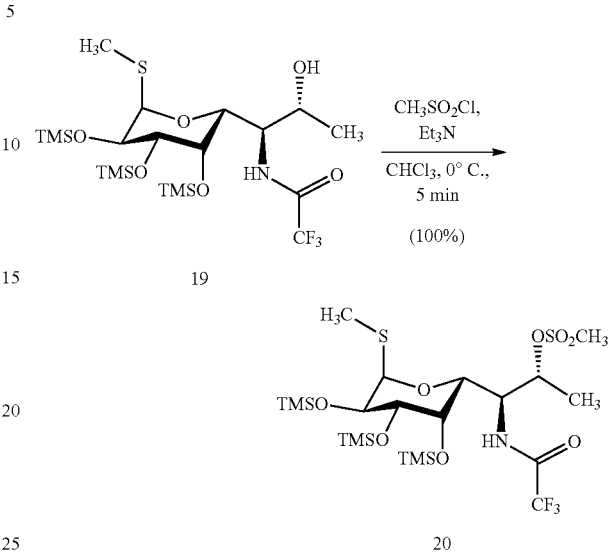

19

20

In a 25-mL round-bottomed flask, N-trifluoroacetyl methylthiolincosamine (18, 400 mg, 1.15 mmol, 1 equiv) was dissolved in pyridine 1.91 mL, and this solution was chilled to 0° C. Hexamethyldisilazane (607 μL, 2.90 mmol, 2.53 equiv) and chlorotrimethylsilane (840 μL, 6.57 mmol, 5.74 equiv) were then added sequentially, dropwise. Addition of chlorotrimethylsilane caused the formation of a white precipitate. The mixture was warmed to 23° C., and was stirred at that temperature for 2 h before it was concentrated to dryness in vacuo. To the dried, white solid residue were added hexanes (7 mL) and water (7 mL), and the mixture was stirred until both phases were clear and all solids were dissolved. The mixture was then transferred into a separatory funnel containing an additional portion of hexanes (20 mL); the layers were shaken, then separated. The organic phase was then washed with a fresh portion of water (10 mL), dried over sodium sulfate, filtered, and concentrated to provide tetrakis-O-trimethylsilylated intermediate as a white solid.

This residue was dissolved in methanol (850 μL), and 80% v/v acetic acid-water (141 μL) was added to this solution at 23° C. After 24 h of stirring, TLC demonstrated complete consumption of tetrakis-O-trimethylsilyl intermediate (R$_f$=0.66, 20% ethyl acetate-hexanes, CAM). The mixture was neutralized with the addition of saturated aqueous sodium bicarbonate solution (400 μL). After gas evolution ceased, the neutralized solution was transferred to a separatory funnel containing hexanes (25 mL) and water (10 mL). The layers were shaken, then separated; the organic phase was washed with a fresh portion of saturated aqueous sodium bicarbonate solution (10 mL), water (10 mL), and saturated aqueous sodium chloride solution (10 mL). The organic layer was then dried over sodium sulfate, filtered, and concentrated to provide the product as a foaming white, amorphous solid (535 mg, 83%, 2 steps). $^1$H NMR (500 MHz, CDCl$_3$) δ 7.64 (d, J=8.3 Hz, 1H), 5.18 (d, J=5.3 Hz, 1H), 4.35 (dd, J=6.1, 1.2 Hz, 1H), 4.18-4.14 (m, 2H), 4.06 (dd, J=9.5, 5.3 Hz, 1H), 3.90-3.84 (m, 1H), 3.71 (dd, J=9.5, 2.7 Hz, 1H), 2.15 (br, 1H), 2.00 (s, 3H), 1.26 (d, J=6.4 Hz, To a magnetically stirred, ice-cold solution of alcohol 19 (399 mg, 705 μmol, 1 equiv) and triethylamine (246 μL, 1.76 mmol, 2.50 equiv) in chloroform (2.20 mL) was added methanesulfonyl chloride (110 μL, 1.41 mmol, 2.00 equiv) dropwise. After stirring for 5 min at 0° C., TLC analysis (15% diethyl ether-dichloromethane, CAM) showed complete consumption of starting material. The reaction mixture was diluted with dichloromethane (7 mL), and saturated aqueous sodium bicarbonate solution (7 mL) was added to destroy any residual methanesulfonyl chloride. The biphasic mixture was stirred at 23° C. for 5 min before the layers were separated. The aqueous phase was extracted with dichloromethane (2×15 mL), and the combined organic extracts were dried over sodium sulfate. The dried solution was filtered and concentrated to provide methanesulfonate ester product as a bright white, amorphous solid (456 mg, 100%). $^1$H NMR (500 MHz, CDCl$_3$) δ 7.51 (d, J=8.8 Hz, 1H), 5.15 (d, J=5.4 Hz, 1H), 4.92 (app p, J=6.3 Hz, 1H), 4.48 (app dt, J=68.4, 6.5 Hz, 1H), 4.25 (d, J=7.2 Hz, 1H), 4.08-4.05 (m, 2H), 3.63 (dd, J=9.6, 2.5 Hz, 1H), 3.04 (s, 3H), 2.02 (s, 3H), 1.45 (d, J=6.5 Hz, 3H), 0.16 (s, 9H), 0.13 (s, 9H), 0.12 (s, 9H). $^{19}$F NMR (376 MHz, CDCl$_3$) δ -75.6 (s, 3F). HRMS (ESI+, m/z): [M+Na]$^+$ calcd for C$_{21}$H$_{44}$F$_3$NO$_8$S$_2$Si$_3$, 666.1660; found 666.1673.

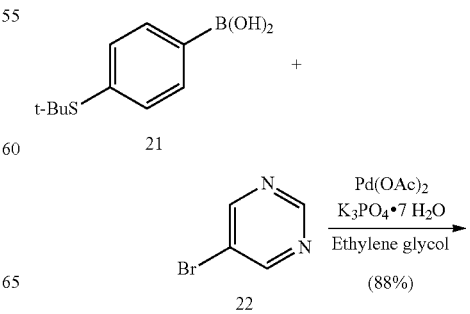

21

22

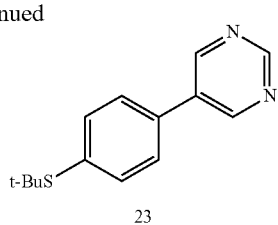

23

Taking no special precautions to exclude air or moisture, a 25-mL round-bottomed flask was charged with a magnetic stir bar, 5-bromopyrimidine (22, 180 mg, 1.13 mmol, 1 equiv), 4-(tert-butylthio)phenylboronic acid (21, 357 mg, 1.70 mmol, 1.50 equiv), potassium phosphate heptahydrate (766 mg, 2.26 mmol, 2.00 equiv), palladium(II) acetate (12.7 mg, 0.0566 mmol, 0.0500 equiv), and ethylene glycol (8.71 mL). The heterogeneous, light-yellow mixture was heated to 80° C. with stirring in a pre-heated oil bath. After 20 min, the mixture had become a dark gray suspension, and LCMS analysis indicated that no 5-bromopyrimidine remained. The mixture was cooled to room temperature before it was poured into a separatory funnel containing saturated aqueous sodium chloride solution (25 mL). This mixture was then extracted with diethyl ether (3×15 mL). In order to remove excess boronic acid coupling partner, the combined organic extracts were washed with 1N aqueous sodium hydroxide solution (2×10 mL), and saturated sodium chloride solution (10 mL). The dried organic solution was dried over sodium sulfate, filtered, and concentrated to give off-white milky oil, which was purified by flash-column chromatography (12 g silica gel, eluting with 20% diethyl ether-hexanes initially, grading to 45% diethyl ether-hexanes) to furnish the product as a white crystalline solid (244 mg, 88%). Melting point: 64-66° C. H NMR (600 MHz, CDCl$_3$) δ 9.12 (s, 1H), 8.88 (s, 2H), 7.60-7.57 (m, 2H), 7.48-7.45 (m, 2H), 1.23 (s, 9H). HRMS (ESI+, m/z): [M+H]$^+$ calcd for C$_{14}$H$_{16}$N$_2$S, 245.1107; found 245.1117.

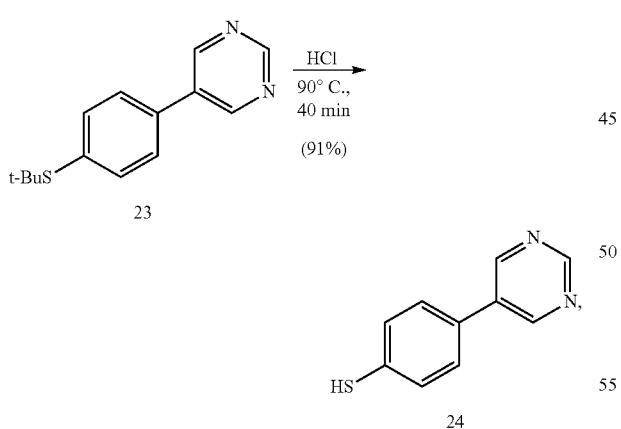

In a 100-mL round-bottomed flask, concentrated hydrochloric acid (35% w/v, 40.9 mL) was added to tert-butane sulfide 23 (500 mg, 2.05 mmol, 1 equiv). The headspace of the flask was flushed with argon, and the mixture was heated to 90° C. Upon heating, the mixture became a vibrant yellow, homogeneous solution, and gas bubbling was noted. After 40 min, the bubbling had subsided, and LCMS analysis indicated that the reaction was complete. The mixture was cooled to 23° C., and was then transferred to a 250-mL round-bottomed flask, where it was chilled to 0° C. A steady stream of nitrogen was maintained over the mixture in order to minimize oxidative dimerization of the thiol product. A solution of 6N aqueous sodium hydroxide solution (ca. 60 mL) was added to neutralize excess hydrochloric acid; when all the acid was neutralized, a persistent precipitate had formed. The mixture was diluted with 1M sodium phosphate buffer solution (pH 7.0, 50 mL), and the resulting neutral solution was extracted with ethyl acetate (3×25 mL). The combined organic extracts were dried over sodium sulfate, filtered, and concentrated to give a faint gray crystalline solid. This crude product was purified by flash-column chromatography (12 g silica gel, eluting with 30% ethyl acetate-dichloromethane initially, grading to 50% ethyl acetate-dichloromethane) to furnish the product as a gleaming white crystalline solid (352 mg, 91%). Melting point: 98-100° C. $^1$H NMR (500 MHz, CDCl$_3$) δ 9.19 (s, 1H), 8.92 (s, 2H), 7.46 (d, J=8.5 Hz, 2H), 7.41 (d, J=8.5 Hz, 2H), 3.57 (s, 1H). HRMS (ESI+, m/z): [M+H]$^+$ calcd for C$_{10}$H$_8$N$_2$S, 189.0481; found 189.0482.

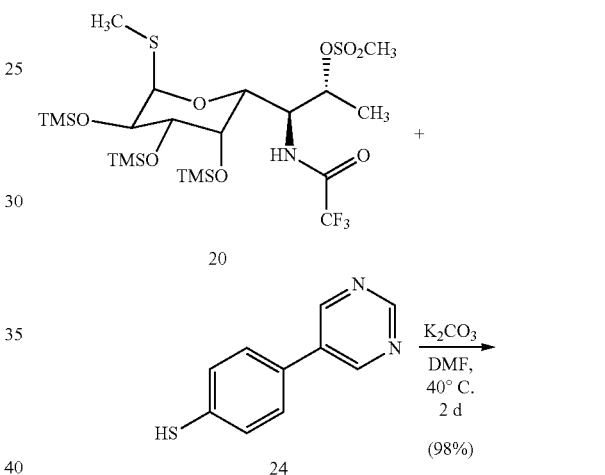

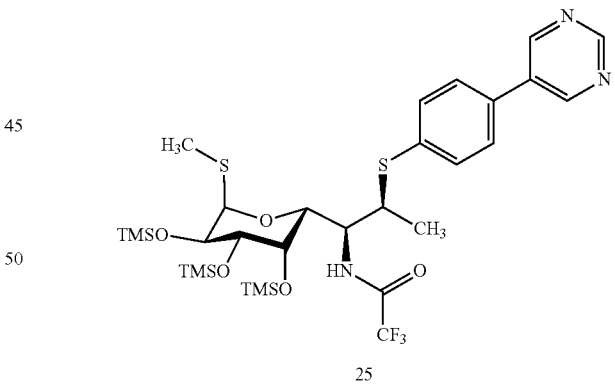

25

In a 0.5-2 mL conical glass microwave vial fitted with a magnetic stir bar, methanesulfonate ester 20 (75 mg, 0.12 mmol, 1 equiv) and 4-(pyrimidin-5-yl)benzenethiol (24, 66 mg, 0.35 mmol, 3.0 equiv) were mixed, and these starting materials were dried together by azeotropic removal of benzene. The dried mixture was then dissolved in N,N-dimethylformamide (290 µL), and potassium carbonate (19 mg, 0.14 mmol, 1.2 equiv) was added to the solution, causing a vibrant canary yellow color to evolve. The vial was sealed, and the mixture was heated to 40° C. for 2 d, at which point TLC analysis (40% ethyl acetate-hexanes, UV+CAM) showed that no electrophile remained. The mixture was diluted withyl acetate (30 mL), and the diluted mixture was washed sequentially with saturated aqueous sodium bicarbonate solution (15 mL) and saturated aqueous sodium chloride solution (15 mL). The washed organic solution was then dried over sodium sulfate, filtered, and concentrated to give a colorless oil. This residue was subjected to flash-column chromatography (12 g silica gel, eluting with 10% ethyl acetate-hexanes initially, grading to 30% ethyl acetate-hexanes) to furnish the product as a colorless, viscous oil (84 mg, 98%). $^1$H NMR (500 MHz, CDCl$_3$) δ 9.21 (s, 1H), 8.93 (s, 3H), 7.53 (app d, J=0.9 Hz, 4H), 6.93 (d, J=9.6 Hz, 1H), 5.21 (d, J=5.5 Hz, 1H), 4.62 (ddd, J=9.6, 8.4, 3.8 Hz, 1H), 4.34 (d, J=8.4 Hz, 1H), 4.11 (dd, J=9.6, 5.4 Hz, 1H), 3.92 (dd, J=2.7, 1.0 Hz, 1H), 3.85 (qd, J=7.0, 3.9 Hz, 1H), 3.67 (dd, J=9.6, 2.6 Hz, 1H), 1.97 (s, 3H), 1.33 (d, J=7.0 Hz, 3H), 0.17 (s, 9H), 0.14 (s, 9H), 0.13 (s, 9H). $^{19}$F NMR (471 MHz, CDCl$_3$) δ −75.47 (s, 3F). HRMS (ESI+, m/z): [M+H]$^+$ calcd for C$_3$H$_{48}$F$_3$N$_3$O$_5$S$_2$Si$_3$, 736.2368; found 736.2399.

Hz, 1H), 1.89 (s, 3H), 1.51 (d, J=6.9 Hz, 3H). HRMS (ESI+, m/z): [M+H]$^+$ calcd for C$_{19}$H$_{25}$N$_3$O$_4$S$_2$, 424.1359; found 424.1369.

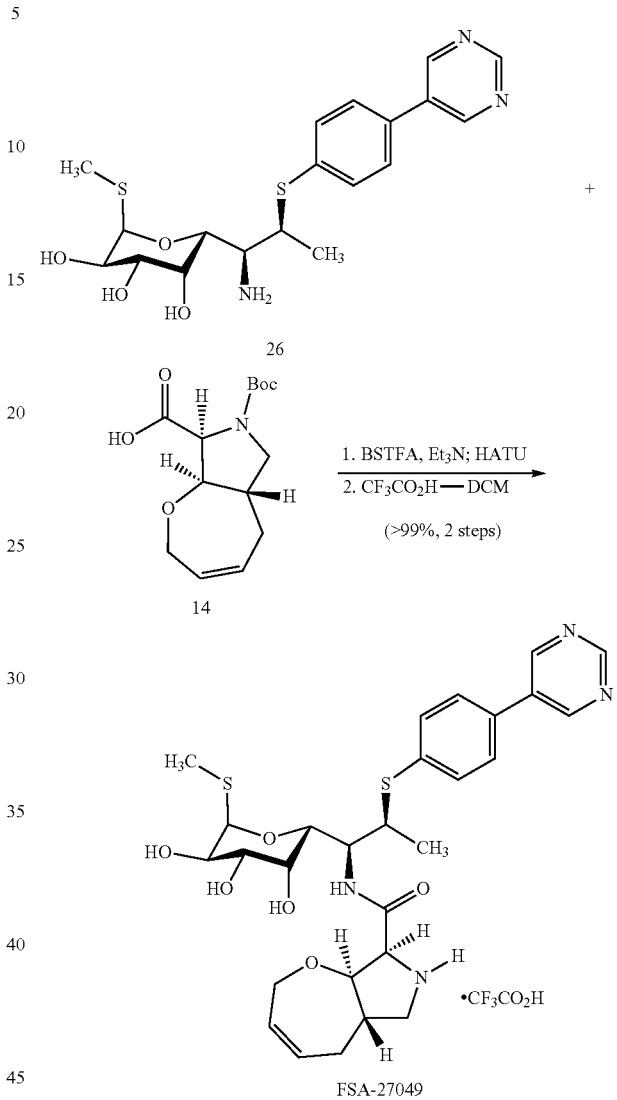

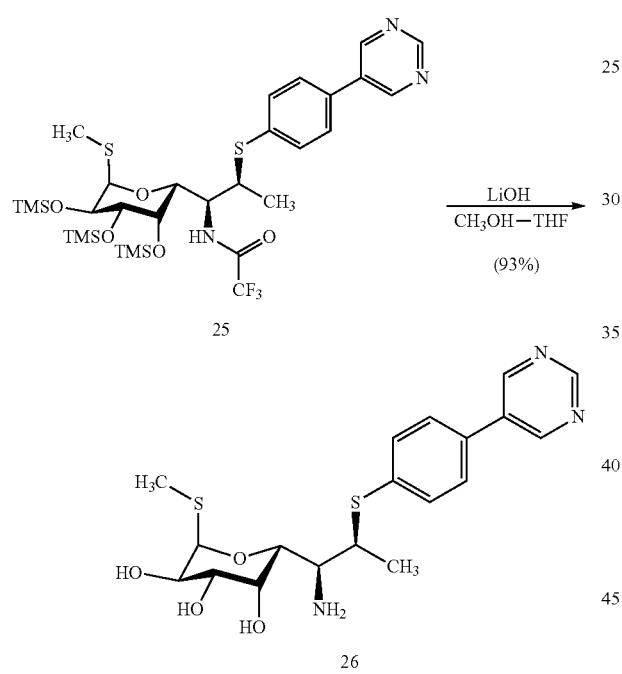

In a 2-5 mL glass microwave vial, trifluoroacetamide 25 (107 mg, 145 μmol, 1 equiv) was dissolved in 50% v/v tetrahydrofuran-methanol (1.45 mL). To this solution was added lithium hydroxide (17.4 mg, 727 μmol, 5.00 equiv) at 23° C.; immediately, the colorless solution attained a canary yellow color. After 2 d, LCMS analysis indicated that global O-desilylation and trifluoroacetamide hydrolysis were complete; the reaction mixture was concentrated directly under a stream of nitrogen. The residue was purified by flash-column chromatography (4 g silica gel, eluting with 1% ammonium hydroxide-7% methanol-dichloromethane initially, grading to 0.1% ammonium hydroxide-10% methanol-dichloromethane) to provide the product as a white powder (57.0 mg, 93%). $^1$H NMR (600 MHz, CD$_3$OD) δ 9.12 (s, 1H), 9.07 (s, 2H), 7.68 (d, J=8.4 Hz, 2H), 7.55 (d, J=8.4 Hz, 1H), 5.24 (d, J=5.5 Hz, 1H), 4.11 (dd, J=3.4, 1.2 Hz, 1H), 4.09 (dd, J=10.2, 5.5 Hz, 1H), 3.83 (qd, J=7.0, 2.8 Hz, 1H), 3.61 (dd, J=10.2, 3.4 Hz, 1H), 3.30 (dd, J=8.6, 2.9

To an ice-cold solution of aminothiol 26 (41.7 mg, 98.5 μmol, 1 equiv) and triethylamine (43.9 μL, 315 μmol, 3.20 equiv) in N,N-dimethylformamide (281 μL) was added N,O-bis(trimethylsilyl)trifluoroacetamide (39.6 μL, 148 μmol, 1.50 equiv). The mixture was then warmed to 23° C., and was stirred for 1 h at this temperature to ensure complete O-silylation. Carboxylic acid 14 (30.7 mg, 108 μmol, 1.10 equiv) and HATU (48.7 mg, 128 μmol, 1.30 equiv) were then added, and the mixture was stirred at 23° C. After 3 h, the reaction mixture was diluted with ethyl acetate (35 mL), and the diluted mixture was washed sequentially with 10% w/v aqueous citric acid solution (2×10 mL), water (10 mL), half-saturated aqueous sodium bicarbonate solution (2×10 mL), and saturated aqueous sodium chloride solution (10 mL). The washed organic phase was then dried over sodium sulfate, filtered, and concentrated.

The crude, coupled residue was then transferred to a 25-mL round-bottomed flask, where it was dissolved in dichloromethane (4.02 mL). Water (80.0 μL), dimethyl sulfide (80.0 μL), and trifluoroacetic acid (803 μL) were then added, and the resulting solution was stirred at 23° C. for 2 h, at which point LCMS analysis indicated that Boc removal was complete. The mixture was diluted with toluene (5 mL), and the diluted mixture was concentrated in vacuo. The residue was subjected to preparative HPLC on a Waters SunFire Prep C18 column (5 µm, 250×19 mm; eluting with 0.1% trifluoroacetic acid-10% acetonitrile-water initially, grading to 0.1% trifluoroacetic acid-40% acetonitrile-water over 40 min, with a flow rate of 15 mL/min; monitored by UV absorbance at 254 nm) to provide FSA-27049.CF$_3$CO$_2$H as a white solid (70.1 mg, 102%, 2 steps). $^1$H NMR (600 MHz, CD$_3$OD) δ 9.15 (s, 1H), 9.10 (s, 2H), 8.33 (d, J=9.9 Hz, 1H), 7.69 (d, J=8.4 Hz, 2H), 7.53 (d, J=8.4 Hz, 2H), 5.85 (app ddt, J=12.5, 7.3, 2.6 Hz, 1H), 5.76 (app ddt, J=12.2, 5.9, 2.9 Hz, 1H), 5.28 (d, J=5.6 Hz, 1H), 4.71 (app td, J=9.9, 2.3 Hz, 1H), 4.64 (d, J=9.1 Hz, 1H), 4.47 (dd, J=10.0, 1.2 Hz, 1H), 4.22-4.19 (m, 2H), 4.11 (dd, J=10.3, 5.6 Hz, 1H), 3.94-3.92 (m, 2H), 3.67 (dd, J=11.4, 7.4 Hz, 1H), 3.59 (dd, J=10.3, 3.3 Hz, 1H), 3.03 (dd, J=12.5, 11.4 Hz, 1H), 2.55 (ddd, J=16.7, 7.4, 3.5 Hz, 1H), 2.26 (app ddtd, J=16.3, 12.5, 7.5, 3.5 Hz, 1H), 2.14-2.08 (m, 1H), 1.86 (s, 3H), 1.44 (d, J=6.9 Hz, 3H). HRMS (ESI+, m/z): [M+H]$^+$ calcd for C$_{28}$H$_{36}$N$_4$O$_6$S$_2$, 589.2149; found 589.2169.

(3.3 mg, 16 µmol, 2.0 equiv) at 23° C. After stirring for 1 h, an additional portion for formalin (1.2 µL, 16 µmol, 2.0 equiv) was added; 1 h later, additional sodium triacetoxyborohydride (3.3 mg, 16 µmol, 2.0 equiv) was added. LCMS analysis 15 min later indicated that no starting material remained. Excess sodium triacetoxyborohydride solution was quenched with the addition of saturated aqueous sodium bicarbonate solution (1 drop) before the mixture was concentrated to dryness in vacuo. The residue was subjected to preparative HPLC on a Waters SunFire Prep C18 column (5 µm, 250×19 mm; eluting with 0.1% formic acid-2% acetonitrile-water initially, grading to 0.1% formic acid-30% acetonitrile-water over 40 min, with a flow rate of 20 mL/min; monitored by UV absorbance at 254 nm) to provide FSA-212034.HCO$_2$H as a colorless film (2.3 mg, 49%). $^1$H NMR (600 MHz, CD$_3$OD) δ 9.13 (s, 1H), 9.08 (s, 2H), 8.24 (s, 2H), 7.72 (d, J=7.7 Hz, 2H), 7.59 (d, J=7.8 Hz, 2H), 5.81 (app ddt, J=9.5, 6.2, 3.7 Hz, 1H), 5.63 (app ddt, J=12.4, 5.6, 2.8 Hz, 1H), 5.27 (d, J=5.5 Hz, 1H), 4.54 (dd, J=10.0, 2.2 Hz, 1H), 4.37-4.33 (m, 2H), 4.14-4.03 (m, 4H), 3.96 (qd, J=7.4, 2.2 Hz, 1H), 3.55 (dd, J=10.3, 3.5 Hz, 1H), 3.53 (d, J=10.2 Hz, 1H), 3.29 (dd, J=8.8, 6.0 Hz, 1H), 2.52-2.47 (m, 1H), 2.50 (s, 3H), 2.41 (app t, J=10.6 Hz, 1H), 2.29 (app tdd, J=14.4, 10.6, 4.9 Hz, 1H), 2.05 (app t, J=14.4 Hz, 1H), 1.95 (s, 3H). HRMS (ESI+, m/z): [M+H]$^+$ calcd for C$_{29}$H$_{38}$N$_4$O$_6$S$_2$, 603.2306; found 603.2319.

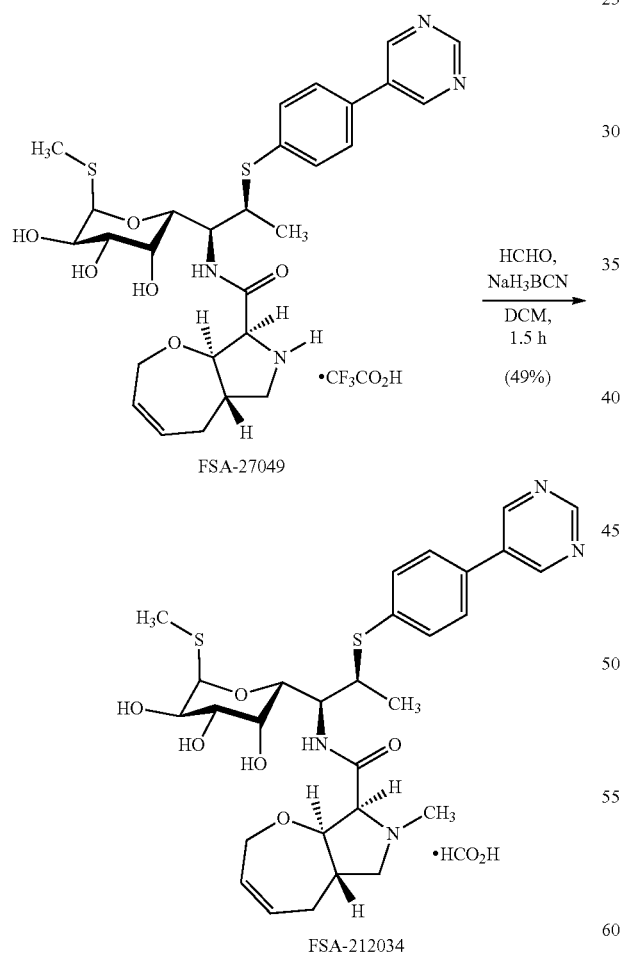

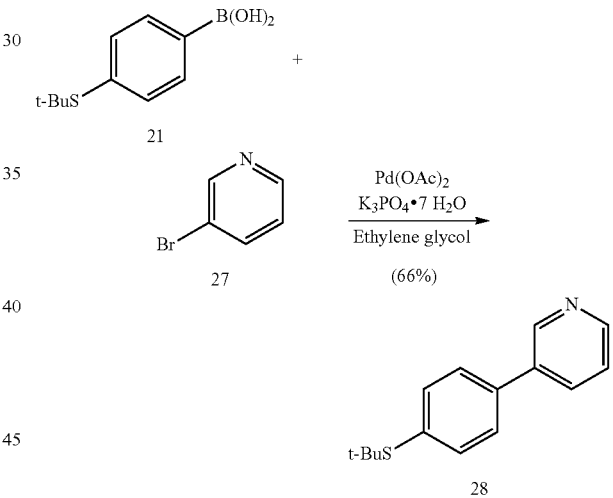

In a 1-mL glass vial fitted with a magnetic stir bar and PTFE-lined screw cap, FSA-27049.CF$_3$CO$_2$H (5.5 mg, 7.8 µmol, 1 equiv) was dissolved in dichloromethane (78 µL). Formalin (1.2 µL, 16 µmol, 2.0 equiv) was then added by micropipette, followed by sodium triacetoxyborohydride Taking no special precautions to exclude air or moisture, a 300-mL round-bottomed flask was charged with a magnetic stir bar, (4-(tert-butylthio)phenyl)boronic acid (21, 4.79 g, 22.8 mmol, 1.20 equiv), potassium phosphate heptahydrate (12.9 g, 38.0 mmol, 2.00 equiv), palladium(II) acetate (43.0 mg, 0.190 mmol, 0.0100 equiv), and ethylene glycol (146 mL). 3-Bromopyridine (27, 1.83 mL, 19.0 mmol, 1 equiv) was added last, stirring was initiated, and the reaction mixture was heated to 80° C. (open to the atmosphere) in a pre-heated oil bath. Within 30 min, the suspension had clarified, forming an amber-brown homogeneous solution; and after 1 h, the mixture became a light tan, turbid suspension. After 2 h of stirring at 80° C., TLC analysis (60% ethyl acetate-hexanes, UV) showed that no starting material remained. The mixture was cooled to 23° C., and was then poured into a separatory funnel containing saturated aqueous sodium chloride solution (250 mL). The aqueous suspension was extracted with diethyl ether (4×50 mL), and the combined organic extracts were washed with a fresh portion of saturated aqueous sodium chloride solution (50 mL). The washed organic product solution was then dried over sodium sulfate, filtered, and concentrated to give a milky, light yellow oil that was purified by flash-column chromatography (120 g silica gel, eluting with 10% ethyl acetate-hexanes initially, grading to 40% ethyl acetate-hexanes) to provide the product as a brilliant white, fluffy powder (3.04 g, 66%). Melting point: 55-57° C. $^1$H NMR (600 MHz, CDCl$_3$) δ 8.86 (d, J=1.7 Hz, 1H), 8.61 (dd, J=4.7, 1.6 Hz, 1H), 7.88 (ddd, J=7.9, 2.4, 1.6 Hz, 1H), 7.64 (d, J=8.3 Hz, 2H), 7.55 (d, J=8.2 Hz, 2H), 7.38 (ddd, J=7.8, 4.8, 0.9 Hz, 1H), 1.33 (s, 9H). HRMS (ESI+, m/z): [M+H]$^+$ calcd for C$_{15}$H$_{17}$NS, 244.1154; found 244.1167.

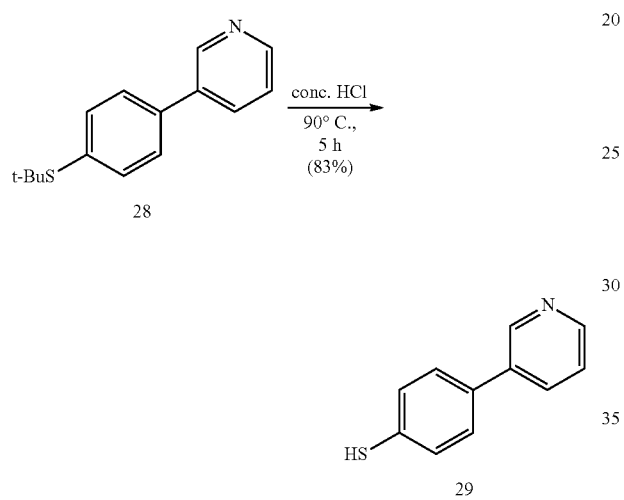

In a 500-mL round-bottomed flask containing a magnetic stir bar, tert-butanesulfide 28 (3.00 g, 12.3 mmol, 1 equiv) and concentrated hydrochloric acid (38% w/w in water, 123 mL) were combined. The headspace was flushed with argon, and the mixture was heated to 90° C. with constant stirring; the starting material gradually dissolved upon warming. After 5 h, LCMS analysis showed that no starting material remained, and the reaction mixture was cooled to 0° C. The chilled solution was basified with the careful addition of aqueous 6N sodium hydroxide solution, until pH=8 was achieved. The aqueous mixture was then extracted with diethyl ether (4×75 mL), the combined extracts were dried over sodium sulfate, the dried solution was filtered, and the filtrate was concentrated to give a colorless oil. This crude residue was finally purified by flash-column chromatography (80 g silica gel, eluting with 20% ethyl acetate-hexanes initially, grading to 60% ethyl acetate-hexanes) to provide arenethiol product as a light yellow solid (1.92 g, 83%). Melting point: 42-44° C. $^1$H NMR (600 MHz, CDCl$_3$) δ 8.79 (d, J=2.4 Hz, 1H), 8.56 (dd, J=4.8, 1.6 Hz, 1H), 7.79 (dt, J=7.9, 2.0 Hz, 1H), 7.42 (d, J=8.3 Hz, 2H), 7.34 (d, J=8.3 Hz, 2H), 7.32 (dd, J=7.9, 4.9 Hz, 1H), 3.55 (s, 1H). HRMS (ESI+, m/z): [M+H]$^+$ calcd for C$_{11}$H$_9$NS, 188.0528; found 188.0526.

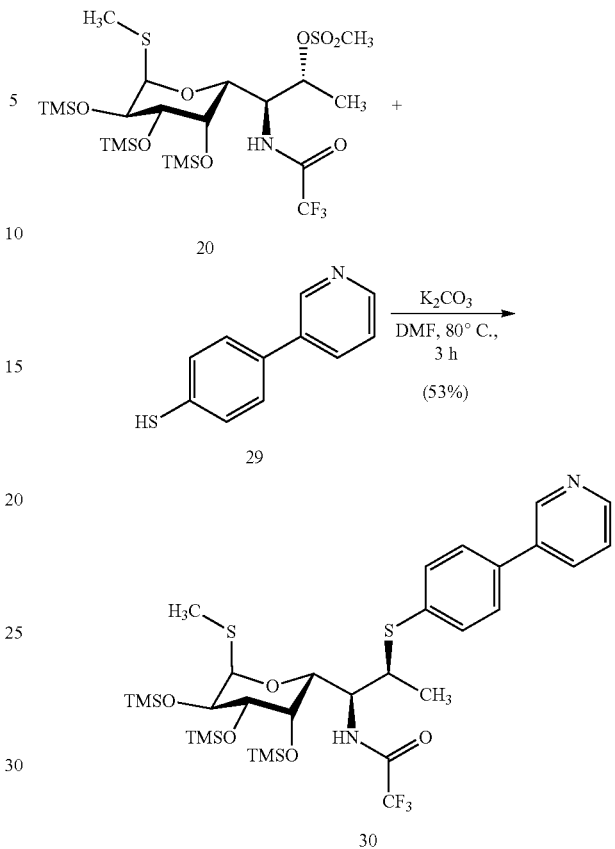

In a 5-10 mL glass microwave vial, methanesulfonate ester 20 (0.400 g, 0.621 μmol, 1 equiv) and arenethiol 29 (233 mg, 1.24 mmol, 2.00 equiv) were dried together by azeotropic removal of benzene. The dried mixture was then dissolved in N,N-dimethylformamide, and potassium carbonate was added. The vial was sealed, and the mixture was heated to 80° C. in a pre-heated oil bath. After 3 h, TLC analysis (30% ethyl acetate-hexanes, UV+CAM) showed complete consumption of starting material, and the mixture was diluted with ethyl acetate (30 mL). The diluted mixture was washed successively with saturated aqueous sodium bicarbonate solution (15 mL) and saturated aqueous sodium chloride solution (15 mL). The washed organic solution was then dried over sodium sulfate, filtered, and concentrated to give a colorless oil. This residue was purified by flash-column chromatography (40 g silica gel, eluting with 15% ethyl acetate-hexanes initially, grading to 50% ethyl acetate-hexanes) to provide the product as a bright white, crystalline solid (242 mg, 53%). Melting point: 134-135° C. $^1$H NMR (500 MHz, CDCl$_3$) δ 8.83 (dd, J=2.4, 0.8 Hz, 1H), 8.60 (dd, J=4.8, 1.6 Hz, 1H), 7.84 (ddd, J=7.9, 2.3, 1.7 Hz, 1H), 7.51 (ABq, Δδ$_{AB}$=0.01, J$_{AB}$=8.7 Hz, 4H), 7.36 (ddd, J=7.9, 4.9, 0.9 Hz, 1H), 7.02 (d, J=9.6 Hz, 1H), 5.22 (d, J=5.4 Hz, 1H), 4.62 (app td, J=9.0, 3.7 Hz, 1H), 4.36 (d, J=8.4 Hz, 1H), 4.12 (dd, J=9.6, 5.4 Hz, 1H), 3.92 (d, J=2.6 Hz, 1H), 3.83 (qd, J=7.0, 3.7 Hz, 1H), 3.67 (dd, J=9.6, 2.6 Hz, 1H), 2.00 (s, 3H), 1.33 (d, J=7.0 Hz, 3H), 0.17 (s, 9H), 0.14 (s, 9H), 0.14 (s, 9H). HRMS (ESI+, m/z): [M+H]$^+$ calcd for C$_{31}$H$_{50}$F$_3$N$_2$O$_6$S$_2$Si$_3$, 735.2416; found 735.2398.

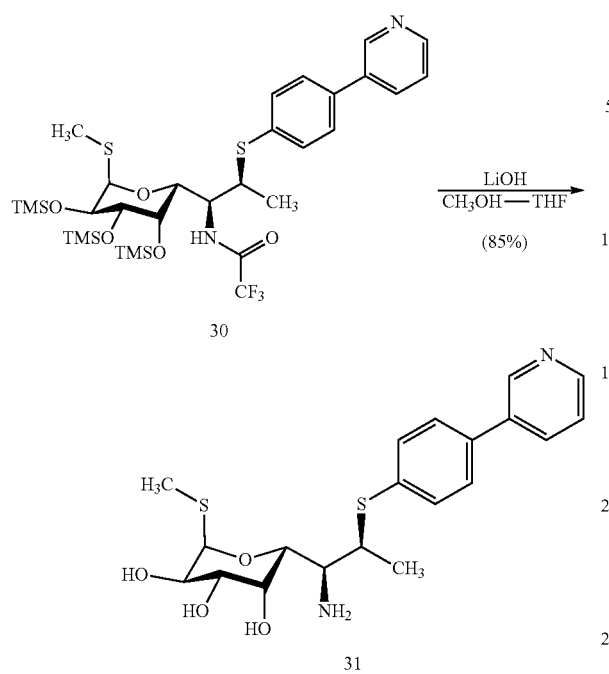

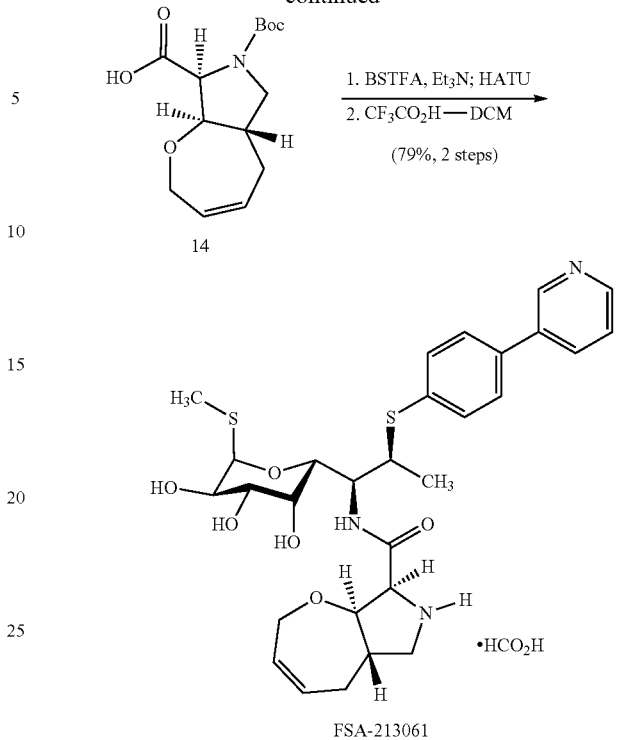

In a 5-10 mL glass microwave vial fitted with a magnetic stir bar, a solution of trifluoroacetamide 30 (240 mg, 326 µmol, 1 equiv) in methanol (2.00 mL) was treated with aqueous sodium hydroxide solution (1.00 M, 2.61 mL, 2.61 mmol, 8.00 equiv) at 23° C. A white, frothy mixture resulted as the trimethylsilyl ether groups were rapidly solvolyzed; the mixture was heated to 40° C., and after 7 h of stirring at that temperature, cleavage of the trifluoroacetamide was complete as well, as indicated by LCMS. The white pasty mixture was chilled to 0° C. before it was subjected to vacuum filtration; the collected solids were washed with ice-cold water (2×2 mL), and were dried on high vacuum (0.1 mmHg) to provide the product as a brilliant white, crystalline solid (118 mg, 85%). Melting point: 157-160° C. $^1$H NMR (500 MHz, CD$_3$OD) δ 8.80 (d, J=2.3 Hz, 1H), 8.51 (dd, J=4.9, 1.5 Hz, 1H), 8.09 (dt, J=7.9, 1.9 Hz, 1H), 7.62 (d, J=8.4 Hz, 2H), 7.52 (d, J=8.1 Hz, 2H), 7.51 (dd, J=7.9, 4.9 Hz, 1H), 5.23 (d, J=5.6 Hz, 1H), 4.26 (d, J=9.1 Hz, 1H), 4.11 (d, J=2.7 Hz, 1H), 4.09 (dd, J=10.3, 5.6 Hz, 1H), 3.81 (qd, J=6.9, 2.3 Hz, 1H), 3.61 (dd, J=10.2, 3.4 Hz, 1H), 3.28 (dd, J=9.0, 2.5 Hz, 1H), 1.90 (s, 3H), 1.50 (d, J=7.0 Hz, 3H). HRMS (ESI+, m/z): [M+H]$^+$ calcd for C$_2$H$_{26}$N$_2$O$_4$S$_2$, 423.1407; found 423.1417.

In a 4-mL glass vial fitted with a magnetic stir bar and a PTFE-lined screw cap, a solution of aminotriol 31 (40 mg, 95 µmol, 1 equiv) and triethylamine (42 µL, 0.30 mmol, 3.20 equiv) in N,N-dimethylformamide (270 µL) was cooled to 0° C. To this chilled solution was added N,O-bis(trimethylsilyl)trifluoroacetamide (38 µL, 0.14 mmol, 1.5 equiv); the mixture was then warmed to 23° C. and stirred for 1 h to ensure complete O-silylation. Carboxylic acid 14 (30 mg, 0.10 mmol, 1.1 equiv) and HATU (47 g, 0.12 mmol, 1.3 equiv) were added next, and the mixture was stirred at 23° C. for 6 h, until LCMS indicated complete consumption of aminotriol starting material and its (oligo)trimethylsilylated congeners. The mixture was diluted with ethyl acetate (10 mL), and the diluted mixture was washed with saturated aqueous sodium chloride solution (2×5 mL). The washed organic solution was dried over sodium sulfate, filtered, and concentrated; residual N,N-dimethylformamide was removed by repeated concentration of the residue from 10% v/v methanol-toluene (2×5 mL).

The dried residue was then dissolved in dichloromethane (900 µL). Water (20 µL) and dimethylsulfide (20 µL) were added, followed by trifluoroacetic acid (300 µL); the resulting solution was stirred at 23° C. for 30 min, at which point LCMS analysis indicated that Boc removal was complete. The mixture was diluted with toluene (2 mL), and the diluted mixture was concentrated to dryness in vacuo. The residue was subjected to preparative HPLC on a Waters SunFire Prep C18 column (5 µm, 250×19 mm; eluting with 0.1% formic acid-5% acetonitrile-water initially, grading to 0.1% formic acid-40% acetonitrile-water over 40 min, with a flow rate of 15 mL/min; monitored by UV absorbance at 280 nm) to provide FSA-213061.HCO$_2$H as a white solid (48 mg, 79%). $^1$H NMR (500 MHz, CD$_3$OD) δ 8.79 (s, 1H), 8.51 (d, J=4.8 Hz, 1H), 8.37 (br, 1H), 8.07 (d, J=8.0 Hz, 1H), 7.61 (d, J=8.3 Hz, 2H), 7.50 (d, J=8.1 Hz, 2H), 5.83 (dd, J=12.5, 7.0 Hz, 1H), 5.75 (ddd, J=12.5, 6.0, 2.8 Hz, 1H), 5.30 (d,

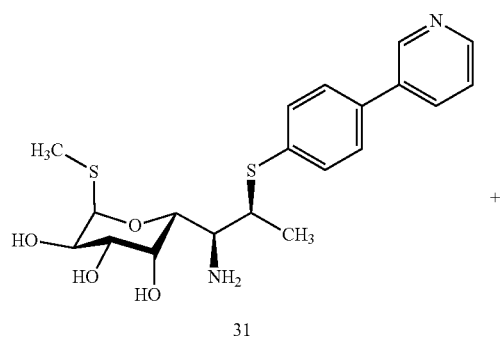

J=5.6 Hz, 1H), 4.70 (d, J=10.0 Hz, 1H), 4.64 (d, J=6.9 Hz, 1H), 4.48 (d, J=10.1 Hz, 1H), 4.38 (dd, J=16.0, 5.8 Hz, 1H), 4.21-4.17 (m, 2H), 4.12 (dd, J=10.2, 5.5 Hz, 1H), 3.95 (d, J=3.3 Hz, 1H), 3.89 (qd, J=7.1, 1.9 Hz, 1H), 3.66 (dd, J=11.4, 7.6 Hz, 1H), 3.61 (dd, J=10.3, 3.2 Hz, 1H), 3.02 (app t, J=11.2 Hz, 1H), 2.53 (ddd, J=17.0, 7.4, 3.4 Hz, 1H), 2.31-2.22 (m, 1H), 2.10 (app t, J=13.7 Hz, 1H), 1.88 (s, 3H), 1.43 (d, J=6.9 Hz, 3H). HRMS (ESI+, m/z): [M+H]$^+$ calcd for $C_{29}H_{37}N_3O_6S_2$, 588.2197; found 588.2193.

4.16-4.11 (m, 2H), 4.10 (ddd, J=10.3, 5.6, 0.9 Hz, 1H), 4.00 (dd, J=3.3, 1.6 Hz, 1H), 3.92 (qt, J=6.9, 1.8 Hz, 1H), 3.74 (d, J=9.9 Hz, 1H), 3.57 (ddd, J=10.2, 3.4, 1.4 Hz, 1H), 3.39 (dd, J=9.2, 6.4 Hz, 1H), 2.60 (s, 3H), 2.56 (dd, J=12.1, 10.8 Hz, 1H), 2.50 (ddd, J=17.2, 7.2, 3.7 Hz, 1H), 2.29 (app dtdd, J=14.9, 12.0, 6.1, 2.6 Hz, 1H), 2.06 (app t, J=14.2 Hz, 1H), 1.95 (s, 3H), 1.41 (d, J=6.9 Hz, 3H). HRMS (ESI+, m/z): [M+H]$^+$ calcd for $C_{30}H_{39}N_3O_6S_2$, 602.2353; found 602.2353.

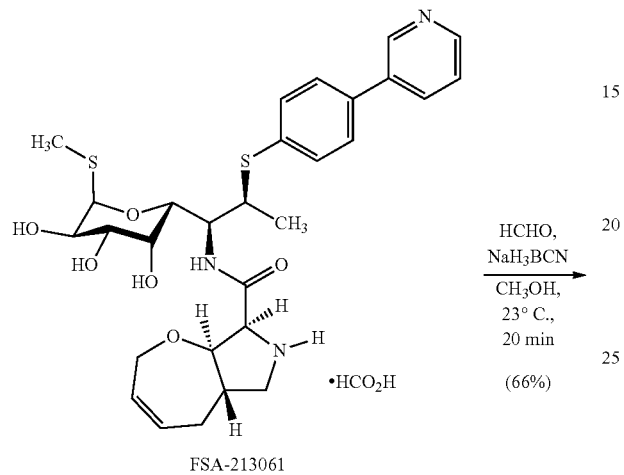

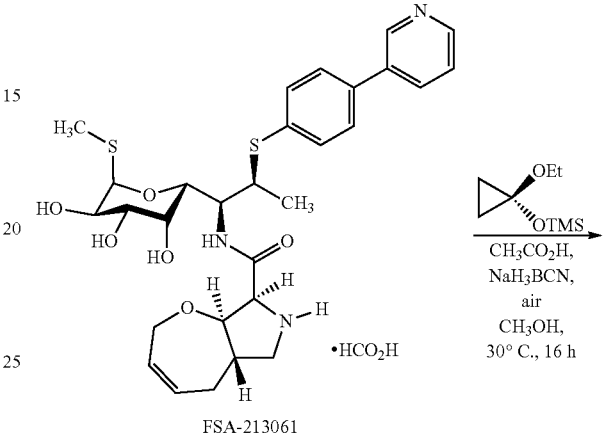

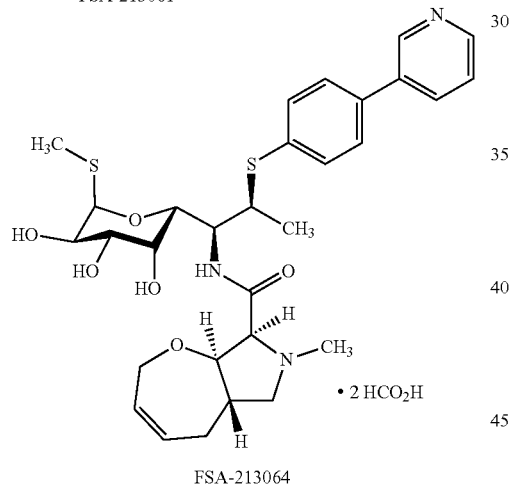

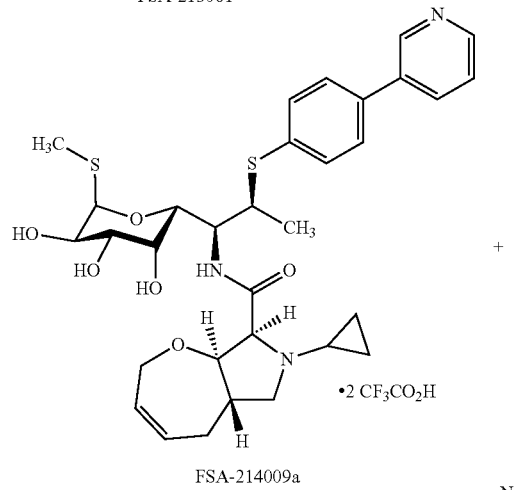

To a solution of FSA-213061·HCO$_2$H (15 mg, 24 μmol, 1 equiv) in methanol (470 μL) was added formalin (3.5 μL, 47 μmol, 2.0 equiv). After stirring the resulting solution for 5 min at 23° C., sodium cyanoborohydride (4.5 mg, 71 μmol, 3.0 equiv) was added. After 20 min, LCMS analysis indicated that no starting material remained. The reaction mixture was directly subjected to preparative HPLC on a Waters SunFire Prep C18 column (5 μm, 250×19 mm; eluting with 0.1% formic acid-5% acetonitrile-water initially, grading to 0.1% formic acid-40% acetonitrile-water over 25 min, with a flow rate of 15 mL/min; monitored by UV absorbance at 280 nm) to provide FSA-213064·2 HCO$_2$H as a white solid (11 mg, 66%). $^1$H NMR (600 MHz, CD$_3$OD) δ 8.81 (s, 1H), 8.52 (d, J=4.6 Hz, 1H), 8.18 (s, 2H), 8.10 (app dq, J=8.0, 1.7 Hz, 1H), 7.66 (d, J=8.3 Hz, 2H), 7.56 (d, J=8.1 Hz, 2H), 7.53 (dd, J=7.9, 4.9 Hz, 1H), 5.83-5.79 (m, 1H), 5.67-5.63 (m, 1H), 5.27 (d, J=5.6 Hz, 1H), 4.58 (app dt, J=10.0, 1.9 Hz, 1H), 4.41 (d, J=10.0 Hz, 1H), 4.36 (dd, J=16.4, 5.7 Hz, 1H),

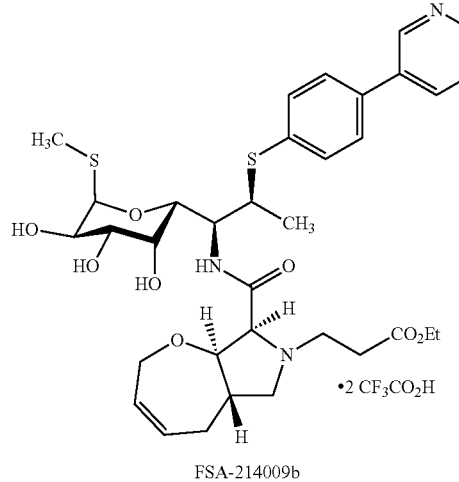

A 1-mL glass vial was charged sequentially with pyrrolidine hydroformate salt FSA-213061·HCO$_2$H (8.5 mg, 0.013 mmol, 1 equiv), methanol (150 µL), activated powdered 4 Å molecular sieves (10 mg), acetic acid (7.7 µL, 0.13 mmol, 10 equiv), and (1-ethoxycyclopropoxy)trimethylsilane (16 µL, 0.080 mmol, 6.0 equiv). The vial, originally open to air, was sealed, and the resulting white suspension was stirred at 23° C. for 10 min. Sodium cyanoborohydride (3.8 mg, 0.060 mmol, 4.5 equiv) was then added, the vial was re-sealed, and the mixture was heated at 30° C. for 16 h. At this point LCMS analysis indicated complete consumption of starting material, with concomitant formation of N-cyclopropanated product FSA-214009a and ester FSA-214009b (ca. 2:1 mixture), the latter likely arising through the generation of ethyl acrylate in situ via aerobic ring-opening fragmentation of (1-ethoxycyclopropoxy)trimethylsilane or a derivative thereof. The reaction mixture was diluted with dichloromethane (2 mL), and saturated aqueous sodium bicarbonate solution (2 mL) was added. The mixture was agitated, and the layers were separated. The aqueous phase was extracted with additional dichloromethane (3×2 mL), and the combined organic extracts were dried over sodium sulfate. The dried product solution was filtered, and the filtrate was concentrated to afford a colorless film. This residue was purified by preparative HPLC on a Waters SunFire Prep C18 column (5 µm, 250×19 mm; eluting with 0.1% trifluoroacetic acid-10% acetonitrile-water, grading to 0.1% trifluoroacetic acid-40% acetonitrile-water over 40 min, with a flow rate of 15 mL/min; monitored by UV absorbance at 280 nm; FSA-214009a $R_t$=18.3 min, FSA-214009b $R_t$=21.5 min) to provide FSA-214009a.2 $CF_3CO_2H$ (3.9 mg, 34%) and FSA-214009b.2 $CF_3CO_2H$ (3.5 mg, 29%).

FSA-214009a.2 $CF_3CO_2H$: $^1H$ NMR (600 MHz, $CD_3OD$) δ 9.07 (br, 1H), 8.73 (br, 1H), 8.70-8.26 (m, 1H), 8.00-7.93 (m, 1H), 7.74 (d, J=8.4 Hz, 2H), 7.55 (d, J=8.5 Hz, 2H), 5.86-5.80 (m, 1H), 5.73-5.68 (m, 1H), 5.27 (d, J=5.7 Hz, 1H), 4.75 (dd, J=10.1, 2.2 Hz, 1H), 4.65-4.61 (m, 1H), 4.49 (d, J=10.2 Hz, 1H), 4.38-4.30 (m, 2H), 4.22 (dd, J=16.0, 1.9 Hz, 1H), 4.12 (dd, J=10.2, 5.6 Hz, 1H), 3.98 (qd, J=7.0, 2.2 Hz, 1H), 3.88 (dd, J=3.1, 1.0 Hz, 1H), 3.75 (dd, J=10.8, 6.3 Hz, 1H), 3.59 (dd, J=10.2, 3.3 Hz, 1H), 3.21 (app t, J=11.3 Hz, 1H), 2.90 (br, 1H), 2.55 (ddd, J=17.0, 7.3, 3.5 Hz, 1H), 2.29 (br, 1H), 2.14 (app t, J=14.6 Hz, 1H), 1.87 (s, 3H), 1.46 (d, J=6.9 Hz, 3H), 1.13-1.09 (m, 1H), 1.05-1.01 (m, 1H), 0.93-0.87 (m, 2H). HRMS (ESI+, m/z): $[M+H]^+$ calcd for $C_{32}H_{41}N_3O_6S_2$, 628.2510; found 628.2509.

FSA-214009b.2 $CF_3CO_2H$: $^1H$ NMR (500 MHz, $CD_3OD$) δ 9.04 (s, 1H), 8.71 (d, J=5.4, 1H), 8.63 (d, J=8.1 Hz, 1H), 7.94 (dd, J=8.2, 5.4 Hz, 1H), 7.73 (d, J=8.4 Hz, 2H), 7.55 (dd, J=8.5 Hz, 2H), 5.86-5.81 (m, 1H), 5.76-5.71 (m, 1H), 5.26 (d, J=5.6 Hz, 1H), 4.74 (dd, J=10.0, 2.3 Hz, 1H), 4.51 (dd, J=10.0, 4.0 Hz, 2H), 4.40 (dd, J=16.3, 5.7 Hz, 1H), 4.31 (app t, J=9.4 Hz, 1H), 4.27-4.19 (m, 3H), 4.10 (dd, J=10.2, 5.6 Hz, 1H), 3.96 (qd, J=7.3, 2.6 Hz, 1H), 3.91 (d, J=2.5 Hz, 1H), 3.81 (dd, J=10.8, 6.3 Hz, 1H), 3.59 (dd, J=10.2, 3.3 Hz, 1H), 3.55-3.49 (m, 2H), 3.08 (app t, J=12.0 Hz, 1H), 2.83 (t, J=7.2 Hz, 2H), 2.56 (ddd, J=16.5, 6.7, 3.2 Hz, 1H), 2.35-2.25 (br, 1H), 2.13 (app t, J=14.0 Hz, 1H), 1.85 (s, 3H), 1.48 (d, J=7.0 Hz, 3H), 1.29 (t, J=7.1 Hz, 3H). HRMS (ESI+, m/z): $[M+H]^+$ calcd for $C_{34}H_{45}N_3O_8S_2$, 688.2721; found 688.2724.

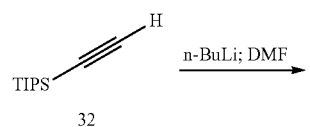

To a solution of ethynyltriisopropylsilane (32, 20.0 g, 110 mmol, 1 equiv) in diethyl ether (100 mL) was added n-butyllithium solution (2.12 M in hexane, 51.7 mL, 110 mmol, 1.00 equiv) slowly by cannula at 0° C. over approximately 15 min. The resulting solution was stirred at 0° C. for an additional 40 min. This lithium acetylide solution was then transferred via cannula over a period of 5-10 min to a 500-mL round-bottomed flask containing a mixture of N,N-dimethylformamide (25.5 mL, 329 mmol, 3.00 equiv) and diethyl ether (100 mL) chilled to −78° C. A white suspension formed. The reaction mixture was stirred at −78° C. for 1 h before warming to 0° C., at which temperature the mixture became homogeneous. After 1 h of stirring at 0° C., the mixture was transferred to an ice-cold aqueous sulfuric acid solution (5% v/v, 250 mL). The resulting biphasic mixture was stirred at 0° C. for 1 h, and then the layers were separated. The aqueous phase was extracted with diethyl ether (3×150 mL), and the combined organic extracts were washed with saturated aqueous sodium chloride solution (150 mL). The washed organic solution was dried over sodium sulfate, the dried solution was filtered, and the filtrate was concentrated to give 3-(triisopropylsilyl)propiolaldehyde (33) as a colorless oil that was used in the next step without further purification. The $^1H$ NMR data matched literature values.

Horner-Wadsworth-Emmons olefination of the crude ynal formed in the preceding formylation reaction was performed according to the procedure reported by Bode and co-workers. An oven-dried 2-L round-bottomed flask was charged with lithium chloride (5.60 g, 132 mmol, 1.20 equiv), and the apparatus was flame-dried. Once cooled, the flask was charged with a magnetic stir bar and acetonitrile (1.3 L), and the resulting suspension was stirred at 23° C. for 10 min (lithium chloride does not fully dissolve). 3-(Triisopropylsilyl)propriolaldehyde (33, theoretically 110 mmol, 1 equiv) and triethyl phosphonoacetate (22.5 mL, 112 mmol, 1.02 equiv) were then added sequentially. 1,8-Diazabicyclo [5.4.0]undec-7-ene (DBU, 16.6 mL, 110 mmol, 1.00 equiv) was added dropwise over 5 min, causing the mixture to warm to approximately 40° C. with concomitant transformation of the originally colorless reaction solution to an opaque, off-white suspension. Progress was monitored by TLC (20% dichloromethane-hexanes, UV+PAA); after 10 min, the reaction was judged to be complete. The mixture was concentrated by rotary evaporation to a volume of approximately 300 mL, and the concentrated mixture was transferred to a separatory funnel containing saturated aqueous ammonium chloride solution (400 mL) and diethyl ether (300 mL). The mixture was shaken, and the layers were separated. The aqueous phase was extracted with diethyl ether (3×300 mL); the combined organic layers were then washed sequentially with water (250 mL) and saturated aqueous sodium chloride solution (250 mL). The washed organic solution was dried over sodium sulfate, the dried solution was filtered, and the filtrate was concentrated to give ethyl (E)-5-(triisopropylsilyl)pent-2-en-4-ynoate as a colorless oil that was used in the next step without further purification. The $^1$H NMR data matched literature values.

Reduction of the crude ester formed in the preceding Horner-Wadsworth-Emmons olefination reaction was performed according to the procedure reported by Bressy and co-workers. To a rapidly stirred solution of crude ethyl (E)-5-(triisopropylsilyl)pent-2-en-4-ynoate (theoretically 110 mmol, 1 equiv) in diethyl ether (220 mL) was added diisobutyl aluminum hydride (1.0 M solution in hexane, 243 mL, 2.2 equiv) by cannula at −78° C. The mixture was stirred at −78° C. for 1 h, then at 0° C. for 1.5 h. The reaction mixture was then transferred by wide-bore cannula to a 2-L round-bottomed flask containing a rapidly stirred aqueous Rochelle salt solution (potassium sodium tartrate, 0.80 M, 410 mL, 328 mmol, 3.0 equiv) pre-chilled to 0° C. A cloudy slurry formed immediately upon aqueous quenching of the reaction mixture; after approximately 3 min of stirring at 0° C., this suspension thickened to form a gel. Gas evolution was then observed, followed by gradual collapse of the gel to form a cloudy, light yellow emulsion. The mixture was stirred at 23° C. overnight under an atmosphere of nitrogen gas, during which time the emulsion separated into a biphasic mixture. The layers were separated at the end of this period, and the aqueous phase was extracted with diethyl ether (3×200 mL). The combined organic layers were then washed with saturated aqueous sodium chloride solution (200 mL), and the washed organic product solution was dried over sodium sulfate. The dried solution was filtered, and the filtrate was concentrated to give a light yellow oil. This residue was purified by flash-column chromatography (500 g silica gel, eluting with 5% ethyl acetate-hexanes initially, grading to 10% ethyl acetate-hexanes) to afford allylic alcohol 34 as a colorless oil (19.7 g, 75%, 3 steps). The $^1$H NMR data matched literature values.

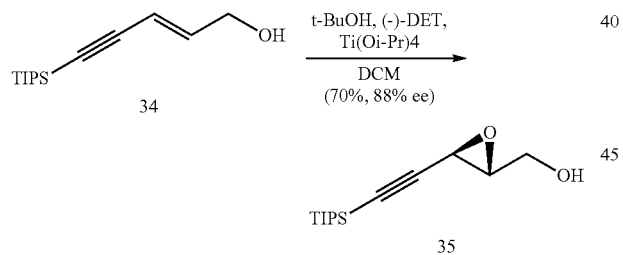

A 1-L, 2-necked round-bottomed flask was oven-dried. Once cooled, the flask was charged with a magnetic stir bar and powdered 4-Å molecular sieves (20.0 g, Sigma-Aldrich, activated by heating overnight in a vacuum drying oven [200° C., 70 Torr]). A thermocouple probe was fitted to one neck of the flask, while the other neck was sealed with a rubber septum. Dichloromethane (229 mL) was added, and the resulting slurry was cooled to −30° C. in a CryoCool bath. (−)-Diethyl-D-tartrate (7.21 mL, 41.9 mmol, 0.500 equiv) was added. Titanium(IV) isopropoxide (9.83 mL, 33.6 mmol, 0.400 equiv) was then added dropwise over 2 min, causing the internal temperature to rise to −26° C. briefly. The resulting mixture was stirred at −30° C. for 20 min, after which time a solution of allylic alcohol 34 (20.0 g, 84.0 mmol, 1 equiv) in dichloromethane (295 mL) was added slowly by cannula over 10 min. The mixture was incubated at −30° C. for 30 min. tert-Butylhydroperoxide solution (TBHP, ~5.5 M solution in decane, 30.5 mL, 170 mmol, 2.0 equiv) was finally added at a rate of 2.0 mL/min with a syringe pump, such that the internal temperature of the mixture did not rise above −28° C. Stirring was maintained at −30° C. following the addition of TBHP, and progress was monitored by TLC (10% ethyl acetate-dichloromethane, UV+PAA). After 21 h, the reaction was judged to be complete. A solution comprising iron(II) sulfate heptahydrate (27 g, 97 mmol, 1.2 equiv), DL-tartaric acid (62 g, 0.41 mol, 4.9 equiv), and water (517 mL) was added to the reaction mixture, and the resulting biphasic mixture was stirred at 0° C. for 10 min at a moderate stir rate (350 rpm) The mixture was then transferred to a separatory funnel where the layers were separated. The aqueous phase was extracted with diethyl ether (3×300 mL), and the combined organic layers were washed with saturated aqueous sodium chloride solution (2×200 mL). The washed organic solution was dried over sodium sulfate, the dried solution was filtered, and the filtrate was concentrated to give a slightly cloudy colorless oil. This residue was purified by flash-column chromatography (800 g silica gel, eluting with 5% ethyl acetate-hexanes initially, grading to 15% ethyl acetate-hexanes) to give epoxyalcohol product as a colorless, viscous oil (14.9 g, 70%). The $^1$H NMR data matched reported values.

The enantiomeric excess was determined by conversion to the corresponding Mosher esters. In this procedure, a solution of epoxyalcohol 35 (10 mg, 39 μmol, 1 equiv) in 4:1 dichloromethane-pyridine (200 μL) was treated with (R)-3,3,3-trifluoro-2-methoxy-2-phenylpropanoyl chloride (8.8 μL, 47 μmol, 1.2 equiv) at 23° C. The mixture was stirred at 23° C. for 30 min, at which point TLC analysis (50% ethyl acetate-hexanes, UV+KMnO$_4$) indicated complete consumption of starting material. The reaction mixture was concentrated, and the crude residue was subjected to $^1$H NMR analysis (600 MHz, CDCl$_3$). Integration of the major methylene resonance at δ 4.60 (dd, J=12.3, 3.2 Hz, 1H) relative to its minor diastereomeric counterpart at δ 4.66 (dd, J=12.5, 3.0 Hz, 1H, derived from undesired (2S,3S)-product enantiomer) demonstrated an enantiomeric ratio of 94:6 (88% ee). Use of the enantiomeric (S)-Mosher acyl chloride reagent gave the same result.

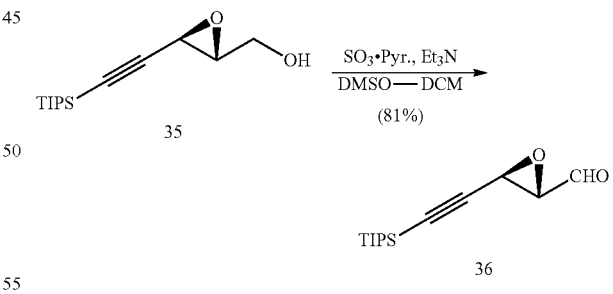

A solution of epoxyalcohol 35 (14.9 g, 58.6 mmol, 1 equiv) in dichloromethane (468 mL) and anhydrous dimethyl sulfoxide (117 mL) was treated with triethylamine (65.3 mL, 468 mmol, 8.00 equiv). Sulfur trioxide-pyridine complex (37.3 g, 234 mmol, 4.00 equiv) was then added in three portions over 15 min at 23° C. The resulting salmon-pink solution was stirred at 23° C., and after 2 h, TLC analysis (30% ethyl acetate-hexanes, PAA) indicated complete consumption of starting material. The reaction mixture was transferred to a separatory funnel containing 1.2 L of 0.5 M copper(II) sulfate solution. The layers were shaken, then separated, and the aqueous phase was extracted with dichloromethane (3×300 mL). The combined organic layers were then washed with saturated aqueous sodium chloride solution (200 mL), and the washed organic product solution was dried over sodium sulfate.

The dried solution was filtered, and the filtrate was concentrated to give a brown oil. This residue was purified by flash-column chromatography (600 g silica gel, eluting with 5% ethyl acetate-hexanes initially, grading to 10% ethyl acetate-hexanes) to afford the product as a colorless oil (12.0 g, 81%). $^1$H NMR (500 MHz, CDCl$_3$): δ 9.02 (d, J=6.1 Hz, 1H), 3.69 (d, J=1.8 Hz, 1H), 3.54 (dd, J=6.1, 1.8 Hz, 1H), 1.07 (s, 21H). HRMS (ESI+, m/z): [M+H]$^+$ calcd for C$_{14}$H$_{24}$O$_2$Si, 252.1542; found 252.1540.

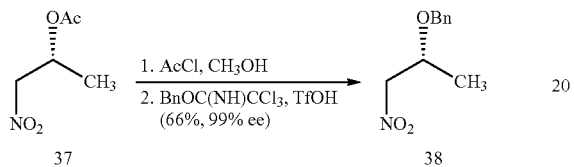

Acetyl chloride (123 mL, 1.73 mol, 12.8 equiv) was added dropwise over 15 min to a solution of (R)-1-nitropropan-2-yl acetate (37, 20.0 g, 136 mmol, 1 equiv) in methanol (1.23 L) at 0° C. Following the addition of acetyl chloride, the mixture was allowed to warm to 23° C.; progress was monitored by TLC (40% ethyl acetate-hexanes, KMnO$_4$). After 2 h, complete consumption of starting material was noted, and the mixture was concentrated by rotary evaporation to obtain (R)-1-nitropropan-2-ol as a faint yellow oil. Residual methanol present in the crude product was removed azeotropic removal of benzene. The crude product thus obtained was used in the next step without further purification.

To a solution of (R)-1-nitropropan-2-ol (theoretically 136 mmol) in 1:2 dichloromethane-hexane (412 mL) was added benzyl 2,2,2-trichloroacetimidate (30.5 mL, 163 mmol, 1.20 equiv). Trifluoromethanesulfonic acid (1.21 mL, 13.6 mmol, 0.100 equiv) was then added dropwise over 30 min at 23° C., causing a white precipitate to appear. After 5 h, TLC analysis (20% ethyl acetate-hexanes, UV+KMnO$_4$) indicated that all starting material had been consumed. The reaction mixture was filtered through a pad of Celite to remove the trichloroacetamide precipitate, and the filter pad was washed with hexanes (2×50 mL). The filtrate was concentrated to give a muddy brown slurry, which was purified by two sequential recrystallizations from 1% ethyl acetate-hexanes (200 mL) to give benzyl ether 7 as a brilliant white, fluffy powder (17.4 g, 66%, 2 steps). The $^1$H NMR and melting-point data matched reported values. Enantiomeric excess was determined to be ≥99% by chiral HPLC analysis using a chiral stationary-phase AD-H column using 2% isopropanol-hexanes as eluent at a flow rate of 1.0 mL/min, with detection at 300 nm. Major enantiomer R$_t$=14.7 min, minor enantiomer R$_t$=11.7 min.

To a mixture of (R,R)-diaminocyclohexane ligand 39 (1.75 g, 47.5 mmol, 0.0100 equiv) and anhydrous copper(II) acetate (863 mg, 4.75 mmol, 0.0100 equiv) was added 1,4-dioxane (47.5 mL mL). The resulting dark forest-green solution was stirred at 23° C. for 30 min before N,N-diisopropylethylamine (830 μL, 4.75 mmol, 0.0100 equiv) was added. The catalyst mixture was then stirred an additional 10 min at 23° C. before cooling to 5-10° C. in an ice-water bath. Nitropropane 38 (12.1 g, 61.8 mmol, 1.30 equiv) was added in one portion, followed by the epoxyaldehyde 36 (12.0 g, 47.5 mmol, 1 equiv), which was added by cannula transfer (transfer was quantitated with 2×2 mL 1,4-dioxane rinses). The mixture was then transferred to a 4° C. coldroom, where constant stirring was maintained at that temperature. Progress was monitored by NMR as follows: Aliquots of the reaction mixture (ca. 50 μL) were diluted with ethyl acetate (2 mL), and the diluted samples were washed with saturated aqueous ammonium chloride solution (1 mL). The washed samples were then dried by passage through a short plug of sodium sulfate (1×2 cm), and the dried filtrate was concentrated. The green-brown residue thus obtained was analyzed by $^1$H NMR (CDCl$_3$), where consumption of aldehyde 36 was gauged relative to the triisopropylsilyl signal (δ 1.15-1.00, 21H). After 48 h at 4° C., conversion of aldehyde 36 had reached ≥95%, and triethylamine (13.3 mL, 95.0 mmol, 2.00 equiv) was added to induce cyclization. The mixture was warmed to 23° C. and stirred for 20 h, whereupon aliquot NMR analysis (as above) showed the absence of epoxide methine resonances (ca. δ 3.45, 3.30), with concomitant formation of isoxazoline N-oxide products as a 98:2 diastereomeric mixture. The product mixture was poured into a separatory funnel containing 175 mL saturated aqueous ammonium chloride solution, and the resulting mixture was extracted with ethyl acetate (3×150 mL). The combined organic extracts were washed with saturated aqueous sodium chloride solution (50 mL), and the washed organic phase was dried over sodium sulfate. The dried product solution was filtered, and the filtrate was concentrated to afford crude product as a dark brown oil. This residue was purified by flash-column chromatography (2.0 kg silica; eluting 10% ethyl acetate-hexanes initially, grading to 30% ethyl acetate-hexanes) to afford the isoxazoline N-oxide product as an amber-brown, viscous oil (16.4 g, 77%). $^1$H NMR (600 MHz, CDCl$_3$): δ 7.37-7.29 (m, 5H), 5.14 (app t, J=6.9 Hz, 1H), 4.77 (app t, J=5.4 Hz, 1H), 4.66 (d, J=12.1 Hz, 1H), 4.63 (q, J=6.7 Hz, 1H), 4.43 (d, J=12.2 Hz, 1H), 3.92 (dd, J=6.7, 5.6 Hz, 1H), 3.60 (d, J=7.2 Hz, 1H), 3.35 (d, J=5.8 Hz, 1H), 1.49 (d, J=6.7 Hz, 3H), 1.09 (br s, 21H). HRMS (ESI+, m/z): [M+H]$^+$ calcd for C$_{24}$H$_{37}$NO$_5$Si, 448.2514; found 448.2529.

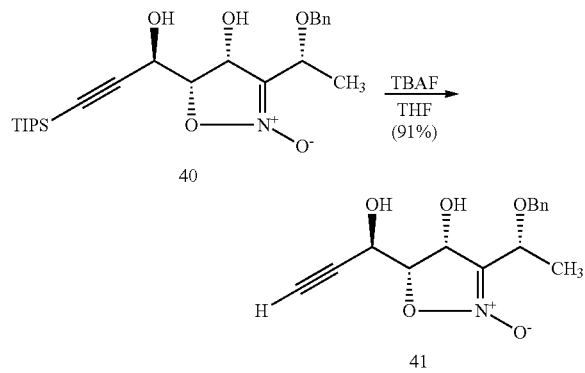

A solution of tetrabutylammonium fluoride (1.0 M in tetrahydrofuran, 88 mL, 88 mmol, 2.5 equiv) was added via cannula over 5 min to a solution of alkynyl silane 40 (15.8 g, 35.3 mmol, 1 equiv) in tetrahydrofuran (118 mL) at 0° C. The mixture was then warmed to 23° C., and after 90 min of stirring at this temperature, TLC analysis (50% ethyl acetate-hexanes, UV+KMnO4) indicated full conversion of starting material. The product solution was then poured into a separatory funnel containing 350 mL of water to which 35 mL of saturated aqueous sodium chloride solution had been added. The resulting biphasic mixture was extracted with ethyl acetate (3×150 mL). The organic layers were combined, and the organic solution was washed with saturated aqueous sodium chloride solution (100 mL). The washed product solution was dried over sodium sulfate, and the dried solution was filtered. The filtrate was concentrated to afford crude product as a light amber oil. This residue was purified by flash-column chromatography (500 g silica; eluting 35% ethyl acetate-hexanes initially, grading to 50% ethyl acetate-hexanes) to afford the product as a sand-colored, powdery solid (9.38 g, 91%). $^1$H NMR (600 MHz, CDCl$_3$): δ 7.37-7.29 (m, 5H), 5.22 (d, J=6.7 Hz, 1H), 4.77 (dd, J=6.3, 2.3 Hz, 1H), 4.61 (q, J=6.7 Hz, 1H), 4.60 (d, J=12.2 Hz, 1H), 4.45 (d, J=12.1 Hz, 1H), 4.06 (app t, J=6.5 Hz, 1H), 4.03 (br s, 1H), 2.59 (d, J=2.2 Hz, 1H), 1.48 (d, J=6.7 Hz, 3H). HRMS (ESI+, m/z): [M+Na]$^+$ calcd for C$_{15}$H$_{17}$NO$_5$, 314.0999; found 314.1009.

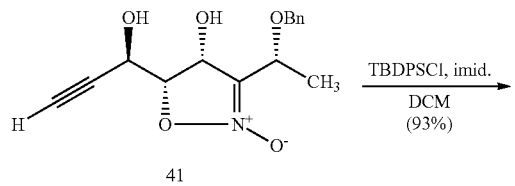

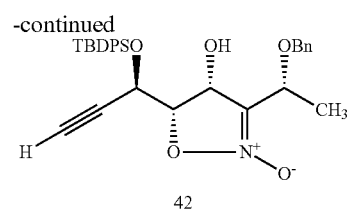

A mixture of diol 41 (9.38 g, 32.2 mmol, 1 equiv) and imidazole (6.58 g, 97.0 mmol, 3.00 equiv) was dissolved in dichloromethane (161 mL), and the resulting solution was cooled to 0° C. tert-Butyl(chloro)diphenylsilane (12.4 mL, 48.3 mmol, 1.50 equiv) was then added in one portion, and the solution was warmed to 23° C. Within 2-5 min of addition of the silyl chloride, a precipitate formed, imparting a cloudy appearance to the reaction mixture. Progress was monitored by TLC (60% ethyl acetate-hexanes, UV+KMnO4), and after 45 min, full consumption of starting material was observed. The reaction mixture was quenched with the addition of 150 mL saturated aqueous sodium bicarbonate solution, and the mixture was stirred rapidly at 23° C. for 10 min. The biphasic mixture was then extracted with dichloromethane (3×50 mL), and the combined organic extracts were washed with brine (50 mL). The organic solution was then dried over sodium sulfate, and the dried solution was filtered. The filtrate was concentrated to give a peach-colored oil, which was purified by flash-column chromatography (700 g silica; eluting with hexanes initially, grading to 25% ethyl acetate-hexanes) to give the product as a colorless, highly viscous oil (15.8 g, 93%). $^1$H NMR (500 MHz, CDCl$_3$): δ 7.75-7.68 (m, 4H), 7.49-7.44 (m, 2H), 7.43-7.28 (m, 9H), 5.17 (app t, J=7.6 Hz, 1H), 4.72 (dd, J=4.6, 2.2 Hz, 1H), 4.66 (q, J=6.8 Hz, 1H), 4.64 (d, J=12.2 Hz, 1H), 4.46 (d, J=12.1 Hz, 1H), 4.02 (dd, J=6.9, 4.7 Hz, 1H), 3.59 (d, J=8.3 Hz, 1H), 2.45 (d, J=2.3 Hz, 1H), 1.50 (d, J=6.8 Hz, 3H), 1.09 (s, 9H). HRMS (ESI+, m/z): [M+Na]$^+$ calcd for C$_{31}$H$_{35}$NO$_5$Si, 552.2177; found 552.2177.

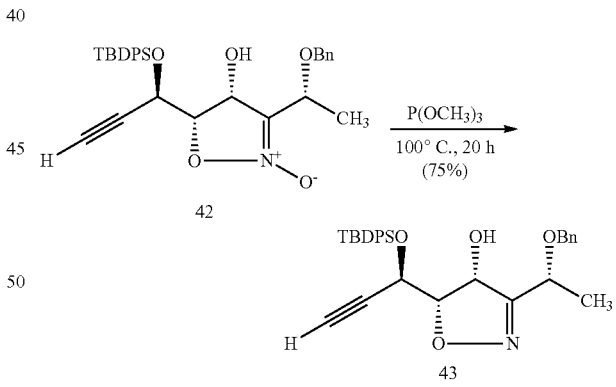

A 500-mL round-bottomed flask was charged with isoxazoline N-oxide 42 (15.7 g, 29.6 mmol), and this substrate was dried by azeotropic removal of benzene. Once dried, the starting material was dissolved in trimethyl phosphite (119 mL; CAUTION: Trimethyl phosphite is a highly malodorous, volatile substance—all operations up to and including the aqueous acid quench should be carried out in a well-ventilated fume hood), and the flask was sealed. The mixture was heated to 100° C. in a pre-heated oil bath for 20 h, at which point TLC analysis (30% ethyl acetate-hexanes, UV+PAA) indicated full consumption of starting material. The solution was cooled to 23° C., and the cooled product solution was transferred to a 2-L round-bottomed flask containing 500 mL of diethyl ether. The product solution was cooled to 5° C. in an ice-water bath, and the chilled mixture was treated very carefully with 1N aqueous hydrochloric acid solution (100 mL, added in 1-mL portions over 30 minutes). Care was taken not to allow the internal temperature of the mixture rise above 15° C. during the acidification procedure. The acidified mixture was transferred to a separatory funnel, where the layers were separated. The organic layer was washed with 1N aqueous hydrochloric acid solution (2×75 mL). The combined aqueous washes were extracted with fresh portions of diethyl ether (2×75 mL). The combined organic phases were then washed sequentially with half-saturated aqueous sodium chloride solution (50 mL), and saturated aqueous sodium chloride solution (50 mL). The organic layer was then dried over sodium sulfate, the dried solution was filtered, and the filtrate was concentrated to afford crude product as a light yellow oil. The crude material was purified by flash-column chromatography (700 g silica; eluting with 5% ethyl acetate-hexanes initially, grading to 25% ethyl acetate-hexanes) to provide the isoxazoline product as a light peach-colored, highly viscous oil (11.5 g, 75%). $^1$H NMR (600 MHz, CDCl$_3$): δ 7.79-7.76 (m, 4H), 7.50-7.46 (m, 2H), 7.44-7.41 (m, 4H), 7.37-7.34 (m, 4H), 7.32-7.29 (m, 1H), 5.28 (app t, J=8.3 Hz, 1H), 4.88 (dd, J=4.0, 2.3 Hz, 1H), 4.58 (q, J=6.8 Hz, 1H), 4.56 (d, J=12.3 Hz, 1H), 4.53 (d, J=12.0 Hz, 1H), 4.23 (d, J=8.2, 4.0 Hz, 1H), 4.15 (d, J=8.6 Hz, 1H), 2.48 (d, J=2.3 Hz, 1H), 1.59 (d, J=6.8 Hz, 3H), 1.10 (s, 9H). HRMS (ESI+, m/z): [M+H]$^+$ calcd for C$_{31}$H$_{35}$NO$_4$Si, 514.2408; found 514.2424.

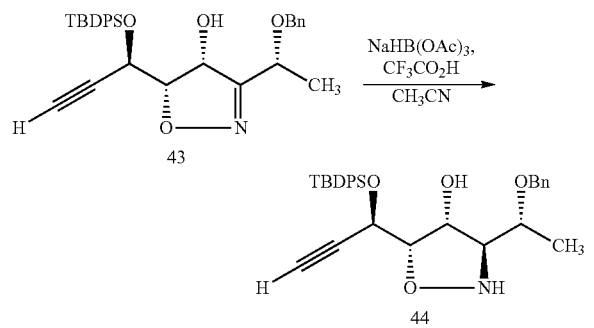

A mixture of isoxazoline 43 (11.4 g, 22.1 mmol, 1 equiv) and sodium triacetoxyborohydride (23.4 g, 110 mmol, 5.00 equiv) was suspended in anhydrous acetonitrile (184 mL). The resulting milky-white suspension was cooled to 0° C. in an ice-water bath with constant stirring, and to the cooled suspension was added trifluoroacetic acid (170 mL, 2.21 mol, 100 equiv) over 10 min via an oven-dried pressure-equalizing addition funnel. Addition of trifluoroacetic acid caused the suspension to resolve into a colorless solution; following this addition, the ice-water bath was removed, and the reaction solution was allowed to warm to 23° C. Progress was monitored by TLC (30% ethyl acetate-hexanes, UV+PAA), and after 2.5 h, starting material was fully consumed. The mixture was cooled to 0° C., and was then transferred via cannula to a stirred, ice-cold mixture of dichloromethane (300 mL) and 2N aqueous sodium hydroxide solution (1.10 L, 2.21 mol). The resulting biphasic mixture was stirred rapidly for 10 min. Additional sodium hydroxide solution was added as necessary, until the aqueous phase attained pH >8. The mixture was then transferred to a separatory funnel, and the layers were separated. The aqueous layer was extracted with dichloromethane (3×300 mL), and the combined organic extracts were washed with brine (300 mL). The washed organic layer was dried over sodium sulfate, the dried solution was filtered, and the filtrate was concentrated to afford crude isoxazolidine product as a colorless oil. This material was used in the next step without further purification.

For characterization purposes, a small quantity (ca. 25 mg) of crude residue was purified by HPLC (eluting with 0.1% trifluoroacetic acid-25% acetonitrile-water, grading to 0.1% trifluoroacetic acid-95% acetonitrile-water over 45 min, with a flow rate of 15 mL/min; monitored by UV absorbance at 254 nm; product R$_t$=33.5 min). The trifluoroacetic acid salt thus obtained (44.CF$_3$CO$_2$H) exhibited the following spectral properties: $^1$H NMR (600 MHz, CDCl$_3$) δ 7.76-7.69 (m, 4H), 7.48-7.43 (m, 2H), 7.42-7.28 (m, 9H), 4.91 (dd, J=5.1, 2.8 Hz, 1H), 4.74 (dd, J=4.9, 2.2 Hz, 1H), 4.66 (d, J=11.5 Hz, 1H), 4.40 (d, J=11.6 Hz, 1H), 3.98 (app t, J=5.0 Hz, 1H), 3.81 (m, 1H), 3.51 (app t, J=3.3 Hz, 1H), 2.40 (d, J=2.2 Hz, 1H), 1.39 (d, J=6.2 Hz, 3H), 1.09 (s, 9H). HRMS (ESI+, m/z): [M+Na]$^+$ calcd for C$_{31}$H$_{37}$NO$_4$Si, 538.2384; found 538.2385.

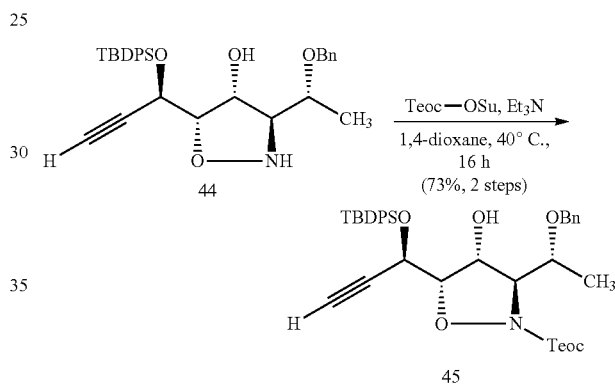

A 200-mL round-bottomed flask was charged with isoxazolidine 44 (crude product from the preceding directed reduction step, theoretically 22.1 mmol). The starting material was dissolved in 1,4-dioxane (55 mL) and to the resulting solution, triethylamine (15.4 mL, 110 mmol, 5.00 equiv) and N-[2-(trimethylsilyl)ethoxycarbonyloxy]succinimide (Teoc-OSu, 8.59 g, 33.1 mmol, 1.50 equiv) were added sequentially. The reaction mixture was heated to 40° C., and consumption of starting material was monitored by LCMS. After 16 h, the reaction was judged to be complete. The reaction mixture was then diluted in 450 mL of ethyl acetate, and the diluted product solution was washed with saturated aqueous ammonium chloride solution (3×50 mL). The combined aqueous washes were extracted with a portion of fresh ethyl acetate (100 mL), and the combined organic layers were then washed with saturated aqueous sodium chloride solution (50 mL). The washed organic product solution was dried over sodium sulfate, the dried solution was filtered, and the filtrate was concentrated to give a viscous orange oil. This material was purified by flash-column chromatography (1.00 kg silica gel, eluting with 5% ethyl acetate-hexanes initially, grading to 20% ethyl acetate-hexanes) to afford the product as a highly viscous, colorless oil (10.6 g, 73%, 2 steps). $^1$H NMR (600 MHz, CDCl$_3$): δ 7.78-7.74 (m, 4H), 7.48-7.44 (m, 2H), 7.42-7.36 (m, 4H), 7.35-7.27 (m, 5H), 4.90 (app t, J=3.8 Hz, 1H), 4.79 (dd, J=6.2, 2.2 Hz, 1H), 4.67 (d, J=11.8 Hz, 1H), 4.48 (d, J=11.8

Hz, 1H), 4.25-4.12 (m, 4H), 3.65 (app p, J=6.3 Hz, 1H), 3.31 (d, J=3.9 Hz, 1H), 2.36 (d, J=2.2 Hz, 1H), 1.33 (d, J=6.2 Hz, 3H), 1.10 (s, 9H), 1.05-0.94 (m, 2H), 0.04 (s, 9H). HRMS (ESI+, m/z): [M+H]+ calcd for $C_{37}H_{49}NO_6Si_2$, 660.3171; found 660.3161.

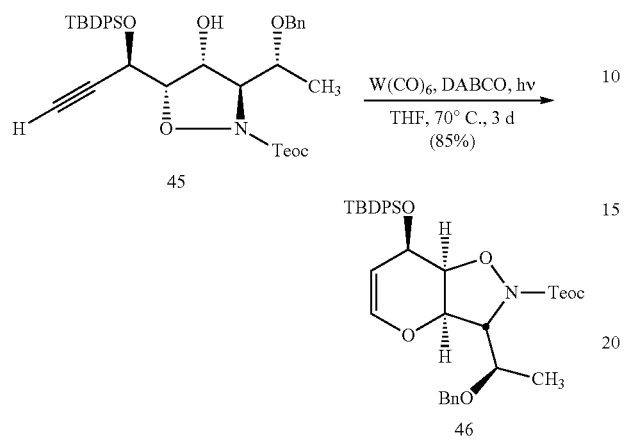

In a 200-mL round-bottomed flask, alkynol 45 (4.17 g, 6.32 mmol, 1 equiv) was dried by azeotropic removal of benzene under vacuum. The flask was back-filled with argon, and tungsten hexacarbonyl (556 mg, 1.58 mmol, 0.250 equiv), 1,4-diazabicyclo[2.2.2]octane (DABCO, 1.42 g, 12.6 mmol, 2.00 equiv), and degassed, anhydrous tetrahydrofuran (63.2 mL) were then added sequentially (CAUTION: Tungsten hexacarbonyl is a volatile source of metal and of carbon monoxide. Manipulations of this reagent should be conducted within a well-ventilated fume hood.). The flask was fitted with an oven-dried reflux condenser, and the apparatus was transferred to a pre-heated oil bath (70° C.) positioned inside a photochemistry safety cabinet. A positive pressure of dry argon was maintained via tubing connected to an argon-filled balloon placed outside of the lightbox. The reaction mixture was refluxed with constant UV irradiation from an adjacent 200-Watt mercury-vapor bulb filtered through a water-cooled Pyrex glass jacket (CAUTION: Exposure to high-intensity UV light can cause irreversible vision loss—never open the safety cabinet when the UV lamp is on.). Progress was monitored by TLC (20% ethyl acetate-hexanes, UV+KMnO4). After 3 d, full consumption of the alkynol substrate was achieved, and the crude product mixture was concentrated under a stream of dry nitrogen. The canary-yellow residue was purified by flash-column chromatography (eluting with hexanes initially, grading to 20% ethyl acetate-hexanes) to provide the product as a viscous, colorless oil (3.53 g, 85%). 1H NMR (500 MHz, CDCl3): 7.77-7.74 (m, 2H), 7.70-7.67 (m, 2H), 7.44-7.38 (m, 2H), 7.37-7.31 (m, 4H), 7.27-7.23 (m, 3H), 7.22-7.19 (m, 2H), 6.10 (dd, J=6.4, 2.3 Hz, 1H), 4.67 (app dt, J=6.5, 1.9 Hz, 1H), 4.62 (d, J=2.9 Hz, 1H), 4.56-4.51 (m, 2H), 4.36 (d, J=11.7 Hz, 1H), 4.36-4.31 (m, 1H), 4.24 (td, J=10.4, 6.9 Hz, 1H), 4.20 (app dt, J=4.6, 2.3 Hz, 1H), 4.10 (d, J=5.1 Hz, 1H), 3.72 (app p, J=6.2 Hz, 1H), 1.27 (d, J=6.4 Hz, 3H), 1.08 (s, 9H), 0.07 (s, 9H). HRMS (ESI+, m/z): [M+H]+ calcd for $C_{37}H_{49}NO_6Si_2$, 660.3171; found 660.3164.

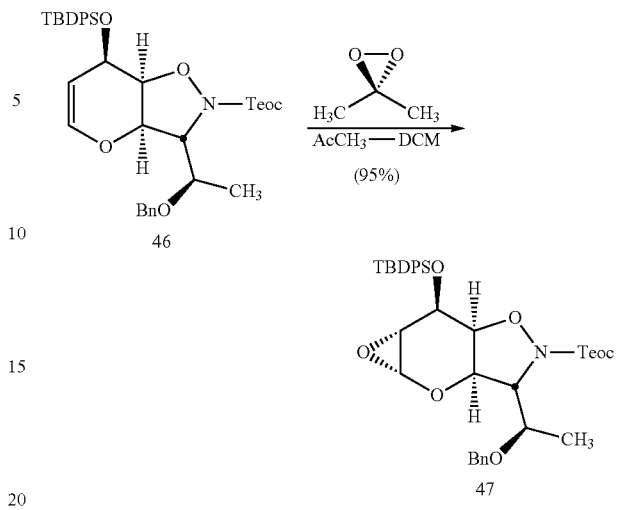

A solution of glycal 46 (1.45 g, 2.20 µmol, 1 equiv) in dichloromethane (22.0 mL) was cooled to 0° C., whereupon dimethyldioxirane solution (0.0997 M, 26.4 mL, 2.64 µmol, 1.20 equiv) was added dropwise over 1 min. The reaction mixture was stirred at 0° C. for 15 min, at which point TLC analysis (20% ethyl acetate-hexanes, UV+PAA) indicated full consumption of starting material. The mixture was then concentrated under a stream of dry argon, and the residue was dried by azeotropic removal of benzene to provide the product as a colorless oil that was suitable for use without further purification (quantitative yield, ≥95% purity by NMR). H NMR (500 MHz, $C_6D_6$) δ 7.89-7.83 (m, 2H), 7.77-7.71 (m, 2H), 7.21-7.09 (m, 7H), 7.08-7.00 (m, 4H), 4.66 (dd, J=2.6, 1.0 Hz, 1H), 4.42 (d, J=5.1 Hz, 1H), 4.34-4.21 (m, 4H), 4.21 (d, J=11.8 Hz, 1H), 4.12-4.08 (m, 1H), 4.05 (d, J=11.8 Hz, 1H), 3.56 (app p, J=6.2 Hz, 1H), 2.97-2.92 (m, 1H), 1.19 (d, J=0.7 Hz, 9H), 0.95 (d, J=6.4 Hz, 3H), 0.91 (ddd, J=9.4, 6.7, 3.9 Hz, 2H), −0.11 (d, J=0.7 Hz, 9H). HRMS (ESI+, m/z): [M+H]+ calcd for $C_{37}H_{49}NO_7Si_2$, 676.3120; found 676.3118.

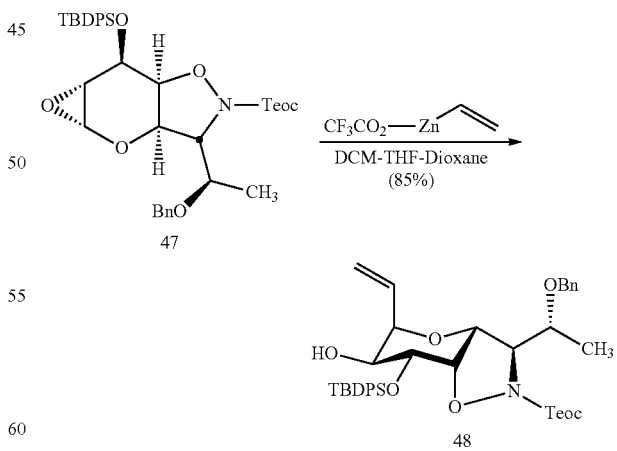

An oven-dried 100-mL round-bottom flask was charged with a stir bar and divinylzinc solution (0.15 M solution in tetrahydrofuran-dioxane, 22 mL, 3.3 mmol, 2.3 equiv). This solution was chilled to 0° C., and trifluoroacetic acid (250 µL, 3.3 mmol, 2.3 equiv) was then added dropwise. The resulting solution was stirred for 30 min at 0° C. prior to use. In a separate 100-mL round-bottom flask, epoxide 47 (954 mg, 1.41 mmol, 1 equiv) was dried by azeotropic removal of benzene. The dried epoxide was dissolved in anhydrous dichloromethane (14.1 mL), and the resulting solution was chilled to 0° C. This epoxide solution was then transferred by cannula to the flask containing freshly prepared vinylzinc trifluoroacetate, also at 0° C. The resulting solution was stirred at 0° C. for 4 h, at which point TLC analysis ($NH_2$ silica gel, 20% ethyl acteate-hexanes+2% methanol, UV+CAM) indicated full consumption of epoxide starting material. The reaction was quenched with the addition of 35 mL of saturated aqueous ammonium chloride solution, and the resulting biphasic mixture was stirred for 10 min. The layers were then separated, and the aqueous phase was extracted with dichloromethane (3×20 mL). The combined organic extracts were washed with saturated aqueous sodium chloride solution, and the washed organic product solution was dried over sodium sulfate. The dried solution was filtered, and the filtrate was concentrated to afford crude product as a faint yellow oil. The product was purified by flash-column chromatography (40 g silica, eluting with 5% ethyl acetate-hexanes initially, grading to 20% ethyl acetate-hexanes) to afford the product as a colorless oil (846 mg, 1.20 mmol, 85%). $^1$H NMR (600 MHz, $C_6D_6$) δ 7.96-7.94 (m, 2H), 7.83-7.79 (m, 2H), 7.22-7.19 (m, 2H), 7.18-7.16 (m, 1H), 7.15-7.11 (m, 4H), 7.07-7.00 (m, 4H). 5.74 (ddd, J=17.6, 11.0, 4.1 Hz, 1H), 5.20 (app dt, J=17.6, 2.1 Hz, 1H), 4.95 (app dt, J=11.1, 2.1 Hz, 1H), 4.57 (app dt, J=9.7, 5.0 Hz, 1H), 4.53 (d, J=2.4 Hz, 1H), 4.50 (app ddt, J=6.1, 4.3, 2.2 Hz, 1H), 4.40 (d, J=5.4 Hz, 1H), 4.33 (app td, J=10.3, 6.5 Hz, 1H), 4.30-4.25 (m, 2H), 4.23 (app t, J=3.0 Hz, 1H), 4.09 (d, J=11.8 Hz, 1H), 4.01 (dd, J=9.7, 3.6 Hz, 1H), 3.60 (app qn, J=6.2 Hz, 1H), 1.71 (d, J=4.2 Hz, 1H), 1.18 (s, 9H), 1.07 (d, J=6.3 Hz, 3H), 0.97-0.91 (m, 2H), −0.09 (s, 9H). HRMS (ESI+, m/z): [M+H]$^+$ calcd for $C_{39}H_{53}NO_7Si_2$, 704.3433; found 704.3418.

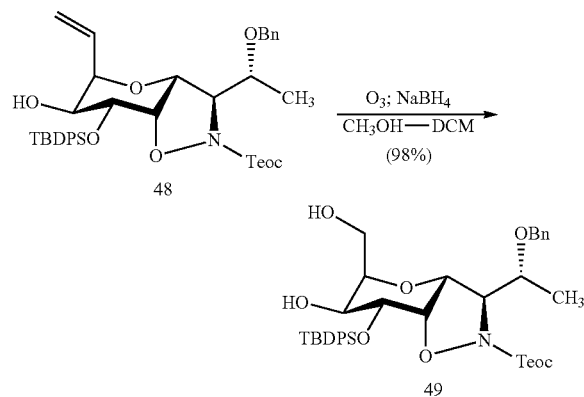

A solution of 48 (654 mg, 0.929 mmol, 1 equiv) in 50% v/v dichloromethane-methanol (18.6 mL) was chilled to −78° C. A mixture of ozone and dioxygen from an ozone generator was bubbled gently through the reaction solution, until an azure color appeared and persisted for 15 seconds, signaling saturation of the solution with ozone gas with concomitant disappearance of starting material. Ozone bubbling was then discontinued, and nitrogen gas was bubbled through the solution for 5 minutes in order to flush the solution of residual ozone. The resulting colorless solution was treated with sodium borohydride (351 mg, 9.29 mmol, 10.0 equiv) at −78° C., and the mixture was subsequently allowed to warm to 23° C. with constant stirring (Note: gas evolution occurs upon warming, and the reaction flask should be adequately vented to avoid overpressurization). After stirring for 1 h at 23° C., the mixture was carefully treated with 30 mL of half-saturated aqueous sodium chloride solution (Caution: gas evolution!). The resulting mixture was stirred for 5 minutes, or until gas evolution ceased; and the mixture was then extracted with ethyl acetate (3×20 mL). The combined organic extracts were washed with saturated aqueous sodium chloride solution, the washed solution was dried over sodium sulfate, and the dried solution was concentrated to provide the product as a brilliant white solid (644 mg, 98%). This material was suitable for use without further purification. $^1$H NMR (500 MHz, $CDCl_3$) δ 7.78-7.75 (m, 2H), 7.69-7.66 (m, 2H), 7.46-7.41 (m, 2H), 7.40-7.35 (m, 4H), 7.25-7.22 (m, 3H), 7.17-7.13 (m, 2H), 4.51 (d, J=11.6 Hz, 1H), 4.39 (d, J=3.1 Hz, 1H), 4.35-4.26 (m, 4H), 4.03 (t, J=3.3 Hz, 1H), 4.00 (app q, J=5.9 Hz, 1H), 3.95 (d, J=5.2 Hz, 1H), 3.92 (dd, J=8.8, 3.3 Hz, 1H), 3.67 (dd, J=11.9, 4.7 Hz, 1H), 3.61 (app tt, J=11.8, 6.7 Hz, 2H), 2.06 (s, 1H), 1.89 (s, 1H), 1.24 (d, J=6.4 Hz, 3H), 1.09 (s, 9H), 1.07 (m, 2H), 0.08 (s, 9H). HRMS (ESI+, m/z): [M+H]$^+$ calcd for $C_{38}H_{53}NO_8Si_2$, 708.3382; found 708.3366.

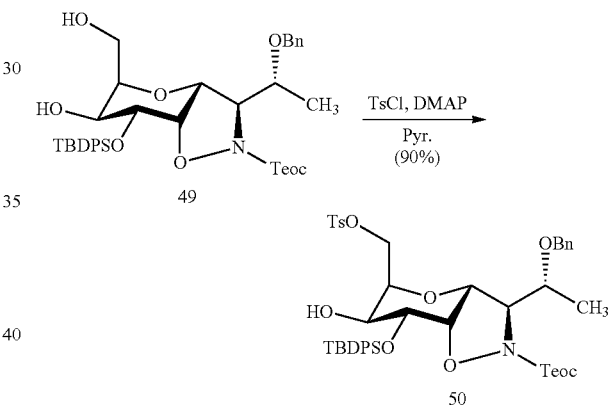

A flame-dried 25-mL round-bottomed flask was charged with diol 49 (1.05 g, 1.48 mmol, 1 equiv), and this starting material was dried by azeotropic removal of benzene. Anhydrous pyridine (5.0 mL) was then added, and the resulting solution was chilled to 0° C. Solid p-toluenesulfonyl chloride (481 mg, 2.52 mmol, 1.70 equiv) was added to the ice-cold solution, causing a golden yellow color to evolve. 4-Dimethylaminopyridine (DMAP, 9.1 mg, 74 μmol, 0.050 equiv) was then added, and the resulting solution was stirred at 0° C. for 5 minutes; the cooling bath was then removed and the mixture was allowed to warm to 23° C. with constant stirring. The golden color dissipated within 30 minutes, leaving a colorless solution. Progress was monitored by TLC (60% ethyl acetate-hexanes, UV+CAM), and after 48 h, the reaction was judged to be complete. The mixture was concentrated in vacuo, and the residue was purified by flash-column chromatography (80 g silica, eluting with 10% ethyl acetate-hexanes initially, grading to 30% ethyl acetate-hexanes) to give the product as a white foaming solid (1.15 g, 90%). $^1$H NMR (500 MHz, $CDCl_3$) δ 7.75-7.72 (m, 2H), 7.68-7.64 (m, 4H), 7.46-7.41 (m, 2H), 7.39-7.34 (m, 4H), 7.26-7.22 (m, 3H), 7.19-7.16 (m, 2H), 4.51 (d, J=11.7 Hz, 1H), 4.44 (d, J=2.8 Hz, 1H), 4.30 (d, J=11.8 Hz, 1H), 4.28-4.24 (m, 3H), 4.10-4.00 (m, 3H), 3.96 (t, J=3.2 Hz, 1H), 3.93 (d, J=5.4 Hz, 1H), 3.83 (dd, J=9.2, 3.4 Hz, 1H), 3.57 (app p, J=6.2 Hz, 1H), 2.41 (s, 3H), 1.86 (d, J=3.7 Hz, 1H), 1.22 (d, J=6.3 Hz, 3H), 1.07 (s, 9H), 1.07-1.03 (m, 2H), 0.07 (s, 9H). HRMS (ESI+, m/z): [M+Na]$^+$ calcd for C$_{45}$H$_{59}$NO$_{10}$SSi$_2$, 884.3290; found 884.3262.

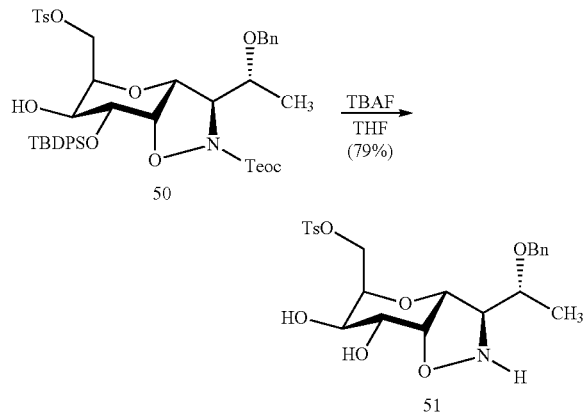

In a 100-mL round-bottomed flask, a solution of carbamate 50 (1.15 g, 1.34 mmol, 1 equiv) in tetrahydrofuran (13.4 mL) was chilled to 0° C. was treated with tetrabutylammonium fluoride (1.0 M solution in tetrahydrofuran, 4.0 mL, 4.0 mmol, 3.0 equiv). Following the addition of TBAF, the ice-water cooling bath was removed, and the reaction solution was allowed to warm to 23° C. Progress was monitored by LCMS; cleavage of the (trimethylsilyl)ethyl carbamate was observed within 15 minutes, while cleavage of the tert-butyldiphenylsilyl ether was comparatively slower. After 2 hours, the reaction was judged to be complete, and 20 mL of saturated aqueous sodium bicarbonate solution was added. The resulting mixture was extracted with dichloromethane (4×15 mL), and the combined organic layers were dried over sodium sulfate. The dried product solution was filtered, and the filtrate was concentrated to afford a colorless oil. This material was purified by flash-column chromatography (40 g silica, eluting with 1% methanol-dichloromethane initially, grading to 10% methanol-dichloromethane) to afford the product as a white foaming solid (508 mg, 79%). $^1$H NMR (600 MHz, CDCl$_3$) δ 7.76 (d, J=8.3 Hz, 2H), 7.34-7.30 (m, 2H), 7.29-7.25 (m, 5H), 4.70 (dd, J=4.1, 2.1 Hz, 1H), 4.61 (d, J=11.6 Hz, 1H), 4.32 (d, J=11.7 Hz, 1H), 4.26-4.21 (m, 2H), 4.18 (app dt, J=6.9, 5.0 Hz, 1H), 3.97 (dd, J=8.4, 5.3 Hz, 1H), 3.88 (app t, J=4.0 Hz, 1H), 3.79 (dd, J=8.4, 3.8 Hz, 1H), 3.57 (br s, 1H), 3.23 (dd, J=3.9, 2.1 Hz, 1H), 2.39 (s, 3H), 1.27 (d, J=6.3 Hz, 3H). HRMS (ESI+, m/z): [M+H]$^+$ calcd for C$_{23}$H$_{29}$NO$_8$S, 480.1687; found 480.1711.

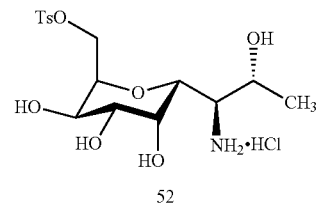

In a 25-mL round-bottomed flask, a solution of isoxazolidine 51 (368 mg, 767 µmol, 1 equiv) in methanol (8.00 mL) was cooled to 0° C., and was treated with hydrogen chloride solution (4.0 M in 1,4-dioxane, 770 µL, 3.1 mmol, 4.0 equiv). This solution was immediately concentrated to dryness, and the white residue obtained was re-dissolved in fresh methanol (7.67 mL). This solution was treated with palladium on carbon (10 wt %, 82.0 mg), the headspace of the flask was flushed with nitrogen gas, and the apparatus was fitted with a 3-way stopcock to which one arm was affixed to a high-vacuum line, and the other was affixed to a hydrogen gas-filled balloon. The headspace of the flask was replaced by briefly evacuating, then back-filling the flask with hydrogen gas using the stopcock (3 evacuation-backfill cycles), and the black suspension was stirred at 23° C. under 1 atm of hydrogen gas. After 5 h, LCMS analysis indicated that isoxazolidine ring and benzyl ether hydrogenolysis were complete, and the headspace of the flask was flushed with nitrogen gas. The reaction mixture was filtered through a Celite pad, and the filter cake was rinsed with methanol (2×3 mL). The filtrate was concentrated to give the product as a dull white crystalline solid (327 mg, 100%). This material was suitable for use in subsequent transformations without further purification.

Crystals suitable for X-ray analysis were prepared as follows: In a 1-mL glass sample vial, 52.HCl (3 mg) was deposited, and this material was dissolved in approximately 200 µL of 190-proof ethanol. The vial containing the ethanolic solution was then placed inside a 20-mL scintillation vial containing approximately 3 mL of acetonitrile. The large vial was capped, and the assembly was allowed to stand undisturbed at 23° C. After 2 days, needle-shaped crystals of sufficient size for X-ray analysis had formed. X-ray diffraction analysis confirmed the structure of 52. $^1$H NMR (600 MHz, CD$_3$OD) δ 7.80 (d, J=8.0 Hz, 2H), 7.46 (d, J=8.0 Hz, 2H), 4.35 (dd, J=11.7, 9.6 Hz, 1H), 4.24-4.21 (m, 2H), 4.18 (app s, 1H), 4.09 (app p, J=6.3 Hz, 1H), 3.99 (dd, J=7.1, 2.8 Hz, 1H), 3.95 (dd, J=8.3, 5.0 Hz, 1H), 3.66 (dd, J=8.3, 3.0 Hz, 1H), 3.56 (app t, J=6.4 Hz, 1H), 2.46 (s, 3H), 1.26 (d, J=6.4 Hz, 3H). HRMS (ESI+, m/z): [M+Na]$^+$ calcd for C$_{1-6}$H$_{25}$NO$_8$S, 414.1193; found 414.1203.

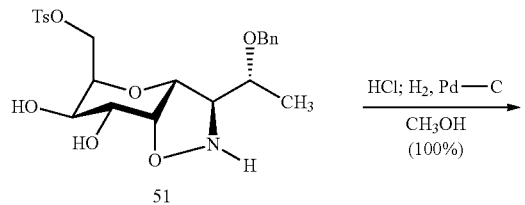

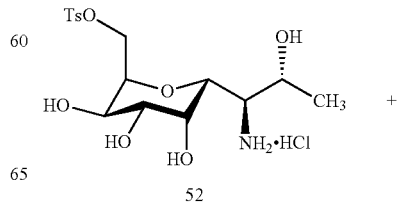

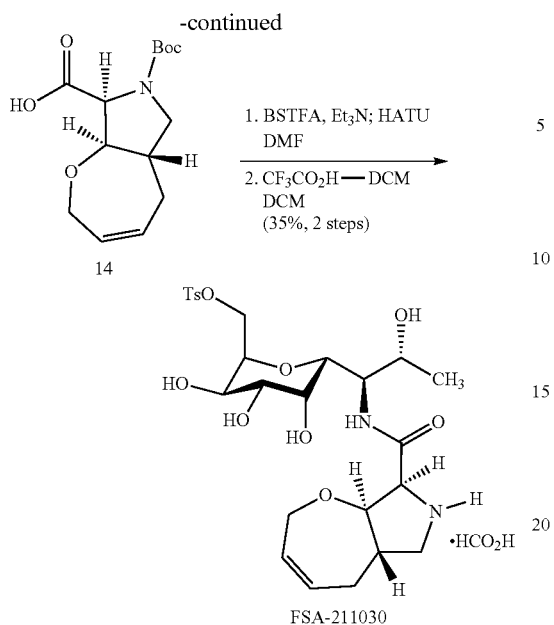

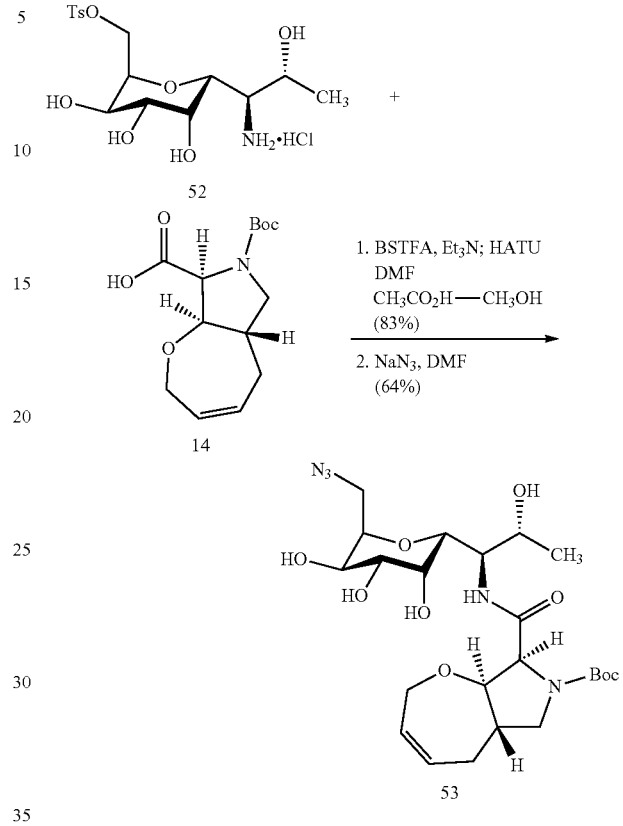

To a solution of aminotetraol 52.HCl (9.7 mg, 23 μmol, 1 equiv) and triethylamine (13 μL, 95 μmol, 4.2 equiv) in N,N-dimethylformamide (110 μL) was added N,O-bis(trimethylsilyl)trifluoroacetamide (12 μL, 45 μmol, 2.0 equiv). The mixture was stirred at 23° C. for 1 h in order to ensure complete O-silylation. Carboxylic acid 14 (7.1 mg, 25 μmol, 1.1 equiv) and HATU (11 mg, 29 μmol, 1.3 equiv) were then added sequentially, the vial was sealed, and the mixture was stirred at 23° C. for 1 h, at which point LCMS analysis showed complete consumption of aminotetraol starting material and its (oligo)trimethylsilylated congeners. The reaction mixture was diluted with ethyl acetate (15 mL), and this diluted solution was washed sequentially with 10% w/v aqueous citric acid solution (5 mL), water (5 mL), half-saturated aqueous sodium bicarbonate solution (5 mL), and saturated aqueous sodium chloride solution (5 mL). The washed organic solution was dried over sodium sulfate, filtered, and concentrated to provide crude (oligo)trimethylsilylated, N-Boc-protected coupled intermediate.

This residue was dissolved in dichloromethane (1.1 mL); and water (25 μL), dimethyl sulfide (25 μL), and trifluoroacetic acid (370 μL) were added. The mixture was stirred at 23° C. for 20 min, whereupon LCMS analysis showed that Boc removal was complete. The mixture was diluted with toluene (2 mL), and the diluted mixture was concentrated to provide a light tan solid residue that was finally subjected to preparative HPLC on a Waters SunFire Prep C18 column (5 μm, 250×19 mm; eluting with 0.1% formic acid-10% acetonitrile-water initially, grading to 0.1% formic acid-50% acetonitrile-water over 40 min, with a flow rate of 15 mL/min; monitored by UV absorbance at 254 nm) to provide FSA-211030.HCO$_2$H as a white solid (4.8 mg, 35%). $^1$H NMR (600 MHz, CD$_3$OD) δ 8.28 (br, 1H), 7.82 (d, J=8.4 Hz, 2H), 7.46 (d, J=8.0 Hz, 2H), 5.88 (app ddt, J=12.5, 7.5, 2.6 Hz, 1H), 5.79 (app ddt, J=12.2, 6.1, 3.0 Hz, 1H), 4.52 (d, J=8.8 Hz, 1H), 4.39 (dd, J=11.6, 10.1 Hz, 1H), 4.33 (dd, J=15.8, 6.1 Hz, 1H), 4.23-4.21 (m, 3H), 4.18-4.13 (m, 2H), 4.00-3.94 (m, 3H), 3.80 (d, J=7.1 Hz, 1H), 3.63 (dd, J=11.4, 7.5 Hz, 1H), 3.49 (dd, J=9.9, 3.2 Hz, 1H), 2.96 (app t, J=11.8 Hz, 1H), 2.54 (ddd, J=16.7, 7.6, 3.3 Hz, 1H), 2.46 (s, 3H), 2.21 (app qd, J=13.1, 11.4, 7.3 Hz, 1H), 2.12-2.06 (m, 1H), 1.20 (d, J=6.4 Hz, 3H). HRMS (ESI+, m/z): [M+H] calcd for C$_{25}$H$_{36}$N$_2$O$_{10}$S, 557.2163; found 557.2181.

In a 4-mL glass vial fitted with a magnetic stir bar and a silicone septum screw cap, an ice-cold suspension of aminosugar salt 52.HCl (35.7 mg, 83.5 μmol, 1 equiv) and triethylamine (48.8 μL, 0.350 mmol, 4.20 equiv) in N,N-dimethylformamide (417 μL) was treated with N,O-bis(trimethylsilyl)trifluoroacetamide (44.7 μL, 0.167 mmol, 2.00 equiv). A colorless solution formed immediately, and this mixture was warmed to 23° C. to stir for 1 h so as to ensure complete O-silylation. Next, carboxylic acid 14 (26.0 mg, 91.8 μmol, 1.10 equiv) and HATU (41.2 mg, 0.108 mmol, 1.30 equiv) were added, and the resulting yellow solution was stirred at 23° C. for 3.5 h, at which point LCMS analysis showed complete consumption of aminotetraol starting material and its (oligo)trimethylsilylated congeners. The reaction mixture was consequently diluted with ethyl acetate (30 mL), and the diluted solution was washed sequentially with aqueous citric acid solution (10% w/v, 2×10 mL), saturated aqueous sodium chloride solution (10 mL), half-saturated aqueous sodium bicarbonate solution (10 mL), and a fresh portion of saturated aqueous sodium chloride solution (10 mL). The washed organic layer was dried over sodium sulfate, filtered, and concentrated. The residue, containing (oligo)trimethylsilylated coupled product congeners, was dissolved in 50% v/v acetic acid-methanol (2.00 mL). The solution was heated to 40° C. for 4 h, at which point LCMS analysis showed that global desilylation was complete. The mixture was diluted with toluene, and the diluted mixture was concentrated in vacuo. The residue thus obtained was purified by flash-column chromatography (12 g silica gel, eluting with 1% methanol-dichloromethane initially, grading to 10% methanol-dichloromethane), and fractions containing N-Boc-protected coupled product were identified by TLC ($R_f$=0.41 (10% methanol-dichloromethane, UV+CAM). These fractions were pooled and concentrated to provide coupled, N-Boc protected product as a colorless solid (45.4 mg, 83%). Due to substantial amide and carbamate rotamerism observed in the $^1$H-NMR spectrum, this material was carried forward through $S_N2$ displacement with sodium azide prior to full characterization.

A portion of this N-Boc-protected p-toluenesulfonate ester intermediate (33 mg, 50 μmol, 1 equiv) was introduced to a 0.5-2 mL conical glass microwave vial. A magnetic stir bar, sodium azide (33 mg, 0.50 mmol, 10 equiv), and N,N-dimethylformamide (250 μL) were then added. The vial was sealed, stirring was initiated, and the reaction mixture was heated to 80° C. in a pre-heated oil bath. After 22 h, LCMS analysis indicated that no starting material remained. The reaction mixture was diluted with saturated aqueous sodium chloride solution (10 mL) and the mixture was extracted with ethyl acetate (3×5 mL). The combined organic extracts were dried over sodium sulfate, filtered, and concentrated; the residue thus obtained was subjected to flash-column chromatography (4 g silica gel, eluting with dichloromethane initially, grading to 10% methanol-dichloromethane) to provide the product as a white solid (17 mg, 64%). $^1$H NMR (1:1 mixture of rotamers, asterisk [*] denotes rotameric signals that could be resolved, 500 MHz, CD$_3$OD) δ 5.91-5.84 (m, 1H), 5.80-5.73 (m, 1H), 4.43 (app t, J=8.0 Hz, 1H), 4.31 (d, J=6.1 Hz, 1H), 4.28 (d, J=6.1 Hz, 1H),* 4.25-4.08 (m, 3H), 4.04-3.95 (m, 4H), 3.80-3.65 (m, 3H), 3.58-3.49 (m, 2H), 2.94 (app q, J=10.9 Hz, 1H), 2.50-2.39 (m, 2H), 2.08 (app q, J=14.7, 13.8 Hz, 1H), 1.46 (s, 9H), 1.45 (s, 9H),* 1.25 (d, J=6.0 Hz, 3H), 1.22 (d, J=6.2 Hz, 3H). HRMS (ESI+, m/z): [M+H]$^+$ calcd for C$_{23}$H$_{37}$N$_5$O$_9$, 528.2664; found 528.2680.

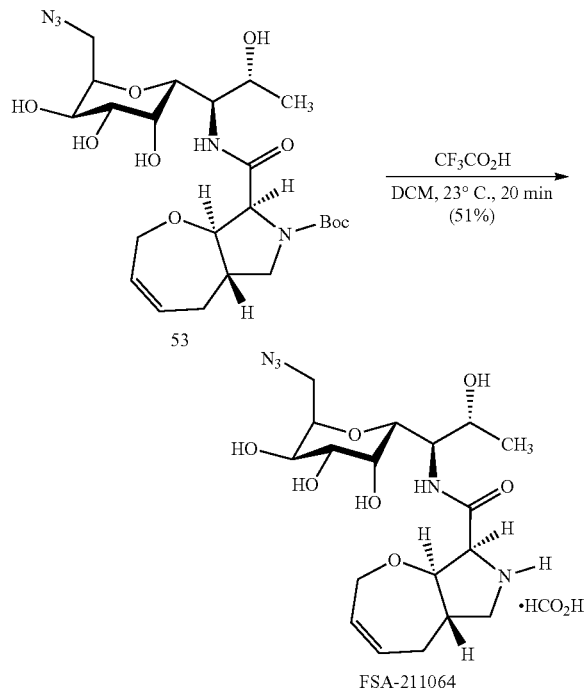

53

FSA-211064

In a 4-mL glass vial, tert-butyl carbamate 53 (6.1 mg, 12 μmol, 1 equiv) was dissolved in dichloromethane (170 μL). Water (3.7 μL), dimethyl sulfide (3.7 μL), and trifluoroacetic acid (170 μL) were then added sequentially, and the reaction mixture was stirred at 23° C. for 20 min, whereupon LCMS analysis showed that Boc removal was complete. The reaction mixture was diluted with toluene (1 mL), and the diluted mixture was concentrated to dryness in vacuo. The residue was then purified by preparative HPLC on a Waters SunFire Prep C18 column (5 μm, 250×19 mm; eluting with 0.1% formic acid-5% acetonitrile-water initially, grading to 0.1% formic acid-50% acetonitrile-water over 40 min, with a flow rate of 15 mL/min; monitored by UV absorbance at 210 nm) to furnish FSA-211064.HCO$_2$H as a white solid (2.8 mg, 51%). $^1$H NMR (600 MHz, CD$_3$OD) δ 5.87 (app ddt, J=12.5, 7.4, 2.5 Hz, 1H), 5.77 (app ddt, J=12.3, 6.1, 3.0 Hz, 1H), 4.41 (d, J=8.7 Hz, 1H), 4.33 (dd, J=15.8, 6.2 Hz, 1H), 4.28 (app t, J=7.1 Hz, 1H), 4.18-4.10 (m, 3H), 4.03-3.97 (m, 3H), 3.86 (d, J=7.6 Hz, 1H), 3.70 (dd, J=13.8, 10.5 Hz, 1H), 3.58-3.55 (m, 2H), 3.49 (dd, J=13.9, 3.0 Hz, 1H), 2.90 (app t, J=11.6 Hz, 1H), 2.53 (ddd, J=16.6, 7.5, 3.2 Hz, 1H), 2.19 (app p, J=10.4 Hz, 1H), 2.07 (app td, J=14.1, 12.3, 3.1 Hz, 1H), 1.23 (d, J=6.3 Hz, 3H). HRMS (ESI+, m/z): [M+H]$^+$ calcd for C$_{18}$H$_{29}$N$_5$O$_7$, 428.2140; found 428.2154.

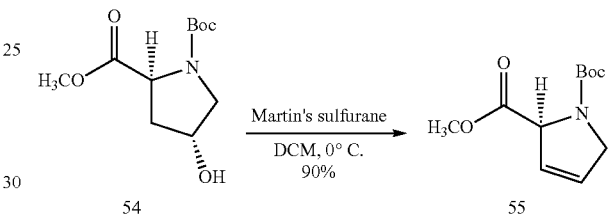

54 → 55

A solution of 54 (2.88 g, 11.74 mmol, 1.0 equiv.) in DCM (59 mL) was added via cannula over 10 min to a suspension of Martin's sulfurane (11.85 g, 17.61 mmol, 1.5 equiv.) in DCM (59 mL) at 0° C. The resultant faintly orange solution was stirred under argon, allowing reaction to warm to room temperature as the ice-water bath expired. Consumption of 54 was monitored by TLC analysis (50% EtOAc in hexanes). After starting material was completely consumed by TLC analysis, the solution was concentrated under reduced pressure and purified directly by column chromatography (10-20-30% EtOAc in hexanes) to yield 55 (2.41 g, 10.59 mmol, 90%) as a colorless oil. $^1$H NMR (asterisk denotes minor rotamer peaks, 500 MHz, CDCl$_3$) δ 6.02, 5.97* (m, 1H), 5.77*, 5.73 (m, 1H), 5.04*, 4.97 (m, 1H), 4.24 (m, 2H), 3.75 (s, 3H), 1.50*, 1.45 (s, 9H).

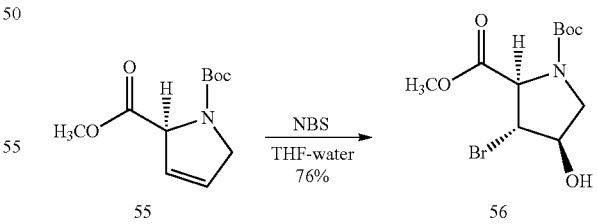

55 → 56

N-bromosuccinimide (2.83 g, 15.91 mmol, 1.5 equiv.) was added in a single portion to a stirring solution of 55 (2.41 g, 10.60 mmol, 1.0 equiv.) in THF (53 mL) and water (53 mL) at 0° C. The resulting yellow solution was stirred under air, allowing reaction to warm to room temperature as the ice-water bath expired. Consumption of 55 was monitored by TLC analysis (30% EtOAc in hexanes). After starting material was completely consumed by TLC analysis, the reaction solution was diluted with water and extracted with ether (3×100 mL). The combined organic layers were washed with brine, dried over sodium sulfate, filtered, and concentrated under reduced pressure to give an orange oil. The crude product was purified by column chromatography (20-30-40% EtOAc in hexanes) to yield 56 (2.60 g, 8.01 mmol, 76%) as a colorless oil. ¹H NMR (asterisk denotes minor rotamer peaks, 500 MHz, CDCl₃) δ 4.66*, 4.54 (s, 1H), 4.42*, 4.35 (m, 2H), 3.94 (m, 1H), 3.79 (s, 3H), 3.59 (dd, J=19.5, 11.8 Hz, 1H) 1.50*, 1.44 (s, 9H).

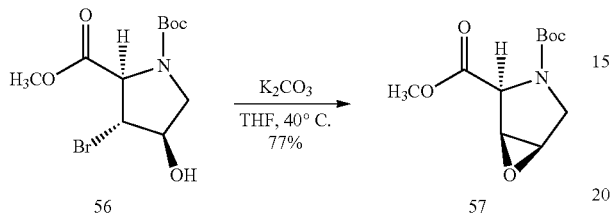

Potassium carbonate (1.663 g, 12.03 mmol, 1.5 equiv.) was added in one portion to a stirred solution of 56 (2.60 g, 8.02 mmol, 1.0 equiv.) in DMF (27 mL) and THF (54 mL). The resulting colorless solution was stirred at room temperature under argon and gradually became cloudy and faintly violet in color. After 16 hours, the reaction solution was filtered through a pad of Celite, the filter cake was washed with ether, and the filtrate was concentrated under reduced pressure. The crude product was purified by column chromatography (30-40-50% EtOAc in hexanes) to yield 57 (1.50 g, 6.18 mmol, 77%) as a colorless oil. ¹H NMR (asterisk denotes minor rotamer peaks, 500 MHz, CDCl₃) δ 4.37*, 4.32 (s, 1H), 3.92 (s, 1H), 3.85-3.76 (m, 2H), 3.80 (s, 3H), 3.50 (dd, J=19.0, 12.7 Hz, 1H), 1.40*, 1.38 (s, 9H).

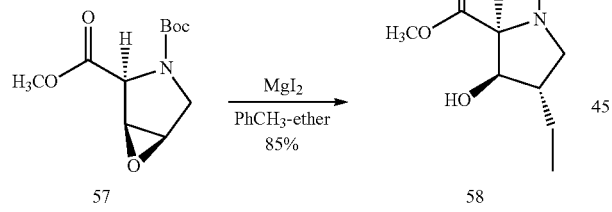

A 0.3 M solution of magnesium iodide (26.5 mL, 7.95 mmol, 1.125 equiv.) in ether was added dropwise by syringe to a stirring solution of 57 (1.72 g, 7.07 mmol, 1.0 equiv.) in toluene (141 mL) at 0° C. The resultant cloudy orange solution was stirred at 0° C. under argon. After 3 hours, the reaction was quenched with saturated aq. sodium thiosulfate and extracted with EtOAc (3×100 mL). The combined organic layers were washed with brine, dried over sodium sulfate, filtered, and concentrated under reduced pressure to give a faintly yellow oil. The crude product was purified by column chromatography (20-30% EtOAc in hexanes) to yield 58 (2.26 g, 6.09 mmol, 86%) as a faintly yellow oil. ¹H NMR (asterisk denotes minor rotamer peaks, 600 MHz, CDCl₃) δ 4.63 (m, 1H), 4.58*, 4.55 (d, J=6.6 Hz, 1H), 4.21 (m, 1H), 4.12 (m, 1H), 3.78-3.69 (m, 1H), 3.76*, 3.75 (s, 3H), 1.45*, 1.40 (s, 9H).

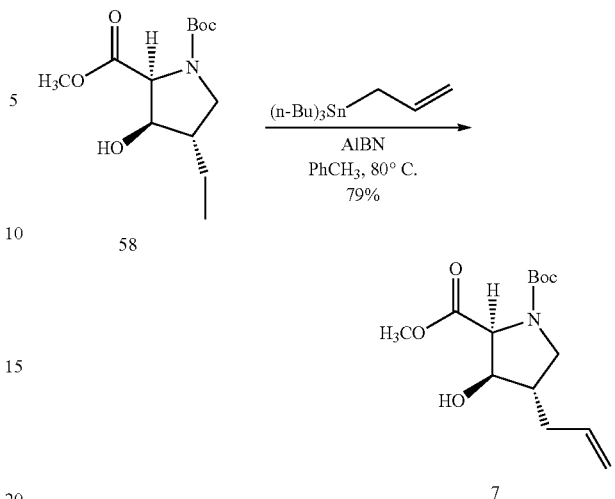

AIBN (0.134 g, 0.814 mmol, 0.2 equiv.) was added to a stirring solution of 58 (1.51 g, 4.07 mmol, 1.0 equiv.) and allyltri-n-butyltin (12.6 mL, 40.7 mmol, 10.0 equiv.) in toluene (40.7 mL). The resultant colorless solution was heated to 80° C. and stirred at 80° C. under argon. After 12 hours, the reaction solution was concentrated under reduced pressure and purified directly by column chromatography (5-20-30-40-50% EtOAc in hexanes to yield 7 (0.915 g, 3.21 mmol, 79%) as a colorless oil. ¹H NMR (asterisk denotes minor rotamer peaks, 500 MHz, CDCl₃) δ 5.80 (m, 1H), 5.09 (d, J=17.1 Hz, 1H), 5.03 (m, 1H), 4.43*, 4.37 (d, J=7.6 Hz, 1H), 4.20 (m, 1H), 4.12 (m, 1H), 3.82-3.71 (m, 1H), 3.75 (s, 3H), 3.04 (m, 1H), 2.41 (m, 2H), 1.47*, 1.41 (s, 9H).

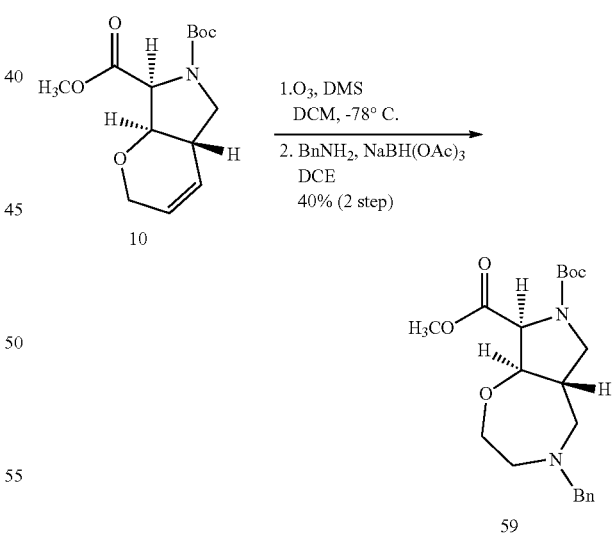

Ozone was bubbled through a stirring solution of 10 (0.577 g, 2.037 mmol, 1.0 equiv.) in DCM (41 mL) at −78° C. until a blue color persisted for 2 min. Nitrogen was bubbled through the solution until the color subsided, and dimethyl sulfide (4.25 mL, 57.4 mmol, 28.2 equiv.) was added to the solution. The resultant solution was stirred at room temperature and consumption of the ozonide intermediate was monitored by aliquot NMR. After 2 hours, the reaction solution was concentrated to give the bis-aldehyde intermediate, which was taken forward without further purification.

Benzylamine (0.23 mL, 2.117 mmol, 1.04 equiv.) and sodium triacetoxyborohydride (0.949 g, 4.48 mmol, 2.20 equiv.) were added sequentially to a stirring solution of the bis-aldehyde prepared above (0.642 g, 2.036 mmol, 1.0 equiv.) in DCE (41 mL). The resultant solution was stirred at room temperature under argon. After 3 hours, the reaction solution was concentrated under reduced pressure, the residue was partitioned between water and DCM, and extracted with DCM (3×50 mL). The combined organic layers were washed with brine, dried over sodium sulfate, filtered, and concentrated to give a yellow oil. The crude product was purified by column chromatography (5-10% i-PrOH+1% aq. NH$_4$OH in hexanes) to yield 59 (0.313 g, 0.802 mmol, 39% over 2 steps). $^1$H NMR (asterisk denotes minor rotamer peaks, 500 MHz, CDCl$_3$) δ 7.36-7.27 (m, 5H), 4.52*, 4.43 (d, J=8.3 Hz, 1H), 4.44-4.39 (m, 1H), 3.97-3.87 (m, 2H), 3.83-3.78 (m, 1H), 3.78*, 3.77 (s, 3H), 3.72-3.65 (m, 1H), 3.68 (t, J=6.1 Hz, 1H), 3.05-2.97 (m, 1H), 2.95-2.90 (m, 1H), 2.83 (dd, J=14.2, 6.8 Hz, 1H), 2.71 (ddd, J=14.8, 9.0, 7.3 Hz, 1H), 2.48 (br, 1H), 2.39-2.33 (m, 1H), 1.47*, 1.43 (s, 9H).

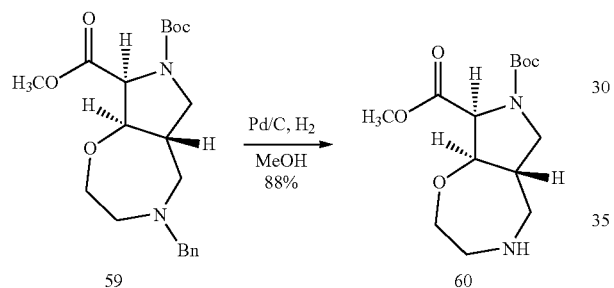

Palladium on carbon (10% wt, 0.126 g, 0.118 mmol, 0.2 equiv.) was added to a stirring solution of 59 (0.231 g, 0.592 mmol, 1.0 equiv.) in methanol (0.8 mL). The resultant black suspension was stirred under hydrogen. The reaction solution was filtered through a pad of Celite, washing with methanol, and concentrated to yield 60 (0.157 g, 0.523 mmol, 88%). $^1$H NMR (asterisk denotes minor rotamer peaks, 500 MHz, CDCl$_3$) δ 4.39*, 4.31 (d, J=8.2 Hz, 1H), 4.23 (m, 1H), 3.81-3.66 (m, 3H), 3.65 (s, 3H), 3.17 (ddd, J=16.9, 12.5, 5.0 Hz, 1H), 2.98-2.80 (m, 3H), 2.74-2.60 (m, 1H), 2.48 (dd, J=12.6, 10.4 Hz, 1H), 2.35 (br, 1H), 1.34*, 1.30 (s, 9H).

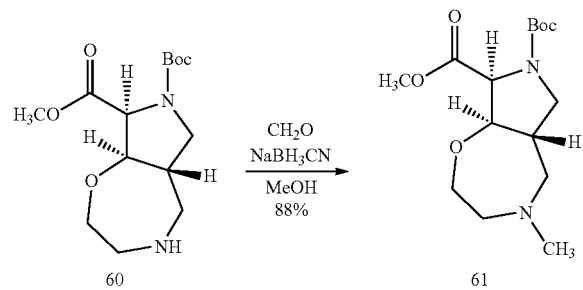 [SMILES: COC(=O)[C@@H]1[C@@H]2OCCNC[C@H]2CN1C(=O)OC(C)(C)C ; "CH2ONaBH3CN" ; COC(=O)[C@@H]1[C@@H]2OCCN(C)C[C@H]2CN1C(=O)OC(C)(C)C]

Formaldehyde (37% aq. solution, 0.03 mL, 0.346 mmol, 2.00 equiv.) and sodium cyanoborohydride (0.022 g, 0.346 mmol, 2.0 equiv.) were added to a stirred solution of 60 (0.052 g, 0.173 mmol, 1 equiv.) in methanol (0.9 mL). The resultant solution was stirred at room temperature. Consumption of 60 was monitored by mass spectrometry. After 1 hour, the reaction was concentrated, redissolved in DCM, passed through a plug of sodium sulfate, and concentrated under reduced pressure. The crude product was purified by column chromatography (2-5% methanol+1% aq. ammonium hydroxide in DCM) to yield 61 (0.037 g, 0.118 mmol, 68%). $^1$H NMR (asterisk denotes minor rotamer peaks, 500 MHz, CDCl$_3$) δ 4.46*, 4.38 (d, J=8.2 Hz, 1H), 4.33 (m, 1H), 3.94 (dd, J=8.1, 1.7 Hz, 1H), 3.87-3.79 (m, 2H), 3.73*, 3.72 (s, 3H), 2.95-2.88 (m, 2H), 2.80-2.74 (m, 2H), 2.67-2.62 (m, 1H), 2.38 (s, 3H), 2.24 (dd, J=11.9, 9.8 Hz, 1H), 1.42*, 1.38 (s, 9H).

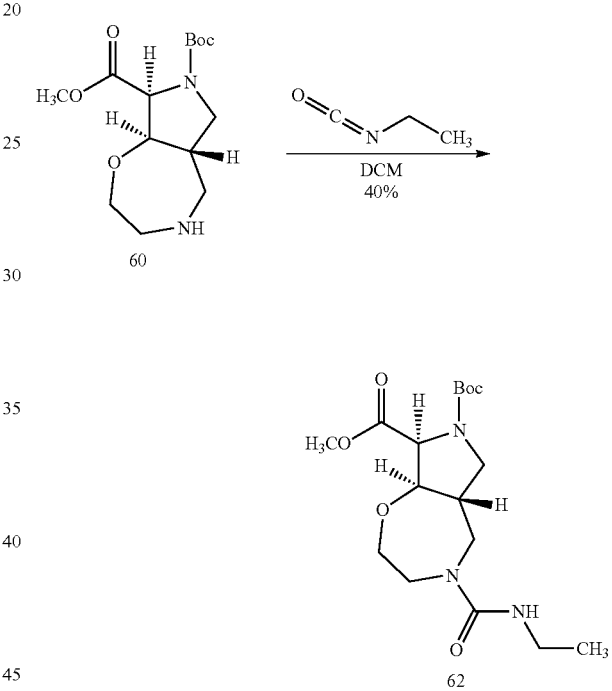

Isocyanatoethane (0.02 mL, 0.260 mmol, 1.5 equiv.) was added via syringe to a stirred solution of 60 (0.052 g, 0.173 mmol, 1 equiv.) in DCM (1.7 mL) at 0° C. The resultant solution was stirred under argon, gradually warming to room temperature as ice-water bath expired. Consumption of 60 was monitored by TLC (10% methanol+1% aq. ammonium hydroxide in DCM). After 14 hours, the reaction was quenched with brine and extracted with DCM (3×10 mL). The combined organic layers were washed with brine, dried over sodium sulfate, and concentrated over reduced pressure. The crude product was purified by column chromatography (75-90% EtOAc in hexanes) to yield 62 (0.026 g, 0.070 mmol, 40%). $^1$H NMR (asterisk denotes minor rotamer peaks, 500 MHz, CDCl$_3$) δ 4.54*, 4.46 (d, J=8.2 Hz, 1H), 4.40 (m, 1H), 4.34*, 4.19 (m, 1H), 4.12*, 4.06 (m, 1H), 4.02-3.89 (m, 2H), 3.75*, 3.74 (s, 3H), 3.62-3.51 (m, 2H), 3.29-3.15 (m, 4H), 3.04-2.97 (m, 1H), 2.88 (m, 1H), 1.43*, 1.39 (s, 9H), 1.13 (td, J=7.2, 2.5 Hz, 3H).

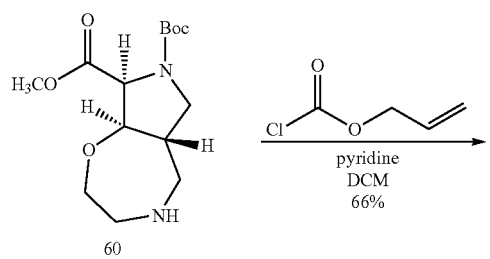

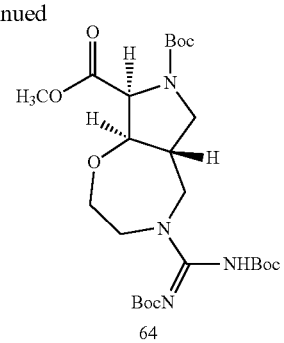

Mercuric oxide (0.041 g, 0.190 mmol, 1.10 equiv.) and triethylamine (0.07 mL, 0.519 mmol, 3.00 equiv.) were added sequentially to a stirred solution of 60 (0.052 g, 0.173 mmol, 1 equiv.) and 1,3-bis(tert-butoxycarbonyl)-2-methyl-2-thiopseudourea (0.053 g, 0.182 mmol, 1.05 equiv.) in DCM (1.2 mL). The resulting suspension was stirred at room temperature under argon with exclusion of light. Consumption of 60 was monitored by TLC (20% isopropanol+1% aq. ammonium hydroxide in hexanes). After 20 hours, the reaction was filtered through a plug of Celite, washed with DCM, and concentrated under reduced pressure. The crude product was purified by column chromatography (5-10% isopropanol+1% aq. ammonium hydroxide in hexanes) to yield 64 (0.063 g, 0.117 mmol, 68%). $^1$H NMR (asterisk denotes minor rotamer peaks, 500 MHz, CDCl$_3$) δ 9.99 (br, 1H), 4.52*, 4.44 (d, J=8.2 Hz, 1H), 4.05 (m, 1H), 4.00 (dd, J=13.2, 4.4 Hz, 1H), 3.92 (m, 1H), 3.85 (m, 1H), 3.75 (m, 1H), 3.74*, 3.73 (s, 3H), 3.49 (m, 1H), 3.38 (m, 1H), 2.98 (m, 1H), 2.93-2.85 (m, 1H), 1.48 (s, 9H), 1.46 (s, 9H), 1.42*, 1.38 (s, 9H).

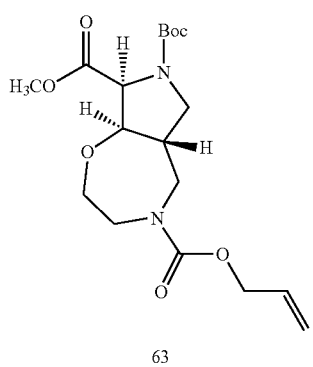

Pyridine (0.08 mL, 0.959 mmol, 3.00 equiv.) was added to a stirred solution of 60 (0.096 g, 0.320 mmol, 1 equiv.) in DCM (0.8 mL). The solution was cooled to 0° C. and allyl chloroformate (0.04 mL, 0.384 mmol, 1.20 equiv.) was added dropwise by syringe. The resultant solution was stirred at 0° C. for 10 minutes and then stirred at room temperature under argon. Consumption of 60 was monitored by mass spectrometry. After 2 hours, the reaction was concentrated, and the residue was redissolved in 1 N aq. hydrochloric acid and EtOAc. The product was extracted with EtOAc (3×15 mL). The combined organic layers were washed with saturated aq. sodium bicarbonate, washed with brine, dried over sodium sulfate, and concentrated under reduced pressure. The crude product was purified by column chromatography (40% EtOAc in hexanes) to yield 63 (0.081 g, 0.210 mmol, 66%). $^1$H NMR (asterisk denotes minor rotamer peaks, 500 MHz, CDCl$_3$) δ 5.90 (m, 1H), 5.26 (dd, J=16.9, 10.8 Hz, 1H), 5.19 (m, 1H), 4.57 (d, J=5.5 Hz, 2H), 4.50*, 4.42 (dd, J=8.7 Hz, 1H), 4.05 (m, 2H), 3.99-3.85 (m, 3H), 3.72*, 3.71 (s, 3H), 3.71-3.66 (m, 1H), 3.55 (m, 1H), 3.42-3.27 (m, 2H), 2.99 (m, 1H), 2.81 (m, 1H), 1.41*, 1.37 (s, 9H).

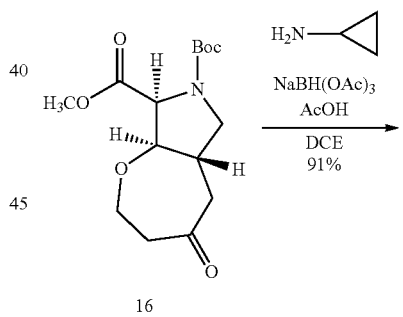

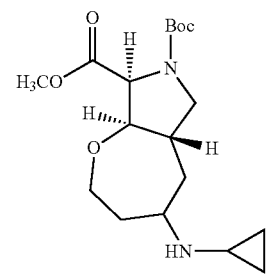

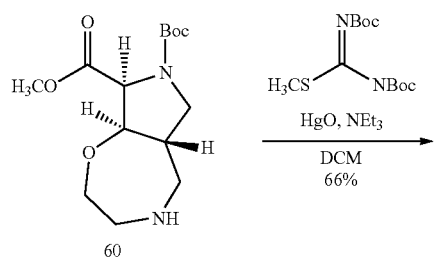

Acetic acid (0.03 mL, 0.536 mmol, 3.00 equiv.) and cyclopropylamine (0.03 mL, 0.357 mmol, 2.00 equiv.) were added to a stirred solution of 16 (0.056 g, 0.179 mmol, 1 equiv.) in DCE (0.9 mL). The resultant solution was stirred at room temperature for 30 min, then sodium triacetoxyborohydride (0.057 g, 0.268 mmol, 1.50 equiv.) was added. Consumption of 16 was monitored by TLC (70% EtOAc in hexanes). After 18 hours, the reaction was quenched with saturated aq. sodium bicarbonate and extracted with DCM (3×10 mL). The combined organic layers were washed with brine, dried over sodium sulfate, and concentrated under reduced pressure. The crude product was purified by column chromatography (2-5% methanol+1% aq. ammonium hydroxide in DCM) to yield 65 (0.058 g, 0.162 mmol, 91%). $^1$H NMR (asterisk denotes minor rotamer peaks, 500 MHz, CDCl$_3$) δ 4.45*, 4.36 (d, J=8.0 Hz, 1H), 4.11*, 3.99 (m, 2H), 3.91-3.82 (m, 2H), 3.79-3.76 (m, 1H), 3.74*, 3.72 (s, 3H), 3.63 (m, 1H), 2.90 (m, 2H), 2.05 (m, 1H), 2.00-1.95 (m, 2H), 1.88-1.81 (m, 1H), 1.43*, 1.38 (s, 9H), 0.45 (m, 2H), 0.31 (m, 2H).

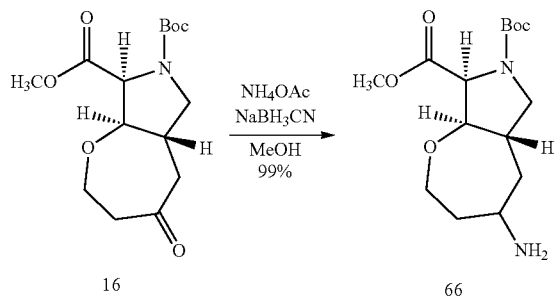 [SMILES: COC(=O)[C@@H]1[C@@H]2OCCC(=O)C[C@H]2CN1C(=O)OC(C)(C)C ; COC(=O)[C@@H]1[C@@H]2OCCC(N)C[C@H]2CN1C(=O)OC(C)(C)C]

Sodium cyanoborohydride (0.017 g, 0.268 mmol, 1.50 equiv.) was added to a stirred solution of 16 (0.056 g, 0.179 mmol, 1 equiv.) and ammonium acetate (0.138 g, 1.79 mmol, 10.0 equiv.) in methanol (0.9 mL). The resultant solution was stirred at room temperature under argon. Consumption of 16 was monitored by TLC (70% EtOAc in hexanes). The reaction was concentrated under reduced pressure and the residue was redissolved in saturated aq. sodium bicarbonate and DCM. The reaction was extracted with DCM (3×10 mL). The combined organic layers were washed with brine, dried over sodium sulfate, and concentrated under reduced pressure to yield 66 (0.059 g, 0.188 mmol, 99%) which was taken forward without further purification. $^1$H NMR (asterisk denotes minor rotamer peaks, 500 MHz, CDCl$_3$) δ 4.43*, 4.35 (d, J=8.2 Hz, 1H), 4.14*, 3.98 (m, 2H), 3.90-3.82 (m, 1H), 3.80-3.75 (m, 2H), 3.73*, 3.71 (s, 3H), 3.62 (m, 1H), 3.35 (m, 1H), 3.09 (m, 1H), 2.88 (m, 1H), 2.61-2.49 (m, 1H), 2.07 (m, 1H), 1.89-1.77 (m, 1H), 1.82 (d, J=4.9 Hz, 1H), 1.42*, 1.37 (s, 9H).

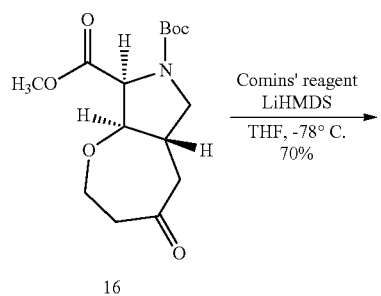

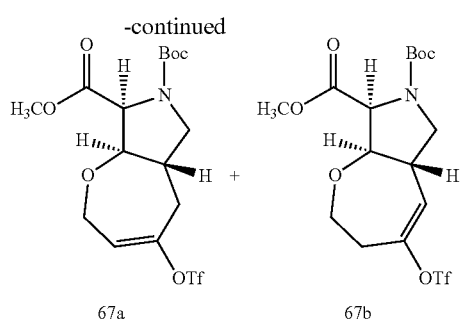

A 1.0 M solution of lithium bis(trimethylsilyl)amide (1.54 mL, 1.543 mmol, 1.2 equiv.) in THF was added dropwise by syringe to a stirring solution of 16 (0.403 g, 1.286 mmol, 1.0 equiv.) in THF (13 mL) at −78° C. The resultant solution was stirred at −78° C. under argon for 1 hour, then Comins' reagent (0.606 g, 1.543 mmol, 1.2 equiv.) was added in a single portion and stirring was continued at −78° C. Consumption of 16 was monitored by TLC (60% EtOAc in hexanes). After 3 hour, the reaction solution was quenched with saturated aq. ammonium chloride, warmed to room temperature while stirring, and extracted with EtOAc (3×50 mL). The combined organic layers were washed with brine, dried over sodium sulfate, and concentrated under reduced pressure. The crude product was purified by column chromatography (20-30-40-50% ether in hexanes) to yield 67a (0.213 g, 0.477 mmol, 37%) and 67b (0.187 g, 0.419 mmol, 33%).

67a $^1$H NMR: (asterisk denotes minor rotamer peaks, 500 MHz, CDCl$_3$) δ 5.83, 5.81* (s, 1H), 4.46*, 4.38 (d, J=8.1 Hz, 1H), 4.08-3.91 (m, 3H), 3.77-3.64 (m, 1H), 3.74*, 3.73 (s, 3H), 3.42-3.22 (m, 1H), 3.13-3.02 (m, 2H), 2.42 (d, 17.1, 1H), 1.42*, 1.37 (s, 9H).

67b $^1$H NMR: (asterisk denotes minor rotamer peaks, 500 MHz, CDCl$_3$) δ 5.84 (s, 1H), 4.49*, 4.41 (d, J=8.2 Hz, 1H), 4.36*, 4.33 (d, J=6.8 Hz, 1H), 4.19, 4.16* (s, 1H), 3.95-3.83 (m, 2H), 3.71*, 3.70 (s, 3H), 2.91 (m, 1H), 2.71-2.56 (m, 3H), 1.40*, 1.36 (s, 9H).

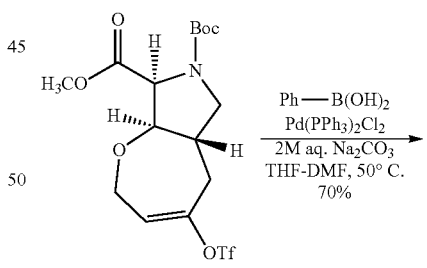

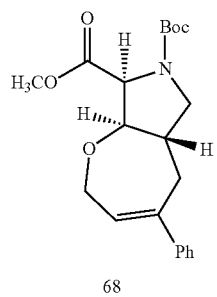

A 2M aq. solution of sodium carbonate (0.04 mL, 0.078 mmol, 0.64 equiv.) was added to a stirring solution of 67a (0.054 g, 0.121 mmol, 1.0 equiv.), phenylboronic acid (0.022 g, 0.182 mmol, 1.5 equiv.), and triphenylphosphine palladium (II) chloride (0.004 g, 0.006 mmol, 0.05 equiv.) in THF (0.3 mL) and DMF (0.3 mL). The resultant yellow solution was heated to 50° C. and stirred at 50° C. under argon. After 24 hours, reaction solution was diluted with saturated aq. sodium bicarbonate and extracted with EtOAc (3×10 mL). The combined organic layers were washed with brine, dried over sodium sulfate, filtered, and concentrated under reduced pressure. The crude product was purified by column chromatography (5-10-20% EtOAc in hexanes) to yield 68 (0.032 g, 0.085 mmol, 70%). $^1$H NMR (asterisk denotes minor rotamer peaks, 500 MHz, CDCl$_3$) δ 7.34-7.26 (m, 5H), 6.01 (m, 1H), 4.58*, 4.49 (d, J=8.2 Hz, 1H), 4.51-4.41 (m, 1H), 4.22 (dt, J=15.1, 4.4 Hz, 1H), 4.04 (m, 2H), 3.92 (dd, J=10.5, 7.6 Hz, 1H), 3.79*, 3.78 (s, 3H), 2.99 (dd, J=10.4, 6.6 Hz, 1H), 2.86 (m, 1H), 2.65-2.60 (m, 1H), 1.47*, 1.43 (s, 9H).

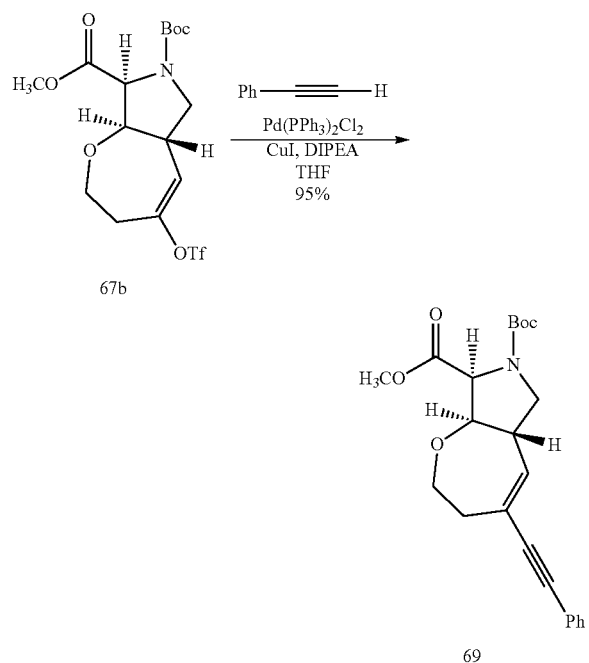

67b

N,N-Diisopropylethylamine (0.03 mL, 0.180 mL, 2.0 equiv.) and ethynylbenzene (0.014 g, 0.135 mmol, 1.5 equiv.) were added sequentially to a stirring solution of 67b (0.040 g, 0.090 mmol, 1.0 equiv.), cuprous iodide (0.002 g, 0.009 mmol, 0.10 equiv.), and triphenylphosphine palladium (II) chloride (0.003 g, 0.005 mmol, 0.05 equiv.) in THF (1 mL). The resultant black solution was stirred at room temperature under argon. After 20 hours, reaction solution was diluted with ether, filtered through a plug of Celite, washing with ether, and concentrated under reduced pressure. The crude product was purified by column chromatography (10-20-30-40% EtOAc in hexanes) to yield 69 (0.034 g, 0.086 mmol, 95%). $^1$H NMR (asterisk denotes minor rotamer peaks, 500 MHz, CDCl$_3$) δ 7.35-7.24 (m, 5H), 6.17, 6.14* (s, 1H), 4.43*, 4.35 (d, J=8.1 Hz, 1H), 4.00-3.95 (m, 2H), 3.92-3.86 (m, 2H), 3.72*, 3.71 (s, 3H), 3.56 (m, 1H), 3.11 (m, 1H), 2.83 (m, 1H), 2.41 (dd, J=16.4, 4.9 Hz, 1H), 1.41*, 1.36 (s, 9H).

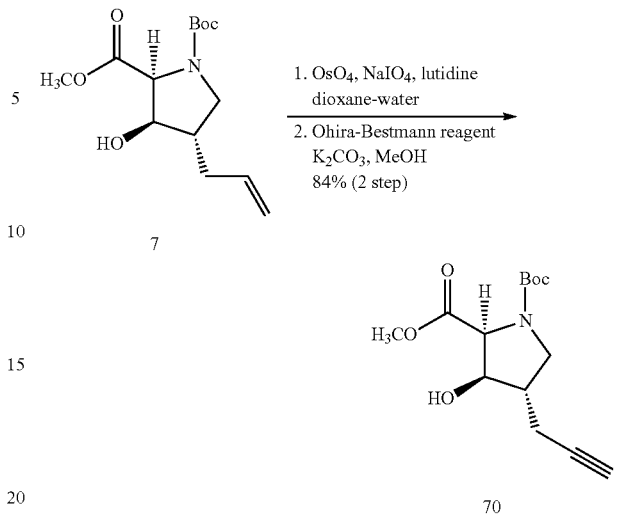

2,6-Lutidine (0.408 mL, 3.50 mmol, 2.0 equiv.), osmium tetroxide (2.5% wt. in t-BuOH, 0.36 mL, 0.035 mmol, 0.02 equiv.), and sodium periodate (1.499 g, 7.01 mmol, 4.0 equiv.) were added sequentially to a stirring solution of 7 (0.500 g, 1.752 mmol, 1.0 equiv.) in dioxane (13.1 mL) and water (4.4 mL). The resultant solution was stirred at room temperature. Consumption of 7 was monitored by TLC (70% EtOAc in hexanes). After 12 hours, the reaction solution was diluted with water and extracted with EtOAc (3×50 mL). The combined organic layers were washed with brine, dried over sodium sulfate, and concentrated to give a yellow oil, which was taken forward to the next step without further purification.

Potassium carbonate (0.842 g, 6.09 mmol, 3.5 equiv.) and Ohira-Bestmann reagent (0.863 g, 4.49 mmol, 2.58 equiv.) were added sequentially to a stirring solution of the aldehyde prepared above (0.500 g, 1.740 mmol, 1.0 equiv.) in anhydrous methanol (8.7 mL) at 0° C. Consumption of the aldehyde was monitored by TLC (70% EtOAc in hexanes). After 5 hours, the reaction solution was quenched with saturated aq. sodium bicarbonate and extracted with EtOAc (3×50 mL). The combined organic layers were washed with brine, dried over sodium sulfate, and concentrated to give a light brown oil. The crude product was purified by column chromatography (25-30% EtOAc in hexanes) to yield 70 (0.415 g, 1.466 mmol, 84% over 2 steps). $^1$H NMR (asterisk denotes minor rotamer peaks, 500 MHz, CDCl$_3$) δ 4.38*, 4.32 (d, J=7.8 Hz, 1H), 4.32-4.24 (m, 1H), 3.77-3.69 (m, 1H), 3.68 (s, 3H), 3.63 (m, 1H), 3.14 (m, 1H), 2.46-2.28 (m, 3H), 1.97 (m, 1H), 1.38*, 1.33 (s, 9H).

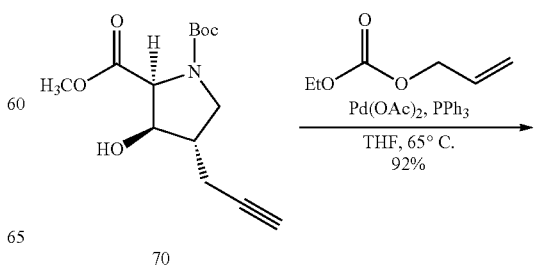

70

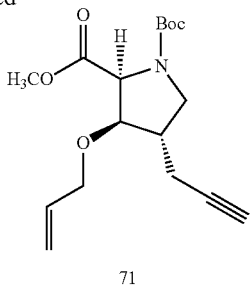

71

A solution of palladium acetate (0.017 g, 0.078 mmol, 0.1 equiv.) and triphenylphosphine (0.102 g, 0.388 mmol, 0.5 equiv.) in THF (3 mL) was transferred via cannula into a stirring solution of 70 (0.220 g, 0.776 mmol, 1.0 equiv.) and allyl ethyl carbonate (0.152 g, 1.165 mmol, 1.5 equiv.) in THF (2 mL); the transfer was quantitated with additional THF (3 mL). The resultant yellow solution was shielded from light, heated to reflux, and stirred while refluxing under argon. Consumption of 70 was monitored by TLC analysis (50% EtOAc in hexanes). After 7 hours, the reaction solution was cooled to room temperature and filtered through a pad of silica gel, washing with MTBE, and concentrated to give an orange oil. The crude product was purified by column chromatography (5-10-20% EtOAc in hexanes) to yield 71 (0.200 g, 0.776 mmol, 80%) as a yellow oil. $^1$H NMR (asterisk denotes minor rotamer peaks, 500 MHz, CDCl$_3$) δ 5.82 (m, 1H), 5.23 (d, J=17.2 Hz, 1H), 5.15 (d, J=10.4 Hz, 1H), 4.54*, 4.45 (d, J=7.6 Hz, 1H), 4.14 (m, 1H), 3.99 (m, 2H), 3.77-3.69 (m, 1H), 3.68 (s, 3H), 3.16 (dd, J=20.8, 10.8 Hz, 1H), 2.58-2.46 (m, 1H), 2.38-2.29 (m, 2H), 1.97 (m, 1H), 1.40*, 1.36 (s, 9H).

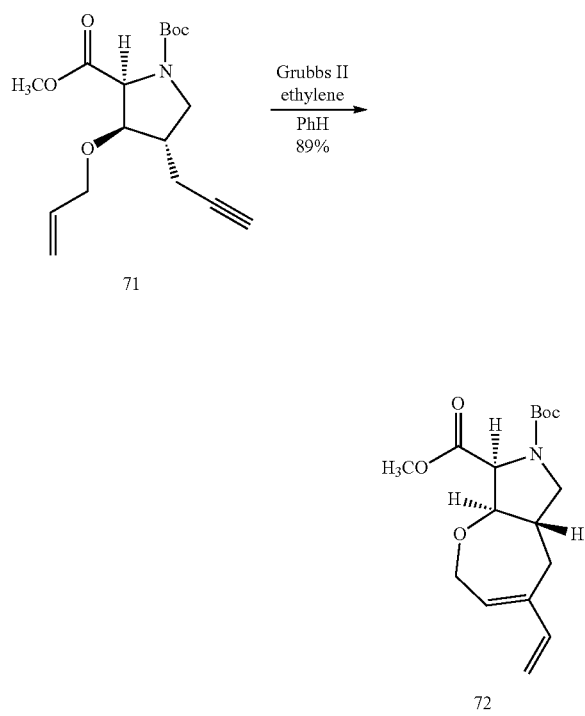 [SMILES: C#CC[C@H]1CN(C(=O)OC(C)(C)C)[C@H](C(=O)OC)[C@@H]1OCC=C ; C=CC1=CCO[C@@H]2[C@@H](C1)CN(C(=O)OC(C)(C)C)[C@@H]2C(=O)OC]

Grubbs 2nd generation catalyst (0.026 g, 0.031 mmol, 0.05 equiv.) was added to a solution of 71 (0.200 g, 0.618 mmol, 1.0 equiv.) in benzene (62 mL). The resultant faintly red solution was stirred at room temperature under ethylene (1 atm, supplied via balloon). Consumption of 71 was monitored by TLC analysis (20% EtOAc in hexanes). After 12 hours, the reaction solution was concentrated under reduced pressure and directly purified by column chromatography (10-20% EtOAc in hexanes) to yield 72 (0.141 g, 0.435 mmol, 70%) as a faintly brown oil. $^1$H NMR (asterisk denotes minor rotamer peaks, 500 MHz, CDCl$_3$) δ 6.29 (dd, J=17.4, 10.8 Hz, 1H), 5.81 (m, 1H), 5.18 (t, J=16.7 Hz, 1H), 5.03 (m, 1H), 4.52*, 4.44 (d, J=8.2 Hz, 1H), 4.37 (dd, J=15.4, 7.0 Hz, 1H), 4.14-4.10 (m, 1H), 3.98-3.81 (m, 2H), 3.75-3.71 (m, 1H), 3.74*, 3.73 (s, 3H), 2.97 (td, J=10.8, 8.6 Hz, 1H), 2.76 (t, J=16.8 Hz, 1H), 2.51-2.38 (m, 1H), 1.44*, 1.39 (s, 9H).

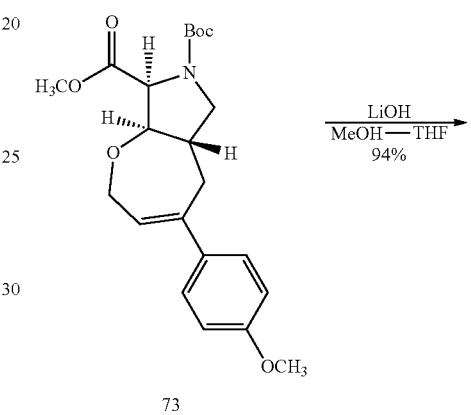

73

74

A 1.0 N aq. solution of lithium hydroxide (0.18 mL, 0.178 mmol, 2.0 equiv.) was added to a solution of 73 (0.036 g, 0.089 mmol, 1.0 equiv.) in methanol (0.22 mL) and THF (0.22 mL). The resultant solution was stirred at room temperature until complete consumption of the methyl ester was observed by mass spectrometry. The reaction solution was acidified with 1 N aq. hydrochloric acid until it reached pH 2, and was extracted with EtOAc (5×3 mL). The combined organic layers were dried over sodium sulfate, filtered, and concentrated to yield 74 (0.033 g, 0.084 mmol, 94%), which was taken forward without further purification.

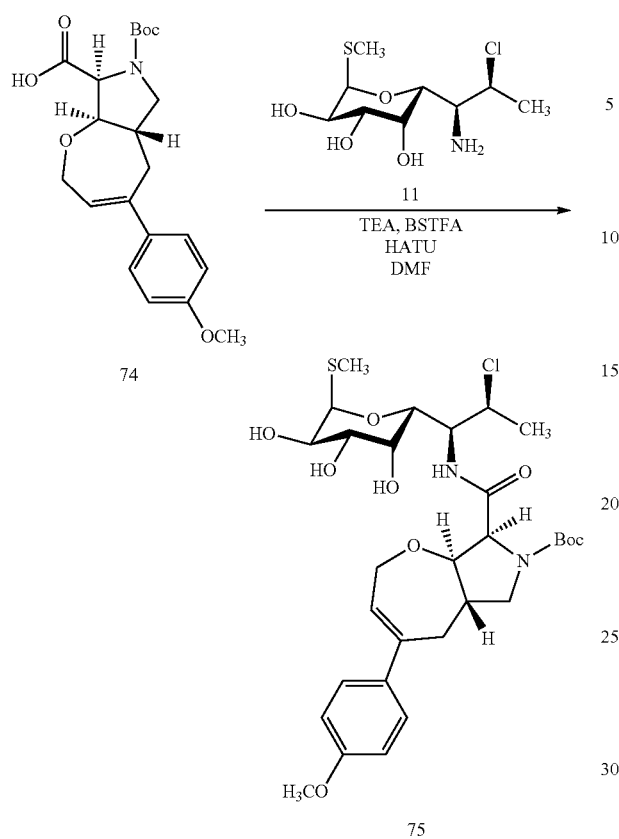

74

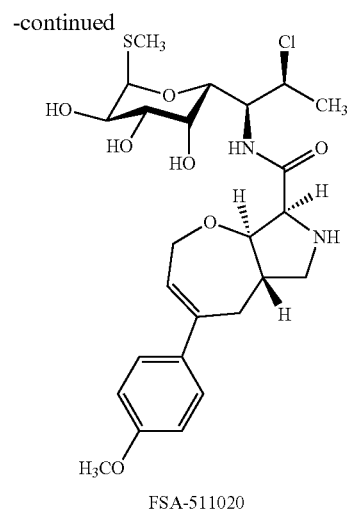

FSA-511020

Triethylamine (0.04 mL, 0.271 mmol, 3.2 equiv.) and bis(trimethylsilyl)trifluoroacetamide (0.03 mL, 0.127 mmol, 1.5 equiv.) were added sequentially to a solution of 11 (0.025 g, 0.093 mmol, 1.1 equiv.) in DMF (0.4 mL) at 0° C. The resultant colorless solution was stirred for 10 min at 0° C., stirred for 1 hour at room temperature, then cannulated into a flask charged with 74 (0.033 g, 0.085 mmol, 1.0 equiv.). HATU (0.042 g, 0.110 mmol, 1.3 equiv.) was added in a single portion and the resultant solution was stirred at room temperature under argon. After complete consumption of 74 was observed by mass spectrometry, the reaction solution was concentrated under reduced pressure and directly purified by column chromatography (2-5-10% MeOH in DCM) to yield 75.

Bis(trimethylsilyl)trifluoroacetamide (0.08 mL, 0.299 mmol, 3.5 equiv.) was added by syringe to a solution of 75 (0.055 g, 0.086 mmol, 1.0 equiv.) in acetonitrile (0.9 mL) at 0° C. The resultant solution was stirred at 0° C. for 5 min, stirred at room temperature for 15 min, then cooled back to 0° C. Trimethylsilyl iodide (0.01 mL, 0.086 mmol, 1.0 equiv.) was added dropwise by syringe to the reaction solution at 0° C. The resultant solution was stirred at 0° C. until complete N-Boc deprotection was observed by mass spectrometry. The reaction solution was quenched with dropwise addition of methanol and concentrated under reduced pressure. The crude product was purified on reverse-phase HPLC (10-50% gradient of MeCN in water over 30 minutes) to yield FSA-511020 (0.011 g, 0.020 mmol, 23%). $^1$H NMR (600 MHz, CD$_3$OD) δ 7.28 (d, J=8.8 Hz, 2H), 6.86 (d, J=8.8 Hz, 2H), 5.93 (s, 1H), 5.31 (d, J=5.7 Hz, 1H), 4.59 (q, J=6.8 Hz, 1H), 4.52 (d, J=10.0 Hz, 1H), 4.40 (d, J=8.9 Hz, 1H), 4.27 (d, J=10.2 Hz, 1H), 4.17 (ddd, J=12.0, 5.0, 2.3 Hz, 1H), 4.09 (m, 2H), 3.90 (s, 1H), 3.77 (s, 3H), 3.69-3.57 (m, 3H), 3.19 (m, 1H), 3.13 (m, 1H), 2.94 (dd, J=16.8, 10.5 Hz, 1H), 2.76 (dd, J=16.5, 4.8 Hz, 1H), 2.15 (s, 3H), 1.57 (d, J=6.8 Hz, 3H).

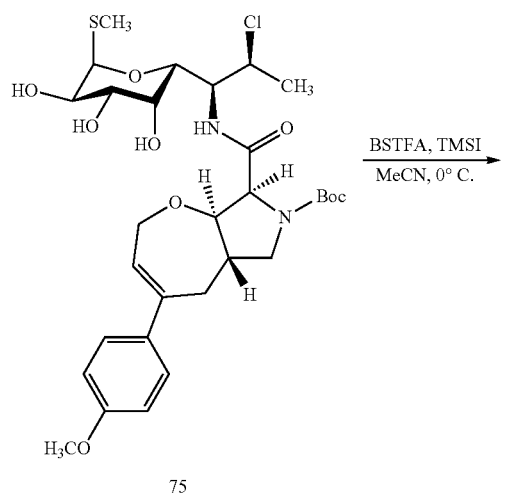

75

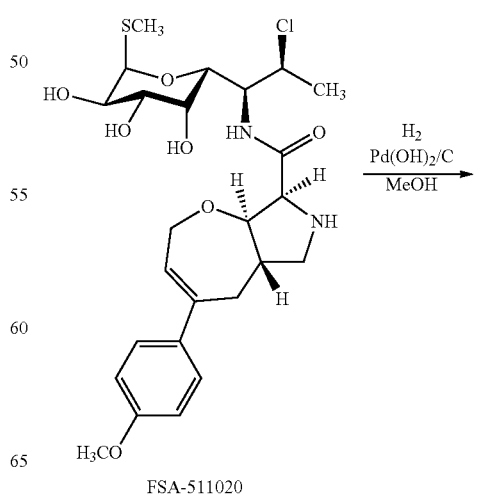

FSA-511020

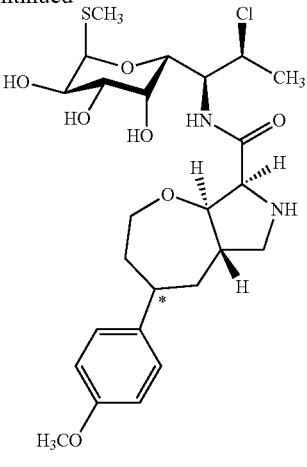

FSA-511045

A suspension of FSA-511020 (0.009 g, 0.017 mmol, 1.0 equiv.) and palladium hydroxide (20% on carbon, 0.012 g, 0.017 mmol, 1.0 equiv.) in anhydrous methanol (0.2 mL) was stirred under hydrogen until complete hydrogenation was observed by mass spectrometry. The reaction solution was filtered through a pad of Celite. The filter pad was washed with methanol, and the filtrate was concentrated. The crude product was purified on reverse-phase HPLC (20-50% gradient of MeCN in water over 30 minutes) to yield FSA-511045 (0.006 g, 0.012 mmol, 69%) as a 50:50 mixture of diastereomers (starred benzylic stereocenter). $^1$H NMR (600 MHz, CD$_3$OD) δ 7.15 (d, J=8.6 Hz, 2H), 6.83 (dd, J=6.9, 2.0 Hz, 2H), 5.30 (dd, J=5.8, 2.0 Hz, 1H), 4.59 (m, 1H), 4.49 (m, 2H), 4.33 (m, 2H), 4.26 (dd, J=10.0, 4.3 Hz, 1H), 4.12-4.07 (m, 2H), 3.88 (dd, J=11.3, 3.4 Hz, 1H), 3.75 (s, 3H), 3.66 (t, J=11.5 Hz, 1H), 3.59 (dt, J=10.0, 3.5 Hz, 1H), 3.51-3.46 (m, 1H), 3.18 (m, 1H), 2.81 (m, 1H), 2.29-2.21 (m, 1H), 2.15 (s, 3H), 2.07-1.97 (m, 1H), 1.91-1.78 (m, 2H), 1.54 (dd, J=13.0, 6.8 Hz, 3H).

The diastereomers of FSA-511045 were separated to provide FSA-512080b and FSA-512080c:

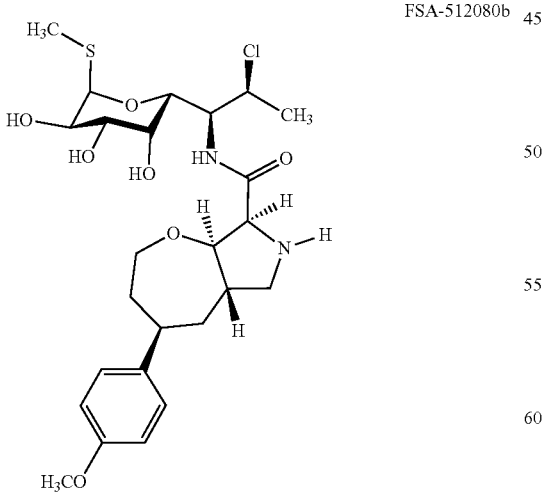

FSA-512080b

FSA-512080b: $^1$H NMR (600 MHz, CD$_3$OD) δ 7.14 (d, J=8.7 Hz, 2H), 6.83 (d, J=8.7 Hz, 2H), 5.30 (d, J=5.6 Hz, 1H), 4.59 (dd, J=6.8, 1.6 Hz, 1H) 4.45 (d, J=9.9, 1.6 Hz, 1H), 4.27 (t, J=9.0 Hz, 1H), 4.23 (d, J=10.2 Hz, 1H), 4.19 (d, J=8.8 Hz, 1H), 4.12 (m, 1H), 4.08 (dd, J=10.3, 5.7 Hz, 1H), 3.93 (m, 1H), 3.75 (s, 3H), 3.64 (m, 1H), 3.58 (dd, J=10.2, 3.3 Hz, 1H), 3.38 (m, 1H), 3.17 (m, 1H), 2.71 (t, J=11.1 Hz, 1H), 2.54 (m, 1H), 2.23 (m, 1H), 2.15 (s, 3H), 1.98 (m, 1H), 1.84 (m, 1H), 1.77 (m, 1H), 1.52 (d, J=6.8 Hz, 3H).

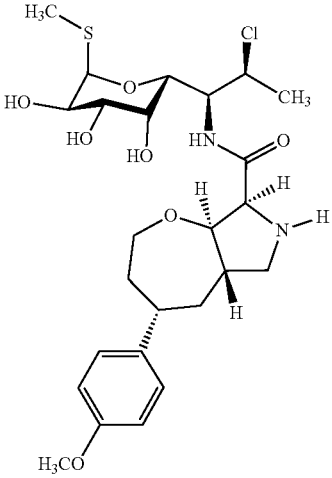

FSA-512080c

FSA-512080c $^1$H NMR (600 MHz, CD$_3$OD) δ 7.14 (d, J=8.7 Hz, 2H), 6.83 (d, J=8.7 Hz, 2H), 5.30 (d, J=5.6 Hz, 1H), 4.60 (dd, J=6.7, 1.6 Hz, 1H), 4.47 (d, J=9.9 Hz, 1H), 4.44 (t, J=9.2 Hz, 1H), 4.25 (d, J=10.1 Hz, 1H), 4.22 (d, J=9.2 Hz, 1H), 4.10-4.05 (m, 2H), 3.93 (dd, J=11.6, 3.1 Hz, 1H), 3.89 (d, J=3.4 Hz, 1H), 3.75 (s, 3H), 3.59 (dd, J=10.2, 3.4 Hz, 1H), 3.42 (m, 1H), 2.82 (t, J=11.3 Hz, 1H), 2.75 (t, J=11.2 Hz, 1H), 2.34 (m, 1H), 2.29-2.23 (m, 1H), 2.15 (s, 3H), 2.05 (m, 1H), 1.88 (m, 1H), 1.54 (d, J=6.8 Hz, 3H), 1.47 (m, 1H).

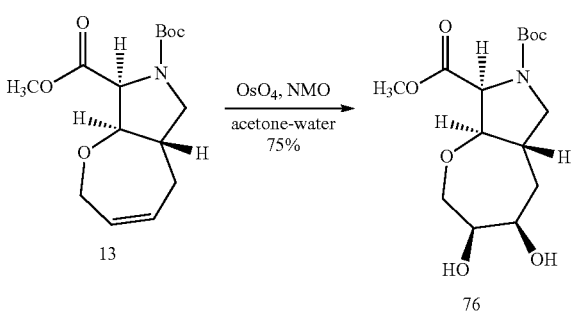 [SMILES: COC(=O)[C@@H]1[C@@H]2OCC=CC[C@H]2CN1C(=O)OC(C)(C)C ; COC(=O)[C@@H]1[C@@H]2OC[C@H](O)[C@H](O)C[C@H]2CN1C(=O)OC(C)(C)C]

N-methylmorpholine N-oxide (0.066 g, 0.565 mmol, 1.50 equiv.) and osmium tetroxide (2.5% wt in t-BuOH, 0.236 mL, 0.019 mmol, 0.05 equiv.) were added sequentially to a stirring solution of 13 (0.112 g, 0.377 mmol, 1 equiv.) in acetone (1.5 mL) and water (0.4 mL) at 0° C. The resultant light brown solution was stirred at room temperature. Consumption of 13 was monitored by TLC analysis (50% EtOAc in hexanes). After 30 min, the reaction was quenched with saturated aq. sodium bicarbonate and extracted with EtOAc (3×10 mL). The combined organic layers were washed with brine, dried over sodium sulfate, and concentrated under reduced pressure. The crude product was purified by column chromatography (80-90-100% EtOAc in hexanes) to yield 76 (0.093 g, 0.282 mmol, 75%). $^1$H NMR (asterisk denotes minor rotamer peaks, 500 MHz, CDCl$_3$) δ 4.38*, 4.31 (d, J=8.2 Hz, 1H), 4.07 (m, 1H), 4.00-3.94 (m, 2H), 3.88 (m, 1H), 3.82-3.72 (m, 2H), 3.69*, 3.68 (s, 3H), 3.54 (d, J=12.2 Hz, 1H), 2.97-2.89 (m, 1H), 2.84 (m, 1H), 2.02 (m, 1H), 1.52 (m, 1H), 1.39*, 1.34 (s, 9H).

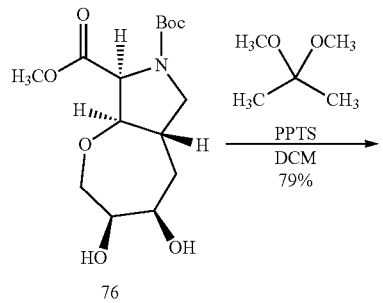

76

2,2-Dimethoxypropane (0.479 mL, 3.89 mmol, 30 equiv.) and pyridinium p-toluenesulfonate (0.016 g, 0.065 mmol, 0.50 equiv.) were added sequentially to a stirring solution of 76 (0.043 g, 0.130 mmol, 1 equiv.) in DCM (2.6 mL). The resultant solution was heated to reflux and stirred at reflux under argon. Consumption of 76 was monitored by TLC (70% EtOAc in hexanes). After 16 hours, the reaction was cooled to room temperature, quenched with saturated aq. sodium bicarbonate, and extracted with EtOAc (3×10 mL). The combined organic layers were washed with brine, dried over sodium sulfate, and concentrated under reduced pressure. The crude product was purified by column chromatography (10-20-30% EtOAc in hexanes) to yield 77 (0.038 g, 0.102 mmol, 79%). $^1$H NMR (asterisk denotes minor rotamer peaks, 500 MHz, CDCl$_3$) δ 4.48-4.45 (m, 1H), 4.46*, 4.38 (d, J=8.0 Hz, 1H), 4.26-4.21 (m, 2H), 3.79-3.66 (m, 2H), 3.74*, 3.74 (s, 3H), 3.50 (d, J=13.4 Hz, 1H), 3.01-2.92 (m, 1H), 2.88 (m, 1H), 2.13 (m, 1H), 1.58 (m, 1H), 1.48 (s, 3H), 1.44*, 1.39 (s, 9H), 1.32 (s, 3H).

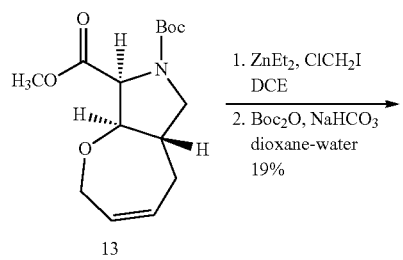

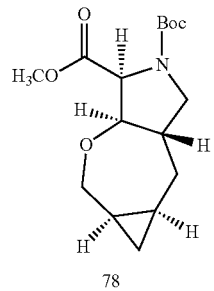

78

Chloroiodomethane (0.10 mL, 1.34 mmol, 4.00 equiv.) was added dropwise by syringe to a stirring solution of diethylzinc (0.07 mL, 0.673 mmol, 2.00 equiv.) in DCE (0.7 mL) at 0° C. The solution was stirred at 0° C. for 10 min, during which time formation of a fine white precipitate was observed. A solution of 13 (0.100 g, 0.336 mmol, 1 equiv.) in DCE (1.0 mL) was added to the organozinc solution via cannula. The resultant solution was stirred at 0° C. under argon. Consumption of 13 was monitored by TLC (30% EtOAc in hexanes). After 4 hours, another portion each of diethylzinc and chloroiodomethane were added to the reaction mixture, and the reaction was allowed to gradually warm to room temperature as the ice-water bath expired. After 16 hours, the reaction was cooled to 0° C., quenched with saturated aq. ammonium chloride, and extracted with EtOAc (3×10 mL). The combined organic layers were washed with brine, dried over sodium sulfate, and concentrated under reduced pressure.

Boc-anhydride (0.23 mL, 0.994 mmol, 2.00 equiv.) and sodium bicarbonate (0.063 g, 0.746 mmol, 1.50 equiv.) were added to a stirring solution of the crude cyclopropanation product in dioxane (2.5 mL) and water (2.5 mL). The resultant solution was stirred at room temperature. After 16 hours, the reaction was diluted with water and EtOAc and extracted with EtOAc (3×10 mL). The combined organic layers were washed with brine, dried over sodium sulfate, and concentrated under reduced pressure. The crude product was purified by column chromatography (10-20% EtOAc in hexanes) to yield 78 (0.030 g, 0.096 mmol, 19%). $^1$H NMR (asterisk denotes minor rotamer peaks, 500 MHz, CDCl$_3$) δ 4.38*, 4.31 (d, J=8.3 Hz, 1H), 4.22 (dd, J=12.8, 3.0 Hz, 1H), 3.77*, 3.75 (m, 2H), 3.73*, 3.72 (s, 3H), 3.48-3.44 (m, 1H), 3.41-3.37 (m, 1H), 2.41-2.28 (m, 1H), 2.23-2.15 (m, 1H), 1.64 (dd, J=12.0, 2.4, 1H), 1.42*, 1.37 (s, 9H), 1.06 (m, 1H), 0.95 (m, 1H), 0.59 (m, 1H), 0.38 (m, 1H).

The following compounds were prepared in an analogous manner to those prepared above using the appropriate starting materials:

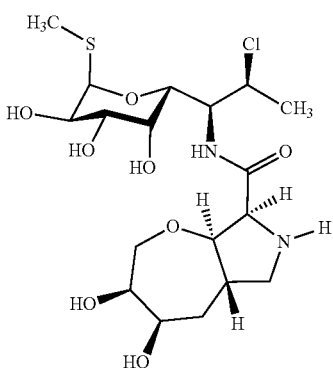

FSA-501076

FSA-501076:
¹H NMR (500 MHz, CD₃OD) δ 5.31 (d, J=5.6 Hz, 1H), 4.60 (dd, J=7.5, 6.1 Hz, 1H), 4.41 (d, J=10.0 Hz, 1H), 4.22 (d, J=9.8 Hz, 1H), 4.14-4.08 (m, 4H), 4.05-3.98 (m, 3H), 3.94 (m, 1H), 3.63-3.59 (m, 2H), 3.36 (d, J=0.9 Hz, 1H), 3.29 (m, 1H), 2.69-2.62 (m, 2H), 2.15 (s, 3H), 1.52 (d, J=6.6 Hz, 3H).

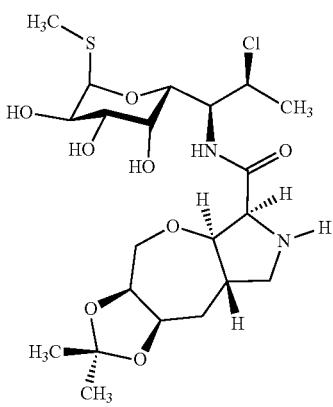

FSA-501099

FSA-501099:
¹H NMR (600 MHz, CD₃OD) δ 5.28 (d, J=5.6 Hz, 1H), 4.63 (m, 1H), 4.56 (m, 2H), 4.46 (m, 1H), 4.31 (d, J=10.0, 1H), 4.27-4.24 (m, 2H), 4.22 (m, 1H), 4.13 (d, J=10.0 Hz, 1H), 4.08-4.05 (m, 2H), 3.96 (d, J=9.2 Hz, 1H), 3.76 (t, J=9.4 Hz, 1H), 3.61 (m, 2H), 3.07 (m, 1H), 2.61 (m, 1H), 2.13 (s, 3H), 1.53 (d, J=6.8 Hz, 3H), 1.46 (s, 3H), 1.31 (s, 3H).

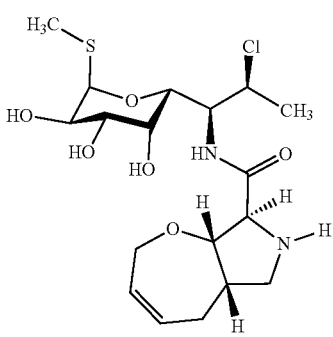

FSA-504059

FSA-504059:
¹H NMR (500 MHz, CD₃OD) δ 5.76 (m, 1H), 5.51 (m, 1H), 5.33 (d, J=5.7 Hz, 1H), 4.61 (qd, J=6.8, 1.6 Hz, 1H), 4.58-4.52 (m, 2H), 4.29 (d, J=10.1 Hz, 1H), 4.27-4.22 (m, 2H), 4.11 (dd, J=10.2, 5.6 Hz, 1H), 3.99 (d, J=6.2 Hz, 1H), 3.84 (dd, J=3.4, 1.1 Hz, 1H), 3.61 (dd, J=10.2, 3.3 Hz, 1H), 3.44 (dd, J=11.5, 7.7 Hz, 1H), 2.89 (dd, J=11.5, 7.9 Hz, 1H), 2.77 (dqd, J=11.4, 7.7, 3.6 Hz, 1H), 2.65 (ddt, J=15.0, 11.7, 3.2 Hz, 1H), 2.16 (s, 3H), 2.04 (m, 1H), 1.48 (d, J=6.8 Hz, 3H).

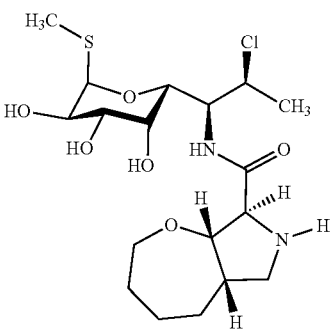

FSA-504062

FSA-504062:
¹H NMR (500 MHz, CD₃OD) δ 5.32 (d, J=5.8 Hz, 1H), 4.61 (dd, J=6.8, 1.6 Hz, 1H), 4.57 (d, J=10.0 Hz, 1H), 4.36-4.28 (m, 3H), 4.21 (d, J=12.2 Hz, 1H), 4.11 (dd, J=10.2, 5.6 Hz, 1H), 3.86 (d, J=3.4 Hz, 1H), 3.66 (ddd, J=11.3, 8.1, 3.0 Hz, 1H), 3.61 (dt, J=10.2, 2.5 Hz, 1H), 3.50 (ddd, J=12.2, 10.3, 3.8 Hz, 1H), 3.10 (t, J=10.7 Hz, 1H), 2.59 (m, 1H), 2.17 (s, 3H), 1.97-1.86 (m, 2H), 1.83-1.75 (m, 2H), 1.66-1.57 (m, 1H), 1.53-1.46 (m, 1H), 1.48 (d, J=6.8 Hz, 3H).

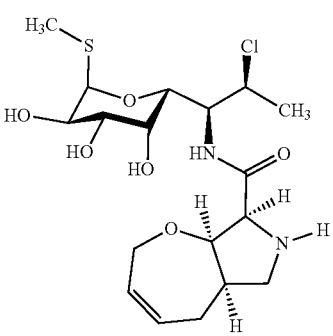

FSA-507051

FSA-507051:
¹H NMR (500 MHz, CD₃OD) δ 5.76 (m, 1H), 5.56 (m, 1H), 5.32 (d, J=5.6 Hz, 1H), 4.60-4.56 (m, 2H), 4.54 (m, 1H), 4.40-4.36 (m, 2H), 4.31 (dq, J=17.2, 2.8 Hz, 1H), 4.25 (d, J=5.7 Hz, 1H), 4.11 (dd, J=10.2, 5.6 Hz, 1H), 3.83 (d, J=3.2 Hz, 1H), 3.60 (m, 2H), 3.10 (dd, J=11.6, 8.3 Hz, 1H), 2.87 (m, 1H), 2.67 (m, 1H), 2.16 (s, 3H), 2.15-2.11 (m, 1H), 1.51 (d, J=6.7 Hz, 3H).

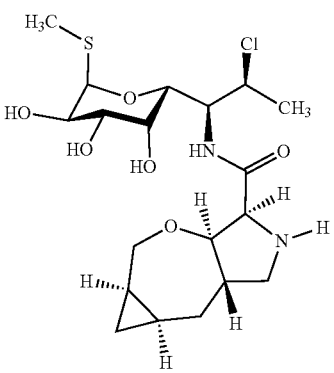

FSA-507007

FSA-507007:
¹H NMR (600 MHz, CD₃OD) δ 5.30 (d, J=5.6 Hz, 1H), 4.56 (qd, J=6.8, 1.7 Hz, 1H), 4.51 (dd, J=10.0, 1.6 Hz, 1H), 4.37 (d, J=8.8 Hz, 1H), 4.28 (m, 2H), 4.08 (dd, J=10.2, 5.6 Hz, 1H), 3.88 (d, J=12.8 Hz, 1H), 3.83 (d, J=3.0 Hz, 1H), 3.65 (t, J=9.5 Hz, 1H), 3.57 (dd, J=10.2, 3.3 Hz, 1H), 3.48 (dd, J=11.1, 7.2 Hz, 1H), 2.84 (t, J=11.7 Hz, 1H), 2.27 (dt, J=14.1, 3.6 Hz, 1H), 2.14 (s, 3H), 2.08 (m, 1H), 1.75 (ddd, 14.3, 12.1, 2.4 Hz, 1H), 1.52 (d, J=6.8 Hz, 3H), 1.17 (m, 1H), 1.07 (m, 1H), 0.55 (q, J=5.8 Hz, 1H), 0.44 (td, J=9.1, 4.8 Hz, 1H).

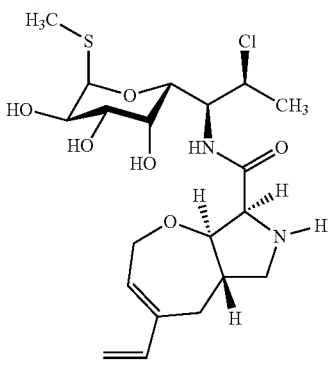

FSA-507041

FSA-507041:
¹H NMR (500 MHz, CD₃OD) δ 6.34 (dd, J=17.4, 10.9 Hz, 1H), 5.86 (m, 1H), 5.29 (d, J=5.5 Hz, 1H), 5.25 (d, J=17.5 Hz, 1H), 5.05 (d, J=10.9 Hz, 1H), 4.57 (m, 1H), 4.50-4.40 (m, 3H), 4.26-4.22 (m, 2H), 4.14 (m, 1H), 4.08 (m, 2H), 3.84 (m, 1H), 3.57 (d, J=10.0 Hz, 2H), 2.97-2.85 (m, 2H), 2.14 (s, 3H), 2.13-2.09 (m, 1H), 1.50 (d, J=6.8 Hz, 3H).

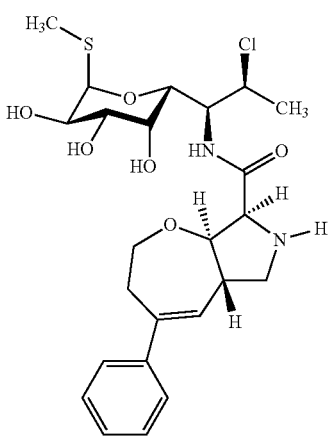

FSA-507031

FSA-507031:
¹H NMR (600 MHz, CD₃OD) δ 7.33 (m, 2H), 7.29 (m, 2H), 7.22 (t, J=7.1 Hz, 1H), 5.98 (s, 1H), 5.29 (d, J=5.6 Hz, 1H), 4.58 (m, 1H), 4.47 (dd, J=9.7, 1.7 Hz, 1H), 4.25 (d, J=10.1 Hz, 1H), 4.16 (m, 2H), 4.08 (dd, J=10.1, 5.7 Hz, 1H), 3.88 (d, J=8.5 Hz, 1H), 3.83 (d, J=3.3 Hz, 1H), 3.75-3.69 (m, 2H), 3.64-3.59 (m, 1H), 3.57 (dd, J=10.2, 3.3 Hz, 1H), 3.48 (t, J=9.6 Hz, 1H), 3.10-3.01 (m, 1H), 2.79 (dd, J=16.5, 5.2 Hz, 1H), 2.14 (s, 3H), 1.48 (d, J=6.8 Hz, 3H).

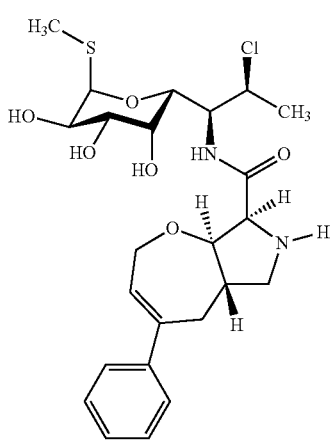

FSA-507056

FSA-507056:
¹H NMR (500 MHz, CD₃OD) δ 7.34 (m, 4H), 7.27 (m, 1H), 6.07 (s, 1H), 5.34 (d, J=5.3 Hz, 1H), 4.68 (d, J=8.0 Hz, 1H), 4.59-4.49 (m, 3H), 4.33 (m, 3H), 4.12 (m, 1H), 3.88 (s, 1H), 3.74 (t, J=9.6 Hz, 1H), 3.62 (d, J=9.9 Hz, 1H), 3.10 (t, J=12.2 Hz, 1H), 2.96 (d, J=15.2 Hz, 1H), 2.74 (t, J=13.6 Hz, 1H), 2.34 (m, 1H), 2.17 (s, 3H), 2.06 (d, J=3.8 Hz, 1H), 1.54 (d, J=6.6 Hz, 3H).

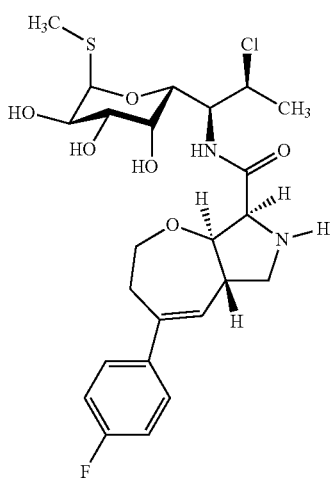

FSA-507052

FSA-507052:
¹H NMR (500 MHz, CD₃OD) δ 7.40 (dd, J=8.6, 5.4 Hz, 2H), 7.07 (t, J=8.7 Hz, 2H), 6.01 (s, 1H), 5.33 (d, J=5.6 Hz, 1H), 4.62 (d, J=8.4 Hz, 1H), 4.61-4.57 (m, 2H), 4.32 (d,

J=10.0 Hz, 1H), 4.23-4.16 (m, 2H), 4.11 (dd, J=10.2, 5.6 Hz, 1H), 3.84 (m, 2H), 3.71 (t, J=11.5 Hz, 1H), 3.60 (dd, J=10.2, 3.4 Hz, 1H), 3.01 (m, 1H), 2.80 (dd, J=16.5, 4.8 Hz, 1H), 2.18 (s, 3H), 1.62 (d, J=6.8 Hz, 3H).

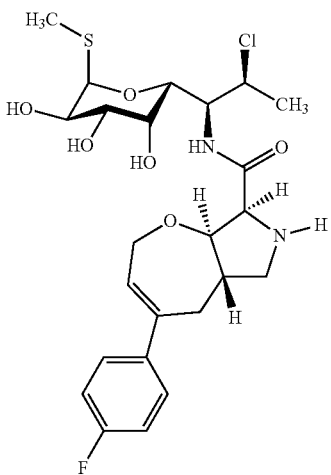

FSA-507057

FSA-507057:
$^1$H NMR (500 MHz, CD$_3$OD) δ 7.35 (dd, J=8.6, 5.4 Hz, 2H), 7.03 (t, J=8.7 Hz, 2H), 6.00 (m, 1H), 5.30 (d, J=5.5 Hz, 1H), 4.57 (dd, J=7.1, 6.4 Hz, 1H), 4.53-4.47 (m, 2H), 4.34-4.29 (m, 1H), 4.27 (d, J=9.9 Hz, 1H), 4.24-4.16 (m, 2H), 4.08 (dd, J=10.2, 5.5 Hz, 1H), 3.88-381 (m, 1H), 3.59 (m, 2H), 3.01-2.95 (m, 1H), 2.90-2.82 (m, 1H), 2.73-2.61 (m, 1H), 2.32 (m, 1H), 2.15 (s, 3H), 1.52 (d, J=6.8 Hz, 3H).

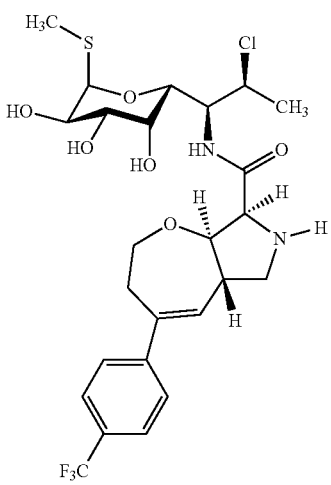

FSA-507053

FSA-507053:
$^1$H NMR (500 MHz, CD$_3$OD) δ 7.64 (d, J=8.1 Hz, 2H), 7.57 (d, J=8.2 Hz, 2H), 6.17 (s, 1H), 5.35 (d, J=5.5 Hz, 1H), 4.65 (m, 2H), 4.59 (m, 2H), 4.33 (d, J=10.0 Hz, 1H), 4.22 (m, 2H), 4.12 (m, 2H), 3.89 (s, 2H), 3.73 (t, J=11.5 Hz, 1H), 3.63 (d, J=10.1 Hz, 1H), 3.04 (m, 1H), 2.83 (dd, J=16.6, 4.5 Hz, 1H), 2.17 (s, 3H), 1.61 (d, J=6.7 Hz, 3H).

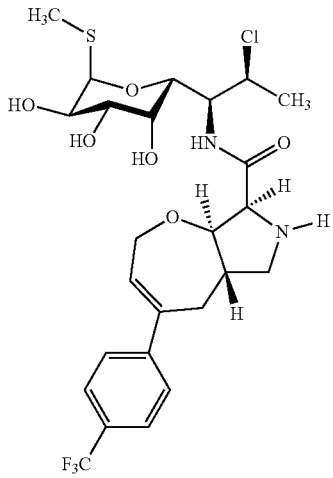

FSA-507060

FSA-507060:
$^1$H NMR (500 MHz, CD$_3$OD) δ 7.61 (d, J=8.2 Hz, 2H), 7.52 (d, J=8.1 Hz, 2H), 6.15 (s, 1H), 5.30 (d, J=5.6 Hz, 1H), 4.59-4.51 (m, 4H), 4.34 (d, J=15.5 Hz, 1H), 4.29-4.24 (m, 2H), 4.09 (dd, J=10.2, 5.6 Hz, 1H), 3.87 (s, 1H), 3.63 (dd, J=11.0, 7.3 Hz, 1H), 3.59 (dd, J=10.2, 3.1 Hz, 1H), 3.01 (t, J=11.8 Hz, 1H), 2.93 (d, J=16.0 Hz, 1H), 2.74 (t, J=13.7 Hz, 1H), 2.34 (m, 1H), 2.15 (s, 3H), 1.53 (d, J=6.8 Hz, 3H).

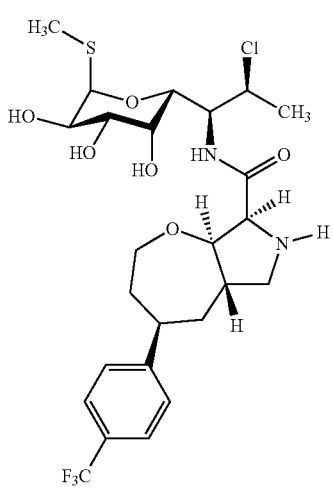

FSA-507019

FSA-509019:
$^1$H NMR (600 MHz, CD$_3$OD) δ 7.59 (d, J=8.0 Hz, 2H), 7.45 (d, J=8.1 Hz, 2H), 5.31 (d, J=5.5 Hz, 1H), 4.57 (dd, J=7.4, 6.8 Hz, 1H), 4.52 (d, J=10.0 Hz, 1H), 4.50-4.45 (m, 1H), 4.44-4.38 (m, 1H), 4.28 (d, J=10.1 Hz, 1H), 4.14 (ddd, J=12.4, 4.4, 2.2 Hz, 1H), 4.09 (dd, J=10.2, 5.6 Hz, 1H), 3.90 (s, 1H), 3.71 (t, J=11.6 Hz, 1H), 3.60 (m, 1H), 3.55 (m, 1H), 3.37 (q, J=9.4 Hz, 1H), 2.93 (s, 1H), 2.68 (s, 1H), 2.30 (m, 1H), 2.15 (s, 3H), 2.03 (ddd, J=13.3, 9.3, 6.8 Hz, 1H), 1.94 (m, 1H), 1.84 (dd, J=15.2, 4.3 Hz, 1H), 1.52 (d, J=6.8 Hz, 3H).

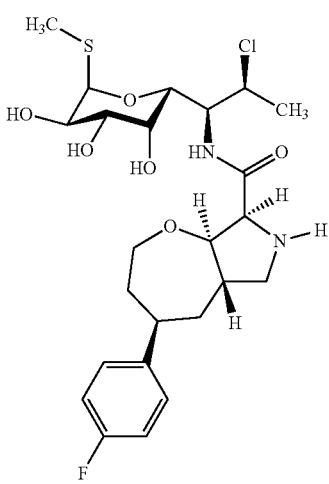

FSA-507061:
¹H NMR (500 MHz, CD₃OD) δ 7.27 (dd, J=8.5, 5.3 Hz, 2H), 7.02 (td, J=8.8 Hz, 1.2 Hz, 2H), 5.32 (d, J=5.5 Hz, 1H), 4.60 (q, J=6.8 Hz, 1H), 4.53 (d, J=9.9 Hz, 1H), 4.47-4.35 (m, 2H), 4.29 (d, J=10.0 Hz, 1H), 4.16-4.09 (m, 2H), 3.90 (s, 1H), 3.70 (t, J=11.6 Hz, 1H), 3.60 (d, J=10.1 Hz, 1H), 3.54 (m, 1H), 3.28 (m, 1H), 2.89 (m, 1H), 2.64 (s, 1H), 2.27 (dd, J=12.3, 11.6 Hz, 1H), 2.17 (s, 3H), 2.02 (dt, J=15.8, 7.9 Hz, 1H), 1.91 (m, 1H), 1.82 (d, J=11.4 Hz, 1H), 1.55 (d, J=6.7 Hz, 3H).

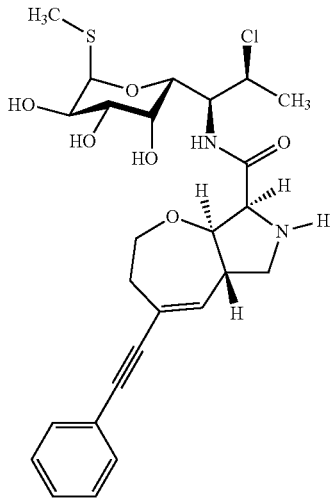

FSA-510002:
¹H NMR (600 MHz, CD₃OD) δ 7.38 (m, 2H), 7.33 (m, 3H), 6.27 (s, 1H), 5.31 (d, J=5.6 Hz, 1H), 4.58 (qd, J=6.7, 1.5 Hz, 1H), 4.52 (dd, J=10.0, 1.6 Hz, 1H), 4.45 (d, J=8.8 Hz, 1H), 4.28 (d, J=10.0 Hz, 1H), 4.09 (m, 3H), 3.89 (d, J=3.4 Hz, 1H), 3.70-3.63 (m, 2H), 3.60 (dd, J=10.2, 3.4 Hz, 1H), 3.25 (m, 1H), 3.15 (t, J=11.8 Hz, 1H), 2.87 (dd, J=15.2, 11.0 Hz, 1H), 2.50 (dd, J=16.3, 4.6 Hz, 1H), 2.15 (s, 3H), 1.56 (d, J=6.7 Hz, 3H).

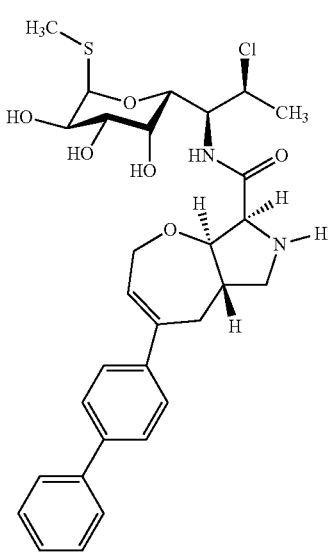

FSA-510001:
¹H NMR (500 MHz, CD₃OD) δ 7.59 (m, 4H), 7.43 (m, 4H), 7.33 (m, 1H), 6.12 (m, 1H), 5.30 (d, J=5.6 Hz, 1H), 4.58 (qd, J=6.7, 1.6 Hz, 1H), 4.54-4.50 (m, 2H), 4.47 (d, J=8.7 Hz, 1H), 4.32 (ddd, J=15.2, 4.2, 2.0 Hz, 1H), 4.27 (d, J=10.0 Hz, 1H), 4.23 (t, J=7.7 Hz, 1H), 4.09 (dd, J=10.2, 5.7 Hz, 1H), 3.86 (dd, J=3.4, 1.2 Hz, 1H), 3.61-3.57 (m, 2H), 2.96 (m, 2H), 2.71 (m, 1H), 2.33-2.26 (m, 1H), 2.15 (s, 3H), 1.54 (d, J=6.8 Hz, 3H).

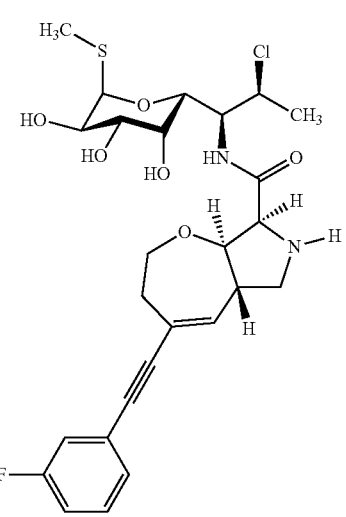

FSA-510003:
¹H NMR (600 MHz, CD₃OD) δ 7.35 (td, J=8.0, 5.9 Hz, 1H), 7.20 (dt, J=7.7, 1.2 Hz, 1H), 7.12 (ddd, J=9.5, 2.7, 1.4 Hz, 1H), 7.08 (tdd, J=8.7, 2.6, 1.0 Hz, 1H), 6.31 (s, 1H), 5.31 (d, J=5.6 Hz, 1H), 4.58 (qd, J=6.8, 1.6 Hz, 1H), 4.51 (dd, J=10.0, 1.6 Hz, 1H), 4.40 (d, J=8.8 Hz, 1H), 4.27 (dd, J=10.0, 1.2 Hz, 1H), 4.10-4.06 (m, 3H), 3.88 (d, J=3.4 Hz, 1H), 3.66-3.62 (m, 2H), 3.59 (dd, J=10.2, 3.3 Hz, 1H), 3.23 (m, 1H), 3.11 (dd, J=12.6, 10.8 Hz, 1H), 2.88 (m, 1H), 2.50 (dd, J=16.4, 4.5 Hz, 1H), 2.15 (s, 3H), 1.55 (d, J=6.8 Hz, 3H).

FSA-510006

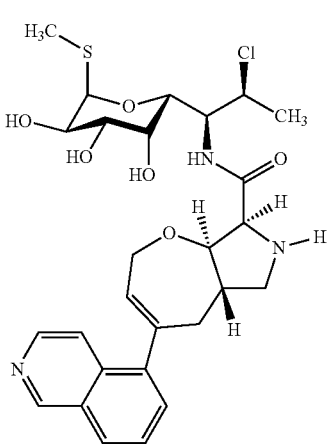

FSA-510006:
¹H NMR (600 MHz, CD₃OD) δ 9.25 (s, 1H), 8.45 (d, J=6.0 Hz, 1H), 8.05 (d, J=8.2 Hz, 1H), 7.82 (d, J=6.0 Hz, 1H), 7.67 (dd, J=8.2, 7.1 Hz, 1H), 7.61 (dd, J=7.0, 1.2 Hz, 1H), 5.99 (m, 1H), 5.32 (d, J=5.7 Hz, 1H), 4.68 (dd, J=9.3, 5.4 Hz, 1H), 4.62-4.55 (m, 3H), 4.47-4.40 (m, 2H), 4.33 (d, J=9.9 Hz, 1H), 4.10 (dd, J=10.2, 5.7 Hz, 1H), 3.88 (s, 1H), 3.64 (dd, J=11.5, 7.4 Hz, 1H), 3.61 (dd, J=10.2, 3.3 Hz, 1H), 3.04 (td, J=12.0, 3.0 Hz, 1H), 2.89 (m, 1H), 2.72 (dd, J=16.2, 2.9 Hz, 1H), 2.53 (m, 1H), 2.16 (s, 3H), 1.61 (d, J=6.7 Hz, 3H).

FSA-510011

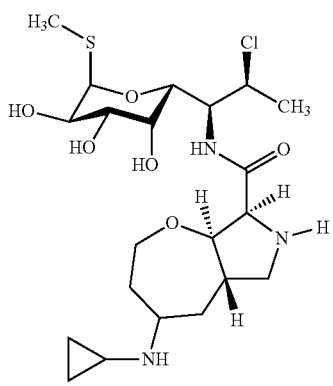

FSA-510011:
¹H NMR (600 MHz, CD₃OD) δ 5.31 (d, J=5.6 Hz, 1H), 4.57-4.50 (m, 3H), 4.30-4.23 (m, 2H), 4.14-4.05 (m, 2H), 3.94-3.86 (m, 2H), 3.81 (m, 1H), 3.71-3.63 (m, 2H), 3.59 (m, 1H), 3.02 (m, 1H), 2.72 (m, 1H), 2.59-2.40 (m, 1H), 2.26 (m, 1H), 2.22-2.05 (m, 2H), 2.15 (s, 3H), 1.52 (d, J=6.7 Hz, 3H), 0.90 (m, 4H).

FSA-510012

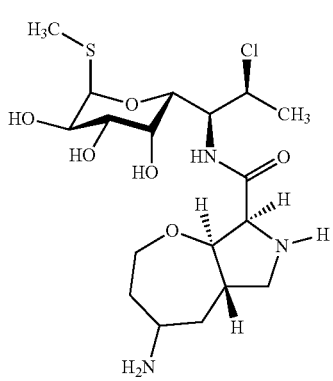

FSA-510012:
¹H NMR (600 MHz, CD₃OD) δ 5.31 (d, J=5.4 Hz, 1H), 4.55-4.42 (m, 3H), 4.31-4.22 (m, 1H), 4.26 (d, J=9.8 Hz, 1H), 4.11-4.02 (m, 2H), 3.89 (m, 1H), 3.75 (m, 1H), 3.66 (m, 2H), 3.58 (m, 1H), 3.46 (m, 1H), 2.38-2.22 (m, 2H), 2.16-2.00 (m, 3H), 2.14 (s, 3H), 1.51 (m, 3H).

FSA-511033

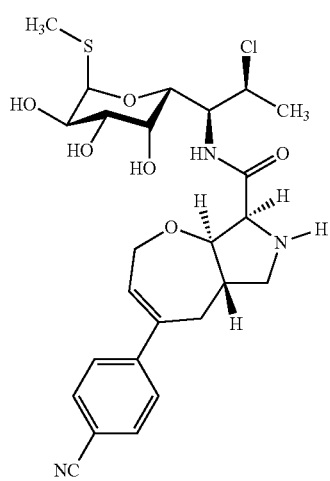

FSA-511033:
¹H NMR (600 MHz, CD₃OD) δ 7.67 (d, J=8.4 Hz, 2H), 7.54 (d, J=8.3 Hz, 2H), 6.19 (s, 1H), 5.31 (d, J=5.6 Hz, 1H), 4.59 (qd, J=6.8, 1.6 Hz, 1H), 4.53 (d, J=11.6 Hz, 1H), 4.43 (d, J=8.8 Hz, 1H), 4.28 (d, J=10.0 Hz, 1H), 4.18 (ddd, J=12.2, 5.0, 2.3 Hz, 1H), 4.14-4.08 (m, 2H), 3.91 (s, 1H), 3.75-3.65 (m, 2H), 3.60 (dd, J=10.2, 3.3 Hz, 1H), 3.30-3.25 (m, 1H), 3.19 (t, J=11.6 Hz, 1H), 3.02 (m, 1H), 2.78 (dd, J=16.5, 4.7 Hz, 1H), 2.15 (s, 3H), 1.57 (d, J=6.8 Hz, 3H).

FSA-510021

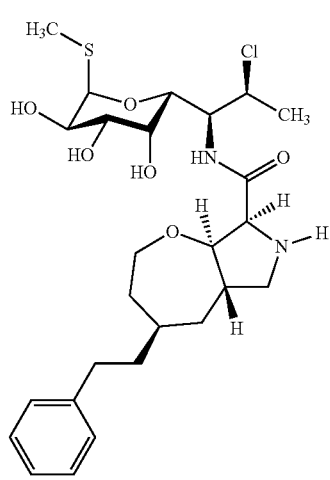

FSA-510021:
¹H NMR (600 MHz, CD₃OD) δ 7.24 (m, 2H), 7.16 (m, 3H), 5.30 (d, J=5.6 Hz, 1H), 4.57 (m, 1H), 4.51 (m, 2H), 4.28 (m, 1H), 4.25-4.19 (m, 1H), 4.10-4.00 (m, 2H), 3.83-3.77 (m, 1H), 3.65-3.56 (m, 3H), 2.93 (m, 1H), 2.63 (m, 2H), 2.42 (m, 1H), 2.14 (s, 3H), 2.08-1.97 (m, 1H), 1.86 (m, 1H), 1.76 (m, 2H), 1.65 (m, 3H), 1.50 (d, J=6.8 Hz, 3H). J=10.0

Hz, 1H), 4.23-4.16 (m, 2H), 4.11 (dd, J=10.2, 5.6 Hz, 1H), 3.84 (m, 2H), 3.71 (t, J=11.5 Hz, 1H), 3.60 (dd, J=10.2, 3.4 Hz, 1H), 3.01 (m, 1H), 2.80 (dd, J=16.5, 4.8 Hz, 1H), 2.18 (s, 3H), 1.62 (d, J=6.8 Hz, 3H).

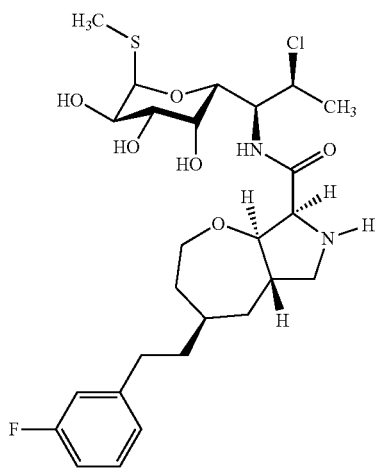

FSA-510022

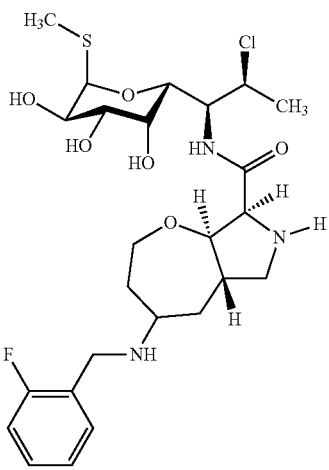

FSA-510072

FSA-510022:

¹H NMR (600 MHz, CD₃OD) δ 7.25 (tdd, J=8.1, 6.0, 2.0 Hz, 1H), 6.99 (dt, J=7.8, 1.9 Hz, 1H), 6.92 (dt, J=10.1, 2.2 Hz, 1H), 6.88 (m, 1H), 5.30 (d, J=5.6 Hz, 1H), 4.57 (m, 1H), 4.51 (m, 1H), 4.43 (d, J=8.9 Hz, 1H), 4.27 (dd, J=10.0, 1.3 Hz, 1H), 4.09-3.99 (m, 3H), 3.82 (m, 1H), 3.63 (ddd, J=11.7, 8.7, 2.6 Hz, 1H), 3.57 (m, 2H), 2.90 (m, 1H), 2.66 (m, 2H), 2.44-2.34 (m, 1H), 2.14 (s, 3H), 2.08-1.96 (m, 1H), 1.85 (m, 1H), 1.75 (m, 1H), 1.69-1.60 (m, 3H), 1.55-1.48 (m, 1H), 1.51 (d, J=6.8 Hz, 3H).

FSA-510072:

¹H NMR (600 MHz, CD₃OD) δ 7.55 (td, J=7.6, 1.7 Hz, 1H), 7.47 (ddd, J=8.6, 7.2, 1.8 Hz, 1H), 7.26 (td, J=7.5, 1.2 Hz, 1H), 7.22 (ddd, J=9.7, 8.4, 1.1 Hz, 1H), 5.30 (d, J=5.6 Hz, 1H), 4.56 (qd, J=6.8, 1.5 Hz, 1H), 4.50 (dd, J=10.0, 1.6 Hz, 1H), 4.46 (d, J=8.9 Hz, 1H), 4.28-4.25 (m, 3H), 4.21-4.14 (m, 2H), 4.09 (dd, J=10.2, 5.6 Hz, 1H), 3.88 (m, 1H), 3.77 (d, J=11.1 Hz, 2H), 3.72 (m, 1H), 3.66 (t, J=11.1 Hz, 1H), 3.62-3.55 (m, 2H), 2.96 (t, J=11.5 Hz, 1H), 2.58 (dt, J=13.3, 7.4 Hz, 1H), 2.19-2.10 (m, 3H), 2.14 (s, 3H), 1.51 (d, J=6.8 Hz, 3H).

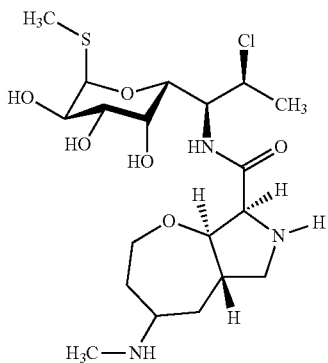

FSA-510065

FSA-510073

FSA-510065:

¹H NMR (600 MHz, CD₃OD) δ 5.31 (d, J=5.6 Hz, 1H), 4.56 (q, J=7.1 Hz, 1H), 4.49 (m, 2H), 4.29 (m, 1H), 4.13 (m, 1H), 4.08 (m, 2H), 3.94-3.86 (m, 1H), 3.75-3.70 (m, 1H), 3.65 (d, J=11.2 Hz, 2H), 3.60-3.57 (m, 2H), 3.04 (t, J=11.7 Hz, 1H), 2.43-2.35 (m, 1H), 2.26 (m, 1H), 2.20-2.15 (m, 1H), 2.15 (s, 3H), 2.11-2.05 (m, 1H), 1.52-1.46 (m, 1H), 1.51 (d, J=6.7 Hz, 3H).

FSA-510073:

¹H NMR (600 MHz, CD₃OD) δ 7.46 (dd, J=8.0, 5.8 Hz, 1H), 7.30 (m, 2H), 7.17 (td, J=8.6, 2.4 Hz, 1H), 5.30 (d, J=5.7 Hz, 1H), 4.57 (q, J=6.9 Hz, 1H), 4.49 (dd, J=10.0, 3.3 Hz, 1H), 4.46-4.37 (m, 1H), 4.26 (dd, J=10.1, 3.2 Hz, 1H), 4.23-4.18 (m, 2H), 4.17-4.12 (m, 2H), 4.08 (dd, J=10.3, 5.6 Hz, 1H), 3.88 (m, 1H), 3.77 (d, J=11.0 Hz, 2H), 3.71-3.61

(m, 2H), 3.58 (m, 2H), 2.93 (m, 1H), 2.57 (m, 1H), 2.18-2.06 (m, 3H), 2.14 (s, 3H), 1.51 (d, J=6.8 Hz, 3H).

1H), 2.63 (t, J=10.4 Hz, 1H), 2.57-2.50 (m, 1H), 2.14 (s, 3H), 1.51-1.47 (m, 1H), 1.49 (d, J=6.9 Hz, 3H).

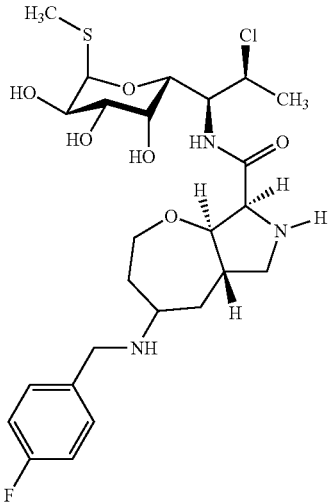

FSA-510074:

$^1$H NMR (600 MHz, CD$_3$OD) δ 7.54 (dd, J=8.6, 5.3 Hz, 2H), 7.18 (t, J=8.7 Hz, 2H), 5.30 (d, J=5.6 Hz, 1H), 4.57 (qd, J=6.7, 1.5 Hz, 1H), 4.48 (dd, J=10.0, 1.6 Hz, 1H), 4.41 (d, J=8.9 Hz, 1H), 4.26 (d, J=10.0 Hz, 1H), 4.22-4.18 (m, 2H), 4.17-4.13 (m, 2H), 4.08 (dd, J=10.2, 5.6 Hz, 1H), 3.88 (m, 1H), 3.77 (d, J=11.1 Hz, 2H), 3.70 (m, 1H), 3.64 (m, 1H), 3.59-3.55 (m, 2H), 2.93 (t, J=11.3 Hz, 1H), 2.57 (dd, J=9.6, 9.1 Hz, 1H), 2.19-2.09 (m, 3H), 2.15 (s, 3H), 1.51 (d, J=6.8 Hz, 3H).

FSA-503002:

$^1$H NMR (600 MHz, CD$_3$OD) δ 5.29 (d, J=5.6 Hz, 1H), 4.59 (qd, J=6.8, 1.6 Hz, 1H), 4.40 (dd, J=10.0, 1.6 Hz, 1H), 4.35 (t, J=9.0 Hz, 1H), 4.18 (d, J=10.0 Hz, 1H), 3.98-3.94 (m, 2H), 3.89 (d, J=3.5 Hz, 1H), 3.84 (ddd, J=12.6, 6.4, 2.0 Hz, 1H), 3.57 (dd, J=10.2, 3.4 Hz, 1H), 3.26 (dd, J=10.0, 7.2 Hz, 1H), 2.95 (dd, J=10.0, 4.3 Hz, 1H), 2.86 (ddt, J=14.8, 6.3, 1.6 Hz, 1H), 2.78 (ddd, J=14.8, 8.1, 2.0 Hz, 1H), 2.59 (dd, J=10.9, 10.0 Hz, 1H), 2.49 (m, 1H), 2.41 (s, 3H), 2.31 (dd, J=11.8, 10.7 Hz, 1H), 2.14 (s, 3H), 1.51-1.48 (m, 1H), 1.49 (d, J=6.8 Hz, 3H).

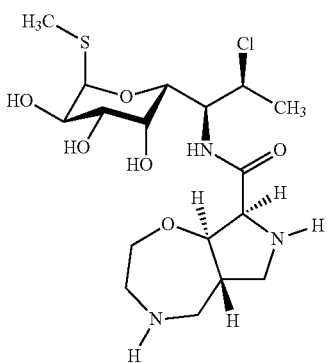

FSA-503001:

$^1$H NMR (600 MHz, CD$_3$OD) δ 5.29 (d, J=5.7 Hz, 1H), 4.60 (q, J=6.8 Hz, 1H), 4.40 (d, J=10.0 Hz, 1H), 4.30 (t, J=9.0 Hz, 1H), 4.19 (d, J=10.0 Hz, 1H), 4.08 (dd, J=10.4, 5.6 Hz, 1H), 4.01-3.95 (m, 2H), 3.89 (d, J=8.5 Hz, 1H), 3.79 (dd, J=13.1, 6.8 Hz, 1H), 3.58 (dd, J=10.2, 3.4 Hz, 1H), 3.33-3.27 (m, 1H), 3.23-3.15 (m, 2H), 2.74 (t, J=12.0 Hz,

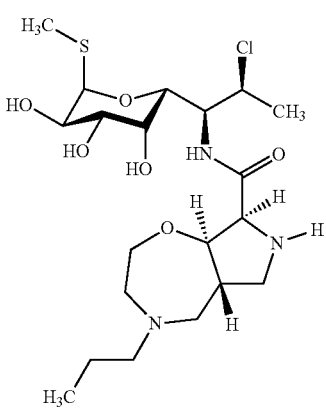

FSA-503003:

$^1$H NMR (600 MHz, CD$_3$OD) δ 5.29 (d, J=5.6 Hz, 1H), 4.59 (qd, J=6.8, 1.7 Hz, 1H), 4.39 (dd, J=10.0, 1.7 Hz, 1H), 4.34 (t, J=9.1 Hz, 1H), 4.18 (dd, J=10.0, 1.2 Hz, 1H), 4.07 (dd, J=10.2, 5.6 Hz, 1H), 3.96-3.92 (m, 2H), 3.90 (d, J=3.5 Hz, 1H), 3.80 (ddd, J=12.4, 6.9, 1.9 Hz, 1H), 3.57 (dd, J=10.2, 3.4 Hz, 1H), 3.25 (dd, J=10.0, 7.2 Hz, 1H), 2.98 (m, 1H), 2.90 (dd, J=14.9, 6.8 Hz, 1H), 2.77 (dd, J=15.0, 7.7 Hz, 1H), 2.58 (t, J=10.4 Hz, 1H), 2.51-2.42 (m, 3H), 2.36 (t, J=11.1 Hz, 1H), 2.13 (s, 3H), 1.55-1.48 (m, 2H), 1.49 (d, J=6.9 Hz, 3H), 0.91 (td, J=7.4, 1.9 Hz, 3H).

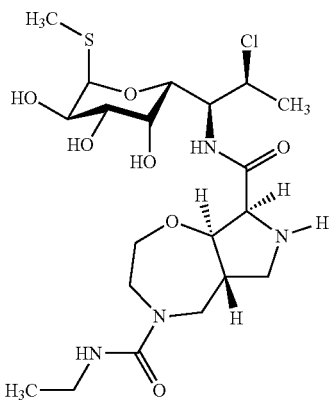

FSA-503004

FSA-503004:
¹H NMR (600 MHz, CD₃OD) δ 5.29 (d, J=5.6 Hz, 1H), 4.59 (qd, J=6.8, 1.7 Hz, 1H), 4.40 (dd, J=10.0, 1.6 Hz, 1H), 4.18 (d, J=10.0 Hz, 1H), 4.07 (m, 1H), 4.03 (d, J=8.7 Hz, 1H), 3.99-3.97 (m, 3H), 3.92 (d, J=3.4 Hz, 1H), 3.57-3.48 (m, 3H), 3.37 (dd, J=10.0, 7.2 Hz, 1H), 3.32-3.28 (m, 1H), 3.28-3.23 (m, 2H), 3.19 (q, J=7.2 Hz, 2H), 2.63 (t, J=10.3 Hz, 1H), 2.54 (m, 1H), 2.13 (s, 3H), 1.49 (d, J=6.9 Hz, 3H), 1.11 (t, J=7.2 Hz, 3H).

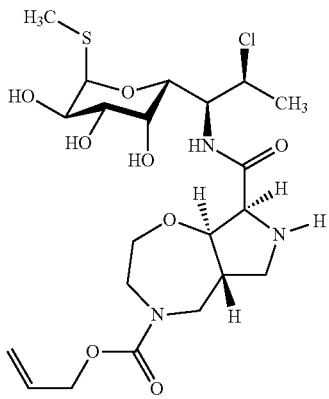

FSA-503073

FSA-503073:
¹H NMR (600 MHz, CD₃OD) δ 5.96 (m, 1H), 5.32-5.28 (m, 1H), 5.29 (d, J=5.6 Hz, 1H), 5.21 (m, 1H), 4.59 (dt, J=5.4, 1.6 Hz, 3H), 4.40 (dt, J=10.1, 2.0 Hz, 1H), 4.19 (d, J=10.0 Hz, 1H), 4.09-4.05 (m, 2H), 4.02-3.96 (m, 3H), 3.92 (d, J=3.5 Hz, 1H), 3.65 (m, 1H), 3.56 (dd, J=10.3, 3.5 Hz, 2H), 3.45-3.34 (m, 3H), 2.64 (dd, J=12.9, 10.4 Hz, 1H), 2.51 (m, 1H), 2.14 (s, 3H), 1.49 (d, J=6.9 Hz, 3H).

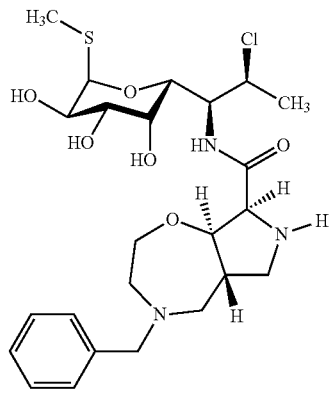

FSA-502002

FSA-502002:
¹H NMR (500 MHz, CD₃OD) δ 7.32 (m, 4H), 7.24 (m, 1H), 5.29 (d, J=5.6 Hz, 1H), 4.59 (qd, J=6.8, 1.6 Hz, 1H), 4.39 (m, 2H), 4.18 (dd, J=10.0, 1.1 Hz, 1H), 4.07 (dd, J=10.2, 5.6 Hz, 1H), 3.93 (d, J=9.0 Hz, 1H), 3.91-3.88 (m, 1H), 3.74 (ddd, J=12.2, 7.2, 1.9 Hz, 1H), 3.69 (s, 2H), 3.57 (dd, J=10.2, 3.4 Hz, 1H), 3.34 (s, 2H), 3.23 (dd, J=9.7, 6.9 Hz, 1H), 2.96 (dd, J=11.2, 4.5 Hz, 1H), 2.85 (dd, J=14.9, 6.8 Hz, 1H), 2.74 (ddd, J=14.9, 7.2, 1.9 Hz, 1H), 2.54 (dd, J=9.8, 9.1 Hz, 1H), 2.38 (m, 1H), 2.13 (s, 3H), 1.49 (d, J=6.8 Hz, 3H).

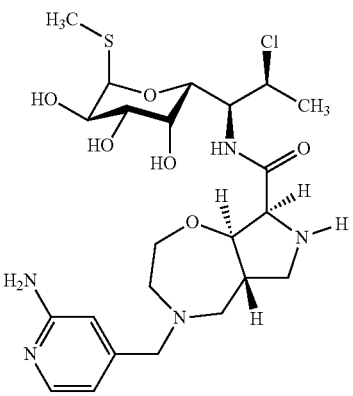

FSA-504049

FSA-504049:
¹H NMR (600 MHz, CD₃OD) δ 7.76 (d, J=6.6 Hz, 1H), 7.02 (s, 1H), 6.91 (dd, J=6.6, 1.6 Hz, 1H), 5.30 (d, J=5.6 Hz, 1H), 4.69 (t, J=9.0 Hz, 1H), 4.59 (d, J=10.0 Hz, 1H), 4.57 (dd, J=6.8, 1.6 Hz, 1H), 4.54 (m, 1H), 4.29 (d, J=10.0 Hz, 1H), 4.09 (dd, J=10.2, 5.6 Hz, 1H), 3.96 (ddd, J=12.1, 6.8, 2.3 Hz, 1H), 3.84 (m, 2H), 3.79 (s, 2H), 3.66 (dd, J=11.4, 7.7 Hz, 1H), 3.59 (dd, J=10.3, 3.2 Hz, 1H), 3.06-3.01 (m, 2H), 2.94 (dd, J=14.1, 6.3 Hz, 1H), 2.87 (ddd, J=15.0, 7.1, 2.2 Hz, 1H), 2.66 (m, 1H), 2.58 (t, J=11.0 Hz, 1H), 2.15 (s, 3H), 1.54 (d, J=6.8 Hz, 3H).

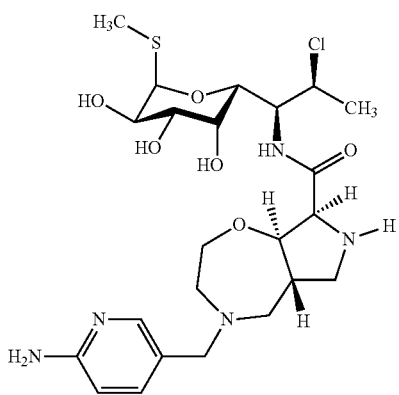

FSA-504050:
¹H NMR (600 MHz, CD₃OD) δ 7.80 (s, 1H), 7.71 (dd, J=14.8, 8.2 Hz, 1H), 6.76 (d, J=8.6 Hz, 1H), 5.30 (d, J=5.6 Hz, 1H), 4.59-4.55 (m, 1H), 4.57 (q, J=6.8 Hz, 1H), 4.50 (d, J=9.8 Hz, 1H), 4.26 (d, J=9.9 Hz, 1H), 4.08 (dd, J=10.2, 5.6 Hz, 1H), 3.92 (m, 1H), 3.84 (m, 1H), 3.80 (m, 1H), 3.65 (s, 2H), 3.57 (d, J=10.0 Hz, 2H), 3.19 (s, 1H), 3.02 (d, J=10.1 Hz, 1H), 2.89 (m, 3H), 2.60 (s, 1H), 2.52 (m, 1H), 2.14 (s, 3H), 1.51 (d, J=6.8 Hz, 3H).

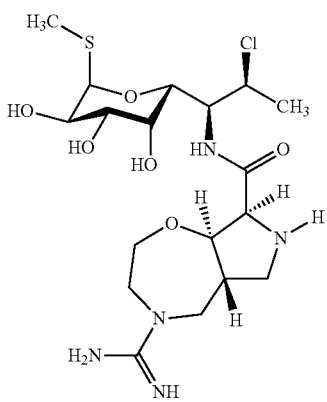

FSA-504057:
¹H NMR (500 MHz, CD₃OD) δ 5.30 (d, J=5.6 Hz, 1H), 4.67 (d, J=8.7 Hz, 1H), 4.58-4.53 (m, 2H), 4.44 (t, J=9.0 Hz, 1H), 4.30 (d, J=10.0 Hz, 1H), 4.08 (ddd, J=10.2, 5.2, 2.3 Hz, 2H), 3.88-3.76 (m, 4H), 3.74-3.58 (m, 2H), 3.58 (dd, J=10.2, 3.3 Hz, 1H), 3.39 (t, J=12.2 Hz, 1H), 3.16 (t, J=11.6 Hz, 1H), 2.80 (m, 1H), 2.14 (s, 3H), 1.51 (d, J=6.6 Hz, 3H).

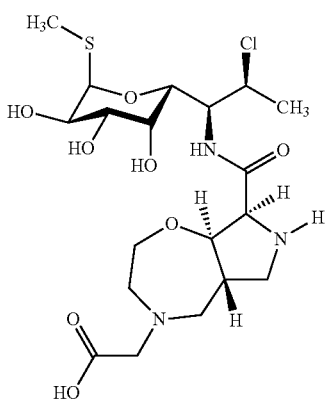

FSA-504063:
¹H NMR (500 MHz, CD₃OD) δ 5.30 (d, J=5.6 Hz, 1H), 4.71-4.65 (m, 2H), 4.58-4.52 (m, 2H), 4.30 (d, J=9.7 Hz, 1H), 4.25-4.19 (m, 3H), 4.16-4.12 (m, 1H), 4.08 (dd, J=10.2, 5.6 Hz, 1H), 3.85 (d, J=3.4 Hz, 1H), 3.79-3.75 (m, 4H), 3.58 (dd, J=10.2, 3.3 Hz, 1H), 3.50 (t, J=12.3 Hz, 1H), 3.17 (t, J=11.8 Hz, 1H), 2.98 (m, 1H), 2.15 (s, 3H), 1.52 (d, J=6.7 Hz, 3H).

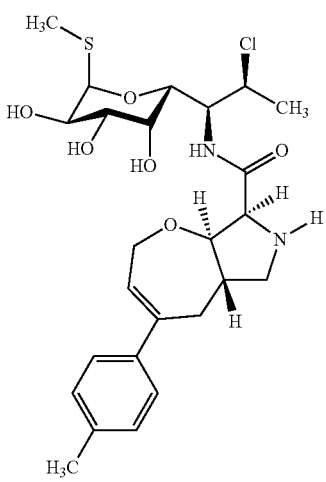

FSA-511019:
¹H NMR (600 MHz, CD₃OD) δ 7.23 (d, J=7.9 Hz, 2H), 7.12 (d, J=7.9 Hz, 2H), 5.97 (s, 1H), 5.31 (d, J=5.5 Hz, 1H), 4.59 (q, J=7.8, 6.9 Hz, 1H), 4.53 (d, J=10.0 Hz, 1H), 4.41 (d, J=8.8 Hz, 1H), 4.28 (d, J=10.0 Hz, 1H), 4.17 (ddd, J=12.1, 5.1, 2.3 Hz, 1H), 4.11-4.06 (m, 2H), 3.91 (m, 1H), 3.69-3.59 (m, 3H), 3.20 (t, J=9.0 Hz, 1H), 3.14 (t, J=11.8 Hz, 1H), 2.95 (dd, J=16.4, 10.9 Hz, 1H), 2.76 (dd, J=16.4, 4.8 Hz, 1H), 2.30 (s, 3H), 2.15 (s, 3H), 1.57 (d, J=6.7 Hz, 3H).

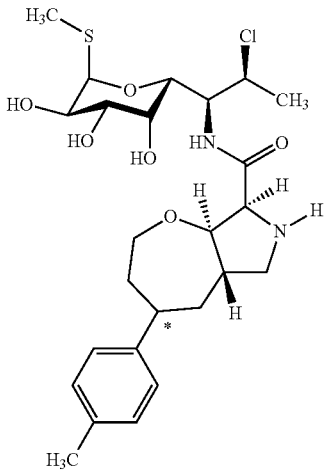

FSA-511044 isolated as a 50:50 mixture of diastereomers (starred benzylic stereocenter): ¹H NMR (600 MHz, CD₃OD) δ 7.09 (m, 4H), 5.30 (d, J=5.7 Hz, 1H), 4.59 (ddd, J=6.8, 5.2, 1.6 Hz, 1H), 4.49 (dt, J=10.4, 5.5, 2.7 Hz, 1H), 4.35 (s, 1H), 4.26 (dd, J=10.0, 4.4 Hz, 1H), 4.13-4.07 (m, 2H), 3.94-3.87 (m, 2H), 3.66 (t, J=11.6 Hz, 1H), 3.59 (m, 1H), 3.49 (m, 1H), 3.18 (m, 1H), 2.83 (t, J=11.7 Hz, 1H), 2.60 (m, 1H), 2.38 (m, 1H), 2.28 (s, 3H), 2.15 (s, 3H), 2.07-1.98 (m, 1H), 1.91-1.78 (m, 2H), 1.54 (dd, J=13.7, 6.8 Hz, 3H).

The diastereomers of FSA-511044 were separated to provide FSA-512079b and FSA-512079c:

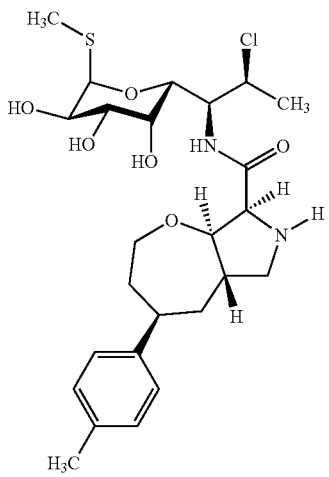

FSA-512079b

FSA-512079b:

$^1$H NMR (600 MHz, CD$_3$OD) δ 7.11 (d, J=8.3 Hz, 2H), 7.08 (d, J=8.2 Hz, 2H), 5.30 (d, J=5.6 Hz, 1H), 4.59 (dd, J=6.8, 1.6 Hz, 1H), 4.46 (d, J=10.1 Hz, 1H), 4.29 (t, J=8.9 Hz, 1H), 4.12-4.06 (m, 3H), 3.91 (m, 1H), 3.64 (t, J=11.6 Hz, 1H), 3.58 (dd, J=10.2, 3.4 Hz, 1H), 3.41 (m, 1H), 3.18 (m, 1H), 2.73 (t, J=11.2 Hz, 1H), 2.56 (m, 1H), 2.28 (s, 3H), 2.25-2.21 (m, 2H), 2.15 (s, 3H), 1.99 (m, 1H), 1.85 (m, 1H), 1.77 (m, 1H), 1.52 (d, J=6.8 Hz, 3H).

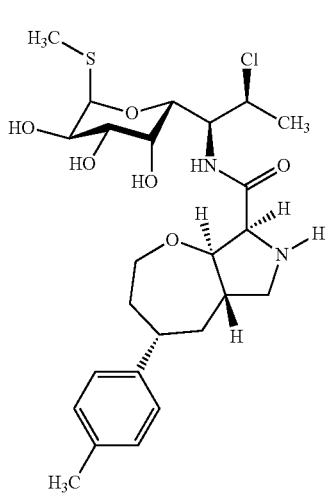

FSA-512079c

FSA-512079c:

$^1$H NMR (600 MHz, CD$_3$OD) δ 7.11 (d, J=8.2 Hz, 2H), 7.08 (d, J=8.2 Hz, 2H), 5.30 (d, J=5.7 Hz, 1H), 4.60 (m, 1H), 4.46 (d, J=10.0 Hz, 1H), 4.42 (t, J=9.1 Hz, 1H), 4.24 (d, J=9.8 Hz, 1H), 4.16 (d, J=9.0 Hz, 1H), 4.10-4.05 (m, 2H), 3.92 (dd, J=11.6, 3.0 Hz, 1H), 3.89 (d, J=3.0 Hz, 1H), 3.59 (dd, J=10.3, 3.4 Hz, 1H), 3.38 (dd, J=10.5, 7.4 Hz, 1H) 2.82 (m, 1H), 2.71 (m, 1H), 2.36-2.26 (m, 2H), 2.28 (s, 3H), 2.15 (s, 3H), 2.05 (m, 1H), 1.87 (m, 1H), 1.54 (d, J=6.8 Hz, 3H). 1.50-1.44 (m, 1H).

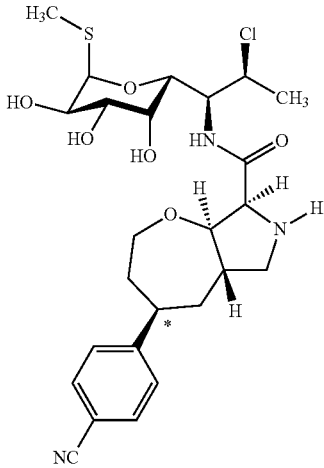

FSA-511046

FSA-511046 isolated as a 60:40 mixture of diastereomers (starred benzylic stereocenter): $^1$H NMR (600 MHz, CD$_3$OD) δ 7.66 (d, J=8.3 Hz, 2H), 7.45 (d, J=8.3 Hz, 2H), 5.31 (d, J=5.7 Hz, 1H), 4.58 (m, 1H), 4.51 (m, 2H), 4.43-4.36 (m, 1H), 4.27 (dd, J=10.0, 5.4 Hz, 1H), 4.19-4.08 (m, 3H), 3.88 (dd, J=8.2, 3.4 Hz, 1H), 3.71-3.63 (m, 1H), 3.59 (m, 1H), 3.53 (m, 1H), 3.00 (m, 1H), 2.88 (t, J=11.6 Hz, 1H), 2.43-2.26 (m, 2H), 2.15 (s, 3H), 1.92 (m, 1H), 1.57-1.52 (m, 1H), 1.54 (dd, J=16.6, 6.8 Hz, 3H).

The diastereomers of FSA-511046 were separated to provide FSA-512081a and FSA-512081b:

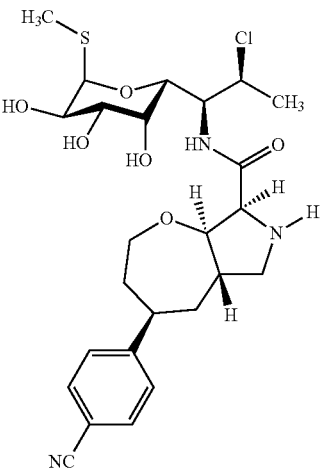

FSA-512081a

FSA-512081a:

$^1$H NMR (600 MHz, CD$_3$OD) δ 7.65 (d, J=8.4 Hz, 2H), 7.44 (d, J=8.4 Hz, 2H), 5.30 (d, J=5.7 Hz, 1H), 4.59 (m, 1H), 4.46 (d, J=10.0 Hz, 1H), 4.30 (t, J=8.9 Hz, 1H), 4.24 (d, J=9.7 Hz, 2H), 4.14 (ddd, J=12.4, 4.6, 2.4 Hz, 1H), 4.08 (dd, J=10.2, 5.6 Hz, 1H), 3.92 (m, 1H), 3.66 (t, J=11.6 Hz, 1H), 3.58 (dd, J=10.1, 3.4 Hz, 1H) 3.42 (m, 1H), 3.34 (m, 1H), 2.75 (t, J=11.1 Hz, 1H), 2.59 (m, 1H), 2.29 (m, 1H), 2.14 (s, 3H), 1.99 (m, 1H), 1.90 (m, 1H), 1.79 (d, J=14.2 Hz, 1H), 1.52 (d, J=6.8 Hz, 3H).

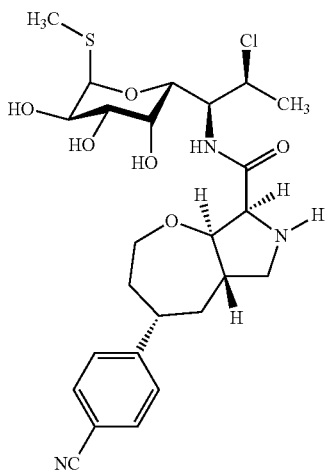

FSA-512081b

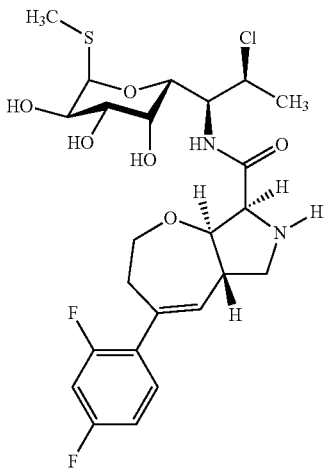

FSA-511072

FSA-512081b:

¹H NMR (600 MHz, CD₃OD) δ 7.66 (d, J=8.1 Hz, 2H), 7.45 (d, J=8.3 Hz, 2H), 5.30 (d, J=5.6 Hz, 1H), 4.59 (m, 1H), 4.49 (t, J=9.4 Hz, 2H), 4.35 (d, J=8.9 Hz, 1H), 4.27 (d, J=10.0 Hz, 1H), 4.09 (m, 2H), 3.95 (td, J=11.7, 3.4 Hz, 1H), 3.87 (m, 1H), 3.59 (dd, J=10.2, 2.4 Hz, 1H), 3.52 (dd, J=11.0, 7.4 Hz, 1H), 3.00 (t, J=11.2 Hz, 1H), 2.85 (t, J=11.5 Hz, 1H), 2.41 (m, 1H), 2.34 (m, 1H), 2.15 (s, 3H), 2.09 (d, J=13.4 Hz, 1H), 1.92 (d, J=15.3 Hz, 1H), 1.55 (d, J=6.6 Hz, 3H), 1.53 (m, 1H).

FSA-511072:

¹H NMR (600 MHz, CD₃OD) δ 7.25 (dd, J=9.2, 8.7 Hz, 1H), 6.93-6.90 (m, 2H), 5.96 (m, 1H), 5.31 (d, J=5.6 Hz, 1H), 4.66 (m, 1H), 4.57-4.53 (m, 2H), 4.48 (dd, J=15.3, 7.0 Hz, 1H), 4.31-4.26 (m, 3H), 4.09 (dd, J=10.2, 5.6 Hz, 1H), 3.88 (s, 1H), 3.65 (t, J=9.1 Hz, 1H), 3.60 (d, J=10.1 Hz, 1H), 3.05 (t, J=11.9 Hz, 1H), 2.73-2.67 (m, 2H), 2.37 (m, 1H), 2.15 (s, 3H), 1.53 (d, J=6.7 Hz, 3H).

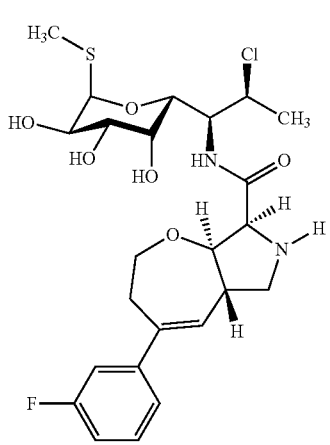

FSA-511071

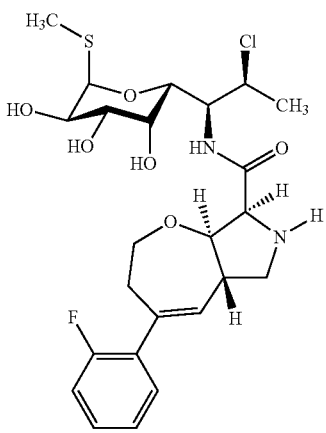

FSA-511073

FSA-511071:

¹H NMR (600 MHz, CD₃OD) δ 7.32 (dd, J=8.0, 6.0 Hz, 1H), 7.15 (d, J=7.6 Hz, 1H), 7.08 (dt, J=10.5, 2.2 Hz, 1H), 6.98 (td, J=8.6, 2.6 Hz, 1H), 6.09 (m, 1H), 5.30 (d, J=5.6 Hz, 1H), 4.65 (dd, J=9.0, 3.7 Hz, 1H), 4.57-4.49 (m, 3H), 4.33-4.26 (m, 3H), 4.09 (dd, J=10.2, 5.6 Hz, 1H), 3.87 (s, 1H), 3.70 (dd, J=10.8, 7.1 Hz, 1H), 3.59 (dd, J=10.2, 3.2 Hz, 1H), 3.07 (t, J=11.9 Hz, 1H), 2.91 (dd, J=16.0, 2.6 Hz, 1H), 2.71 (td, J=16.2, 11.3 Hz, 1H), 2.34 (m, 1H), 2.15 (s, 3H), 1.53 (d, J=6.8 Hz, 3H).

FSA-511073:

¹H NMR (600 MHz, CD₃OD) δ 7.28 (dd, J=7.9, 5.1 Hz, 1H), 7.22 (td, J=7.8, 1.7 Hz, 1H), 7.11 (td, J=7.6, 1H), 7.05 (dd, J=10.8, 8.2 Hz, 1H), 5.97 (m, 1H), 5.31 (d, J=5.7 Hz, 1H), 4.63 (m, 1H), 4.58-4.53 (m, 2H), 4.48 (dd, J=15.2, 7.0 Hz, 1H), 4.31-4.25 (m, 3H), 4.09 (dd, J=10.2, 5.7 Hz, 1H), 3.88 (m, 1H), 3.64-3.59 (m, 2H), 3.01 (td, J=11.9, 4.8 Hz, 1H), 2.75-2.67 (m, 2H), 2.36 (m, 1H), 2.15 (s, 3H), 1.54 (d, J=6.8 Hz, 3H).

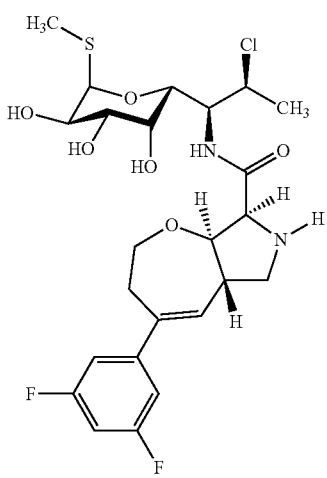

FSA-511074

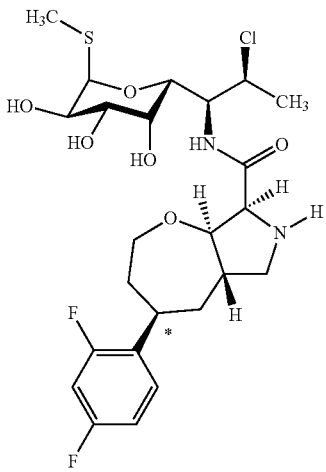

FSA-511078

FSA-511074:

¹H NMR (600 MHz, CD₃OD) δ 6.96 (dt, J=7.3, 2.2 Hz, 2H), 6.84 (tt, J=9.0, 2.3 Hz, 1H), 6.14 (m, 1H), 5.30 (d, J=5.8 Hz, 1H), 4.64 (d, J=8.9 Hz, 1H), 4.57-4.50 (m, 3H), 4.33-4.25 (m, 3H), 4.09 (dd, J=10.2, 5.6 Hz, 1H), 3.86 (m, 1H), 3.70 (dd, J=11.3, 7.4 Hz, 1H), 3.59 (dd, J=10.2, 3.4 Hz, 1H), 3.06 (dd, J=12.5, 11.4 Hz, 1H), 2.88 (dd, J=16.2, 2.7 Hz, 1H), 2.69 (tt, J=16.3, 11.2, 2.6 Hz, 1H), 2.34 (m, 1H), 2.15 (s, 3H), 1.52 (d, J=6.8 Hz, 3H).

FSA-511078 isolated as an 80:20 mixture of diastereomers (starred benzylic stereocenter): ¹H NMR (600 MHz, CD₃OD) δ 7.34 (ddd, J=8.8, 8.3, 6.3 Hz, 1H), 6.94-6.87 (m, 2H), 5.31 (d, J=5.6 Hz, 1H), 4.58 (q, J=6.9 Hz, 1H), 4.51 (d, J=10.0 Hz, 1H), 4.41 (d, J=9.2 Hz, 1H), 4.35 (t, J=8.9 Hz, 1H), 4.27 (d, J=10.0 Hz, 1H), 4.14 (ddd, J=12.4, 4.5, 2.3 Hz, 1H), 4.09 (dd, J=10.1, 5.5 Hz, 1H), 3.91 (d, J=3.4 Hz, 1H), 3.67 (t, J=11.6 Hz, 1H), 3.59 (dd, J=10.1, 3.5 Hz, 1H), 3.54-3.49 (m, 2H), 2.87 (t, J=11.6 Hz, 1H), 2.63 (m, 1H), 2.32 (m, 1H), 2.15 (s, 3H), 2.04-1.99 (m, 1H), 1.94-1.88 (m, 1H), 1.77 (dd, J=15.1, 4.3 Hz, 1H), 1.55 (d, J=6.8 Hz, 3H).

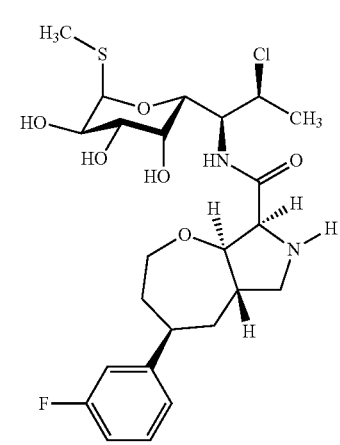

FSA-511077

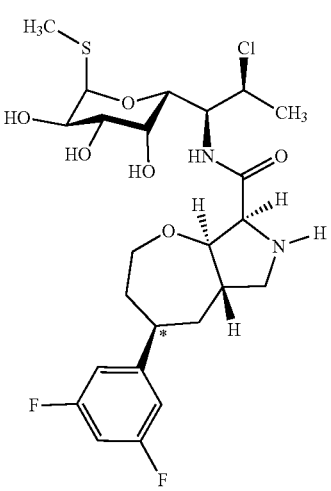

FSA-511080

FSA-511077:

¹H NMR (500 MHz, CD₃OD) δ 7.29 (dd, J=8.0, 6.1 Hz, 1H), 7.06 (d, J=7.1 Hz, 1H), 7.00 (dt, J=10.2, 2.1 Hz, 1H), 6.90 (m, 1H), 5.31 (d, J=5.6 Hz, 1H), 4.59-4.49 (m, 3H), 4.40 (t, J=8.9 Hz, 1H), 4.29 (d, J=9.9 Hz, 1H), 4.14-4.08 (m, 3H), 3.91 (m, 1H), 3.69 (t, J=11.6 Hz, 1H), 3.61-3.55 (m, 1H), 3.31-3.26 (m, 1H), 2.94 (m, 1H), 2.66 (m, 1H), 2.25 (dd, J=13.4, 10.9 Hz, 1H), 2.15 (s, 3H), 2.02 (m, 1H), 1.94-1.88 (m, 1H), 1.83 (dd, J=15.4, 3.6 Hz, 1H), 1.53 (d, J=6.7 Hz, 3H).

FSA-511080 isolated as a 70:30 mixture of diastereomers (starred benzylic stereocenter): ¹H NMR (600 MHz, CD₃OD) δ 6.89-6.87 (m, 2H), 6.76-6.71 (m, 1H), 5.30 (d, J=5.6 Hz, 1H), 4.58 (dd, J=6.9, 6.3 Hz, 1H), 4.50 (d, J=10.0 Hz, 1H), 4.37 (d, J=9.2 Hz, 1H), 4.34 (t, J=8.8 Hz, 1H), 4.26 (d, J=10.1 Hz, 1H), 4.18-4.12 (m, 1H), 4.10-4.06 (m, 1H), 3.88 (d, J=3.3 Hz, 1H), 3.67 (t, J=11.6 Hz, 1H), 3.58 (dd, J=10.2, 3.2 Hz, 1H), 3.50 (dd, J=10.9, 7.4 Hz, 1H), 3.30-3.19 (m, 1H), 2.85 (t, J=11.6 Hz, 1H), 2.69-2.57 (m, 1H), 2.34-2.20 (m, 1H), 2.14 (s, 3H), 2.00 (dd, J=9.2, 6.8 Hz, 1H), 1.90 (m, 1H), 1.81 (dd, J=15.3, 4.3 Hz, 1H), 1.53 (d, J=6.8 Hz, 3H).

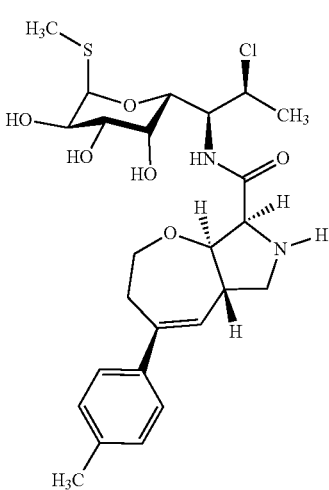

FSA-512075:
¹H NMR (600 MHz, CD₃OD) δ 7.23 (d, J=8.1 Hz, 2H), 7.12 (d, J=8.0 Hz, 2H), 5.97 (s, 1H), 5.31 (d, J=5.6 Hz, 1H), 4.58 (m, 1H), 4.54 (d, J=9.5 Hz, 1H), 4.50 (d, J=7.7 Hz, 1H), 4.29 (d, J=10.0 Hz, 1H), 4.17 (ddd, J=12.1, 4.9, 2.3 Hz, 1H), 4.09 (m, 2H), 3.89 (br, 1H), 3.74 (m, 1H), 3.66 (t, J=11.4 Hz, 1H), 3.60 (dd, J=10.2, 2.9 Hz, 1H), 3.22 (m, 2H), 2.95 (dd, J=16.2, 11.3 Hz, 1H), 2.77 (dd, J=16.4, 4.7 Hz, 1H), 2.31 (s, 3H), 2.15 (s, 3H), 1.58 (d, J=6.8 Hz, 3H).

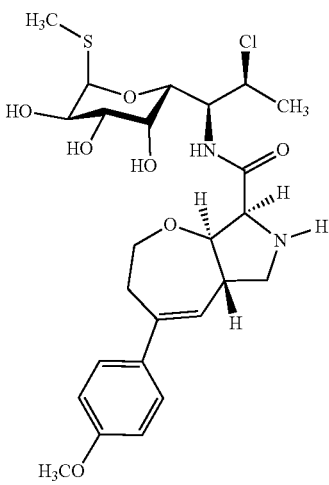

FSA-512076:
¹H NMR (600 MHz, CD₃OD) δ 7.32 (d, J=8.6 Hz, 2H), 6.89 (d, J=8.6 Hz, 2H), 5.96 (s, 1H), 5.33 (d, J=5.6 Hz, 1H), 4.66 (d, J=8.9 Hz, 1H), 4.60 (m, 2H), 4.32 (d, J=10.1 Hz, 1H), 4.20 (m, 2H), 4.11 (dd, J=10.2, 5.6 Hz, 1H), 3.86 (m, 2H), 3.80 (s, 3H), 3.70 (t, J=11.4 Hz, 1H), 3.61 (dd, J=10.2, 3.3 Hz, 1H), 3.32 (m, 2H), 2.97 (dd, J=16.2, 11.1 Hz, 1H), 2.81 (dd, J=16.5, 4.7 Hz, 1H), 2.17 (s, 3H), 1.61 (d, J=6.8 Hz, 3H).

FSA-512077:
¹H NMR (600 MHz, CD₃OD) δ 7.70 (d, J=8.5 Hz, 2H), 7.56 (d, J=8.5 Hz, 2H), 6.21 (s, 1H), 5.33 (d, J=5.6 Hz, 1H), 4.61-4.56 (m, 3H), 4.31 (d, J=10.0 Hz, 1H), 4.20 (m, 1H), 4.12 (m, 1H), 3.90 (br, 1H), 3.81 (m, 1H), 3.71 (m, 1H), 3.61 (m, 1H), 3.36-3.29 (m, 2H), 3.03 (m, 1H), 2.17 (s, 3H), 2.04 (d, J=11.4 Hz, 2H), 1.60 (d, J=6.7 Hz, 3H).

Biological Assays

Minimum inhibitory concentrations (MICs) for compounds described herein have been determined for strains of several Gram positive and Gram negative strains. Data for exemplary compounds described herein is shown in Tables 2-13.

TABLE 2

MIC (μg/mL) of compounds against Gram positive and Gram negative strains

| Species | Genotype | Clindamycin | FSA-24039 | FSA-24041 | FSA-22091 | FSA-24040 | FSA-24035 |
|---|---|---|---|---|---|---|---|
| S. aureus | ATCC 29213 | 0.25 | 1 | 0.5 | 0.125 | ≤0.0313 | 0.12 |
| S. aureus | BAA 977 iErmA | 0.25 | — | — | — | — | 0.25 |
| S. aureus | MP-549 msr(a) USA 300 | 0.125 | — | — | — | — | 0.5 |
| S. aureus | Micromyx USA 300 | 0.25 | — | — | — | — | 0.12 |
| S. aureus | MP-513 clinical cErm | >64 | — | — | — | — | — |
| S. aureus | MMX 3035 cErmA | >64 | — | — | — | — | >64 |

TABLE 2-continued

MIC (μg/mL) of compounds against Gram positive and Gram negative strains

| Species | Genotype | Clindamycin | FSA-24039 | FSA-24041 | FSA-22091 | FSA-24040 | FSA-24035 |
|---|---|---|---|---|---|---|---|
| S. aureus | BAA-1556 (USA 300) | >32 | >32 | >32 | >32 | >32 | >32 |
| S. aureus | UNT96, NRS710, MP-618 (USA 100, Erythro > 8) | >32 | >32 | >32 | >32 | >32 | >32 |
| S. aureus | UNT-146, MP-620, TP 506 (ermA) | >32 | >32 | >32 | >32 | >32 | >32 |
| S. aureus | UNT-120, MP-619, NRS22 (USA 600, GISA) | >32 | >32 | >32 | >32 | >32 | >32 |
| S. pneumoniae | ATCC 49619 | 0.12 | 0.0625 | 0.0625 | <0.0313 | ≤0.0313 | ≤0.06 |
| S. pneumoniae | MMX 3028 cErmB | >64 | — | — | — | — | 64 |
| S. pneumoniae | MMX 3031 cMefA | 0.06 | — | — | — | — | ≤0.06 |
| S. pneumoniae | UNT-038, MP-626, TP 160 (mefA) | ≤0.0313 | 0.125 | 0.0625 | <0.0313 | ≤0.0313 | ≤0.0313 |
| S. pneumoniae | UNT-039, MP-627, TP1517 (mefA) | ≤0.0313 | ≤0.0313 | ≤0.0313 | <0.0313 | ≤0.0313 | ≤0.0313 |
| S. pneumoniae | TP 1579 (ermB + tet(M, O)) | ≤0.0313 | 0.0625 | ≤0.0313 | <0.0313 | ≤0.0313 | ≤0.0313 |
| S. pneumoniae | TP 1537 (ermB + mefA) | >32 | >32 | >32 | 32 | >32 | 32 |
| S. pyogenes | ATCC 19615 | 0.06 | 0.125 | ≤0.0313 | <0.0313 | ≤0.0313 | ≤0.0313 |
| S. pyogenes | MMX 946 Macrolide-Resistant | >64 | — | — | — | — | 16 |
| S. pyogenes | UNT-014, MP-625 MacRes | ≤0.0313 | 0.125 | 0.0625 | <0.0313 | ≤0.0313 | ≤0.0313 |
| E. faecalis | ATCC 29212 | 16 | 32 | 32 | >32 | 32 | 16 |
| E. faecalis | MMX 847 Macrolide-Resistant | >64 | — | — | — | — | >64 |
| E. faecalis | UNT-047 VRE | >32 | >32 | >32 | >32 | >32 | >32 |
| C. difficile | BAA 1805 | 8 | — | — | — | — | 2 |
| B. fragilis | ATCC 25285 | 0.5 | — | — | — | — | 8 |
| K. pneumoniae | ATCC 10031 | 8 | >32 | >32 | 8 | 8 | 64 |
| K. pneumoniae | IHMA 658692; KPC-2 | >32 | >32 | >32 | >32 | >32 | 32 |
| K. pneumoniae | UNT TEM-10 | >32 | — | — | — | — | 32 |
| E. coli | ATCC 25922 | >64 | >32 | >32 | 32 | >32 | >64 |
| E. coli | MMX TolC parent strain | >64 | — | — | — | — | >64 |
| E. coli | MMX 0121 ΔTolC | 4 | — | — | — | — | 4 |
| E. coli | MP-9 ΔTolC | 8 | — | — | — | — | — |
| E. coli | MP-74 LptD mutant | 2 | — | — | — | — | — |
| E. coli | GUEST131 (NDM-1) | >32 | >32 | >32 | >32 | >32 | >32 |
| P. aeruginosa | ATCC 27853 | >64 | >32 | >32 | >32 | >32 | >64 |
| P. aeruginosa | MMX Mex parent strain | >64 | — | — | — | — | >64 |
| P. aeruginosa | MMX 3476 Δmex | >64 | — | — | — | — | 16 |
| H. influenzae | ATCC 49247 | 16 | 32 | 32 | 8 | 8 | 1 |

TABLE 3

MIC (μg/mL) of compounds against Gram positive and Gram negative strains

| Species | Genotype | FSA-24036 | FSA-27049 | FSA-212034 | FSA-213061 | FSA-213064 | FSA-214009a |
|---|---|---|---|---|---|---|---|
| S. aureus | ATCC 29213 | 0.25 | 1 | 0.25 | 0.25 | 0.25 | 64 |
| S. aureus | BAA 977 iErmA | 0.5 | 2 | 0.25 | 0.25 | 0.25 | NT |
| S. aureus | MP-549 msr(a) USA 300 | — | 0.25 | 0.5 | 0.5 | 0.25 | — |
| S. aureus | Micromyx USA 300 | 0.12 | 1 | 0.25 | — | — | — |
| S. aureus | MP-513 clinical cErm | — | >64 | — | — | — | — |
| S. aureus | MMX 3035 cErmA | >64 | >64 | 32 | 64 | 16 | — |
| S. aureus | BAA-1556 (USA 300) | >32 | — | — | — | — | — |
| S. aureus | UNT96, NRS710, MP-618 (USA 100, Erythro > 8) | >32 | — | — | — | — | — |
| S. aureus | UNT-146, MP-620, TP 506 (ermA) | >32 | — | — | — | — | — |

TABLE 3-continued

MIC (μg/mL) of compounds against Gram positive and Gram negative strains

| Species | Genotype | FSA-24036 | FSA-27049 | FSA-212034 | FSA-213061 | FSA-213064 | FSA-214009a |
|---|---|---|---|---|---|---|---|
| S. aureus | UNT-120, MP-619, NRS22 (USA 600, GISA) | >32 | — | — | — | — | — |
| S. pneumoniae | ATCC 49619 | ≤0.06 | ≤0.06 | ≤0.06 | ≤0.06 | ≤0.125 | 4 |
| S. pneumoniae | MMX 3028 cErmB | 64 | 32 | 4 | 8 | 8 | — |
| S. pneumoniae | MMX 3031 cMefA | ≤0.06 | ≤0.06 | ≤0.06 | 0.125 | 0.125 | — |
| S. pneumoniae | UNT-038, MP-626, TP 160 (mefA) | ≤0.0313 | — | — | — | — | — |
| S. pneumoniae | UNT-039, MP-627, TP1517 (mefA) | ≤0.0313 | — | — | — | — | — |
| S. pneumoniae | TP 1579 (ermB + tet(M, O)) | ≤0.0313 | — | — | — | — | — |
| S. pneumoniae | TP 1537 (ermB + mefA) | >32 | — | — | — | — | — |
| S. pyogenes | ATCC 19615 | ≤0.0313 | ≤0.06 | ≤0.06 | ≤0.06 | ≤0.125 | 4 |
| S. pyogenes | MMX 946 MacRes | 4 | 2 | 2 | 4 | 2 | — |
| S. pyogenes | UNT-014, MP-625 MacRes | ≤0.0313 | — | — | — | — | — |
| E. faecalis | ATCC 29212 | 4 | 64 | 16 | 16 | 32 | >64 |
| E. faecalis | MMX 847 MacRes | >64 | >64 | >64 | >64 | >64 | — |
| E. faecalis | UNT-047 VRE | >32 | — | — | — | — | — |
| C. difficile | BAA 1805 | 2 | 1 | 0.5 | — | — | — |
| B. fragilis | ATCC 25285 | 4 | >64 | 1 | — | — | — |
| K. pneumoniae | ATCC 10031 | 16 | — | 64 | 32 | 64 | — |
| K. pneumoniae | IHMA 658692; KPC-2 | >32 | — | — | — | — | — |
| K. pneumoniae | UNT TEM-10 | >32 | — | — | — | — | — |
| E. coli | ATCC 25922 | >64 | >64 | >64 | >64 | >64 | >64 |
| E. coli | MMX TolC parent strain | >64 | >64 | >64 | — | — | — |
| E. coli | MMX 0121 ΔTolC | 8 | 8 | 1 | — | — | — |
| E. coli | MP-9 ΔTolC | — | 64 | 16 | 8 | 16 | — |
| E. coli | MP-74 LptD mutant | — | 32 | — | 8 | — | — |
| E. coli | GUEST131 (NDM-1) | >32 | — | — | — | — | — |
| P. aeruginosa | ATCC 27853 | >64 | >64 | >64 | — | >64 | — |
| P. aeruginosa | MMX Mex parent strain | >64 | >64 | >64 | — | — | — |
| P. aeruginosa | MMX 3476 Δmex | 32 | >64 | >64 | — | — | — |
| H. influenzae | ATCC 49247 | 4 | 32 | 4 | — | — | — |

TABLE 4

MIC (μg/mL) of compounds against Gram positive and Gram negative strains

| Species | Genotype | FSA-214009b | FSA-211030 | FSA-211064 | FSA-501076 | FSA-501099 | FSA-504059 |
|---|---|---|---|---|---|---|---|
| S. aureus | ATCC 29213 | ≥64 | >64 | >64 | >64 | >64 | 2 |
| S. aureus | BAA 977 iErmA | — | >64 | >64 | >64 | >64 | — |
| S. aureus | MP-549 msr(a) USA 300 | — | — | — | >64 | >64 | 2 |
| S. aureus | Micromyx USA 300 | — | >64 | >64 | — | — | — |
| S. aureus | MP-513 clinical cErm | — | — | — | >64 | >64 | — |
| S. aureus | MMX 3035 cErmA | — | >64 | >64 | — | — | — |
| S. aureus | UNT96, NRS710, MP-618 (USA 100, Erythro > 8) | — | — | — | >64 | >64 | — |
| S. aureus | UNT-146, MP-620, TP 506 (ermA) | — | — | — | >64 | >64 | — |
| S. aureus | UNT-120, MP-619, NRS22 (USA 600, GISA) | — | — | — | >64 | >64 | — |
| S. pneumoniae | ATCC 49619 | 32 | 32 | 16 | 64 | 8 | 0.25 |
| S. pneumoniae | MMX 3028 cErmB | — | >64 | >64 | — | — | — |
| S. pneumoniae | MMX 3031 cMefA | — | 32 | 16 | — | — | — |
| S. pneumoniae | UNT-038, MP-626, TP 160 (mefA) | — | — | — | 64 | 16 | — |
| S. pneumoniae | UNT-039, MP-627, TP1517 (mefA) | — | — | — | 32 | 2 | — |
| S. pyogenes | ATCC 19615 | 8 | 1 | 4 | >64 | 16 | 0.12 |

TABLE 4-continued

MIC (μg/mL) of compounds against Gram positive and Gram negative strains

| Species | Genotype | FSA-214009b | FSA-211030 | FSA-211064 | FSA-501076 | FSA-501099 | FSA-504059 |
|---|---|---|---|---|---|---|---|
| S. pyogenes | MMX 946 MacRes | — | >64 | >64 | — | — | — |
| S. pyogenes | UNT-014, MP-625 MacRes | — | — | — | >64 | 32 | — |
| E. faecalis | ATCC 29212 | >64 | >64 | >64 | >64 | >64 | 32 |
| E. faecalis | MMX 847 MacRes | — | >64 | >64 | — | — | — |
| E. faecalis | UNT-047 VRE | — | — | — | >64 | >64 | — |
| C. difficile | BAA 1805 | — | >64 | 64 | — | — | — |
| B. fragilis | ATCC 25285 | — | >64 | >64 | — | — | — |
| K. pneumoniae | ATCC 10031 | — | — | — | >64 | >64 | >64 |
| E. coli | ATCC 25922 | >64 | >64 | >64 | >64 | >64 | >64 |
| E. coli | MMX TolC parent strain | — | >64 | >64 | — | — | — |
| E. coli | MMX 0121 ΔTolC | — | >64 | >64 | — | — | — |
| E. coli | MP-9 ΔTolC | — | — | — | >64 | >64 | >64 |
| E. coli | MP-74 LptD mutant | — | — | — | — | — | >64 |
| E. coli | GUEST131 (NDM-1) | — | — | — | — | — | — |
| P. aeruginosa | ATCC 27853 | — | >64 | >64 | >64 | >64 | — |
| P. aeruginosa | MMX Mex parent strain | — | >64 | >64 | — | — | — |
| P. aeruginosa | MMX 3476 Δmex | — | >64 | >64 | — | — | — |
| H. influenzae | ATCC 49247 | — | >64 | >64 | — | — | >64 |

TABLE 5

MIC (μg/mL) of compounds against Gram positive and Gram negative strains

| Species | Genotype | FSA-504062 | FSA-507051 | FSA-507007 | FSA-507041 | FSA-507031 | FSA-507056 |
|---|---|---|---|---|---|---|---|
| S. aureus | ATCC 29213 | 2 | 16 | 0.25 | 0.5 | >32 | 1 |
| S. aureus | BAA 977 iErmA | — | 16 | 0.5 | 0.5 | >32 | 1 |
| S. aureus | MP-549 msr(a) USA 300 | 1 | — | 0.25 | — | — | — |
| S. aureus | Micromyx USA 300 | — | 16 | 0.12 | 0.25 | >32 | 0.5 |
| S. aureus | MMX 3035 cErmA | — | >32 | 64 | >32 | >32 | >32 |
| S. pneumoniae | ATCC 49619 | 0.25 | 1 | 0.12 | ≤0.03 | 32 | 0.25 |
| S. pneumoniae | MMX 3028 cErmB | — | >32 | 64 | 32 | >32 | >32 |
| S. pneumoniae | MMX 3031 cMefA | — | 1 | 0.12 | ≤0.03 | 16 | 0.12 |
| S. pyogenes | ATCC 19615 | 0.12 | 0.5 | ≤0.06 | 0.06 | 32 | 0.25 |
| S. pyogenes | MMX 946 MacRes | — | >32 | 32 | >32 | >32 | >32 |
| E. faecalis | ATCC 29212 | 32 | >32 | 16 | 2 | >32 | 2 |
| E. faecalis | MMX 847 MacRes | — | >32 | >64 | >32 | >32 | >32 |
| C. difficile | BAA 1805 | — | >32 | 4 | 0.5 | >32 | 16 |
| B. fragilis | ATCC 25285 | — | 32 | 32 | 2 | >32 | >32 |
| K. pneumoniae | ATCC 10031 | >64 | — | >64 | — | — | — |
| E. coli | ATCC 25922 | >64 | >32 | >64 | >32 | >32 | >32 |
| E. coli | MMX TolC parent strain | — | >32 | >64 | >32 | >32 | >32 |
| E. coli | MMX 0121 ΔTolC | — | >32 | 8 | 16 | >32 | >32 |
| E. coli | MP-9 ΔTolC | >64 | — | 16 | — | — | — |
| E. coli | MP-74 LptD mutant | >64 | — | 16 | — | — | — |
| E. coli | GUEST131 (NDM-1) | — | — | — | — | — | — |
| P. aeruginosa | ATCC 27853 | — | >32 | >64 | >32 | >32 | >32 |
| P. aeruginosa | MMX Mex parent strain | — | >32 | >64 | >32 | >32 | >32 |
| P. aeruginosa | MMX 3476 Δmex | — | >32 | 64 | >32 | >32 | >32 |
| H. influenzae | ATCC 49247 | >64 | 16 | 2 | 16 | 8 | >32 |

TABLE 6

MIC (μg/mL) of compounds against Gram positive and Gram negative strains

| Species | Genotype | FSA-511019 | FSA-511020 | FSA-511071 | FSA-511072 | FSA-511073 | FSA-511074 |
|---|---|---|---|---|---|---|---|
| S. aureus | ATCC 29213 | 0.5 | 0.5 | 2 | 1 | 1 | 2 |
| S. aureus | BAA 977 iErmA | — | NT | 2 | 1 | 1 | 2 |
| S. aureus | MP-549 msr(a) USA 300 | 0.5 | 1 | 1 | 1 | 1 | 1 |
| S. aureus | MMX 3035 cErmA | — | — | >64 | >64 | >64 | >64 |

TABLE 6-continued

MIC (μg/mL) of compounds against Gram positive and Gram negative strains

| Species | Genotype | FSA-511019 | FSA-511020 | FSA-511071 | FSA-511072 | FSA-511073 | FSA-511074 |
|---|---|---|---|---|---|---|---|
| S. pneumoniae | ATCC 49619 | 0.25 | ≤0.06 | 0.25 | 0.12 | 0.12 | 0.25 |
| S. pneumoniae | MMX 3028 cErmB | — | — | 64 | 64 | 64 | 64 |
| S. pneumoniae | MMX 3031 cMefA | — | — | 0.5 | 0.12 | 0.12 | 0.25 |
| S. pyogenes | ATCC 19615 | 0.125 | ≤0.06 | 0.5 | 0.25 | 0.25 | 0.5 |
| S. pyogenes | MMX 946 MacRes | — | — | >64 | >64 | >64 | >64 |
| E. faecalis | ATCC 29212 | 4 | 4 | 4 | 4 | 4 | 4 |
| E. faecalis | MMX 847 MacRes | — | — | >64 | >64 | >64 | >64 |
| K. pneumoniae | ATCC 10031 | >64 | >64 | 64 | 32 | 64 | 64 |
| E. coli | ATCC 25922 | >64 | >64 | >64 | >64 | >64 | >64 |
| E. coli | MP-9 ΔTolC | 32 | 64 | 64 | 32 | 64 | 64 |
| E. coli | MP-74 LptD mutant | 64 | 64 | 64 | 64 | 64 | 64 |
| H. influenzae | ATCC 49247 | 64 | 64 | >64 | >64 | >64 | >64 |

TABLE 7

MIC (μg/mL) of compounds against Gram positive and Gram negative strains

| Species | Genotype | FSA-507052 | FSA-507057 | FSA-507053 | FSA-507060 | FSA-509019 | FSA-507061 |
|---|---|---|---|---|---|---|---|
| S. aureus | ATCC 29213 | 2 | 2 | 0.25 | 2 | ≤0.06 | 0.12 |
| S. aureus | BAA 977 iErmA | 2 | 1 | 0.25 | 1 | 0.25 | 0.25 |
| S. aureus | MP-549 msr(a) USA 300 | — | — | — | — | 0.5 | 0.125 |
| S. aureus | Micromyx USA 300 | 0.5 | 0.5 | 0.12 | 0.5 | — | ≤0.06 |
| S. aureus | MMX 3035 cErmA | >32 | >64 | >64 | 32 | 64 | 64 |
| S. pneumoniae | ATCC 49619 | 0.25 | ≤0.06 | 0.25 | 0.5 | ≤0.06 | ≤0.06 |
| S. pneumoniae | MMX 3028 cErmB | >32 | 64 | 32 | 16 | 16 | 4 |
| S. pneumoniae | MMX 3031 cMefA | 0.12 | ≤0.06 | 0.12 | 0.25 | 0.125 | ≤0.06 |
| S. pyogenes | ATCC 19615 | 0.25 | 0.12 | ≤0.06 | 0.25 | ≤0.06 | ≤0.06 |
| S. pyogenes | MMX 946 MacRes | >32 | >64 | 32 | 32 | 32 | 4 |
| E. faecalis | ATCC 29212 | 1 | 1 | 2 | 8 | 1 | ≤0.06 |
| E. faecalis | MMX 847 MacRes | >32 | >64 | >64 | 32 | 64 | 32 |
| C. difficile | BAA 1805 | 16 | 16 | 8 | 32 | — | 2 |
| B. fragilis | ATCC 25285 | >32 | 64 | 16 | 32 | — | 64 |
| K. pneumoniae | ATCC 10031 | — | — | — | — | 16 | 16 |
| E. coli | ATCC 25922 | >32 | >64 | >64 | 64 | >64 | 64 |
| E. coli | MMX TolC parent strain | >32 | >64 | >64 | 64 | — | >64 |
| E. coli | MMX 0121 ΔTolC | >32 | 64 | 16 | 16 | — | 2 |
| E. coli | MP-9 ΔTolC | — | — | — | — | 16 | 4 |
| E. coli | MP-74 LptD mutant | — | — | — | — | 32 | 8 |
| P. aeruginosa | ATCC 27853 | >32 | >64 | >64 | >64 | — | >64 |
| P. aeruginosa | MMX Mex parent strain | >32 | >64 | >64 | >64 | — | >64 |
| P. aeruginosa | MMX 3476 Δmex | >32 | >64 | >64 | >64 | — | >64 |
| H. influenzae | ATCC 49247 | >32 | 64 | 16 | 32 | — | 4 |

TABLE 8

MIC (μg/mL) of compounds against Gram positive and Gram negative strains

| Species | Genotype | FSA-511044 | FSA-511045 | FSA-511046 | FSA-511077 | FSA-511078 | FSA-511080 |
|---|---|---|---|---|---|---|---|
| S. aureus | ATCC 29213 | 0.25 | 0.5 | 1 | 0.25 | 0.25 | 0.12 |
| S. aureus | BAA 977 iErmA | NT | NT | NT | 0.25 | 0.25 | 0.25 |
| S. aureus | MP-549 msr(a) USA 300 | 0.5 | 0.25 | 0.5 | 0.25 | 0.12 | 0.25 |
| S. aureus | MMX 3035 cErmA | — | — | — | >64 | >64 | >64 |
| S. pneumoniae | ATCC 49619 | 0.5 | ≤0.06 | ≤0.06 | ≤0.06 | ≤0.06 | ≤0.06 |
| S. pneumoniae | MMX 3028 cErmB | — | — | — | 8 | 4 | 8 |
| S. pneumoniae | MMX 3031 cMefA | — | — | — | ≤0.06 | ≤0.06 | ≤0.06 |
| S. pyogenes | ATCC 19615 | ≤0.06 | ≤0.06 | ≤0.06 | ≤0.06 | ≤0.06 | ≤0.06 |
| S. pyogenes | MMX 946 MacRes | — | — | — | 32 | 16 | 32 |
| E. faecalis | ATCC 29212 | 2 | 1 | 1 | 0.5 | 0.25 | 0.5 |
| E. faecalis | MMX 847 MacRes | — | — | — | 64 | 64 | >64 |
| K. pneumoniae | ATCC 10031 | 32 | 16 | 16 | 8 | 8 | 16 |
| E. coli | ATCC 25922 | >64 | >64 | >64 | >64 | >64 | >64 |
| E. coli | MP-9 ΔTolC | 16 | 8 | 8 | 4 | 2 | 4 |

TABLE 8-continued

MIC (μg/mL) of compounds against Gram positive and Gram negative strains

| Species | Genotype | FSA-511044 | FSA-511045 | FSA-511046 | FSA-511077 | FSA-511078 | FSA-511080 |
|---|---|---|---|---|---|---|---|
| E. coli | MP-74 LptD mutant | 16 | 32 | 32 | 16 | 8 | 16 |
| H. influenzae | ATCC 49247 | 16 | 16 | 16 | 16 | 16 | 16 |

TABLE 9

MIC (μg/mL) of compounds against Gram positive and Gram negative strains

| Species | Genotype | FSA-510001 | FSA-510002 | FSA-510003 | FSA-510006 | FSA-510011 | FSA-510012 |
|---|---|---|---|---|---|---|---|
| S. aureus | ATCC 29213 | 2 | 0.5 | 0.5 | 8 | 32 | >64 |
| S. aureus | BAA 977 iErmA | 2 | 0.25 | 0.25 | 16 | 32 | >64 |
| S. aureus | MP-549 msr(a) USA 300 | — | — | — | — | — | >64 |
| S. pneumoniae | ATCC 49619 | 4 | 0.25 | 0.25 | 1 | 8 | >64 |
| S. pyogenes | ATCC 19615 | 2 | 0.25 | 0.25 | 0.5 | 2 | 32 |
| E. faecalis | ATCC 29212 | 8 | 2 | 1 | 16 | >64 | >64 |
| C. difficile | BAA 1805 | — | — | — | — | — | >64 |
| K. pneumoniae | ATCC 10031 | >64 | 64 | 16 | >64 | >64 | >64 |
| E. coli | ATCC 25922 | >64 | >64 | >64 | >64 | >64 | >64 |
| E. coli | MP-9 ΔTolC | >64 | >64 | >64 | >64 | >64 | >64 |
| E. coli | MP-74 LptD mutant | 8 | 32 | 32 | 64 | >64 | >64 |
| H. influenzae | ATCC 49247 | 16 | 32 | 16 | >64 | >64 | >64 |

TABLE 10

MIC (μg/mL) of compounds against Gram positive and Gram negative strains

| Species | Genotype | FSA-511033 | FSA-510021 | FSA-510022 | FSA-510065 | FSA-510072 | FSA-510073 |
|---|---|---|---|---|---|---|---|
| S. aureus | ATCC 29213 | 0.5 | 0.125 | 0.12 | >64 | 64 | 16 |
| S. aureus | BAA 977 iErmA | NT | 0.125 | 0.12 | >64 | — | — |
| S. aureus | MP-549 msr(a) USA 300 | 1 | 0.125 | 0.12 | >64 | 64 | 16 |
| S. aureus | MMX 3035 cErmA | NT | 4 | 2 | — | — | — |
| S. pneumoniae | ATCC 49619 | ≤0.06 | ≤0.06 | ≤0.06 | >64 | 32 | 8 |
| S. pneumoniae | MMX 3028 cErmB | NT | 4 | 4 | — | — | — |
| S. pneumoniae | MMX 3031 cMefA | NT | ≤0.06 | ≤0.06 | — | — | — |
| S. pyogenes | ATCC 19615 | ≤0.06 | ≤0.06 | ≤0.06 | 32 | 8 | 2 |
| S. pyogenes | MMX 946 MacRes | NT | 1 | 0.5 | — | — | — |
| E. faecalis | ATCC 29212 | 2 | 0.25 | 0.25 | >64 | >64 | >64 |
| E. faecalis | MMX 847 MacRes | — | 4 | 2 | — | — | — |
| C. difficile | BAA 1805 | — | — | — | >64 | — | — |
| K. pneumoniae | ATCC 10031 | 64 | 4 | 2 | >64 | >64 | >64 |
| E. coli | ATCC 25922 | >64 | 64 | 32 | >64 | >64 | >64 |
| E. coli | MP-9 ΔTolC | 32 | 4 | 4 | >64 | >64 | >64 |
| E. coli | MP-74 LptD mutant | 64 | 4 | 4 | >64 | >64 | >64 |
| H. influenzae | ATCC 49247 | 64 | 1 | 1 | >64 | >64 | >64 |

TABLE 11

MIC (μg/mL) of compounds against Gram positive and Gram negative strains

| Species | Genotype | FSA-510074 | FSA-502002 | FSA-503001 | FSA-503002 | FSA-503003 | FSA-503004 |
|---|---|---|---|---|---|---|---|
| S. aureus | ATCC 29213 | 64 | 2 | 64 | 64 | 4 | >64 |
| S. aureus | BAA 977 iErmA | — | 2 | >64 | >64 | 4 | >64 |
| S. aureus | MP-549 msr(a) USA 300 | 64 | 2 | >64 | >64 | 2 | >64 |
| S. aureus | MP-513 clinical cErm | — | >64 | >64 | >64 | >64 | >64 |
| S. aureus | UNT96, NRS710, MP-618 (USA 100, Erythro > 8) | — | >64 | — | — | — | — |
| S. aureus | UNT-146, MP-620, TP 506 (ermA) | — | >64 | — | — | — | — |

TABLE 11-continued

MIC (μg/mL) of compounds against Gram positive and Gram negative strains

| Species | Genotype | FSA-510074 | FSA-502002 | FSA-503001 | FSA-503002 | FSA-503003 | FSA-503004 |
|---|---|---|---|---|---|---|---|
| S. aureus | UNT-120, MP-619, NRS22 (USA 600, GISA) | — | >64 | — | — | — | — |
| S. pneumoniae | ATCC 49619 | 32 | 0.25 | — | — | — | — |
| S. pneumoniae | UNT-038, MP-626, TP 160 (mefA) | — | 0.25 | — | — | — | — |
| S. pneumoniae | UNT-039, MP-627, TP1517 (mefA) | — | 0.125 | — | — | — | — |
| S. pyogenes | ATCC 19615 | 8 | 0.125 | — | — | — | — |
| S. pyogenes | UNT-014, MP-625 MacRes | — | 0.125 | — | — | — | — |
| E. faecalis | ATCC 29212 | >64 | 8 | — | — | — | — |
| E. faecalis | UNT-047 VRE | — | >64 | — | — | — | — |
| K. pneumoniae | ATCC 10031 | >64 | 64 | >64 | >64 | >64 | >64 |
| E. coli | ATCC 25922 | >64 | >64 | >64 | >64 | >64 | >64 |
| E. coli | MP-9 ΔTolC | >64 | >64 | >64 | >64 | >64 | >64 |
| E. coli | MP-74 LptD mutant | >64 | — | — | — | — | — |
| P. aeruginosa | ATCC 27853 | — | >64 | >64 | >64 | >64 | >64 |
| H. influenzae | ATCC 49247 | >64 | — | — | — | — | — |

TABLE 12

MIC (μg/mL) of compounds against Gram positive and Gram negative strains

| Species | Genotype | FSA-503073 | FSA-504049 | FSA-504050 | FSA-504063 | FSA-504057 |
|---|---|---|---|---|---|---|
| S. aureus | ATCC 29213 | 64 | 16 | 32 | >64 | >64 |
| S. aureus | BAA 977 iErmA | 64 | 32 | 64 | NT | NT |
| S. aureus | MP-549 msr(a) USA 300 | 32 | 8 | 32 | NT | NT |
| S. aureus | MP-513 clinical cErm | >64 | >64 | >64 | >64 | >64 |
| K. pneumoniae | ATCC 10031 | >64 | >64 | >64 | >64 | >64 |
| E. coli | ATCC 25922 | >64 | >64 | >64 | >64 | >64 |
| E. coli | MP-9 ΔTolC | >64 | >64 | >64 | >64 | >64 |
| P. aeruginosa | ATCC 27853 | >64 | >64 | >64 | >64 | >64 |

TABLE 13

MIC (μg/mL) of compounds against Gram positive and Gram negative strains

| Species | Genotype | FSA-511100 | FSA-512011 | FSA-512012 | FSA-512075 | FSA-512076 | FSA-512077 |
|---|---|---|---|---|---|---|---|
| S. aureus | ATCC 29213 | 0.25 | 8 | 8 | 0.5 | 0.25 | 0.5 |
| S. aureus | BAA 977 iErmA | 4 | — | — | — | — | — |
| S. aureus | MP-549 msr(a) USA 300 | 0.25 | 8 | 8 | 0.25 | 0.25 | 0.25 |
| S. aureus | MP-513 cErm | >256 | — | — | — | — | — |
| S. pneumoniae | ATCC 49619 | 0.125 | 1 | 1 | 0.25 | ≤0.12 | ≤0.12 |
| S. pneumoniae | MMX 3028 cErmB | >256 | — | — | — | — | — |
| S. pneumoniae | UNT-039, MP-627, TP1517 (mefA) | 1 | — | — | — | — | — |
| S. pyogenes | ATCC 19615 | 0.25 | 4 | 4 | 0.25 | ≤0.12 | ≤0.12 |
| S. pyogenes | MMX 946 MacRes | >256 | — | — | — | — | — |
| E. faecalis | ATCC 29212 | >256 | 64 | 64 | 2 | 2 | 1 |
| K. pneumoniae | ATCC 10031 | >64 | — | — | — | — | — |
| E. coli | ATCC 25922 | >64 | >256 | >256 | >256 | >256 | >256 |
| E. coli | MP-9 ΔTolC | 32 | >256 | >256 | 32 | 64 | 16 |
| E. coli | MP-74 LptD mutant | 16 | >256 | >256 | 64 | 64 | 64 |
| H. influenzae | ATCC 49247 | 64 | >256 | >256 | 64 | 128 | 128 |

TABLE 14

MIC (μg/mL) of compounds against Gram positive and Gram negative strains

| Species | Genotype | FSA-512079b | FSA-512079c | FSA-512080b | FSA-512080c | FSA-512081a | FSA-512081b |
|---|---|---|---|---|---|---|---|
| S. aureus | ATCC 29213 | 0.5 | 0.5 | 0.12 | 0.25 | 0.25 | 0.25 |
| S. aureus | BAA 977 iErmA | — | — | 0.25 | 0.5 | 1 | 1 |
| S. aureus | MMX-3035 cErmA | — | — | 64 | 128 | 128 | 128 |
| S. aureus | MP-549 msr(a) USA 300 | 0.5 | 0.5 | 0.5 | 0.5 | 1 | 1 |
| S. pneumoniae | ATCC 49619 | — | — | ≤0.06 | ≤0.06 | ≤0.06 | ≤0.06 |
| S. pneumoniae | MMX-3028 cErmB | — | — | 4 | 16 | 4 | 16 |
| S. pneumoniae | MMX-3031 cMefA | — | — | ≤0.06 | 0.12 | ≤0.06 | 0.12 |
| S. pyogenes | ATCC 19615 | ≤0.12 | ≤0.12 | ≤0.06 | ≤0.06 | ≤0.06 | ≤0.06 |
| S. pyogenes | MMX-946 MacRes | — | — | 16 | 64 | 16 | 32 |
| E. faecalis | ATCC 29212 | 1 | 2 | 0.5 | 2 | 0.5 | 1 |
| E. faecalis | MMX-8471 | — | — | 64 | 128 | 64 | 128 |
| K. pneumoniae | ATCC 10031 | 16 | 16 | — | — | — | — |
| E. coli | ATCC 25922 | >128 | >128 | 128 | >128 | 128 | 128 |
| E. coli | MP-9 ΔTolC | 8 | 8 | 4 | 8 | 4 | 8 |
| E. coli | MP-74 LptD mutant | 16 | 16 | 8 | 32 | 16 | 32 |
| H. influenzae | ATCC 49247 | 16 | 16 | 16 | 32 | 16 | 16 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

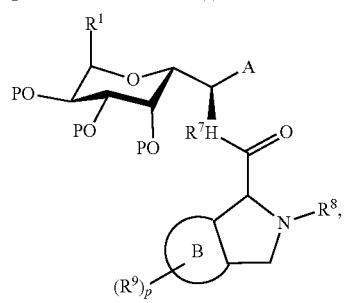

(I)

or a pharmaceutically acceptable salt thereof, wherein:
P is independently hydrogen or a protecting group;
A is substituted or unsubstituted carbocyclyl, substituted or unsubstituted heterocyclyl, substituted or unsubstituted aryl, substituted or unsubstituted heteroaryl, substituted or unsubstituted alkyl, substituted or unsubstituted alkenyl, or substituted or unsubstituted alkynyl;

B is a carbocyclyl or heterocyclyl ring;

$R^1$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, substituted or unsubstituted heteroaliphatic, $-OR^A$, $-N(R^A)_2$, or $-SR^A$;

$R^7$ is hydrogen or unsubstituted alkyl; or A and $R^7$ are joined to form a substituted or unsubstituted heterocyclic ring;

$R^8$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaliphatic, $-C(=NR^A)R^A$, $-C(=NR^A)OR^A$, $-C(=NR^A)N(R^A)_2$, $-C(=O)R^A$, $-C(=O)OR^A$, $-C(=O)N(R^A)_2$, $-S(O)_2R^A$, or a nitrogen protecting group;

each occurrence of $R^9$ is independently, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, substituted or unsubstituted heteroaliphatic, $-OR^A$, $-N(R^A)_2$, $-SR^A$, $-CN$, $-SCN$, $-C(=NR^A)R^A$, $-C(=NR^A)OR^A$, $-C(=NR^A)N(R^A)_2$, $-C(=O)R^A$, $-C(=O)OR^A$, $-C(=O)N(R^A)_2$, $-NO_2$, $-NR^AC(=O)R^A$, $-NR^AC(=O)OR^A$, $-NR^AC(=O)N(R^A)_2$, $-NR^AC(=NR^A)N(R^A)_2$, $-OC(=O)R^A$, $-OC(=O)OR^A$, $-OC(=O)N(R^A)_2$, $-NR^AS(O)_2R^A$, $-OS(O)_2R^A$, or $-S(O)_2R^A$; or two $R^9$ groups are joined to form a substituted or unsubstituted heterocyclyl ring, or a substituted or unsubstituted carbocyclyl ring;

p is 0-4; and each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted carbocyclylalkyl, substituted or unsubstituted heterocyclyl, substituted or unsubstituted aryl, substituted or unsubstituted aralkyl, substituted or unsubstituted heteroaryl, substituted or unsubstituted hetaralkyl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclyl ring, or a substituted or unsubstituted heteroaryl ring.

2. The compound of claim 1, or a pharmaceutically acceptable salt thereof, wherein:

A is substituted or unsubstituted carbocyclyl, substituted or unsubstituted heterocyclyl,

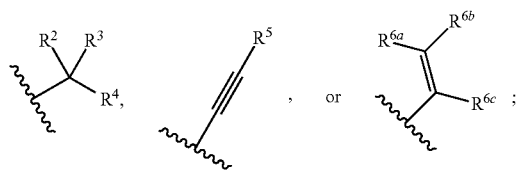

$R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, $-OR^A$, $-N_3$, $-N(R^A)_2$, $-SR^A$, $-CN$, $-SCN$, $-C(=NR^A)R^A$, $-C(=NR^A)OR^A$, $-C(=NR^A)N(R^A)_2$, $-C(=O)R^A$, $-C(=O)OR^A$, $-C(=O)N(R^A)_2$, $-NO_2$, $-NR^AC(=O)R^A$, $-NR^AC(=O)OR^A$, $-NR^AC(=O)N(R^A)_2$, $-NR^AC(=NR^A)N(R^A)_2$, $-OC(=O)R^A$, $-OC(=O)OR^A$, $-OC(=O)N(R^A)_2$, $-NR^AS(O)_2R^A$, $-OS(O)_2R^A$, or $-S(O)_2R^A$;

$R^3$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

$R^4$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

$R^5$ is hydrogen, halogen, substituted or unsubstituted alkyl, substituted or unsubstituted carbocyclyl, substituted or unsubstituted heterocyclyl, substituted or unsubstituted aryl, substituted or unsubstituted heteroaryl, or substituted or unsubstituted heteroaliphatic; and $R^{6a}$, $R^{6b}$, and $R^{6c}$ are each independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, or substituted or unsubstituted acyl.

3. The compound of claim 2, or a pharmaceutically acceptable salt thereof, wherein:

$R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaryl, substituted or unsubstituted heteroalkyl, $-OR^A$, $-N_3$, $-N(R^A)_2$, $-SR^A$, $-NR^AC(=O)R^A$, or $-OC(=O)N(R^A)_2$.

4. The compound of claim 2, or a pharmaceutically acceptable salt thereof, wherein:

$R^3$ is hydrogen, halogen, substituted or unsubstituted alkyl, or substituted or unsubstituted alkenyl.

5. The compound of claim 2, or a pharmaceutically acceptable salt thereof, wherein:

$R^4$ is hydrogen, halogen, substituted or unsubstituted alkyl, or substituted or unsubstituted alkenyl.

6. The compound of claim 1, or a pharmaceutically acceptable salt thereof, wherein:

A is of the formula:

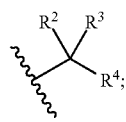

$R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —$OR^A$, —$N_3$, —$N(R^A)_2$, —$SR^A$, —CN, —SCN, —$C(=NR^A)R^A$, —$C(=NR^A)OR^A$, —$C(=NR^A)N(R^A)_2$, —$C(=O)R^A$, —$C(=O)OR^A$, —$C(=O)N(R^A)_2$, —$NO_2$, —$NR^AC(=O)R^A$, —$NR^AC(=O)OR^A$, —$NR^AC(=O)N(R^A)_2$, —$NR^AC(=NR^A)N(R^A)_2$, —$OC(=O)R^A$, —$OC(=O)OR^A$, —$OC(=O)N(R^A)_2$, —$NR^AS(O)_2R^A$, —$OS(O)_2R^A$, or —$S(O)_2R^A$;

$R^3$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic; and $R^4$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic.

7. The compound of claim 1, or a pharmaceutically acceptable salt thereof, wherein:

A is of the formula:

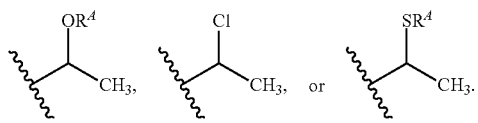

8. The compound of claim 1, or a pharmaceutically acceptable salt thereof, wherein:

$R^1$ is substituted or unsubstituted alkyl, substituted or unsubstituted alkenyl, substituted or unsubstituted carbocyclyl, substituted or unsubstituted heterocyclyl, substituted or unsubstituted heteroaryl, substituted or unsubstituted heteroaralkyl, substituted or unsubstituted heteroalkyl, —$OR^A$, —$N(R^A)_2$, or —$SR^A$.

9. The compound of claim 1, or a pharmaceutically acceptable salt thereof, wherein:

$R^8$ is hydrogen, substituted or unsubstituted alkyl, substituted or unsubstituted carbocyclyl, or —$C(=O)R^A$.

10. The compound of claim 1, or a pharmaceutically acceptable salt thereof, wherein:

$R^9$ is halogen, substituted or unsubstituted alkyl, substituted or unsubstituted alkenyl, substituted or unsubstituted alkynyl, substituted or unsubstituted heterocyclyl, substituted or unsubstituted aryl, substituted or unsubstituted aralkyl, substituted or unsubstituted heteroaryl, substituted or unsubstituted heteroaralkyl, —$OR^A$, or —$N(R^A)_2$; or two $R^9$ groups are joined to form a substituted or unsubstituted heterocyclyl ring, or a substituted or unsubstituted carbocyclyl ring.

11. The compound of claim 1, wherein the compound is of Formula (I-a), (I-b), (I-c), (I-d), (I-e), (I-f), (I-g), (I-i), (I-j), (I-k), (I-l), or (I-m):

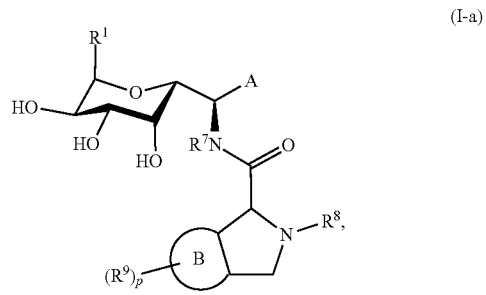

(I-a)

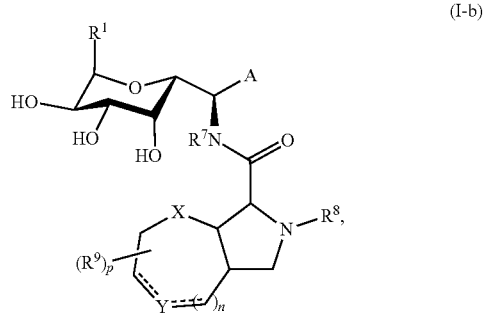

(I-b)

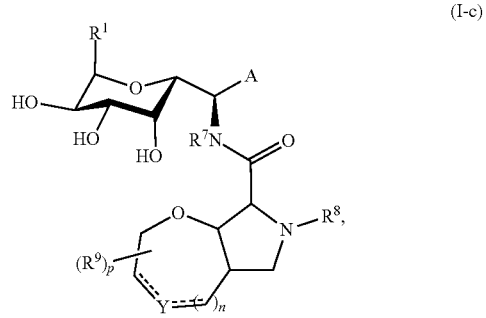

(I-c)

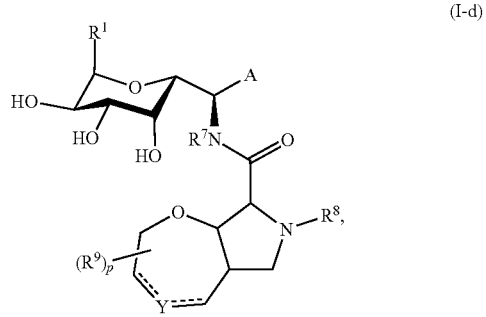

(I-d)

-continued
(I-e)
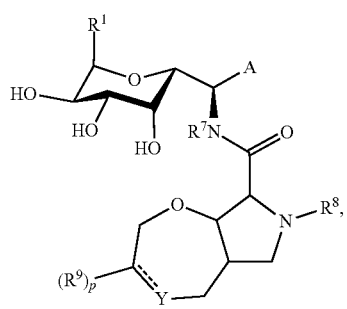
(I-f)
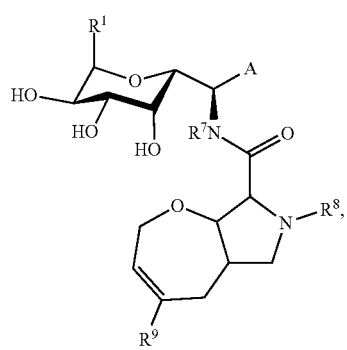
(I-g)
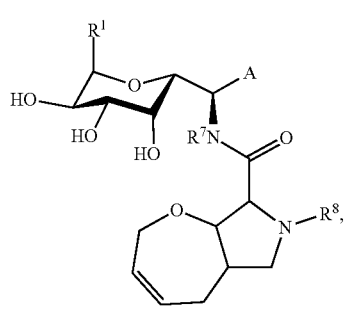
(I-i)
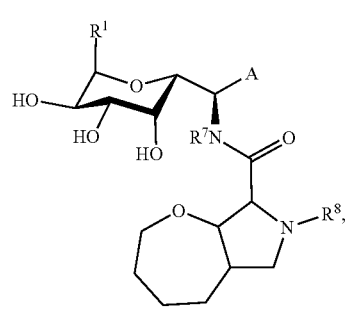
(I-j)
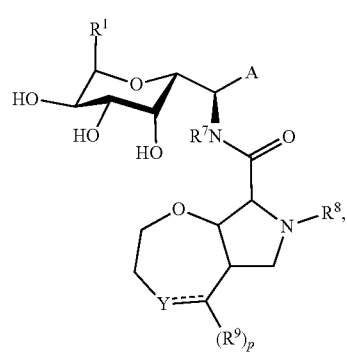
-continued
(I-k)
(I-l)
(I-m)
or a pharmaceutically acceptable salt thereof, wherein:
X is O, S, NR⁹ or C(R⁹)₂;
Y is O, S, NR⁹, C(R⁹)₂, CR⁹, CH₂, or CH;
n is 0 or 1; and
═══ represents a single or double bond; and
p is 0-2.
12. The compound of claim 1, wherein the compound is of Formula (I-h):
(I-h)
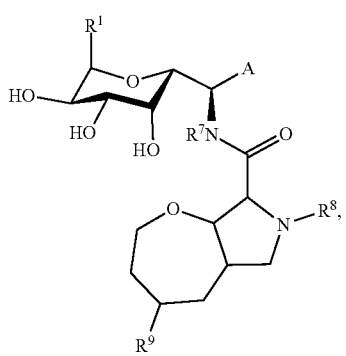
or a pharmaceutically acceptable salt thereof.

13. The compound of claim 2, wherein the compound is of Formula (I-n), (I-o), (I-p), (I-q), (I-r), (I-s), (I-t), (I-u), or (I-v):
(I-n)
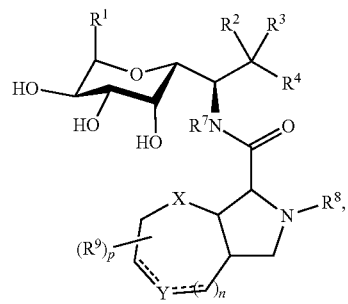
(I-o)
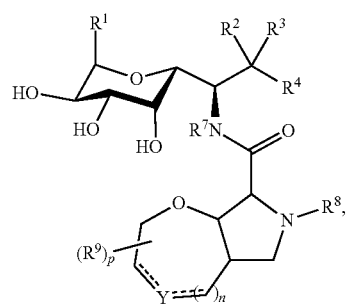
(I-p)
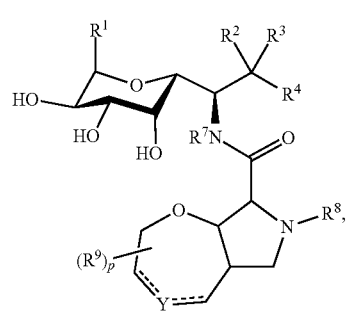
(I-q)
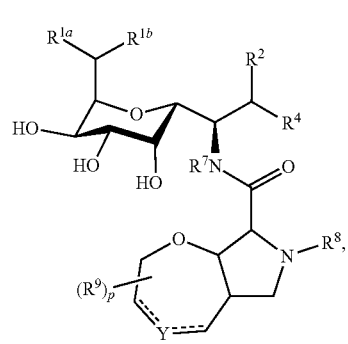
-continued
(I-r)
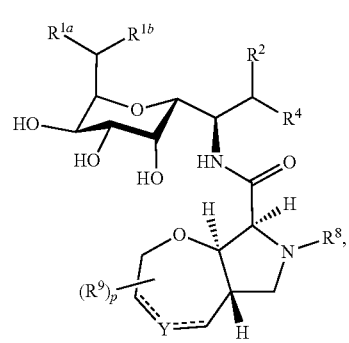
(I-s)
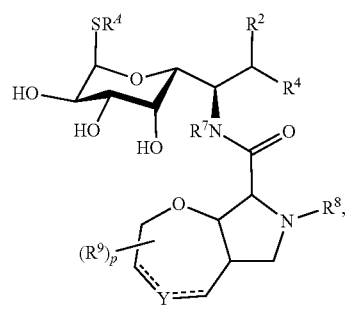
(I-t)
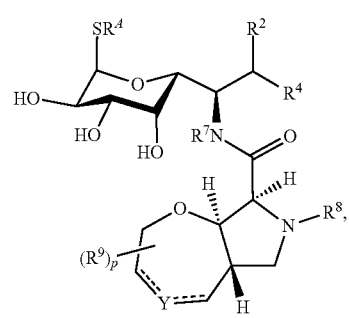
(I-u)
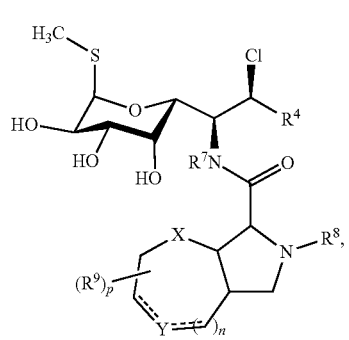

231
-continued (I-v)

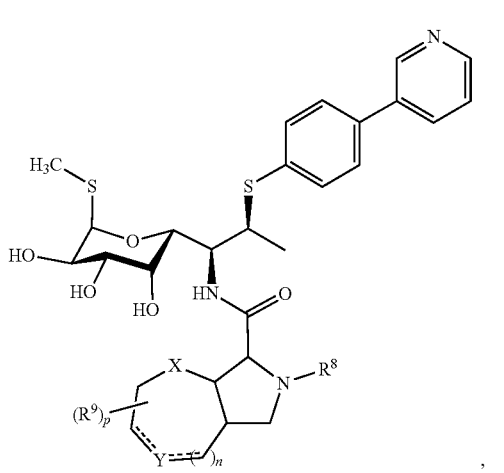

, or a pharmaceutically acceptable salt thereof, wherein:
X is O, S, NR$^9$ or C(R$^9$)$_2$;
Y is O, S, NR$^9$, C(R$^9$)$_2$, CR$^9$, CHR$^9$, CH$_2$, or CH;
n is 0 or 1;
≡≡≡ represents a single or double bond; and
R$^{1a}$ and R$^{1b}$ are each independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —OR$^A$, —N$_3$, —N(R$^A$)$_2$, —SR$^A$, —CN, —SCN, —C(=NR$^A$)R$^A$, —C(=NR$^A$)OR$^A$, —C(=NR$^A$)N(R$^A$)$_2$, —C(=O)R$^A$, —C(=O)OR$^A$, —C(=O)N(R$^A$)$_2$, —NO$_2$, —NR$^A$C(=O)R$^A$, —NR$^A$C(=O)OR$^A$, —NR$^A$C(=O)N(R$^A$)$_2$, —NR$^A$C(=NR$^A$)N(R$^A$)$_2$, —OC(=O)R$^A$, —OC(=O)OR$^A$, —OC(=O)N(R$^A$)$_2$, —NR$^A$S(O)$_2$R$^A$, —OS(O)$_2$R, or —S(O)$_2$R$^A$, or R$^{1a}$ and R$^{1b}$ are joined to form a substituted or unsubstituted heterocyclic ring, or a substituted or unsubstituted carbocyclic ring.

14. The compound of claim 1, or a pharmaceutically acceptable salt thereof, wherein the compound is:

FSA-24039

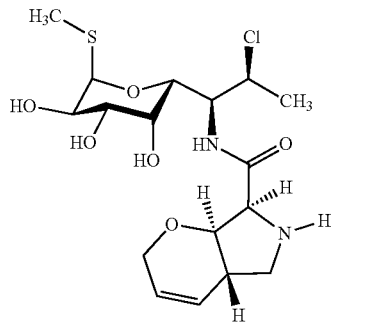

232
-continued

FSA-24041

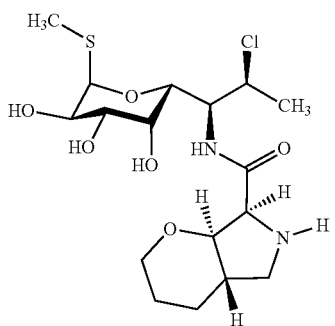

FSA-22091

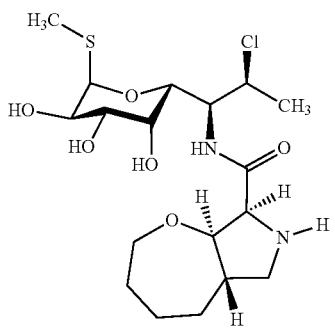

FSA-24040

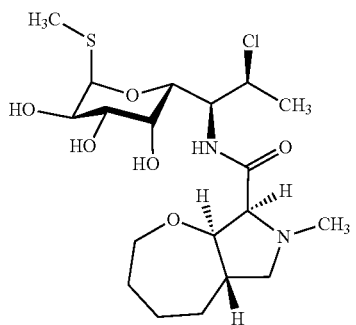

FSA-24035

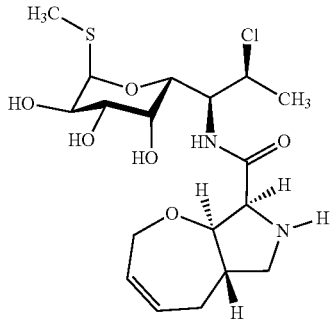

233
-continued
234
-continued
FSA-24036
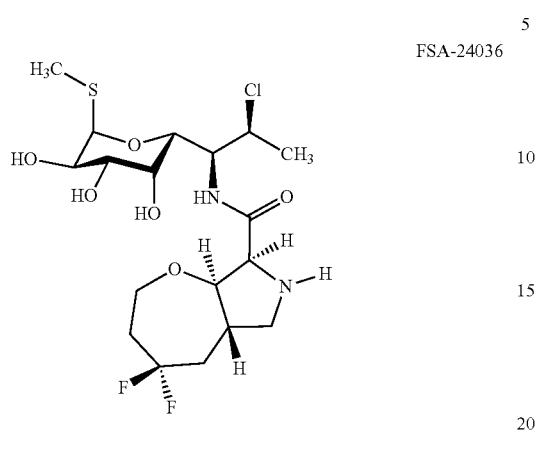
FSA-213061
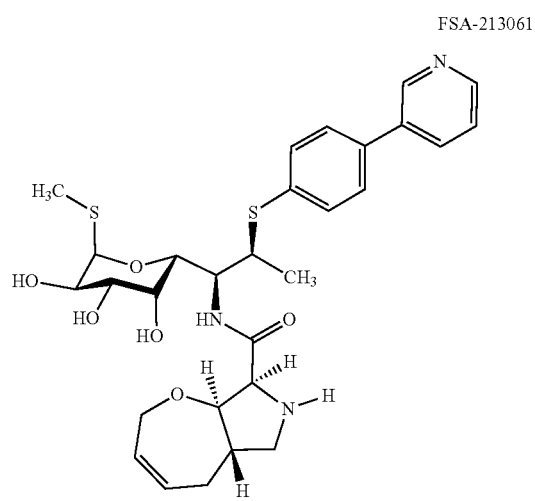
FSA-27049
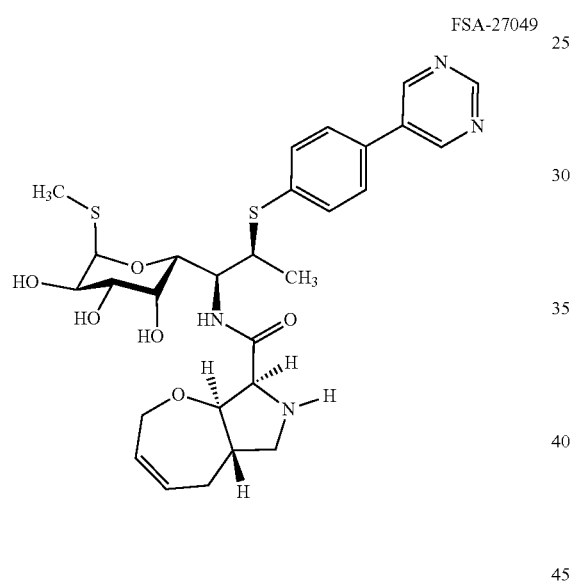
FSA-213064
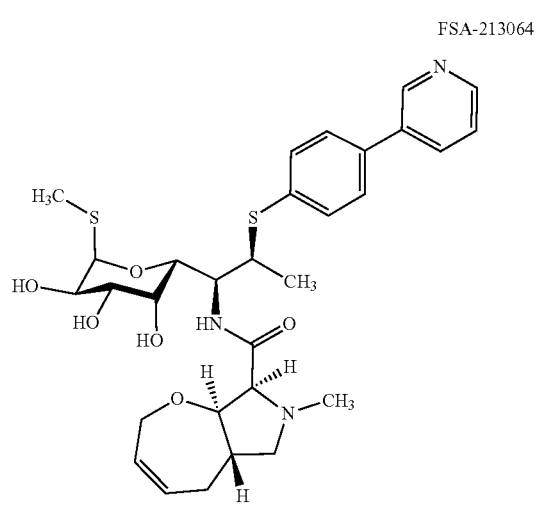
FSA-212034
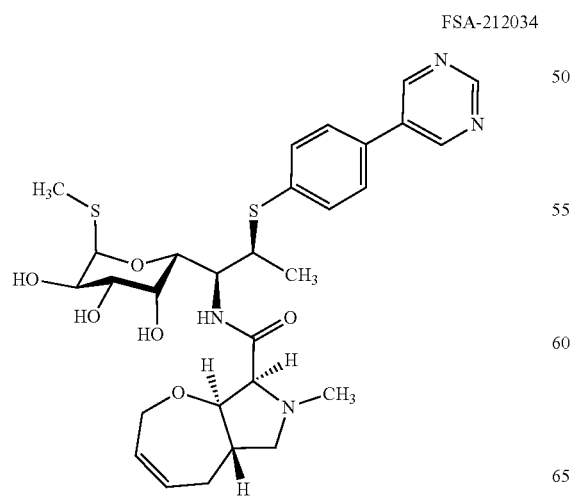
FSA-214009a
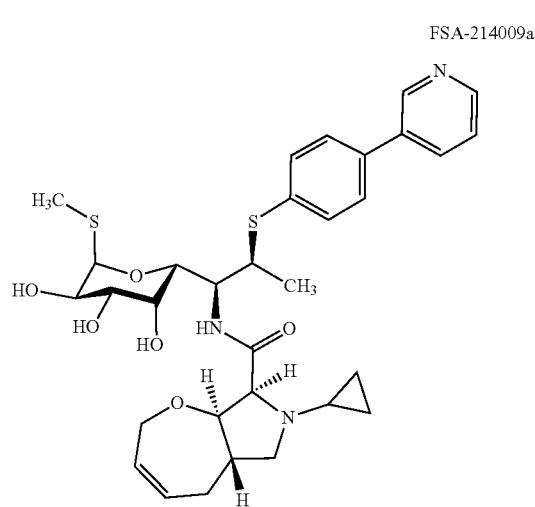

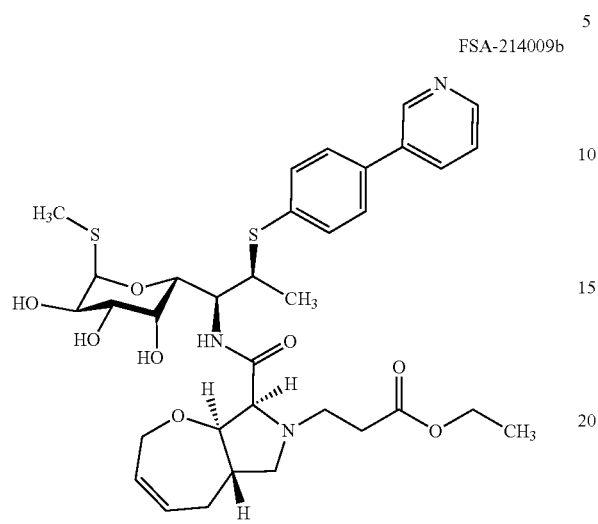
FSA-214009b
FSA-211030
FSA-211064
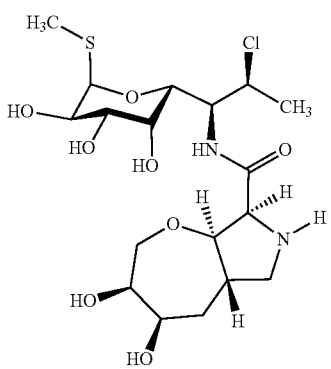
FSA-501076
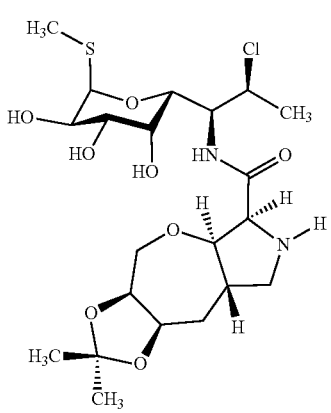
FSA-501099
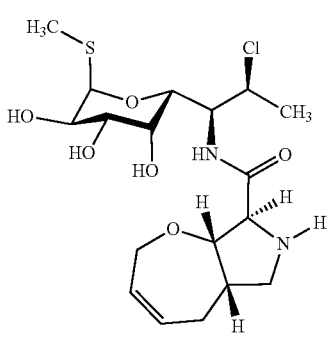
FSA-504059
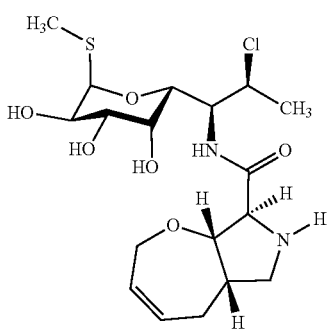
FSA-504059

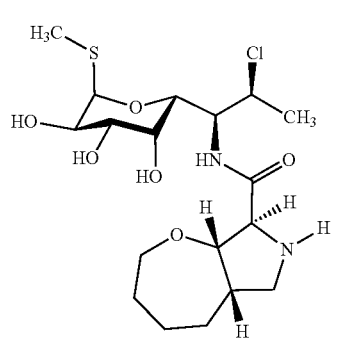
FSA-504062
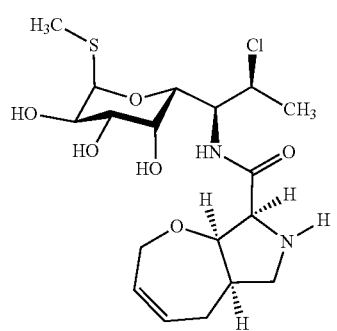
FSA-507051
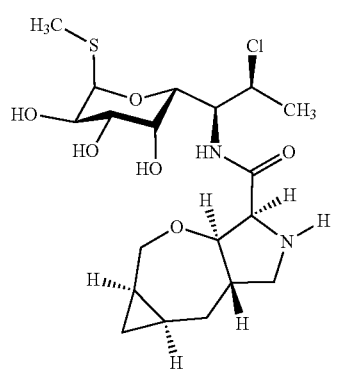
FSA-507007
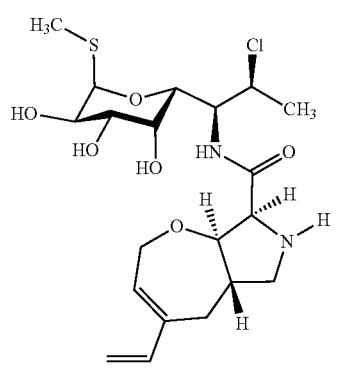
FSA-507041
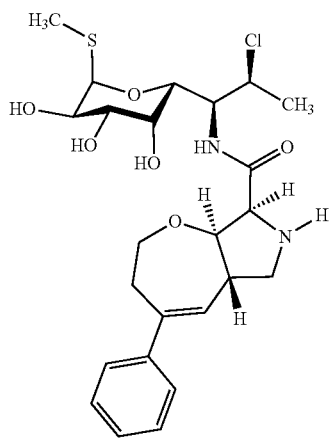
FSA-507031
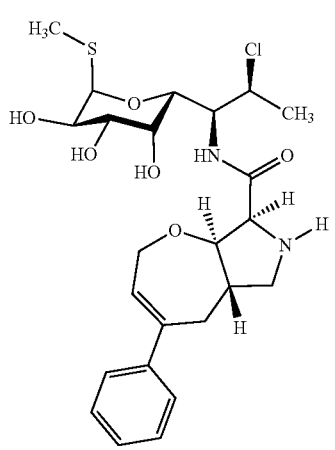
FSA-507056
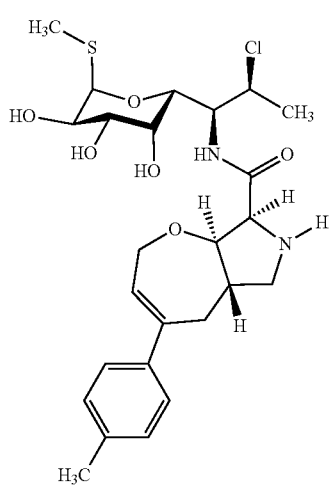
FSA-511019

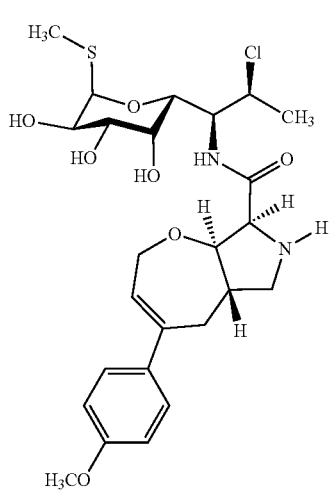
FSA-511020
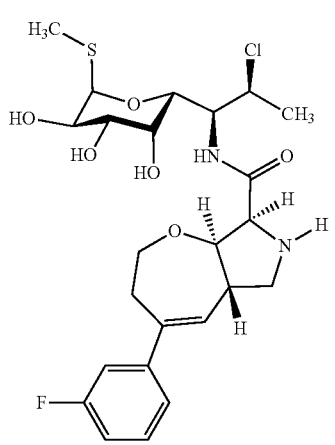
FSA-511071
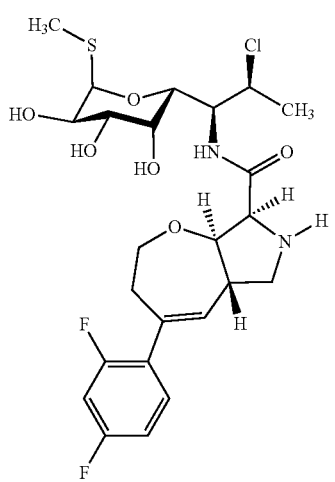
FSA-511072
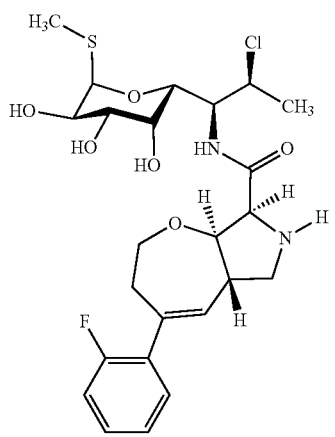
FSA-511073
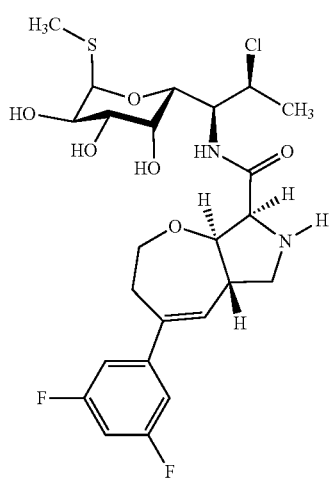
FSA-511074
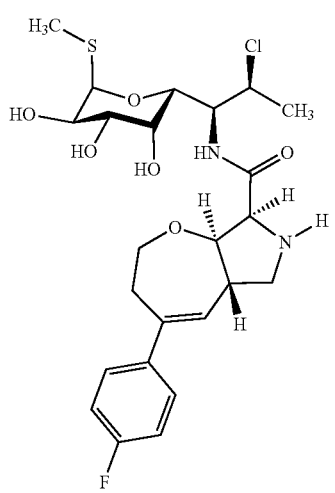
FSA-507052

-continued
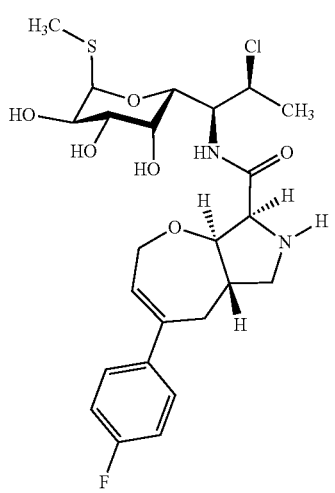
FSA-507057
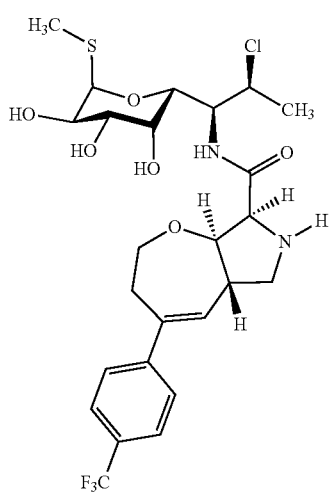
FSA-507053
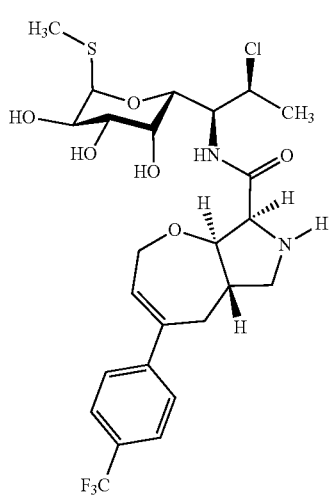
FSA-507060
-continued
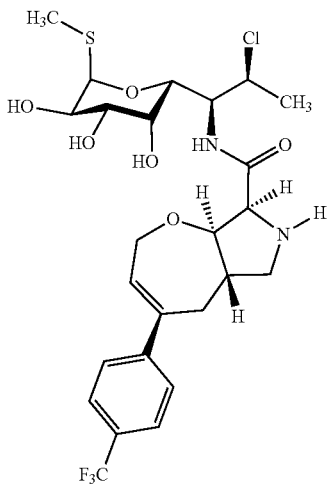
FSA-509019
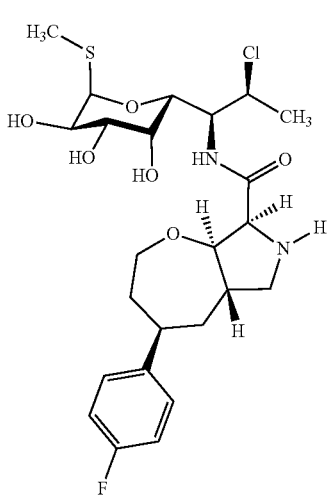
FSA-507061
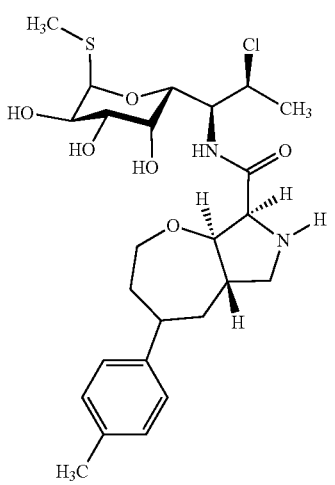
FSA-511044

FSA-511045
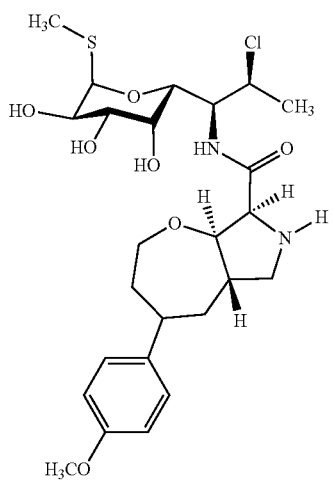
FSA-511046
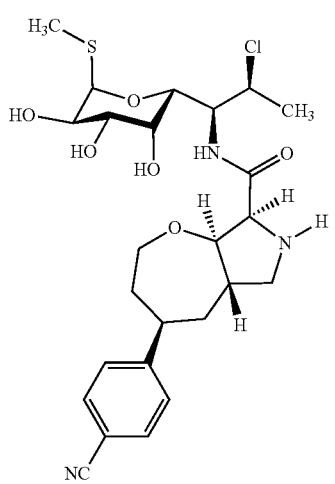
FSA-511077
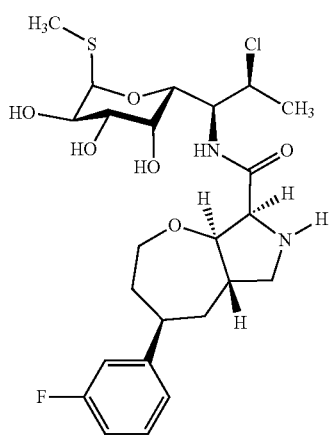
FSA-511078
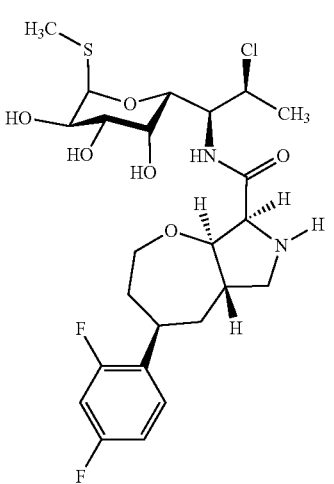
FSA-511080
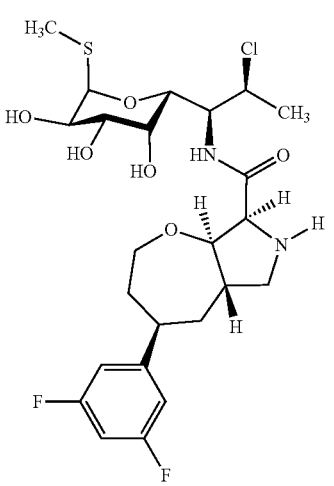
FSA-510001
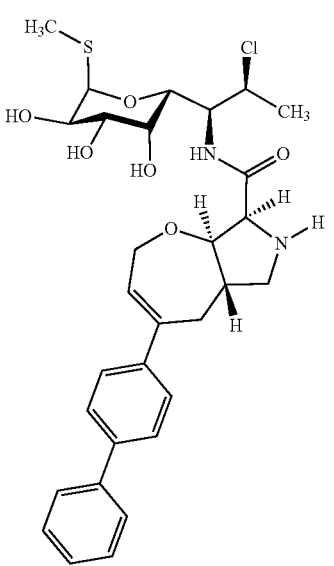

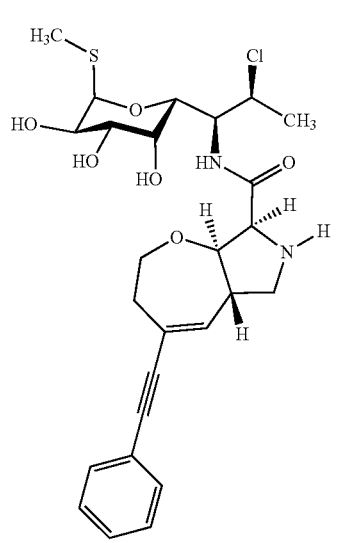
FSA-510002
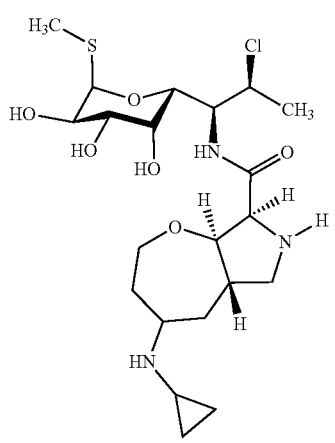
FSA-510011
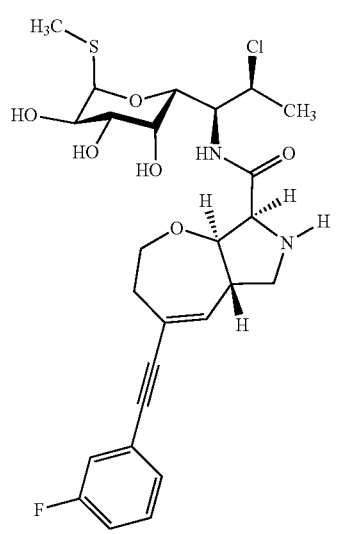
FSA-510003
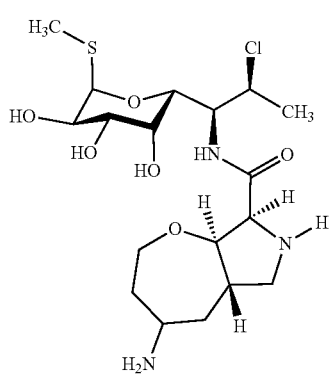
FSA-510012
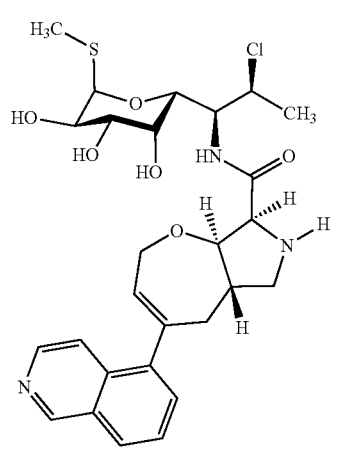
FSA-510006
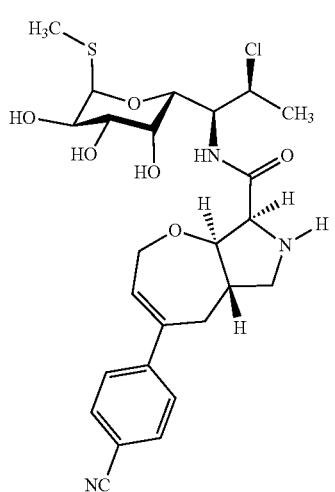
FSA-511033

FSA-510021
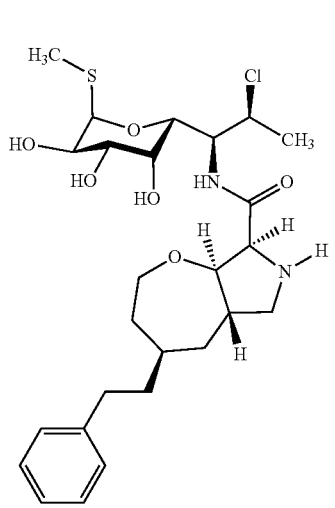
FSA-510072
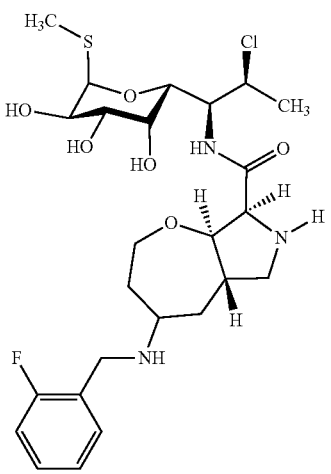
FSA-510022
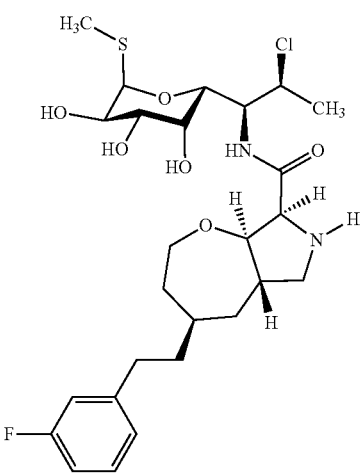
FSA-510073
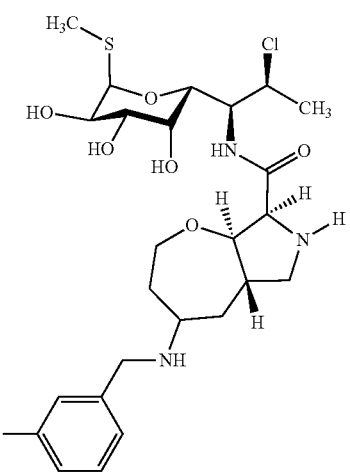
FSA-510065
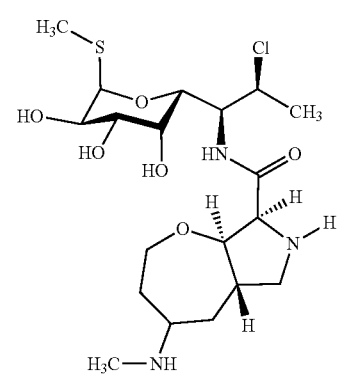
FSA-510074
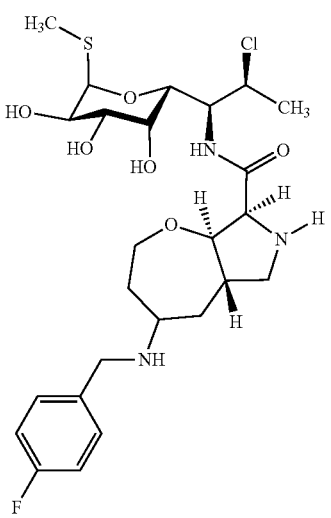

249
-continued
FSA-503001
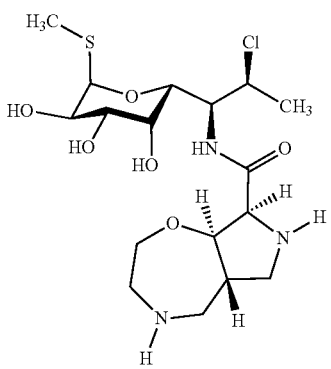
FSA-503002
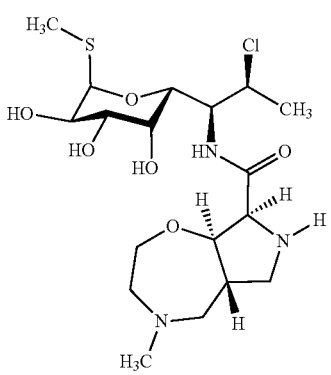
FSA-503003
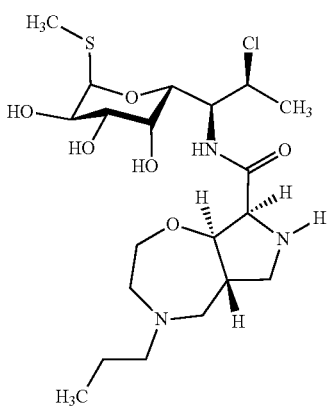
FSA-503004
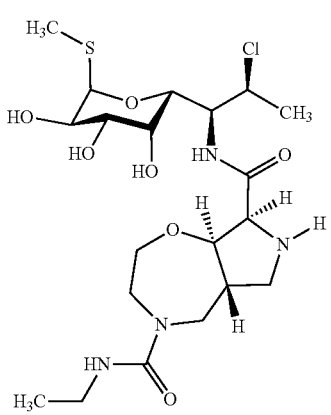
250
-continued
FSA-503073
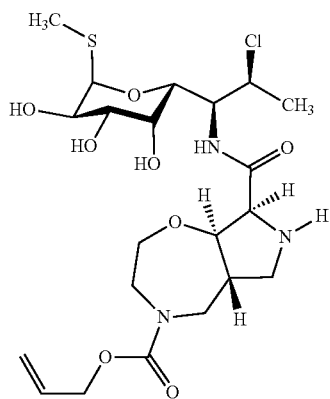
FSA-502002
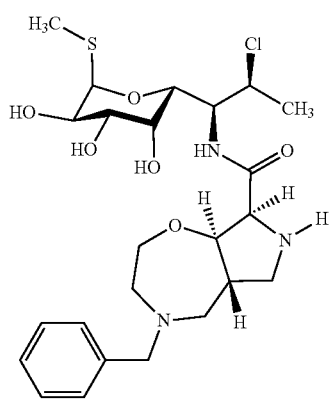
FSA-504049
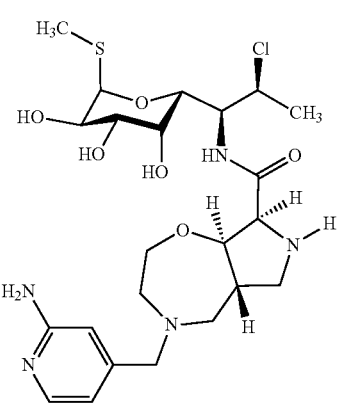
FSA-504050
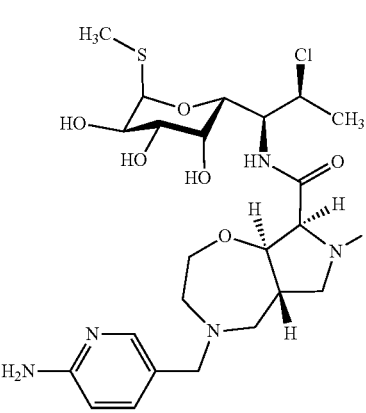

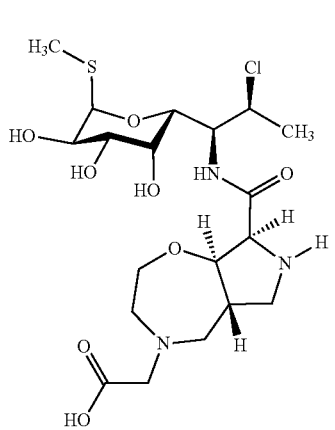
FSA-504063
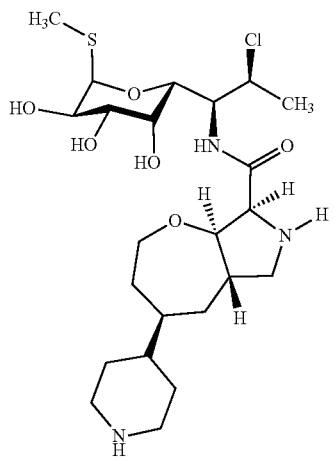
FSA-512011
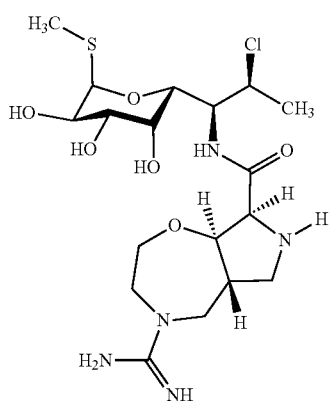
FSA-504057
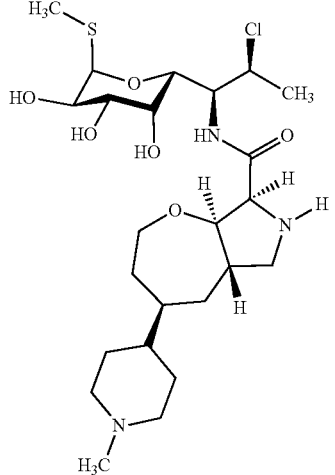
FSA-512012
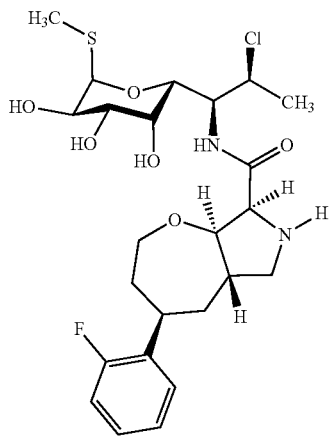
FSA-511100
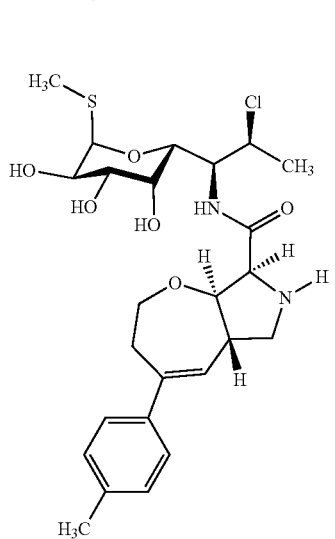
FSA-512075

253
-continued
FSA-512076
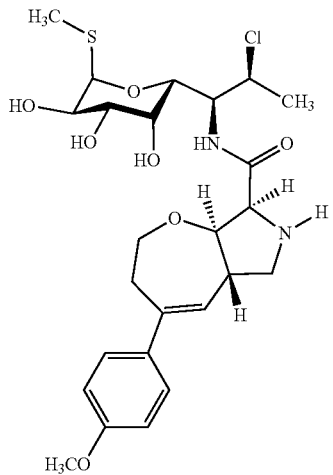
FSA-512077
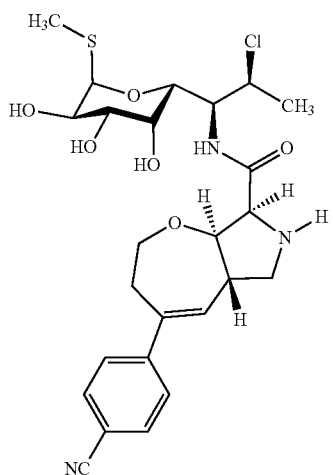
FSA-512079b
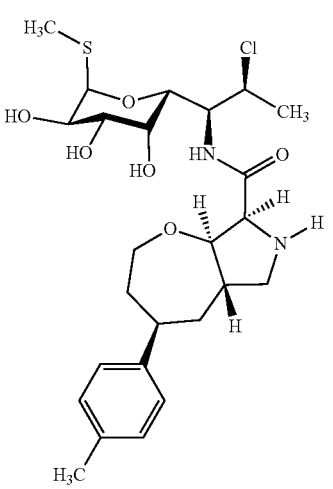
254
-continued
FSA-512079c
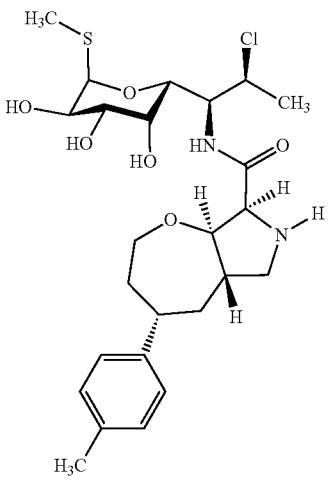
FSA-512080b
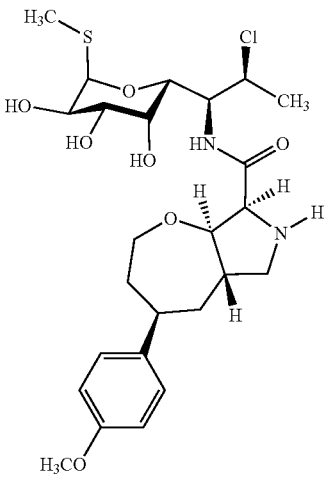
FSA-512080c
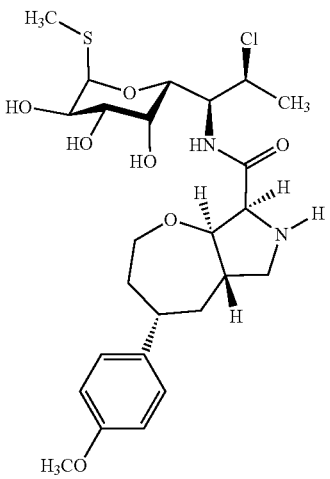

-continued

FSA-512081a

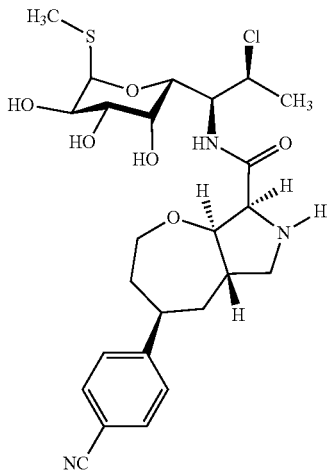

or

FSA-512081b

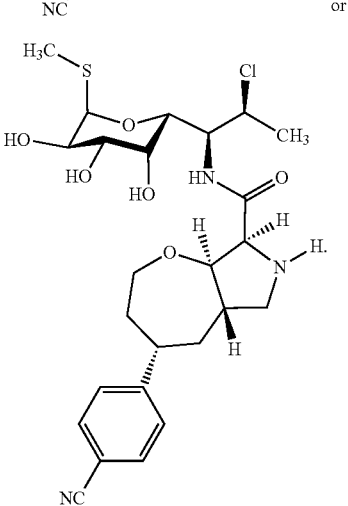

15. A pharmaceutical composition comprising a compound of claim 1, or a pharmaceutically acceptable salt thereof, and a pharmaceutically acceptable excipient.

16. A method of treating an infectious disease comprising administering an effective amount of a compound of claim 1, or pharmaceutically acceptable salt thereof, to a subject in need thereof.

17. A method of killing or inhibiting the growth of a microorganism comprising contacting the microorganism with an effective amount of a compound of claim 1, or pharmaceutically acceptable salt thereof, to a subject in need thereof.

18. A method of preparing a compound of Formula (I):

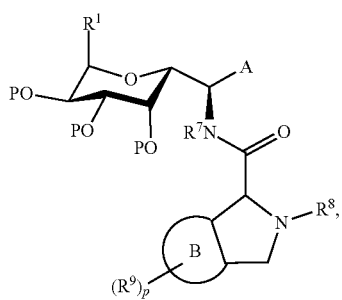

(I)

or a salt thereof, the method comprising coupling a compound of Formula (A):

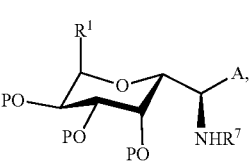

(A)

or salt thereof, with a compound of Formula (B),

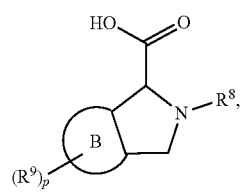

(B)

to yield a compound of Formula (I), wherein A, P, B, $R^1$, $R^7$, $R^8$, $R^9$, and p are as defined in claim 1.

19. A compound of Formula (C):

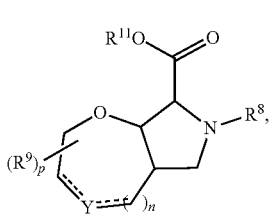

(C-2)

or salt thereof, wherein:

Y is O, S, $NR^9$, $C(R^9)_2$, $CR^9$, $CH_2$, or CH;

$R^8$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaliphatic, $-C(=NR^A)R^A$, $-C(=NR^A)OR^A$, $-C(=NR^A)N(R^A)_2$, $-C(=O)R^A$, $-C(=O)OR^A$, $-C(=O)N(R^A)_2$, $-S(O)_2R^A$, or a protecting group;

each occurrence of $R^9$ is independently, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, substituted or unsubstituted heteroaliphatic, $-OR^A$, $-N(R^A)_2$, $-SR^A$, $-CN$, $-SCN$, $-C(=NR^A)R^A$, $-C(=NR^A)OR^A$, $-C(=NR^A)N(R^A)_2$, $-C(=O)R^A$, $-C(=O)OR^A$, $-C(=O)N(R^A)_2$, $-NO_2$, $-NR^AC(=O)R^A$, $-NR^AC(=O)OR^A$, $-NR^AC(=O)N(R^A)_2$, $-NR^AC(=NR^A)N(R^A)_2$, $-OC(=O)R^A$, $-OC(=O)OR^A$, $-OC(=O)N(R^A)_2$, —NR$^A$S(O)$_2$R$^A$, —OS(O)$_2$R$^A$, or —S(O)$_2$R$^A$; or two R$^9$ groups are joined to form a substituted or unsubstituted heterocyclyl ring, or a substituted or unsubstituted carbocyclyl ring;

R$^{11}$ is hydrogen, substituted or unsubstituted alkyl, substituted or unsubstituted aryl, substituted or unsubstituted heteroaryl, or an oxygen protecting group;

p is 0-3;

n is 0 or 1;

⸗ represents a single or double bond; and each occurrence of R$^A$ is, independently, hydrogen, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted carbocyclylalkyl, substituted or unsubstituted heterocyclyl, substituted or unsubstituted aryl, substituted or unsubstituted aralkyl, substituted or unsubstituted heteroaryl, substituted or unsubstituted hetaralkyl, a nitrogen protecting group when attached to a nitrogen atom, an oxygen protecting group when attached to an oxygen atom, or a sulfur protecting group when attached to a sulfur atom, or two R$^A$ groups are joined to form a substituted or unsubstituted heterocyclyl ring, or a substituted or unsubstituted heteroaryl ring.

20. A method of preparing a compound of Formula (C-4):

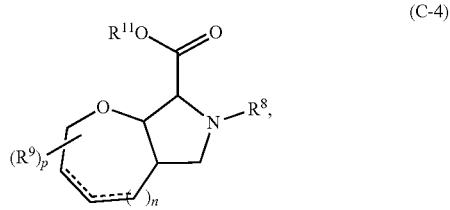

(C-4)

or a salt thereof, the method comprising ring closing metathesis of a compound of Formula (D):

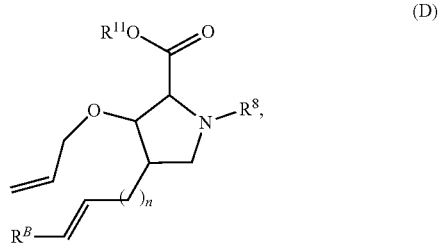

(D)

or salt thereof, wherein R$^8$, R$^9$, R$^{11}$, p, and n are as defined in claim 19; and R$^B$ is hydrogen or methyl.

* * * * *

UNITED STATES PATENT AND TRADEMARK OFFICE
CERTIFICATE OF CORRECTION

PATENT NO. : 11,124,534 B2
APPLICATION NO. : 16/637647
DATED : September 21, 2021
INVENTOR(S) : Andrew G. Myers et al.

It is certified that error appears in the above-identified patent and that said Letters Patent is hereby corrected as shown below:

In the Claims

Claim 1 (Column 222, Lines 51-62), the following structure:

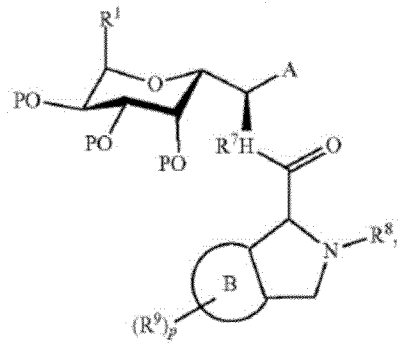

Should be replaced with:

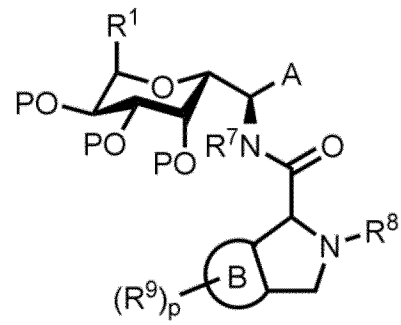

Signed and Sealed this
Seventh Day of December, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)

Claim 13 (Column 230, Lines 5-17), the following structure:

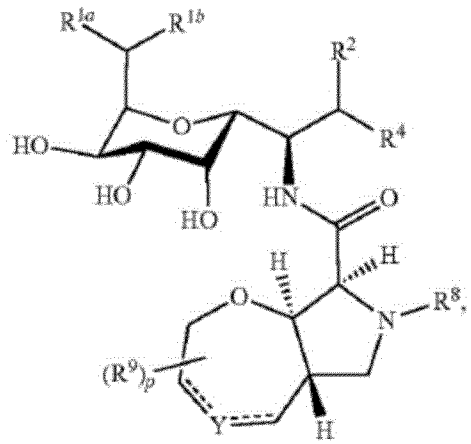

Should be replaced with:

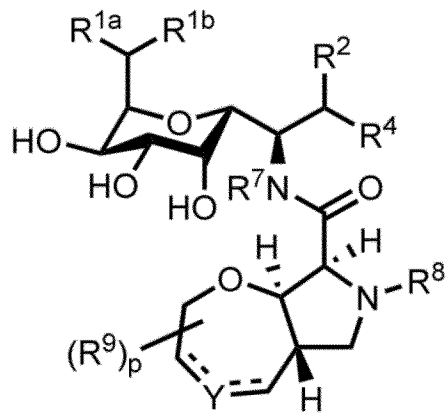

Claim 13 (Column 230, Lines 37-48), the following structure:

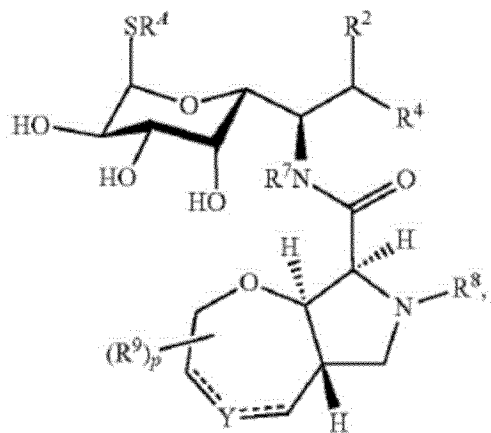

CERTIFICATE OF CORRECTION (continued)
U.S. Pat. No. 11,124,534 B2

Page 3 of 5

Should be replaced with:

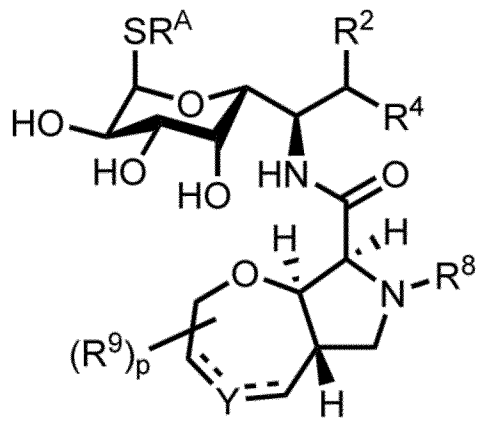

Claim 13 (Column 230, Lines 55-66), the following structure:

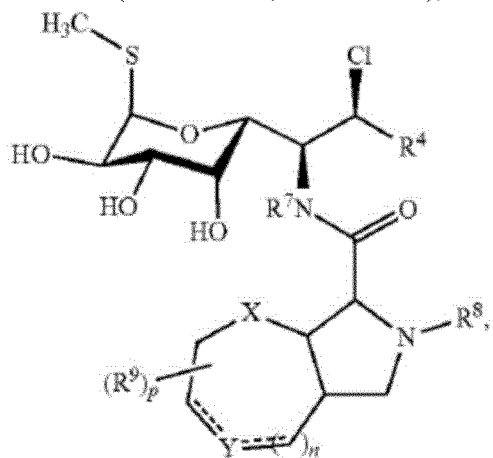

Should be replaced with:

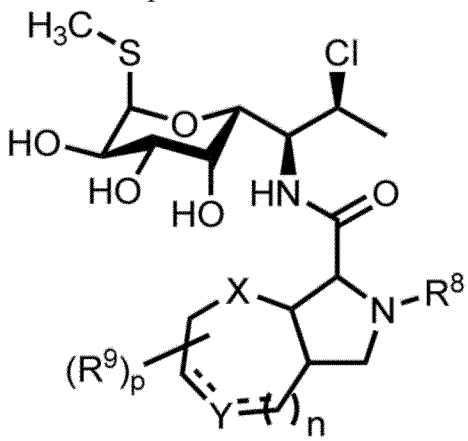

CERTIFICATE OF CORRECTION (continued)

Claim 14 (Column 236, Lines 55-66), the following structure should be deleted:

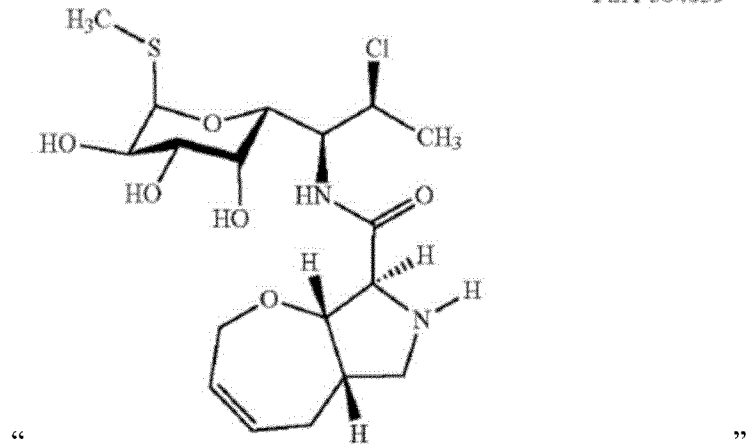

"                                                                                              "

Claim 14 (Column 242, Lines 5-23), the following structure:

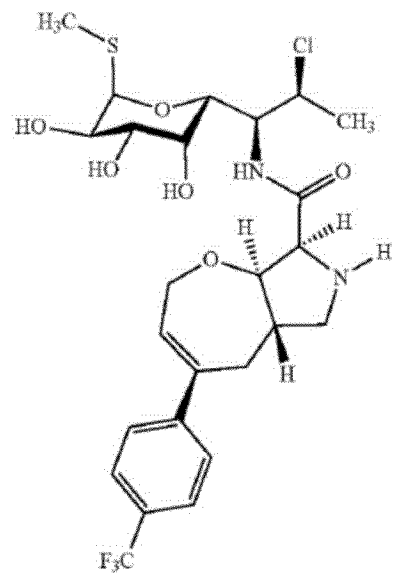

Should be replaced with:
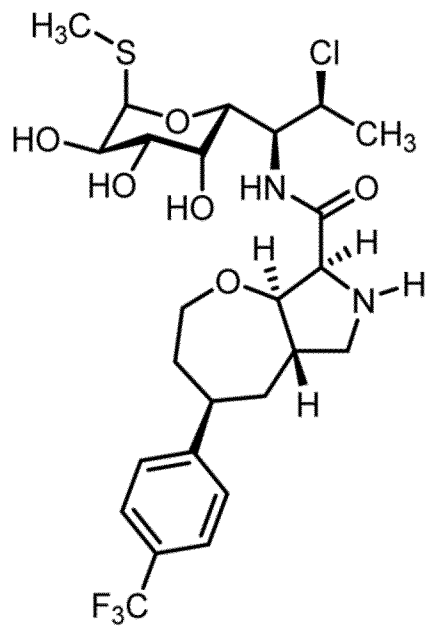
FSA-509019